United States Patent
Negi et al.

(10) Patent No.: US 10,590,398 B2
(45) Date of Patent: Mar. 17, 2020

(54) PRODUCTIVITY AND BIOPRODUCT FORMATION IN PHOTOTROPIN KNOCK/OUT MUTANTS IN MICROALGAE

(71) Applicants: NMC, INC., Los Alamos, NM (US); LOS ALAMOS NATIONAL SECURITY, LLC, Los Alamos, NM (US)

(72) Inventors: Sangeeta Negi, Los Alamos, NM (US); Richard Thomas Sayre, Los Alamos, NM (US); Shawn Robert Starkenburg, Los Alamos, NM (US)

(73) Assignees: NMC, INC., Los Alamos, NM (US); LOS ALAMOS NATIONAL SECURITY, LLC, Los Alamos, NM (US)

(*) Notice: Subject to any disclaimer, the term of this patent is extended or adjusted under 35 U.S.C. 154(b) by 0 days.

(21) Appl. No.: 15/831,178

(22) Filed: Dec. 4, 2017

(65) Prior Publication Data
US 2018/0187170 A1    Jul. 5, 2018

Related U.S. Application Data

(63) Continuation of application No. PCT/IB2016/054466, filed on Jul. 26, 2016.
(Continued)

(51) Int. Cl.
| | |
|---|---|
| *C12N 9/12* | (2006.01) |
| *C12P 19/04* | (2006.01) |
| *C12P 23/00* | (2006.01) |
| *C12N 1/12* | (2006.01) |
| *C12P 7/64* | (2006.01) |

(Continued)

(52) U.S. Cl.
CPC .............. *C12N 9/12* (2013.01); *C07K 14/405* (2013.01); *C12N 1/12* (2013.01); *C12N 9/0051* (2013.01); *C12N 9/1205* (2013.01); *C12N 9/22* (2013.01); *C12N 15/01* (2013.01); *C12N 15/11* (2013.01); *C12P 7/64* (2013.01); *C12P 19/04* (2013.01); *C12P 23/00* (2013.01);
(Continued)

(58) Field of Classification Search
None
See application file for complete search history.

(56) References Cited

U.S. PATENT DOCUMENTS

| | | |
|---|---|---|
| 6,258,588 B1 | 7/2001 | Demetropoulos et al. |
| 8,859,232 B2 | 10/2014 | Hahn et al. |

(Continued)

FOREIGN PATENT DOCUMENTS

| | | |
|---|---|---|
| EP | 2682469 | 1/2014 |
| WO | 2011/133493 | 10/2011 |

(Continued)

OTHER PUBLICATIONS

Thelander et al. Snf1-related protein kinase 1 is needed for growth in a normal day-night light cycle. The EMBO Journal (2004) 23, 1900-1910.*

(Continued)

*Primary Examiner* — Iqbal H Chowdhury
(74) *Attorney, Agent, or Firm* — Peacock Law P.C.; Janeen Vilven

(57) ABSTRACT

Phototropin is a blue light receptor, which mediates a variety of blue-light elicited physiological processes in plants and algae. In higher plants these processes include phototropism, chloroplast movement and stomatal opening. In the green alga *Chlamydomonas reinhardtii*, phototropin plays a vital role in progression of the sexual life cycle and in the control of the eye spot size and light sensitivity Phototropin is also involved in blue-light mediated changes in the synthesis of chlorophylls, carotenoids, chlorophyll binding proteins. We compared the transcriptome of phototropin knock out (PHOT KO) mutant and wild-type parent to analyze differences in gene expression in high light grown cultures (500 µmol photons $m^{-2}$ $s^{-1}$). Our results indicate the up-regulation of genes involved in photosynthetic electron transport chain, carbon fixation pathway, starch, lipid, and cell cycle control genes. With respect to photosynthetic electron transport genes, genes encoding proteins of the cytochrome b6f and ATP synthase complex were up regulated potentially facilitating proton-coupled electron transfer. In addition genes involved in limiting steps in the Calvin cycle Ribulose-1,5-bisphosphate carboxylase/oxygenase (RuBisCO), Sidoheptulose 1,7 bisphosphatase (SBPase), Glyceraldehyde-3-phosphate dehydrogenase (3PGDH) and that mediate cell-cycle control (CDK) were also up regulated along with starch synthase and fatty acid biosynthesis genes involved in starch and lipid synthesis. In addition, transmission electron micrographs show increased accumulation of starch granules in PHOT mutant compared to wild type, which is consistent with the higher expression of starch synthase genes. Collectively, the altered patterns of gene expression in the PHOT mutants were associated with a two-fold increase in growth and biomass accumulation compared to wild type when grown in environmental phototbioreactors (Phenometrics) that simulate a pond environment. In conclusion, our studies suggest that phototropin may be a master gene regulator that suppresses rapid cell growth and promotes gametogenesis and sexual recombination in wild type strains.

9 Claims, 12 Drawing Sheets

Specification includes a Sequence Listing.

Related U.S. Application Data

(60) Provisional application No. 62/171,176, filed on Jun. 4, 2015.

(51) Int. Cl.

| | | |
|---|---|---|
| C07K 14/405 | (2006.01) | |
| C12N 9/02 | (2006.01) | |
| C12N 9/22 | (2006.01) | |
| C12N 15/01 | (2006.01) | |
| C12N 15/11 | (2006.01) | |

(52) U.S. Cl.
CPC ..... *C12Y 108/01009* (2013.01); *C12Y 207/11* (2013.01); *C12N 2310/20* (2017.05); *C12N 2800/80* (2013.01)

(56) References Cited

U.S. PATENT DOCUMENTS

| | | |
|---|---|---|
| 2005/0108791 A1 | 5/2005 | Edgerton |
| 2011/0207117 A1 | 8/2011 | Bock et al. |
| 2012/0322157 A1 | 12/2012 | Yohn et al. |
| 2013/0007916 A1 | 1/2013 | Spalding |
| 2013/0116165 A1 | 5/2013 | Schmidt et al. |
| 2013/0330718 A1 | 12/2013 | Shu et al. |
| 2014/0249295 A1 | 9/2014 | Bonger et al. |

FOREIGN PATENT DOCUMENTS

| | | |
|---|---|---|
| WO | 2013/016267 | 1/2013 |
| WO | 2013/056212 | 4/2013 |
| WO | 2014/085626 | 6/2014 |
| WO | 2016/193959 | 12/2016 |
| WO | 2016/197136 | 12/2016 |

OTHER PUBLICATIONS

Davies et al. Sac3, an Snf1-like Serine/Threonine Kinase That Positively and Negatively Regulates the Responses of Chlamydomonas to Sulfur Limitation. The Plant Cell, vol. 11, 1179-1190, Jun. 1999.*
Arnon, "Copper Enzymes in Isolated Chloroplasts. Polyphenoloxidase in Beta Vulgaris", Plant Physiology, vol. 24, No. 1, 1949, 1-15.
Baena-Gonzalez, "A central integrator of transcription networks in plant stress and energy signalling", Nature, vol. 448, No. 7156, 2007, 938-942.
Bao, et al., "Homologues of bacterial TnpB_IS605 are widespread in diverse eukaryotic transposable elements", Mobile DNA, vol. 4, No. 12, 2013, 1-16.
Briggs, et al., "Photoreceptors in Plant Photomorphogenesis to Date. Five Phytochromes, Two Cryptochromes, One Phototropin, and One Superchrome1", Plant Physiol vol. 125, No. 1, 2001, 85-88.
Chapman, et al., "Conditions for Mutagenesis of the Nitrogen-fixing Cyanobacterium Anabaena variabilis", Journal of General Microbiology, vol. 133, 1987, 111-118.
Chen, "Light Signal Transduction in Higher Plants", Annu. Rev. Genet., vol. 38, 2004, 87-117.
Comai, "Efficient discovery of DNA polymorphisms in natural populations by Ecotilling", The Plant Journal, vol. 37, No. 5, 2004, 778-786.
Dubrow, "The Development and Application of the CRISPR/CAS System as a Powerful New Tool for Genome Editing: A CASe Study", Biochemistry 158, 1-8, 2014.
Ermilova, et al., "Phototropin plays a crucial role in controlling changes in chemotaxis during the initial phase of the sexual life cycle in Chlamydomonas", Planta, vol. 219, No. 3, 2004, 420-427.
Folta, et al., "Primary Inhibition of Hypocotyl Growth and Phototropism Depend Differently on Phototropin-Mediated Increases in Cytoplasmic Calcium Induced by Blue Light1", Plant Physiol., vol. 133, No. 4, 2003, 1464-1470.

Fu, "Time Course Transcriptome Changes in *Shewanella* algae in Response to Salt Stress", PLOS One, vol. 9, No. 5, 2014, e96001 1-8.
Gaj, et al., "ZFN, TALEN, and CRISPR/Cas-based methods for genome engineering", Trends in Biotechnology, vol. 31, No. 7, 2013, 397-405.
Grossman, "Paths toward Algal Genomics", Plant Physiology, vol. 137, No. 2, 2005, 410-427.
Huang, et al., "Localization of the Blue-Light Receptor Phototropin to the Flagella of the Green Alga *Chlamydomonas reinhardtii*", Molecular Biology of the Cell, vol. 15, No. 8, 2004, 3605-3614.
Huang, "Phototropin is the blue-light receptor that controls multiple steps in the sexual life cycle of the green alga *Chlamydomonas reinhardtii*", PNAS, vol. 100, No. 10, 2003, 6269-6274.
Hwang, et al., "Transcriptome analysis of acclimatory responses to thermal stress in Antarctic algae", Biochemical and Biophysical Research Communications, vol. 367, No. 3, 2008, 635-641.
Im, et al., "Phototropin involvement in the expression of genes encoding chlorophyll and carotenoid biosynthesis enzymes and LHC apoproteins in Chlamydomonas reinhardtii", The Plant Journal, vol. 48, No. 1, 2006, 1-16.
Kaftan, "Characterization of Photosystem II Activity and Heterogeneity during the Cell Cycle of the Green Alga *Scenedesmus quadricauda1*", Plant Physiology, vol. 120, No. 2, 1999, 433-441.
Kagawa, et al., "Blue Light-Induced Phototropism of Infl orescence Stems and Petioles is Mediated by Phototropin Family Members phot1 and phot2", Plant Cell Physiol., vol. 50, No. 10, 2009, 1774-1785.
Kanehisa, et al., "Data, information, knowledge and principle: back to metabolism in KEGG", Nucleic Acids Research, vol. 42, 2014, D199-D205.
Kanehisa, et al., "KEGG: Kyoto Encyclopedia of Genes and Genomes", Nucleic Acids Research, vol. 28, No. 1, 2000, 27-30.
Koid, et al., "Comparative Transcriptome Analysis of Four Prymnesiophyte Algae", PLOS One, vol. 9, No. 6, 2014, e97801 1-15.
Kozuka, et al., "Tissue-Autonomous Promotion of Palisade Cell Development by Phototropin 2 in *Arabidopsis*", The Plant Cell, vol. 23, No. 10, 2011, 3684-3695.
Matiolli, et al., "The *Arabidopsis* bZIP Gene AtbZIP63 Is a Sensitive Integrator of Transient Abscisic Acid and Glucose Signals", Plant Physiology, vol. 157, 2011, 692-705.
Matsuoka, et al., "Primary Processes During the Light-signal Transduction of Phototropin", Photochemistry and Photobiology, vol. 83, No. 1, 2007, 122-130.
Molnar, et al., "miRNAs control gene expression in the single-cell alga *Chlamydomonas reinhardtii*", Nature, vol. 447, No. 28, 2007, 1126-1130.
Moni, "The blue light receptor Phototropin 1 suppresses lateral root growth by controlling cell elongation", Plant Biology, vol. 17, No. 1, 2015, 34-40.
Negi, "The blue light photoreceptor phototropin regulates growth and photosynthetic responses in Chlamydomonas reinhardtii", https://ps16stlouis.sched.org/event/12U8bwG/poster-group-19-light-harvesting-b, 2013, 1.
Nieto, et al., "EcoTILLING for the identification of allelic variants of melon eIF4E, a factor that controls virus susceptibility", BMC Plant Biology, vol. 7, No. 34, 2007, 1-9.
Ohsaki, et al., "A pitfall in using BODIPY dyes to label lipid droplets for Xuorescence microscopy", Histochem Cell Biol, vol. 133, No. 4, 2010, 477-480.
Onodera, "Phototropin from Chlamydomonas reinhardtii is Functional in *Arabidopsis thaliana*", Plant Cell Physiol., vol. 46, No. 2, 2005, 367-374.
Perrine, "Optimization of Photosynthetic Light Energy Utilization by Microalgae", Algal Research 1, 2012, 134-142.
Pick, et al., "Kinetic anomalies in the interactions of Nile red with microalgae", Journal of Microbiological Methods, vol. 88, No. 2, 2012, 189-196.
Reeck, et al., ""Homology" in Proteins and Nucleic Acids: A Terminology Muddle and a Way out of It", Cell, vol. 50, No. 5, 1987, 667.

(56) References Cited

OTHER PUBLICATIONS

Rismani-Yazdi, et al., "Transcriptome sequencing and annotation of the microalgae *Dunaliella tertiolecta*: Pathway description and gene discovery for production of next-generation biofuels", BMC Genomics, vol. 12, No. 148, 2011, 1-18.
Sethi, "All-optical switching in LOV2-C250S protein mutant from *Chlamydomonas reinhardtii* green algae", 2009 International Conference on Emerging Trends in Electronic and Photonic Devices & Systems, 2009, 1.
Sizova, et al., "Nuclear gene targeting in Chlamydomonas using engineered zinc-finger nucleases", The Plant Journal, vol. 73, 2013, 873-882.
Suetsugu, et al., "Phytochrome-dependent Photomovement Responses Mediated by Phototropin Family Proteins in Cryptogam Plants†", Photochemistry and Photobiology, vol. 83, No. 1, 2007, 87-93.
Sullivan, "In Vivo Phosphorylation Site Mapping and Functional Characterization of *Arabidopsis* Phototropin 1", Molecular Plant, vol. 1, No. 1, 2008, 178-194.
Takemiya, et al., "Phototropins Promote Plant Growth in Response to Blue Light in Low Light Environments", The Plant Cell, vol. 17, No. 4, 2005, 1120-1127.
Tamaki, et al., "Biochemical and physiological analyses of NADPH-dependent thioredoxin reductase isozymes in Euglena gracilis", Plant Science vol. 236, 2015, 29-36.
Thomas, et al., "Unique Ecophysiology among U(VI)-Reducing Bacteria as Revealed by Evaluation of Oxygen Metabolism in Anaeromyxobacter dehalogenans Strain 2CP-C", Applied and Environmental Microbiology, vol. 76, No. 1, 2010, 176-183.
Tian, "Characterization of a second carotenoid β-hydroxylase gene from *Arabidopsis* and its relationship to the LUT1 locus", Plant Molecular Biology, vol. 47, No. 3, 2001, 379-388.
Trippens, et al., "Phototropin Influence on Eyespot Development and Regulation of Phototactic Behavior in Chlamydomonas reinhardtii", The Plant Cell, vol. 24, No. 11, 2012, 4687-4702.
Veetil, et al., "A conserved isoleucine in the LOV1 domain of a novel phototropin from the marine alga *Ostreococcus tauri* modulates the dark state recovery of the domain", Biochimica et Biophysica Acta, vol. 1810, No. 7, 2011, 675-682.
Wang, et al., "One-Step Generation of Mice Carrying Mutations in Multiple Genes by CRISPR/Cas-Mediated Genome Engineering", Cell, vol. 153, No. 4, 2013, 910-918.
Xiao, et al., "Chromosomal deletions and inversions mediated by TALENs and CRISPR/Cas in zebrafish", Nucleic Acids Research, vol. 41, No. 14, 2013, e141 1-11.
Yan, et al., "Induction and characterization of pigmentation mutants in Porphyra yezoensis (Bangiales, Rhodophyta)", Journal of Applied Phycology, vol. 12, 2000, 69-81.
Zorin, et al., "Nuclear gene targeting in Chlamydomonas as exemplified by distruption of the PHOT gene", Gene, vol. 432, 2008, 91-96.

* cited by examiner

WT Parent

PHOT K/O

SEQUENCE LISTING

```
<160> NUMBER OF SEQ ID NOS: 73

<210> SEQ ID NO 1
<211> LENGTH: 760
<212> TYPE: PRT
<213> ORGANISM: Chlorella sorokiniana

<400> SEQUENCE: 1

Met Ala Pro Thr Val Gln Gly Leu Pro Ala Pro Gln Thr Gln Val Val
1               5                   10                  15

Asn Ala Leu Ser Thr Leu Arg His Thr Phe Val Val Ala Asp Ala Thr
            20                  25                  30

Leu Pro Asp Cys Pro Leu Ile Tyr Ala Ser Glu Gly Phe Val Gln Met
        35                  40                  45

Thr Gly Tyr Ser Met Glu Glu Val Leu Gly His Asn Cys Arg Phe Leu
    50                  55                  60

Gln Gly Glu Gly Thr Asp Pro Lys Asp Val Lys Lys Leu Arg Asp Ala
65                  70                  75                  80
```

-continued

Val Lys Asn Gly Thr Pro Val Cys Thr Arg Leu Leu Asn Tyr Arg Lys
            85              90              95

Asp Gly Thr Pro Phe Trp Asn Leu Leu Thr Met Thr Pro Ile Lys Asp
            100             105             110

Glu Ile Gly Arg Val Ile Lys Phe Val Gly Val Gln Val Asp Val Thr
            115             120             125

Asn Arg Thr Glu Gly Arg Ala Tyr Thr Asp Ser Gln Gly Val Pro Val
            130             135             140

Leu Val His Tyr Asp Asp Arg Leu Lys Glu Thr Val Ala Lys Pro Ile
145             150             155             160

Val Asp Asp Val Leu Met Ala Val Gln Gln Asp Asp Gly Lys Thr Pro
            165             170             175

Val Arg Leu Ser Arg Gly Ser Pro Ser Arg Ala Leu Pro Arg Val Ala
            180             185             190

Leu Asp Leu Ala Thr Thr Val Glu Arg Ile Gln Ser Asn Phe Val Ile
            195             200             205

Ala Asp Pro Thr Leu Pro Asp Cys Pro Ile Val Phe Ala Ser Asp Pro
            210             215             220

Phe Leu Arg Leu Thr Gly Tyr Arg Arg Glu Glu Val Leu Gly Arg Asn
225             230             235             240

Cys Arg Phe Leu Gln Gly Pro Asp Thr Asp Arg Ala Ala Val Leu Glu
            245             250             255

Leu Lys Ala Ala Ile Arg Ala Gly Arg Glu Cys Thr Val Arg Leu Leu
            260             265             270

Asn Tyr Thr Lys Thr Gly Lys Ala Phe Trp Asn Met Leu Thr Val Ala
            275             280             285

Pro Ile Lys Asp Ile Glu Asp Arg Pro Arg Phe Leu Val Gly Val Gln
            290             295             300

Val Asp Val Thr Glu His Pro Thr Val Ala Asp Ala Thr Pro Val Gly
305             310             315             320

Arg Gln Ala Ala Asn Ala Val Gly Gln Ala Leu Gln Ser Met Asn Trp
            325             330             335

Val Gly Val Asp Pro Trp Ala Thr Phe Pro Thr Gly Leu Arg Gln Pro
            340             345             350

Lys Pro His Arg Arg Leu Asp Pro Ala Ala Ala Leu Ala Ala Val
            355             360             365

Val Ala Arg Asp Gly Lys Leu Arg Leu Arg His Phe Ser Arg Val Lys
            370             375             380

Gln Leu Gly Ser Gly Asp Val Gly Met Val Asp Leu Val Gln Leu Val
385             390             395             400

Gly Thr Gly Gln Arg Phe Ala Leu Lys Ser Leu Glu Lys Arg Glu Met
            405             410             415

Leu Glu Arg Asn Lys Val Gly Arg Val Arg Thr Glu Glu Ala Ile Leu
            420             425             430

Ser Thr Val Asp His Pro Phe Leu Ala Thr Leu Tyr Gly Thr Leu Gln
            435             440             445

Thr Asp Thr His Leu His Phe Leu Leu Glu Tyr Cys Asn Gly Gly Glu
            450             455             460

Leu Tyr Ala Leu Leu Asn Ser Gln Pro Asn Lys Arg Leu Lys Glu Asp
465             470             475             480

Val Val Arg Phe Tyr Ala Ala Glu Val Leu Leu Ala Leu Gln Tyr Leu
            485             490             495

His Val Gln Gly Tyr Val Tyr Arg Asp Leu Lys Pro Glu Asn Ile Leu

```
                500                 505                 510
Leu His Ser Thr Gly His Val Met Leu Thr Asp Phe Asp Leu Ser Tyr
            515                 520                 525
Cys Gln Gly Ser Thr Thr Pro Ser Leu Leu Met Leu Pro Gly Glu Ala
            530                 535                 540
Ala Ala Ala Ala Ala Ala Gly Val Pro Arg Ser Ser Gly Ile Asn
545                 550                 555                 560
Cys Ala Gly Ser Lys Gly Glu Arg Gly Ser Glu Ala Ala Pro Ala Leu
            565                 570                 575
Pro Ser Gly Gln Gln Ala Leu Leu Val Ala Gln Pro Asp Gly Arg Ala
            580                 585                 590
Asn Ser Phe Val Gly Thr Glu Glu Tyr Leu Ala Pro Glu Val Ile Thr
            595                 600                 605
Gly Ser Gly His Thr Ser Met Val Asp Trp Trp Ser Phe Gly Ile Leu
            610                 615                 620
Ile Tyr Glu Leu Leu Gly Ala Arg Arg Asp Ala Thr Phe Glu Asn Val
625                 630                 635                 640
Leu Lys Lys Pro Leu Ala Phe Pro Asp Ala Val Ser Val Ser Pro Ala
            645                 650                 655
Cys Lys Asp Leu Ile Thr Lys Leu Leu Asn Lys Glu Pro Gly Lys Arg
            660                 665                 670
Leu Gly Ser Lys Ala Gly Ala Asp Glu Ile Lys Arg His Pro Trp Phe
            675                 680                 685
Ala Ala Thr Asn Trp Ala Leu Val Arg Gln Gln Ser Pro Pro Phe Val
            690                 695                 700
Thr Pro Arg Arg Ser Ser Ala Gly Ala Glu Gly Gly Arg Pro Ser Arg
705                 710                 715                 720
Pro Leu Ser Asp Gly Ser Glu Pro Arg Val His Ser Ala Asp Ser Val
            725                 730                 735
Leu Pro Asp Pro Lys Pro Ala Ala Ala Ala Ala Ala Ala Ala Pro
            740                 745                 750
Gly Gln Gln Pro Lys Ala Lys Ser
            755                 760

<210> SEQ ID NO 2
<211> LENGTH: 2347
<212> TYPE: DNA
<213> ORGANISM: Chlorella sorokiniana

<400> SEQUENCE: 2
cccaagggtc ccggctctgg ggccgtggca gcagcagcga gttggaggga cgcagcgggc    60
tgcaaatatg ccccgaccg tgcagggctt accggcgccc agacgcaag tcgtgaacgc    120 actatcgacc cttcggcaca cctttgtggt ggcggatgcc acgctgccag actgcccgct    180
catctatgcc agcgagggt tgtgcagat gacgggctat agcatggagg aggtgctggg    240
gcacaactgc cgcttcctgc aaggcgaggg caccgaccca aaggatgtga agaagctgcg    300
ggatgctgtg aagaatggca ccccgtgtg cacgcgcctg ctcaactacc ggaaggacgg    360
cacgccattc tggaacctgc tgaccatgac acccatcaag gacgagatcg gcgggtcat    420 caagtttgtg ggcgtgcagg tggatgtgac caaccgcaca gagggccgcg catacaccga    480 ctcccaggc gtgccggtgc tggtccacta cgacgaccgc ctgaaggaga cggtggccaa    540
gccgattgtg gacgatgtgc tgatggcggt gcagcaggat gacggcaaga cgccggtgcg    600
gctgtcgcgc ggctcgccct cgcgcgccct gccccgtgtg gcgctggatc tggccacgac    660
```

```
agtggagcgc atccagtcga actttgtgat tgccgacccc acgctgcccg actgccccat    720
tgtgtttgcc tccgaccccct tcttgcgcct caccggctac cggcgcgagg aggtgctggg   780
ccgaaactgc cgcttcctgc aaggccccga caccgaccgg cggcagtgc tggagctcaa    840 ggcagccatc cgggcggggc gcgagtgcac ggtgcgcctg ctcaactaca ccaagacggg    900
caaggccttc tggaacatgc tcacagtggc gcccatcaag gacattgagg accggccgcg    960
gttcctggtg ggcgtgcaag tagatgtgac agagcacccc acagtggcgg acgccacccc   1020
tgtgggccgc caggcagcca acgcggtcgg ccaggcgctg cagagcatga actgggtggg   1080
cgtggaccca tgggccacgt tccccacagg cctgcggcag cccaagccgc accgccggtt   1140
ggacccggcg gctgcggcgc tggcggcagt ggtggctcgc gacggcaagc tgcgcctgcg   1200
ccacttctcg cgggtgaagc agctgggcag cggcgacgtg ggcatggtgg acctggtgca   1260
gctggtgggc accggccagc gctttgcgct caagtcgctg gagaagcggg agatgctgga   1320
gcgcaacaag gtgggccgcg tgcgcactga ggaggccatc ctgtccacag tggaccaccc   1380
tttcctggcc acgctctacg gcacgctgca gacggacacg cacctccact tcctgctgga   1440
gtactgcaac ggcggcgagc tgtacgcgct gctcaactcg cagcccaaca gcggctgaa    1500 ggaggatgtg gtgcgcttct acgccgccga ggtgctgctg gccctgcagt acctgcacgt   1560
ccagggctac gtgtaccgcg acctgaagcc tgagaacatc ctgctgcact ccaccggcca   1620
cgtcatgctg accgactttg acctgagcta ctgccagggc agcaccacgc cctccctgct   1680
catgctgccg ggcgaagcag cggcagcagc tgcagcgggc gtgccgcgca gcagcagcgg   1740
catcaactgt gcgggttcca aaggcgagcg cggcagcgag gcggcccctg cactgccctc   1800
gggccagcag gcgctgctgg tggcgcagcc ggatgggcgt gccaacagct tgtgggcac    1860 tgaggagtac ctggcaccag aggtcatcac aggctccggc cacacctcca tggtggactg   1920
gtggtctttt ggcatcctca tttatgagct gctgggcgcg cggcgagatg ccacctttga   1980
gaatgtgctg aagaagcctc tggccttccc ggatgcggtg tccgtctcgc ccgcctgcaa   2040
ggacctgatc accaagcttc tgaacaagga gcctggcaag cggctgggca gcaaggcggg   2100
ggcggacgag atcaagcgcc acccatggtt tgcggccacc aactgggcgc ttgtgcggca   2160
gcagtcgccg ccatttgtca cgccgcggcg ctccagtgca ggagcagagg gcggccgccc   2220
gtcgcgcccg ctgtctgatg gctcggagcc acgcgtgcac tctgctgact ctgttctgcc   2280
agatcccaag ccggcggcag cagcggcagc ggcagcagcc ccaggccagc agccgaaagc   2340
caagtca                                                            2347
```

<210> SEQ ID NO 3
<211> LENGTH: 775
<212> TYPE: PRT
<213> ORGANISM: Chlorella sorokiniana

<400> SEQUENCE: 3

Leu Arg His Thr Phe Val Val Ala Asp Ala Thr Gln Pro Asp Cys Pro
1               5                   10                  15

Leu Val Tyr Ala Ser Gln Gly Phe Tyr Asp Met Thr Gly Phe Ser Pro
            20                  25                  30

Glu Glu Val Ile Gly His Asn Cys Arg Phe Leu Gln Gly Pro Asn Thr
        35                  40                  45

Asp Pro Glu His Val Arg Lys Leu Arg Glu Ser Val Gln Asn Gly Thr
    50                  55                  60

-continued

Cys Val Thr Val Arg Leu Leu Asn Tyr Arg Lys Asp Gly Thr Pro Phe
65                  70                  75                  80

Trp Asn Leu Leu Thr Met Thr Pro Val Lys Asp Asp Thr Gly Ala Val
            85                  90                  95

Val Lys Ile Val Gly Val Gln Leu Asp Val Thr Asp Thr Thr Glu Gly
            100                 105                 110

Leu Glu Asp Ala Ala His Gly Val Pro Val Leu Val Arg Tyr Asp Tyr
            115                 120                 125

Arg Leu Gln Asp Lys Leu Val Thr Pro Ala Val Asp Asp Val Leu Leu
            130                 135                 140

Gly Leu Gln Glu Asp Asp Glu Ala Ala Thr Thr Ala Gly Ala Ala Gly
145                 150                 155                 160

Ala Ala Ala Gly Gly Glu Ala His Arg Leu Ser Cys Ser Ala Leu Leu
            165                 170                 175

Arg Gln His His Arg Gly Gln Leu Asp Leu Gly Thr Thr Met Glu Arg
            180                 185                 190

Met Gln His Asn Phe Val Val Ser Asp Pro Thr Leu Pro Asp Cys Pro
            195                 200                 205

Ile Val Phe Ala Ser Asp Gly Phe Leu Glu Leu Thr Gly Tyr Arg Arg
            210                 215                 220

Glu Glu Val Leu Gly His Asn Cys Arg Phe Leu Gln Gly Pro Asp Thr
225                 230                 235                 240

Asp Arg Ala Glu Val Glu Arg Leu Lys Ala Ala Ile Asn Asn Trp Glu
            245                 250                 255

Glu Val Thr Val Lys Leu Leu Asn Tyr Asn Lys Ser Gly Lys Pro Phe
            260                 265                 270

Trp Asn Leu Leu Thr Val Ala Pro Ile Leu Asp Gly Lys Gly His Pro
            275                 280                 285

Arg Leu Leu Val Gly Val Leu Val Asp Val Thr Asn Ile Ser Thr Glu
            290                 295                 300

Gly Val Ala Ala Ala Glu His Gln Ala Ala Thr Ala Val Gly Gln Ala
305                 310                 315                 320

Leu Gly Thr Met Gly Trp Asp Gly Gly Asp Pro Trp Glu His Phe Glu
            325                 330                 335

Thr Ala Leu Ala Pro Ala Lys Pro His Gln Ala Asn Asp Pro Ala Ala
            340                 345                 350

Ala Ala Leu Arg Ala Leu Val Lys Glu Asp Gly Glu Leu Arg Leu Glu
            355                 360                 365

Arg Phe Arg Arg Ile Ala Asp Leu Gly Ala Gly Asp Ala Gly Val Val
            370                 375                 380

Thr Leu Val Glu Leu Gln Pro Leu Asp Gly Met Asp Ala Val Gly Ala
385                 390                 395                 400

Gly Gly Ala Ile Gly Arg His Leu Phe Ala Leu Lys Ser Met Asp Lys
            405                 410                 415

Lys Ala Met Glu Glu Arg Asn Lys Val Gly Arg Val Arg Thr Glu Glu
            420                 425                 430

Thr Ile Leu Arg Ser Val Asp His Pro Tyr Leu Ala Lys Leu Tyr Ala
            435                 440                 445

Thr Ile His Thr Asp Thr His Leu His Phe Leu Glu Tyr Cys Ser
            450                 455                 460

Gly Gly Val Leu Tyr Asp Val Leu Glu Arg Ser Pro Asp His Cys Ile
465                 470                 475                 480

Pro Glu Ala Glu Ala Lys Ser Ile Ala Ala Glu Val Leu Leu Ala Leu

```
                485                 490                 495

Gln Tyr Leu His Leu Arg Gly Phe Ile Tyr Arg Asp Leu Lys Pro Glu
            500                 505                 510

Asn Ile Leu Ile Met Pro Ser Gly His Cys Gln Leu Thr Asp Phe Asp
        515                 520                 525

Leu Ser Phe Thr Cys Gly Thr Asn Gly Ala Ser Val Ala Pro Glu Leu
    530                 535                 540

Val Pro Ala Ala Val Ala Pro Val Pro Ala Pro Gly Thr Pro Pro Gly
545                 550                 555                 560

Ser Thr Ser Gly Arg Gly Gly Ser Gly Ser Ala Met Leu Arg Thr Ser
                565                 570                 575

Ser Thr Ser Leu Arg Ser Asn Gly Ser Ala Ala Ser Pro Met Leu Leu
            580                 585                 590

Ala Ala Gln Pro Ser Val Arg Thr Asn Ser Leu Val Gly Thr Glu Glu
        595                 600                 605

Tyr Leu Ala Pro Glu Ile Ile Ile Gly Glu Gly His Asp Ser Met Val
    610                 615                 620

Asp Trp Trp Ser Phe Gly Ile Leu Leu Tyr Glu Leu Met Tyr Gly Thr
625                 630                 635                 640

Thr Pro Phe Lys Ser Ala Arg Arg Asp Thr Thr Phe Asp Asn Ile Val
                645                 650                 655

Lys Arg Gln Pro His Phe Pro His Arg Gly Val Ser Pro Glu Gly Arg
            660                 665                 670

Asp Leu Ile Ser Lys Leu Leu Ile Lys Asp Pro Thr Gln Arg Leu Gly
        675                 680                 685

Ala Gln Ala Gly Ala Asp Glu Val Arg Gln His Pro Trp Phe Ala Asp
    690                 695                 700

Phe Asp Trp Ala Leu Gly Arg His Ser Glu Ala Thr Leu Ala Arg Ala
705                 710                 715                 720

Ala Ser Arg Ala Gly Val Pro Lys Cys Ala Pro Ser Lys Val Pro Thr
                725                 730                 735

Gly Ile Gly Ser Asn Gly Ile Ser Gly Gly Arg Ser Ser Ala Ser Pro
            740                 745                 750

Pro Thr Pro Lys Arg Ala Gly Glu Gly Gly Ala Val Met Gly Cys Phe
        755                 760                 765

Pro Leu Arg Arg Arg Arg Asn
    770                 775

<210> SEQ ID NO 4
<211> LENGTH: 2328
<212> TYPE: DNA
<213> ORGANISM: Chlorella sorokiniana

<400> SEQUENCE: 4
ctccgccaca cctttgtggt ggccgatgcc acccagccag actgcccgct ggtctatgcc      60
agccagggct tctatgacat gacaggcttt tcgcctgagg aggtgattgg gcacaactgc     120
cgcttcctgc aaggccccaa cacagaccct gagcacgtgc gcaagctgcg ggagtcggtg     180
cagaacggca catgcgtcac tgtgcgcctg ctcaactgtc gcaaggatgg cacgccgttc     240
tggaacctgc tgaccatgac gcctgtcaag gatgacacgg gcgctgtggt caagattgtg     300
ggcgtgcagt tggatgtgac ggacaccaca gaaggcttgg aggacgcagc acacggcgtt     360
ccggtgcttg tgcgctacga ctaccgcctg caagacaagc tggtcacgcc agcggtggac     420
gatgtcctgc tgggcctgca ggaggacgac gaggcggcga ccacagcggg cgcagcgggc     480
```

```
gcagcagcgg cggcgaggc gcaccgcctg tcctgctcgg cgctgctgcg ccagcaccac      540
cgcggccagc tggacctggg tacaaccatg gagcgcatgc agcagaactt tgtggtgtcg      600
gaccccacgc tgcccgactg ccccatcgtg tttgcctcgg acggattcct ggagctcacc      660
ggctaccggc gcgaggaggt gctgggccac aactgccgct tcctgcaagg ccccgacacc      720
gacagggccg aggtggaacg gctgaaggca gccatcaaca actgggagga ggtgactgtg      780
aagctgctga actacaacaa gagcggcaag ccctttggga acctgctcac gtggccccc      840
atcctggatg caagggcca ccccgcctg cttgtgggcg tgctggtgga tgtgaccaac       900
atcagcaccg gggtgttgc agcggcgag caccaggcag caaccgctgt ggggcaggcg        960
ctgggcacaa tgggctggga cggcggcgat ccctgggagc actttgagac cgctctggca     1020
cctgccaagc ccaccaagc caacgaccct gccgccgccg ctctgcgcgc tctggtcaag     1080
gaggatggcg agctgcggct ggagcgcttc cgccgcattg ccgacctggg agccggcgat     1140
gcgggcgtgg tgactctagt ggagcttcag ccgctcgatg gatggatgc ggtgggggcg      1200
ggcggcgcca tcggccgcca cctgtttgcc ctcaagtcca tggacaagaa ggcgatggag     1260
gagcgcaaca aggtgggccg cgtgcgcacc gaggagacga tcctgcggtc ggtggaccac     1320
ccctatctcg ccaagctcta cgccaccatc cacacggaca cacacctgca cttcctgctc     1380
gagtactgct ccggcggcgt gctgtacgac gtgctggagc gctcccccga ccactgcatc     1440
cccgaggcag aggcgaagag cattgctgcc gaggtgctgc tggccctgca gtacctccac     1500
ctgcgtggct tcatctacag ggacctgaag cctgagaaca tcctaatcat gccctccggc     1560
cactgccagc tcaccgattt tgatctgtcc ttcacctgcg gcaccaacgg cgccagtgtg     1620
gcacctgagc tggtcccagc ggcggtcgca cccgtgcccg cccccggcac ccaccgggc     1680
agcaccagcg ggcgcggtgg cagcggcagc gccatgctgc gcaccagttc caccagcctg     1740
cggtccaatg gcagtgcggc cagccccatg ctgctggctg cccagcccag cgtgcgaacc     1800
aactcgctgg tgggcactga ggagtacctg cacctgaga tcatcattgg cgaggggcac     1860
gacagcatgg tggactggtg gtccttggc atcctgctct acgagctgat gtacggcacc     1920
acgcccttca gtcggcgcg gcgcgacacc acctttgaca acattgtgaa gcggcagccg     1980
cacttcccgc accgcggggt gtctccagag gggcgcgacc tcattagcaa gctgctgatc     2040
aaggacccca cgcagcgcct gggggcgcag gcgggtgctg acgaggtgcg gcagcacccc     2100
tggtttgccg actttgactg ggctctgggg cggcactcag aagccaccct ggcccggcg      2160
gccagccggg ccggcgtgcc caagtgtgcc cccagcaagg tgccgaccgg catcggcagc     2220
aacggcatca gcggcggccg cagcagcgca tcgccgccca cgcccaagcg ggctggggag     2280
gggggcgccg tcatgggctg cttcccactg cggcgccgcc gcaactga                 2328
```

<210> SEQ ID NO 5
<211> LENGTH: 730
<212> TYPE: PRT
<213> ORGANISM: Chlorella sorokiniana

<400> SEQUENCE: 5

Asn Cys Arg Phe Leu Gln Gly Glu Gly Thr Asp Pro Lys Asp Val Lys
1               5                   10                  15

Lys Leu Arg Asp Ala Val Lys Asn Gly Thr Pro Val Cys Thr Arg Leu
            20                  25                  30

Leu Asn Tyr Arg Lys Asp Gly Thr Pro Phe Trp Asn Leu Leu Thr Met
        35                  40                  45

```
Thr Pro Ile Lys Asp Glu Leu Gly Arg Val Ile Lys Phe Gly Val
     50                  55                  60

Gln Val Asp Val Thr Asn Arg Thr Glu Gly Arg Ala Tyr Thr Asp Ser
 65                  70                  75                  80

Asn Gly Val Pro Val Leu Val His Tyr Asp Asp Arg Leu Lys Glu Thr
                     85                  90                  95

Val Ala Lys Pro Ile Val Asp Asp Val Leu Met Ala Val Gln Gln Asp
                100                 105                 110

Asp Gly Lys Thr Pro Val Arg Leu Ser Arg Gly Ser Pro Ser Arg Ala
            115                 120                 125

Leu Pro Arg Val Ala Leu Asp Leu Ala Thr Thr Val Glu Arg Ile Gln
    130                 135                 140

Ser Asn Phe Val Ile Ala Asp Pro Thr Leu Pro Asp Cys Pro Ile Val
145                 150                 155                 160

Phe Ala Ser Asp Pro Phe Leu Arg Leu Thr Gly Tyr Arg Arg Glu Glu
                165                 170                 175

Val Leu Gly Arg Asn Cys Arg Phe Leu Gln Gly Pro Asp Thr Asp Arg
                180                 185                 190

Ala Ala Val Leu Glu Leu Lys Ala Ala Ile Arg Ala Gly Arg Glu Cys
                195                 200                 205

Thr Val Arg Leu Leu Asn Tyr Thr Lys Thr Gly Lys Ala Phe Trp Asn
    210                 215                 220

Met Leu Thr Val Ala Pro Ile Lys Asp Ile Glu Asp Arg Pro Arg Phe
225                 230                 235                 240

Leu Val Gly Val Gln Val Asp Val Thr Glu His Pro Thr Val Ala Asp
                245                 250                 255

Ala Thr Pro Val Gly Arg Gln Ala Ala Asn Ala Val Gly Gln Ala Leu
                260                 265                 270

Gln Ser Met Asn Trp Val Gly Val Asp Pro Trp Ala Thr Phe Pro Thr
        275                 280                 285

Gly Leu Arg Gln Pro Lys Pro His Arg Arg Leu Asp Pro Ala Ala Ala
    290                 295                 300

Ala Leu Ala Ala Val Val Ala Arg Asp Gly Lys Leu Arg Leu Arg His
305                 310                 315                 320

Phe Ser Arg Val Lys Gln Leu Gly Ser Gly Asp Val Gly Met Val Asp
                325                 330                 335

Leu Val Gln Leu Val Gly Thr Gly Gln Arg Phe Ala Leu Lys Ser Leu
                340                 345                 350

Glu Lys Arg Glu Met Leu Glu Arg Asn Lys Val Gly Arg Val Arg Thr
            355                 360                 365

Glu Glu Ala Ile Leu Ser Ala Val Asp His Pro Phe Leu Ala Ser Leu
    370                 375                 380

Tyr Gly Thr Leu Gln Thr Asp Thr His Leu His Phe Leu Leu Glu Tyr
385                 390                 395                 400

Cys Asn Gly Gly Glu Leu Tyr Ala Leu Leu Asn Ser Gln Pro Asn Lys
                405                 410                 415

Arg Leu Lys Glu Glu Val Arg Phe Tyr Ala Cys Glu Val Leu Leu
                420                 425                 430

Ala Leu Gln Tyr Leu His Val Gln Gly Tyr Val Tyr Arg Asp Leu Lys
        435                 440                 445

Pro Glu Asn Ile Leu Leu His Ser Thr Gly His Val Met Leu Thr Asp
    450                 455                 460
```

```
Phe Asp Leu Ser Tyr Cys Gln Gly Ser Thr Thr Pro Ser Leu Leu Met
465                 470                 475                 480

Leu Pro Ala Glu Gln Ala Ala Pro Ala Ala Ala Gly Arg Thr Ser
                485                 490                 495

Ser Gly Ile Asn Cys Ala Gly Ser Lys Gly Glu Arg Gly Glu Ala
            500                 505                 510

Ala Ala Ala Leu Pro Ser Gly Gln Gln Ala Leu Leu Val Ala Gln Pro
        515                 520                 525

Asp Gly Arg Ala Asn Ser Phe Val Gly Thr Glu Glu Tyr Leu Ala Pro
    530                 535                 540

Glu Val Ile Thr Gly Ser Gly His Thr Ser Met Val Asp Trp Trp Ser
545                 550                 555                 560

Phe Gly Ile Leu Val Tyr Glu Leu Leu Gly Ala Arg Arg Asp Ala Thr
                565                 570                 575

Phe Glu Asn Val Leu Lys Lys Pro Leu Gly Phe Pro Asp Gly Val Ala
            580                 585                 590

Val Ser Pro Ala Cys Lys Asp Leu Ile Thr Lys Leu Leu Asn Lys Ala
        595                 600                 605

Ser Gly Ala Gly Leu Gly Thr Pro Phe Ile Arg Glu Pro Gly Lys Arg
    610                 615                 620

Leu Gly Ser Lys Ala Gly Ala Asp Glu Ile Lys Arg His Pro Trp Phe
625                 630                 635                 640

Ala Gly Ile Asn Trp Ala Leu Val Arg Gln Gln Ala Pro Pro Phe Val
                645                 650                 655

Thr Pro Arg Arg Ser Ser Ala Gly Glu Gly Arg Pro Ser Arg Pro
            660                 665                 670

Leu Ser Asp Gly Ser Glu Ala Arg Val His Ser Ala Asp Ser Val Leu
    675                 680                 685

Pro Glu Pro Lys Pro Ala Ala Ala Ala Ala Ala Ala Gly Gln
690                 695                 700

Gln Pro Lys Ser Lys Ser Glu Gly Ala Ala Ala Ala Ala Val Ala
705                 710                 715                 720

Arg Glu Gly Pro Gly His Ile Asp Gly Phe
                725                 730

<210> SEQ ID NO 6
<211> LENGTH: 2420
<212> TYPE: DNA
<213> ORGANISM: Chlorella sorokiniana

<400> SEQUENCE: 6
tgtattccca gctttcgctg gccccagcgc agctgcagga gcccaggatg aagcgtgggg      60
gggaggtggg gctccctgcg cgcaatccc aggtcgtgaa cgcgctggcc accctcagac     120
atacgtttgt ggtggccgat gccacgctgc cagactgccc gctcatctat gccagcgagg     180
ggtttgtgca gatgacgggc tacagcatgg aggaggttct ggggcacaac tgccgtttcc     240
tgcaaggcga gggcaccgat cccaaggatg tgaagaagct gcgggatgcg gtgaagaacg     300 gcaccccgt gtgcacgcgc ctgctcaact accgcaagga cggcacccc ttctggaacc     360 tgctgaccat gacgccgatc aaggacgagc tggggcgcgt gatcaagttt gtgggcgtgc     420
aggtggatgt gaccaaccgc accgagggcc gcgcgtacac agactccaac ggcgtgccgg     480
tgctggtgca ctacgacgac cgcctcaagg agacggtggc caagccgatt gtggacgatg     540
tgctgatggc ggtgcagcag gatgacggca agacgccggt gcggctgtca cgcggctcgc     600
```

```
cctcacgggc ctgccccgt gtggcgctgg atctggccac aacggtggag cgcatccagt    660
cgaactttgt gattgccgac ccacgctgc ccgactgccc catcgtgttt gccagcgacc    720
cgttcctgcg gctcaccggc taccgccgag aggaggtgct gggacgcaac tgccgcttcc    780
tgcaaggccc cgacacggat cgtgcggcag tgctggagct gaaggcagcg atccgggcgg    840
ggcgcgagtg cacggtgcgt ctgctcaact acaccaagac gggcaaggcc ttctggaaca    900
tgctcaccgt ggcgcccatc aaggacattg aggaccggcc gcgcttcctg gtgggcgtgc    960
aagtggatgt gacggagcac ccgactgtgg cagatgccac gcccgtgggc cgccaggcag   1020
ccaacgcggt cggccaggcg ctgcagagca tgaactgggt gggtgtggac ccctgggcca   1080
cgttccccac gggcctgcgg cagcccaagc cgcaccgccg cttggaccca gccgcggcag   1140
cgctggcggc agtggtggcg cgcgacggca agctgcgcct cgccacttc tcgcgggtga   1200
agcagctggg cagcggtgac gttggcatgg ttgacctggt gcagctggtg ggcaccggcc   1260
agcgctttgc gctcaagtcg cttgagaagc gggagatgct ggagcgcaac aaggtgggcc   1320
gcgtgcgcac agaggaggca atcctgtcgg ccgtggacca cccttcctg gccagcctgt   1380
atggcacgct gcagacagac acgcacctgc acttcctgct ggagtactgc aacggcggcg   1440
agctgtatgc actgctcaac tcgcagccca caagcgact gaaggaggag gtggtgcgct   1500
tctacgcctg cgaggtgctg ctggcgctgc agtacctgca cgtccagggc tacgtgtacc   1560
gcgacctgaa gcccgagaac atcctgctgc actccacggg ccacgtcatg ctgaccgact   1620
ttgacctgag ctactgccag ggcagcacca cgccctccct gctcatgctg ccggcggagc   1680
aggcggcgcc ggcggcagcc gcagggcgca ccagcagcgg catcaactgc gctgggtcca   1740
agggcgagcg gggcggcgag gcggccgctg cgctgccctc gggccagcag gcgctgctgg   1800
tggcgcagcc agacgggcgc gccaacagct tgtgggcac tgaggaatac ctggcgccag   1860
aggtcatcac cggctccggc cacacatcca tggtggactg gtggtccttt ggcatcctcg   1920
tctacgagct gctgggcgcg cggcgagacg ccacgtttga gaatgtgctg aagaagccgc   1980
tgggcttccc ggatggggtg gccgtctcgc ccgcctgcaa ggacctcatc accaagctgc   2040
tgaacaaggc gagtggggct gggctgggca ctccatttat cagggagcct ggcaagcggc   2100
tgggcagcaa ggctggggca gacgagatca agcggcaccc ctggtttgcc ggcatcaact   2160
gggcgctcgt cgccagcag cgccgccgt tgtcacgcc ccggcgctcc agcgcgggag   2220
agggcgggcg ccctcgcgg ccgctgtcgg acggctccga ggcgcgtgtg cactctgccg   2280
actcagtcct gccagagccc aagcctgcag cggcggcggc ggcggcggcg gccggccagc   2340
agcccaagtc aaagtcggaa ggtgctgctg cggcggcggc ggtggcccgc gagggccctg   2400
gccacatcga cggattctga                                              2420
```

<210> SEQ ID NO 7
<211> LENGTH: 781
<212> TYPE: PRT
<213> ORGANISM: Chlorella sorokiniana

<400> SEQUENCE: 7

Met Val Ser Ala Leu Ala Lys Leu Arg His Thr Phe Val Val Ala Asp
1               5                   10                  15

Ala Thr Gln Pro Asp Cys Pro Leu Val Tyr Ala Ser Gln Gly Phe Tyr
                20                  25                  30

Asp Met Thr Gly Tyr Ser Pro Gln Glu Val Ile Gly His Asn Cys Arg
            35                  40                  45

```
Phe Leu Gln Gly Pro Asp Thr Asp Pro Glu His Val Arg Lys Leu Arg
 50                  55                  60

Asp Ser Val Gln Asn Gly Thr Gly Val Thr Val Arg Leu Leu Asn Tyr
 65                  70                  75                  80

Arg Lys Asp Gly Thr Pro Phe Trp Asn Leu Leu Thr Met Thr Pro Val
                 85                  90                  95

Lys Asp Asp Thr Gly Thr Val Val Lys Ile Val Gly Val Gln Leu Asp
                100                 105                 110

Val Thr Asp Thr Thr Glu Gly Leu Glu Asp Ala Ala His Gly Val Pro
                115                 120                 125

Val Leu Val Arg Tyr Asp Tyr Arg Leu Gln Asp Lys Leu Val Thr Pro
130                 135                 140

Ala Val Asp Asp Val Leu Leu Gly Leu Gln Glu Asp Asp Glu Ala Ala
145                 150                 155                 160

Thr Thr Ala Gly Thr Ala Gly Ala Gly Glu Val His Arg Leu Ser Cys
                165                 170                 175

Ser Thr Leu Leu Arg Gln His His Arg Gly Gln Leu Asp Leu Gly Thr
                180                 185                 190

Thr Met Glu Arg Met Gln Gln Asn Phe Val Val Ser Asp Pro Ser Leu
                195                 200                 205

Pro Asp Cys Pro Ile Val Phe Ala Ser Asp Gly Phe Leu Glu Leu Thr
210                 215                 220

Gly Tyr Arg Arg Glu Glu Val Leu Gly His Asn Cys Arg Phe Leu Gln
225                 230                 235                 240

Gly Pro Glu Thr Asp Arg Ala Glu Val Glu Arg Leu Lys Thr Ala Ile
                245                 250                 255

Ala Asn Trp Glu Glu Val Thr Val Lys Leu Gln Asn Tyr Thr Lys Gly
                260                 265                 270

Gly Lys Pro Phe Trp Asn Leu Leu Thr Val Ala Pro Ile Leu Asp Gly
                275                 280                 285

Lys Gly His Pro Arg Leu Leu Val Gly Val Leu Met Asp Val Thr Asn
290                 295                 300

Ser Ser Val Glu Gly Gly Ala Ala Ala Glu His Gln Ala Ala Thr Ala
305                 310                 315                 320

Val Gly Arg Ala Leu Gly Ala Met Gly Trp Asp Gly Ser Asp Pro Trp
                325                 330                 335

Glu His Phe Glu Thr Ala Leu Ala Pro Ala Lys Pro His Gln Ala Ser
                340                 345                 350

Asp Pro Ala Ala Ala Leu Arg Ala Val Lys Glu Asp Gly Glu
                355                 360                 365

Leu Arg Leu Glu Arg Phe Arg Arg Ile Ala Asp Leu Gly Ala Gly Asp
370                 375                 380

Ala Gly Val Val Thr Leu Val Glu Leu Leu Pro Pro Lys Gly Ala Asp
385                 390                 395                 400

Ala Ala Ala Gly Met Gly Ala Ala Ser Gly Arg His Leu Phe Ala Leu
                405                 410                 415

Lys Ser Met Asp Lys Lys Ala Met Glu Glu Arg Asn Lys Val Gly Arg
                420                 425                 430

Val Arg Thr Glu Glu Thr Ile Leu Arg Ser Val Asp His Pro Tyr Leu
                435                 440                 445

Ala Lys Leu Tyr Ala Thr Leu Gln Thr Asp Thr His Leu His Phe Leu
450                 455                 460

Leu Glu Tyr Cys Ser Gly Gly Val Leu Tyr Asp Val Leu Glu Arg Ala
```

```
        465                 470                 475                 480
Pro Asp His Cys Leu Pro Glu Ala Glu Ala Lys Ser Ile Ala Ala Glu
                        485                 490                 495

Val Leu Leu Ala Leu Gln Tyr Leu His Leu His Gly Phe Ile Tyr Arg
            500                 505                 510

Asp Leu Lys Pro Glu Asn Ile Leu Ile Met Pro Cys Gly His Cys Gln
                515                 520                 525

Leu Thr Asp Phe Asp Leu Ser Phe Ala Gly Thr Gly Ala Ala Ser Val
            530                 535                 540

Ala Pro Glu Leu Val Pro Ala Ser Ala Ala Leu Ala Pro Gly
545                 550                 555                 560

Thr Pro Pro Ala Ala Ser Pro Thr Arg Gly Ser Ser Ser Ser
                565                 570                 575

Met Leu Arg Thr Ser Ser Ala Ser Leu Arg Ser Ser Ser Thr Ala
            580                 585                 590

Ser Pro Met Leu Leu Ala Ala Gln Pro Ser Val Arg Thr Asn Ser Leu
                595                 600                 605

Val Gly Thr Glu Glu Tyr Leu Ala Pro Glu Val Ile Ile Gly Glu Gly
            610                 615                 620

His Asp Ser Met Val Asp Trp Trp Ser Phe Gly Ile Leu Leu Tyr Glu
625                 630                 635                 640

Leu Met Tyr Gly Thr Thr Pro Phe Lys Ser Ala Arg Arg Asp Thr Thr
                645                 650                 655

Phe Asp Asn Ile Val Lys Arg Glu Leu His Phe Pro Ser Arg Gly Pro
                660                 665                 670

Val Val Ser Ala Glu Gly Arg Asp Leu Ile Thr Arg Leu Leu Thr Lys
            675                 680                 685

Asp Pro Thr Gln Arg Leu Gly Ala Gln Ala Gly Ala Asp Glu Val Arg
                690                 695                 700

Gln His Pro Trp Phe Ala Glu Val Asp Trp Ala Leu Gly Arg His Ser
705                 710                 715                 720

Glu Ala Thr Leu Ala Arg Ala Ala Ser Arg Gly Pro Lys Arg Ala Pro
                725                 730                 735

Ser Lys Ala Ala Ser Arg Ala Pro Pro Gly Ile Gly Ser Asn Gly Arg
                740                 745                 750

Gly Ser Ser Ala Ala Pro Pro Thr Pro Lys Arg Ala Gly Glu Gly Gly
            755                 760                 765

Ala Val Met Gly Cys Phe Pro Met Arg Arg Arg Arg Asn
770                 775                 780

<210> SEQ ID NO 8
<211> LENGTH: 2346
<212> TYPE: DNA
<213> ORGANISM: Chlorella sorokiniana

<400> SEQUENCE: 8
atggtgtcgg cgcttgcaaa gctccgccac acctttgtgg tggccgatgc cacccagccg      60
gactgcccgc tggtgtatgc cagccagggt ttctatgaca tgaccggcta cagtccacag     120
gaggtgatcg ccataactg ccggttcctg caaggcccgg acacggaccc agagcacgtg      180
cgcaagctgc gcgactcggt gcaaaacggc acaggcgtca ccgtgcgcct gctcaactac     240
cgcaaggatg cacccccgtt ttggaacctg ctgacaatga cacctgtcaa ggatgacacc     300
ggcactgtgg tcaagattgt gggcgtgcag ctggatgtga ccgacaccac cgaaggcctg     360
```

| gaggatgcgg cgcacggcgt gccagtgctg gtccgatacg actaccgcct gcaggacaag | 420 |
| ctggtgacac ctgcagtgga cgacgtgctt ctgggcctgc aagaggatga cgaggcggcg | 480 |
| accacagcgg gcacagcagg ggcgggcgag gtgcaccgcc tctcctgctc cacgctgctg | 540 |
| cgccagcacc accgcggcca gctggacctg gcaccacca tggagcgcat gcagcagaac | 600 |
| ttcgtggtgt ccgacccttc cctgcccgac tgccccatcg tatttgcgtc cgacgggttc | 660 |
| ctggagctca cgggctaccg cgcgaagaa gtgctgggcc acaactgccg cttcctgcaa | 720 |
| ggccccgaga ctgatcgggc ggaggtggag cggctgaaga cagccattgc caactgggag | 780 |
| gaggtgactg taaagctgca gaactacacc aagggcggca agcctttctg gaacctgctt | 840 |
| acggtggctc ccattctgga tgggaagggc caccccgcc tgcttgtggg cgtgctgatg | 900 |
| gatgtgacca acagcagcgt ggagggcggc gcagcggcgg agcaccaggc ggcgacggct | 960 |
| gtggggcgtg cgctgggagc gatgggctgg gacggcagcg accctgggda gcactttgag | 1020 |
| acagccctgg cgccggccaa gccgcaccag gccagcgacc ccgcggccgc cgccctgcgc | 1080 |
| gctgtggtca aggaggacgg cgagctgcgc ctggagcgct tccgccgcat cgcggatctg | 1140 |
| ggtgctggcg atgcgggcgt ggtgacccta gtggagctgc tgccgcccaa gggagcggac | 1200 |
| gcagcggcgg gcatggggc cgccagcggg cgccacctgt ttgcgcttaa gtccatggac | 1260 |
| aagaaggcga tggaggagcg caacaaggtg ggccgcgtgc gcaccgagga gaccatcctg | 1320 |
| cgctcggtgg accacccta cctcgccaag ctgtacgcca ccctccagac agacacgcac | 1380 |
| ctgcacttcc tgctggagta ctgctcgggc ggtgtgctgt acgacgtgct agagcgcgcc | 1440 |
| cccgaccact gcctgcccga agcggaggcc aagagcatcg cggcagaggt gctgctggcg | 1500 |
| ctgcagtacc tgcacctgca tggcttcatc tacagggacc tgaagcccga aacatcctg | 1560 |
| atcatgccct gcgccactg ccagctcacc gacttcgacc tgtcctttgc cggtaccggc | 1620 |
| gccgccagcg tggcgccaga gctggtgccg gccgcctccg cggcggcact cgcgccgggc | 1680 |
| acgccgccgg ctgccgcctc ccccacgcgc ggcagcagca gcagcagcat gctgcggacc | 1740 |
| agctcggcca gctgcggtc cagcagcagc acggccagcc ccatgctgct ggctgcacag | 1800 |
| cccagcgtgc gcaccaactc gttggtgggc actgaggagt acttggcgcc ggaggtcatc | 1860 |
| attggcgagg gccacgacag catggtggac tggtggtcct ttggcatcct gctgtacgag | 1920 |
| ctgatgtacg gtaccacgcc cttcaagtct gcgcggcggg acaccacttt cgacaacatc | 1980 |
| gtcaagcggg agctgcattt cccgtcccgc gggccggttg tgtctgcaga ggggcgcgac | 2040 |
| ctcatcaccc gcctgctgac caaggacccc acgcaacggt tgggtgccca ggcaggggcg | 2100 |
| gacgaggtgc ggcagcaccc ctggtttgcg gaggtggact gggccctggg gcggcactcc | 2160 |
| gaggccaccc tggctcgtgc cgccagccgt ggacccaagc gcgcacccag caaggccgcc | 2220 |
| agcagggcgc ctcccggcat cggcagcaac ggccgcggca gcgcgcggc gccgcccacg | 2280 |
| cccaagcggg ccggggaggg cggtgcggtg atgggtgct tccccatgcg ccgccggcgc | 2340 |
| aactga | 2346 |

<210> SEQ ID NO 9
<211> LENGTH: 789
<212> TYPE: PRT
<213> ORGANISM: Chlorella sorokiniana

<400> SEQUENCE: 9

Met Ala Pro Ser Ala Ala Gly Leu Pro Ala Pro Gln Thr Gln Val Val
1               5                   10                  15

```
Asp Ala Leu Ser Thr Leu Arg His Thr Phe Val Val Ala Asp Ala Thr
             20                  25                  30
Leu Pro Asp Cys Pro Leu Ile Tyr Ala Ser Glu Gly Phe Val Gln Met
         35                  40                  45
Thr Gly Tyr Ser Met Glu Glu Val Leu Gly His Asn Cys Arg Phe Leu
     50                  55                  60
Gln Gly Glu Gly Thr Asp Pro Lys Asp Val Lys Lys Leu Arg Asp Ala
 65                  70                  75                  80
Val Lys Asn Gly Thr Pro Val Cys Thr Arg Leu Leu Asn Tyr Lys Lys
             85                  90                  95
Asp Gly Thr Pro Phe Trp Asn Leu Leu Thr Met Thr Pro Ile Lys Asp
            100                 105                 110
Glu Ala Gly Arg Val Ile Lys Phe Val Gly Val Gln Val Asp Val Thr
        115                 120                 125
Asn Arg Thr Glu Gly Arg Ala Tyr Thr Asp Ser Asn Gly Val Pro Val
    130                 135                 140
Leu Val His Tyr Asp Asp Arg Leu Lys Glu Thr Val Ala Lys Pro Ile
145                 150                 155                 160
Val Asp Asp Val Leu Met Ala Val Gln Gln Asp Asp Gly Lys Thr Pro
                165                 170                 175
Val Arg Leu Ser Arg Gly Ser Pro Ser Arg Ala Leu Pro Arg Val Ala
            180                 185                 190
Leu Asp Leu Ala Thr Thr Val Glu Arg Ile Gln Ser Asn Phe Val Ile
        195                 200                 205
Ala Asp Pro Thr Leu Pro Asp Cys Pro Ile Val Phe Ala Ser Asp Pro
    210                 215                 220
Phe Leu Arg Leu Ser Gly Tyr Arg Arg Glu Glu Val Leu Gly Arg Asn
225                 230                 235                 240
Cys Arg Phe Leu Gln Gly Pro Asp Thr Asp Arg Ala Ala Val Leu Glu
                245                 250                 255
Leu Lys Ala Ala Ile Arg Ala Gly Arg Glu Cys Thr Val Arg Leu Leu
            260                 265                 270
Asn Tyr Thr Lys Thr Gly Lys Ala Phe Trp Asn Met Leu Thr Val Ala
        275                 280                 285
Pro Ile Lys Asp Ile Glu Glu Arg Pro Arg Phe Leu Val Gly Val Gln
    290                 295                 300
Val Asp Val Thr Glu His Pro Thr Val Ala Asp Ala Thr Pro Val Gly
305                 310                 315                 320
Arg Gln Ala Ala Asn Ala Val Gly Gln Ala Leu Met Ser Met Asn Trp
                325                 330                 335
Val Gly Val Asp Pro Trp Ala Thr Phe Pro Thr Gly Leu Arg Gln Pro
            340                 345                 350
Lys Pro His Arg Arg Met Asp Pro Ala Ala Ala Leu Ala Ala Val
        355                 360                 365
Val Ala Arg Asp Gly Lys Leu Arg Leu Arg His Phe Ser Arg Val Lys
    370                 375                 380
Gln Leu Gly Ser Gly Asp Val Gly Met Val Asp Leu Val Gln Leu Val
385                 390                 395                 400
Gly Thr Ser Gln Arg Phe Ala Leu Lys Ser Leu Glu Lys Arg Glu Met
                405                 410                 415
Leu Glu Arg Asn Lys Val Gly Arg Val Arg Thr Glu Glu Ala Ile Leu
            420                 425                 430
Ser Thr Val Asp His Pro Phe Leu Ala Thr Leu Tyr Gly Thr Leu Gln
```

| | | | | | 435 | | | | | 440 | | | | | 445 | | | |
|---|---|---|---|---|---|---|---|---|---|---|---|---|---|---|---|---|---|---|

Thr Asp Thr His Leu His Phe Leu Leu Glu Tyr Cys Ser Gly Gly Glu
450                 455                 460

Leu Tyr Ala Leu Leu Asn Ser Gln Pro Asn Lys Arg Leu Lys Glu Asp
465                 470                 475                 480

Val Val Arg Phe Tyr Ala Ser Glu Val Leu Ala Leu Gln Tyr Leu
            485                 490                 495

His Val Gln Gly Tyr Val Tyr Arg Asp Leu Lys Pro Glu Asn Ile Leu
                500                 505                 510

Leu His Ser Thr Gly His Val Met Leu Thr Asp Phe Asp Leu Ser Tyr
515                 520                 525

Cys Gln Gly Ser Ala Thr Pro Ser Leu Leu Leu Pro Gly Glu Ala
530                 535                 540

Ala Ala Ala Pro Ala Val Ala Arg Ser Asn Ser Gly Ile Thr Cys Gly
545                 550                 555                 560

Ser Ala Lys Gly Glu Arg Gly Gly Ser Glu Ala Ala Pro Ala Leu Pro
                565                 570                 575

Ser Gly Gln Gln Ala Leu Leu Val Ala Gln Pro Asp Gly Arg Ala Asn
                580                 585                 590

Ser Phe Val Gly Thr Glu Glu Tyr Leu Ala Pro Glu Val Ile Thr Gly
            595                 600                 605

Ser Gly His Thr Ser Leu Val Asp Trp Trp Ser Phe Gly Ile Leu Ile
        610                 615                 620

Tyr Glu Leu Leu Gly Ala Arg Arg Asp Ala Thr Phe Glu Asn Val Leu
625                 630                 635                 640

Lys Lys Pro Leu Gly Phe Pro Glu Ala Val Pro Val Ser Pro Ala Cys
                645                 650                 655

Lys Asp Leu Ile Ala Lys Leu Leu Cys Lys Glu Pro Gly Lys Arg Leu
            660                 665                 670

Gly Ser Lys Ala Gly Ala Asp Glu Ile Lys Arg His Pro Trp Phe Ala
        675                 680                 685

Gly Ile Asn Trp Ala Leu Val Arg Gln Gln Ala Pro Pro Phe Val Thr
    690                 695                 700

Pro Arg Arg Ser Ser Val Gly Gly Glu Gly Arg Pro Ser Arg Pro Leu
705                 710                 715                 720

Ser Asp Arg Ser Glu Pro Arg Val His Ser Ala Asp Ser Val Leu Pro
                725                 730                 735

Asp Ser Lys Ala Ala Ser Ala Ala Ser Gly Lys Gln Ala Lys Ala Lys
            740                 745                 750

Ser Glu Gly Ala Ala Val Ala Ala Ala Pro Ala Ala Val Pro
        755                 760                 765

Ala Ala Ala Pro Ala Ala Ala Ala Pro Gln Gly Pro Gly
    770                 775                 780

His Ile Asp Gly Phe
785

<210> SEQ ID NO 10
<211> LENGTH: 2370
<212> TYPE: DNA
<213> ORGANISM: Chlorella sorokiniana

<400> SEQUENCE: 10
atggccccga gcgctgcggg gctgccggcc ccccagacgc aagtagtaga tgcgttgtcg   60
acgctgcgac acaccttcgt ggtggctgat gccaccctgc cggactgccc gctcatctac  120

```
gccagcgagg ggtttgtgca gatgacgggg tacagcatgg aggaggtgct ggggcacaac      180
tgccgcttcc ttcaaggcga gggcaccgac cccaaggacg tgaagaagct gcgggatgcg      240
gtgaagaacg gcaccccagt gtgcacgcgc ctgctcaact acaagaagga cggcaccccg      300
ttttggaacc tgctgaccat gaccccatc aaggacgagg ccgggcgcgt catcaagttt       360
gtgggcgtgc aggtggatgt gaccaaccgc accgagggcc gggcctacac agacagcaac      420
ggcgtgccgt gctggtcca ctacgatgac cgcctgaagg aaacggtggc caagccgatt      480
gtggatgatg tgctgatggc ggtgcagcag gatgatggca agacgccggt gcggctgtcg      540
cgcggctcgc cctcacgggc cctgcctcgt gtggcgctgg atctggccac cacggtggag      600
cgcattcagt cgaacttcgt gattgccgac cccacgctgc ccgactgccc cattgtcttt      660
gcctccgacc cctcctgcg cctgagtgga taccgccgag aggaggttct gggccgcaac       720
tgccgcttcc tccaagggcc agacacggac agggcagcag tgctggaact gaaggcggcc      780
atccgggcag ggcgcgagtg cacggtgcgc ctgctcaact acaccaagac gggcaaggcc      840
ttttggaaca tgctcactgt ggcgcccatc aaggacattg aggagcggcc gcgcttcctg      900
gtgggcgtgc aagtggacgt gacggagcac cccactgtgg cggacgccac gccggtgggc      960
cgccaggcag ccaacgcggt gggccaggcg ctgatgagca tgaactgggt gggtgtggac     1020
ccttgggcca ccttccccac gggcctgcgg cagcccaagc cgcaccgccg catggacccg     1080
gccgctgcgg cgctggcggc ggtggtggcg cgcgacggca agctgcgcct cgccacttt      1140 tcgcgggtca gcagctggg cagcggcgat gtgggcatgg tggacctggt gcagctggtg      1200
ggcaccagcc agcgctttgc gctcaagtcg ctggagaagc gggagatgct ggagcgcaac     1260
aaggtgggcc gcgtgcgcac cgaggaggcc atcctgtcaa cagtggacca ccccttcctg     1320
gccaccctct atggcacgct gcagacggac acgcacctcc atttcctgct ggagtactgc     1380
agcggcggcg agctgtacgc gctgctcaac tcgcagccta acaagcggct gaaggaggat     1440
gtggtgcgct tctacgccag cgaggtgctg ctggcgctgc agtacctgca cgtccagggc     1500
tacgtgtacc gcgacctgaa gccggagaac atcctgctgc actccacggg ccacgtcatg     1560
ctgaccgact ttgacctcag ctactgccag ggcagcgcca cgccctccct gctgctgctg     1620
cccggcgagg cggcgcggc gccggcggtg gcacgcagca acagcggcat cacgtgcggg     1680
agcgccaagg gcgagcgcgg cggcagcgag gcggcgccgg cgctgccctc gggccagcag     1740
gcgctgctgg tggcgcagcc ggatgggcgc gcaaacagct tgtgggcac tgaggagtac     1800 ttggctccag aggtcatcac cggctccggc cacacctccc tggtggactg gtggtccttt     1860
ggcatcctga tttacgagct gctgggtgcg cggcgagacg ccacctttga gaacgtgctg     1920
aagaagccgc tgggcttccc ggaagcgtg cccgtctcac ccgcctgcaa ggacctcatc     1980
gccaagctgc tgtgcaaaga gcccggcaag cggctgggca gcaaggcggg gcggacgag    2040 atcaagcggg accctggtt tgcgggcatc aactggcgc tggtgcggca gcaggcgccg      2100 cccttttgtca cgccgcggcg ctcgagcgtg ggaggagagg gccgaccgtc ccgcccgctg    2160
tccgaccgct cggagccgcg cgtgcactcc gccgactcag tcctgccaga cagcaaggca    2220
gcatcggctg cctctggcaa gcaggccaag gccagtcgc aaggggcggc tgtggcggcc     2280
gccgcgccgg cagccgccgt gccggcagcc gccgcgccgg ccgctgccgc ggcggccccg    2340
cagggccccg gccacattga cggcttttga                                      2370
```

<210> SEQ ID NO 11

```
<211> LENGTH: 779
<212> TYPE: PRT
<213> ORGANISM: Chlorella sorokiniana

<400> SEQUENCE: 11
```

| | | | | | | | | | | | | | | |
|---|---|---|---|---|---|---|---|---|---|---|---|---|---|---|
|Met|Ser|Ala|Leu|Ala|Lys|Leu|Arg|His|Thr|Phe|Val|Val|Ala|Asp|Ala|
|1| | | |5| | | | |10| | | | |15|
|Thr|Leu|Pro|Asp|Cys|Pro|Leu|Val|Tyr|Ala|Ser|Gln|Gly|Phe|Tyr|Asp|
| | | |20| | | | |25| | | | |30| |
|Met|Thr|Gly|Phe|Ser|Arg|Glu|Glu|Val|Ile|Gly|His|Asn|Cys|Arg|Phe|
| | | |35| | | | |40| | | | |45| |
|Leu|Gln|Gly|Pro|Asp|Thr|Asp|Pro|Glu|His|Val|Lys|Lys|Leu|Arg|Asp|
| |50| | | | |55| | | | |60| | | |
|Ala|Val|Lys|Asn|Gly|Thr|Cys|Val|Thr|Val|Arg|Leu|Leu|Asn|Tyr|Arg|
|65| | | | |70| | | | |75| | | | |80|
|Lys|Asp|Gly|Thr|Pro|Phe|Trp|Asn|Leu|Leu|Thr|Met|Thr|Pro|Val|Lys|
| | | | |85| | | | |90| | | | |95| |
|Asp|Asp|Thr|Gly|Thr|Val|Val|Lys|Ile|Val|Gly|Val|Gln|Leu|Asp|Val|
| | | |100| | | | |105| | | | |110| | |
|Thr|Asp|Thr|Thr|Glu|Gly|Leu|Glu|Asp|Ala|Ala|His|Gly|Val|Pro|Leu|
| | | |115| | | | |120| | | | |125| | |
|Leu|Val|Arg|Tyr|Asp|Tyr|Arg|Leu|Gln|Asp|Lys|Leu|Val|Thr|Pro|Ala|
| |130| | | | |135| | | | |140| | | | |
|Thr|Asp|Asp|Val|Leu|Leu|Gly|Leu|Gln|Glu|Asp|Glu|Leu|Ala|Thr|
|145| | | | |150| | | | |155| | | | |160|
|Lys|Ala|Gly|Ala|Pro|Gly|Ser|Val|His|Pro|Val|His|Arg|Leu|Ser|Thr|
| | | | |165| | | | |170| | | | |175| |
|Ser|Thr|Leu|Leu|Arg|Gln|His|His|Arg|Gly|Gln|Leu|Asp|Leu|Gly|Thr|
| | | |180| | | | |185| | | | |190| | |
|Thr|Phe|Glu|Arg|Met|Gln|Gln|Asn|Phe|Val|Val|Ser|Asp|Pro|Thr|Leu|
| | | |195| | | | |200| | | | |205| | |
|Pro|Asp|Cys|Pro|Ile|Val|Phe|Ala|Ser|Asp|Gly|Phe|Leu|Glu|Leu|Thr|
| |210| | | | |215| | | | |220| | | | |
|Gly|Tyr|Arg|Arg|Glu|Glu|Val|Leu|Gly|His|Asn|Cys|Arg|Phe|Leu|Gln|
|225| | | | |230| | | | |235| | | | |240|
|Gly|Pro|Asp|Thr|Asp|Arg|Ala|Glu|Val|Glu|Lys|Leu|Lys|Ala|Ala|Ile|
| | | |245| | | | |250| | | | |255| | |
|Thr|Asn|Trp|Glu|Glu|Ile|Thr|Val|Arg|Leu|Leu|Asn|Tyr|Thr|Lys|Thr|
| | |260| | | | |265| | | | |270| | | |
|Gly|Thr|Pro|Phe|Trp|Asn|Leu|Leu|Thr|Val|Ala|Pro|Ile|Leu|Asp|Gly|
| | |275| | | | |280| | | | |285| | | |
|Lys|Gly|His|Pro|Arg|Leu|Leu|Val|Gly|Val|Leu|Met|Asp|Ala|Thr|Asn|
| |290| | | | |295| | | | |300| | | | |
|Ile|Ser|Ile|Glu|Gly|Gly|Ala|Ala|Glu|His|Gln|Ala|Ala|Val|Ser|
|305| | | | |310| | | | |315| | | | |320|
|Val|Gly|Arg|Ala|Leu|Gly|Thr|Met|Gly|Trp|Asp|Gly|Ser|Asp|Pro|Trp|
| | | | |325| | | | |330| | | | |335| |
|Glu|His|Phe|Gln|Thr|Ala|Leu|Ala|Pro|Ala|Lys|Pro|His|Gln|Ala|Ser|
| | | |340| | | | |345| | | | |350| | |
|Asp|Pro|Ala|Ala|Ala|Leu|Arg|Ala|Val|Lys|Ala|Asp|Gly|Glu|
| | | |355| | | | |360| | | | |365| | |
|Leu|Arg|Leu|Glu|Arg|Phe|Arg|Arg|Ile|Ala|Asp|Leu|Gly|Ala|Gly|Asp|
| |370| | | | |375| | | | |380| | | | |
|Ala|Gly|Val|Val|Thr|Leu|Val|Glu|Leu|Arg|Pro|Pro|Glu|Ala|Ala|Gly|

```
            385                 390                 395                 400
        Ala Ala Gly Met Thr Ala Ser Gly Gly Arg Phe Leu Phe Ala Leu Lys
                        405                 410                 415

Ser Met Asp Lys Lys Ala Met Glu Glu Arg Asn Lys Val Gly Arg Val
                        420                 425                 430

Arg Thr Glu Glu Thr Ile Leu Arg Thr Val Asp His Pro Tyr Leu Ala
                        435                 440                 445

Lys Met Tyr Ala Thr Ile His Thr Asp Thr His Leu His Phe Leu Leu
                        450                 455                 460

Glu Tyr Cys Ser Glu Gly Val Leu Tyr Asp Val Leu Glu Arg Ser Pro
        465                 470                 475                 480

Asp His Cys Ile Pro Glu Ala Glu Ala Lys Ser Ile Ala Ala Glu Val
                        485                 490                 495

Leu Leu Ala Leu Gln Tyr Leu His Leu His Gly Val Ile Tyr Arg Asp
                        500                 505                 510

Leu Lys Pro Glu Asn Ile Leu Leu Arg Pro Ser Gly His Cys Gln Leu
                        515                 520                 525

Thr Asp Phe Asp Leu Ser Phe Ala Ser Ser Ala Ser Ser Val Ala
                        530                 535                 540

Pro Glu Leu Val Pro Ala Ala Val Pro Ala Pro Ala Pro Ala Ser Ala
        545                 550                 555                 560

Pro Ser Thr Pro Pro Ala Gly Ala Gly Pro Ala Arg Ser Gly Ser Ser
                        565                 570                 575

Met Leu Arg Thr Ser Ser Thr Ser Leu Arg Ser Ser Gly Ser Ala Ala
                        580                 585                 590

Ser Pro Met Leu Leu Ala Ala Gln Pro Ser Val Arg Thr Asn Ser Leu
                        595                 600                 605

Val Gly Thr Glu Glu Tyr Leu Ala Pro Glu Val Ile Ile Gly Glu Gly
                        610                 615                 620

His Asp Ser Met Val Asp Phe Trp Ser Phe Gly Ile Leu Leu Tyr Glu
        625                 630                 635                 640

Leu Leu Tyr Gly Thr Thr Pro Phe Lys Ala Ser Arg Arg Asp Ala Thr
                        645                 650                 655

Phe Asp Asn Ile Val Lys Arg Glu Pro Ser Phe Pro Pro Arg Gly Ala
                        660                 665                 670

Leu Val Ser Gly Glu Ala Lys Asp Leu Ile Arg Arg Leu Leu Val Lys
                        675                 680                 685

Asp Pro Thr Gln Arg Leu Gly Ala Gln Ala Gly Ala Asp Glu Val Arg
                        690                 695                 700

Gln His Pro Trp Phe Ala Gly Val Asp Trp Ala Leu Gly Arg His Ser
        705                 710                 715                 720

Glu Ala Thr Leu Ala Arg Ala Ala Ser Arg Ala Ala Thr Met Lys Arg
                        725                 730                 735

Val Pro Ser Lys Ser Ser Gly Met Ser Gly Met Gly Ser Ser Gly Ser
                        740                 745                 750

Gly Arg Ala Pro Pro Thr Pro Lys Arg Ala Gly Asp Ser Thr Thr Val
                        755                 760                 765

Leu Gly Cys Phe Pro Val Arg Arg Arg Gln
                        770                 775

<210> SEQ ID NO 12
<211> LENGTH: 2340
<212> TYPE: DNA
<213> ORGANISM: Chlorella sorokiniana
```

<400> SEQUENCE: 12

```
atgtcggccc tggccaagct ccgccacacc tttgtggtgg ccgatgccac cctgcccgac      60
tgcccgctgg tgtatgccag ccagggcttt tacgacatga cgggtttcag ccgtgaggag     120
gtcatcggcc acaactgccg cttcctccaa ggaccggaca cagaccctga gcatgtgaag     180
aagctgaggg acgcggtgaa gaacggcacc tgcgtcacag tgcgcctgct caactaccgc     240
aaggatggca ccccttctg gaacctgctg accatgacgc tgtcaagga cgataccggc      300
accgtggtta agattgtggg cgtgcagctg gatgtgaccg acaccacaga aggcctggag     360
gacgctgcgc acgcgtgcc gctgctggtc cgctacgact accgcctgca ggacaagctg      420
gtgacgcctg caacggacga tgtgctgctg gggctgcagg aggacgacga gctggcgacc     480
aaagcaggcg caccaggcag cgtgcacccc gtgcaccgcc tgtccacctc cacgctgctg     540
cggcagcacc accgcgggca gctggatctg gcacgacct ttgagcgcat gcagcagaat      600
ttcgtggtgt cggaccccac gctgcccgac tgccccatcg tgtttgcctc cgacgggttc     660
ctggagctca cggggtaccg gcgtgaggag gtgctgggcc acaactgccg cttcctgcaa     720
ggccccgata cagaccgagc cgaagtggag aagctcaagg cggccatcac caactgggag     780
gagatcactg tgaggctgct caactacacc aagaccggca cgccctttg gaacctgctc      840
acggtggcgc ccattctgga tggcaagggc caccccgcc tgctcgtggg cgtgctgatg      900
gatgcgacca acatcagcat tgagggtggt gcggcagcgg agcaccaggc cgctgtgtca     960
gtggggcgtg cgctgggcac gatgggctgg gacggcagcg acccctggga gcactttcag    1020
acggccctgg ccccggccaa gccccaccag gccagcgacc ccgccgccgc cgctctgcgc    1080
gctgtggtca aggcggatgg cgagctgcga ctggagcgct ccgccgcat tgctgacctg     1140
ggtgcgggcg acgcggggt ggtgaccctg gttgagctgc ggcctccaga ggcagcgggc     1200
gcagcgggca tgaccgccag cggcgggcgc ttcctgttcg cgctgaagtc catggacaaa    1260
aaggcgatgg aggagcgcaa caaggtgggc cgcgtgcgca cggaggaaac cattctgcgg    1320
acagtggacc accctatttt ggccaagatg tacgccacca tccacacaga cacgcacctc    1380
cacttccttc tggagtactg ctccgagggc gtgctgtacg acgtgctgga gcgctccccc    1440
gaccactgta ttccggaggc ggaggccaag agcatcgccg ccgaggtgct gctggcgctg    1500
cagtacctac acctacatgg cgtgatctac cgggacctga gcccgagaa catcctgctg     1560
aggccctccg ccactgcca gctcaccgat ttcgacctgt cctttgcgag cagcagcgcc     1620
tccagcgtag cacccgagct tgtgccagct gccgtccccg ccccggcccc cgcatccgct    1680
cccagcacgc cccagcagg cgccggcccc gcacgaagcg gcagctccat gctgcggacc     1740
agctcaacca gctgcggtc tagtggcagc gcagcgagcc ccatgctgct ggcggcgcag    1800
cccagcgttc ggaccaactc gctggtgggg actgaggagt acctggcccc tgaagtcatc    1860
attgagagg gccacgacag catggtggac ttttggtcct ttggcatcct gctctatgag      1920
ctgctgtacg gcaccacgcc cttcaaggcc tcccgccgcg atgccacttt cgacaacatt    1980
gtgaagcggg agccgagctt cccgccgcgc ggcgccctgg tctcagggga ggccaaggac    2040
ctgatccggc gcctgctggt caaggacccc acgcagcgct gggcgcgca ggcgggtgct     2100
gacgaggtgc ggcagcaccc ctggttcgcc ggcgtggact gggccctggg gcggcactca    2160
gaggccaccc tggctcgtgc cgccagccgg cggcaaccca tgaagcgtgt gcccagcaag    2220
tcctctggaa tgagcggcat gggcagcagc ggtagcggca gggcaccacc gacgcccaag    2280
```
cgggctgggg acagcaccac ggtgctgggg tgcttccccg tgcgccgccg gcgccagtga    2340

<210> SEQ ID NO 13
<211> LENGTH: 724
<212> TYPE: PRT
<213> ORGANISM: Picochlorum soloecismus

<400> SEQUENCE: 13

```
Met Ser Pro Gly Val Arg Glu Gly Gly Val Ala Pro Gly Ala Ala Thr
1               5                   10                  15

Lys Val Pro Glu Pro Gln Ala Lys Leu Thr Thr Ala Leu Ala Gly Leu
            20                  25                  30

Arg His Thr Phe Val Val Ala Asp Ala Thr Leu Pro Asp Cys Pro Leu
        35                  40                  45

Val Tyr Ala Ser Glu Gly Phe Leu Thr Met Thr Gly Tyr Ser Lys Glu
    50                  55                  60

Glu Val Leu Gly His Asn Cys Arg Phe Leu Gln Gly Glu Gly Thr Asp
65                  70                  75                  80

Pro Lys Ser Val Asp Gln Ile Arg Ser Ala Val Lys Lys Gly His Ser
                85                  90                  95

Leu Cys Thr Arg Leu Leu Asn Tyr Lys Lys Asn Gly Thr Pro Phe Trp
            100                 105                 110

Asn Leu Leu Thr Ile Thr Pro Ile Arg Asp Glu Thr Gly Arg Val Val
        115                 120                 125

Lys Phe Val Gly Val Gln Val Asp Val Thr Ser Thr Thr Glu Gly Arg
    130                 135                 140

Ala Ile Lys Asp Ser Glu Gly Val Pro Val Leu Ile Asn Tyr Asp Asp
145                 150                 155                 160

Arg Leu Lys Glu Asn Val Ala Lys Pro Ile Val Asp Asp Val Leu His
                165                 170                 175

Ala Val Gln Arg Asp Glu Gly Lys Ser Pro Lys Arg Leu Ser Arg Thr
            180                 185                 190

Gly Gly Ala Pro Gly Ser Pro Arg Ser Phe Pro Arg Val Ala Leu Asp
        195                 200                 205

Leu Ala Thr Thr Val Glu Arg Ile Gln Ser Asn Phe Val Ile Ala Asp
    210                 215                 220

Pro Thr Leu Pro Asp Cys Pro Ile Val Phe Ala Ser Asp Ala Phe Leu
225                 230                 235                 240

Arg Leu Ser Gly Tyr Arg Arg Glu Glu Val Leu Gly Arg Asn Cys Arg
                245                 250                 255

Phe Leu Gln Gly Asn Glu Thr Asp Arg Ser Thr Val Leu Glu Leu Lys
            260                 265                 270

Ala Ala Ile Lys Ala Gly Lys Glu Ile Thr Val Arg Leu Leu Asn Tyr
        275                 280                 285

Lys Lys Asp Gly Thr Pro Phe Trp Asn Met Leu Thr Val Ala Ser Ile
    290                 295                 300

Arg Asp Val Thr Gly Arg Leu Arg Phe Tyr Val Gly Val Gln Val Asp
305                 310                 315                 320

Val Thr Ala Glu Pro Thr Val Glu Thr Ala Pro Val Gly Met Lys
                325                 330                 335

Ala Ala Ser Ile Val Gly Asp Ala Met Lys Arg Phe Asp Trp Val Gly
            340                 345                 350

Val Asp Pro Trp Ile Ser Phe Lys Ser Gly Val Met Pro Leu Lys Pro
        355                 360                 365
```

His Arg Arg Gln Asp Pro Asn Ala Leu Ile Leu His Glu Leu Ala Lys
370                 375                 380

Lys Glu Gly Lys Leu Arg Leu Lys Asn Phe Phe Arg Ser Lys Gln Leu
385                 390                 395                 400

Gly Ala Gly Asp Val Gly Met Val Asp Leu Leu Thr Leu Asp Gly His
                405                 410                 415

Lys Tyr Ala Met Lys Ser Leu Glu Lys Gln Glu Met Ile Asp Arg Asn
                420                 425                 430

Lys Val Gly Arg Val Lys Thr Glu Gln Thr Ile Leu Glu Asn Ile Asp
                435                 440                 445

His Pro Phe Leu Ala Thr Cys Tyr Ala Lys Ile Gln Thr Asp Thr His
450                 455                 460

Leu His Phe Val Leu Glu Tyr Cys Ser Gly Gly Glu Leu Tyr Gly Leu
465                 470                 475                 480

Met Asn Ser Met Pro Gly Lys Arg Leu Pro Glu Asp Trp Val Lys Phe
                485                 490                 495

Tyr Ala Ala Glu Val Leu Leu Ala Leu Gln Tyr Leu His Leu Met Gly
                500                 505                 510

Tyr Phe Tyr Arg Asp Leu Lys Pro Glu Asn Ile Leu Ile His Ser Ser
                515                 520                 525

Gly His Ile Lys Leu Thr Asp Phe Asp Leu Ser Tyr Cys Gln Gly Glu
530                 535                 540

Thr Val Pro Glu Val Glu Lys Leu Asp Pro Pro Val Arg Asp Pro Ser
545                 550                 555                 560

Asp Val Glu Asn Ser Ile Tyr Asp Lys Arg Glu Met Glu Asp Tyr Leu
                565                 570                 575

Leu Lys Leu Asn Pro Arg Gly Lys Ala Asn Ser Phe Val Gly Thr Glu
                580                 585                 590

Glu Tyr Leu Ala Pro Glu Ile Ile Ala Gly Thr Gly His Asp Ala Met
                595                 600                 605

Val Asp Trp Trp Ser Phe Gly Ile Leu Ile Tyr Glu Leu Ser Tyr Gly
610                 615                 620

Ser Ser Pro Phe Arg Gly Pro Arg Arg Asp Ala Thr Phe Asp Asn Val
625                 630                 635                 640

Leu Lys Lys Pro Leu Lys Phe Pro Gln Arg Glu Glu Asp Leu Ser Asp
                645                 650                 655

Asp Gly Lys Asp Leu Ile Gln Arg Leu Leu His Lys Asp Pro Thr Leu
                660                 665                 670

Arg Leu Gly His Asn Ala Gly Ala Asp Glu Val Lys Arg His Pro Trp
                675                 680                 685

Phe His Asp Ile Asn Trp Ala Leu Leu Arg Asn Ser Thr Pro Pro Met
690                 695                 700

Val Pro Asp Gln Asp Lys Thr Gln Lys Thr Gln Gly Ser Asn Thr Thr
705                 710                 715                 720

Ile Glu Gly Phe

<210> SEQ ID NO 14
<211> LENGTH: 2473
<212> TYPE: DNA
<213> ORGANISM: Picochlorum soloecismus

<400> SEQUENCE: 14
gacgaaataa atcaataaat ttcgaccaat tagtacaaga gagcacacta atgggcttta      60
tgtcctgtgt tgaggagtag cgaaacgggt ttagaaatat cttcgtaggc cgacacttga     120

```
acttctagcc tcacgaagac ggttgaaaca cggatatctt tgtgtattca tgccattcaa    180
gtctctataa tctgataatt gggccgttga aatgagtcct ggcgttcgag aagggggggt    240
tgcacctggc gcagcaacca aggtgcccga acctcaagca aagctgacga ctgcgctggc    300
ggggcttcgc catacctttg ttgtggcaga tgcgacgctt cctgattgtc cactggtata    360
tgctagcgaa gggttttttga caatgactgg ttattccaaa gaagaggtgc ttgggcataa    420
ttgtcgattt cttcaagggg agggcactga tcccaaatct gttgaccaga ttcgatctgc    480
tgtgaaaaag ggacactctc tgtgcaccag gttgcttaat tacaagaaaa atggaactcc    540
attttggaat cttctgacaa taacaccaat aagggatgaa actggtagag tagtaaagtt    600
tgttggcgtt caagtggatg tcacatccac aactgaaggc cgagcaatta aggactctga    660
aggggtgcct gttttgatca actatgatga ccgactgaaa gagaatgtgg cgaaacctat    720
agtggatgat gtcctacatg cggttcaaag agatgaagga aaatctccga agcgactctc    780
tcgtacagga ggagctccag ggtcacccag gtcatttccc cgtgttgctt tagatctggc    840
aacaaccgtg aacgtatac agtccaactt tgtgattgcc gatccaactt taccagattg    900
cccaatcgtt tttgcatctg atgcattttt gcgcctgtct gggtatagac gagaagaggt    960
tctgggaaga aattgtcgct tccttcaggg aaacgaaacc gataggtcaa ctgtcctgga   1020
attgaaagct gctattaagg cagggaaaga gataactgtt cggcttctga actacaaaaa   1080
ggacggaaca ccattttgga acatgttgac tgttgcttcg atacgagatg ttactgggag   1140
actgaggttt tatgtgggtg tacaggtgga tgttactgct gagcccacgg tagagacagc   1200
cgctccagtt gggatgaagg ctgccagtat tgttggcgat gcaatgaaga gatttgattg   1260
ggttggagtc gacccatgga tctcatttaa gagcggggtg atgcctctca agcctcaccg   1320
gcgccaagat ccaaatgctt taattctgca tgagttggca agaaggagg ggaaattgag   1380 attgaagaac ttttttccgat cgaaacaatt gggcgccggt gacgtcggca tggttgattt   1440
actcacatta gatggtcata aatatgcgat gaagtctcta gaaaaacaag aaatgattga   1500
tagaaataaa gttggtcgag tgaagacaga acagacaatt ctggaaaaca ttgaccaccc   1560
cttcctggct acttgctacg caaagataca aacagataca catttacatt tcgtgctcga   1620
atattgctct ggaggagagc tgtatggact gatgaactcc atgccaggta aaaggcttcc   1680
agaggattgg gtcaagtttt atgctgctga agttctgttg gcgctgcagt acctgcatct   1740
catgggctat ttctacagag atttaaagcc agaaaacatc ttaatccata gctctggcca   1800
cataaagttg acagattttg atctttcgta ctgccaaggg gaaactgttc ctgaagttga   1860
aaaattagat cctccagtca gggatccatc tgatgtggaa aatagtatct atgataaacg   1920
agaaatggag gactacttgt tgaaattgaa tccaaggggt aaggccaact cctttgttgg   1980
cactgaagaa tacttggcac cagaaataat agcgggaacc gggcatgatg ccatggttga   2040
ctggtggtcc tttggtattc tgatctacga actatcatac ggctcttctc cctttagggg   2100
cccgagaaga gatgcaacgt tgacaatgt tctaaagaag cctttgaaat ttcctcagcg   2160
agaagaagat ttgtctgacg atggaaaaga ccttatccaa cgtttgttgc acaaagatcc   2220
cacactcaga ttaggccata atgctggagc ggacgaagtc aagcggcatc catggttcca   2280
tgacatcaac tgggcgcttc tacgcaatag cactcctccc atggtaccag atcaagataa   2340
gacacaaaaa actcagggat ctaatactac tatagaaggc ttttaatgtt ctgttcttga   2400
attgttgttt gcattctgca cagcagcatg tccgagttgc tcatagtaac aatgtaatgt   2460
```
tgaatcaata tta                                                               2473

<210> SEQ ID NO 15
<211> LENGTH: 1213
<212> TYPE: PRT
<213> ORGANISM: Chlorella sorokiniana

<400> SEQUENCE: 15

Met Ala Asp Arg Gly Leu Arg Arg Asp Ile Ser Cys Arg Arg
1               5                   10                  15

Leu Arg Cys Thr Arg Leu Pro Ser Arg Pro Ala Ala His Pro His
            20                  25                  30

Val Ala Ala Cys Pro Pro Arg Pro Pro Thr Asp Ala Pro Pro Thr Trp
        35                  40                  45

Asp Leu Gly Ala Ala Gln Gly Gly Ala Ala Thr Ser Gln Arg Pro
    50                  55                  60

Val Thr Pro Gly Leu Gly Ala Leu Gly Asp Gly Gly Ser Arg His Ser
65                  70                  75                  80

Arg Gln Pro Ala Ala Arg Ala Ala Thr Ala Ala Pro Thr Ser Gln Lys
                85                  90                  95

Gln Pro Gly Phe Phe Arg Ala Ala Met Arg Thr Thr Ser Gly Ser Leu
            100                 105                 110

Ser Gly Leu Leu Lys Arg Ser Gly Thr Ala Ala Pro Ala Pro Ala Gly
        115                 120                 125

Ser Ser Pro Leu Phe Glu Val Arg Gly Ala Ala Met Leu Pro Pro Asp
    130                 135                 140

Pro Pro Thr Arg Pro Ala Thr Ala Ala Pro Ala Gly Pro Pro Ser Arg
145                 150                 155                 160

Thr Ser Ala His Gln Gln Gln Gln Gln His Lys Ala Ala Ala Pro
                165                 170                 175

Pro Thr Tyr Asn Val His Ala Arg Ala Ala His Ser Arg Pro Ala Thr
            180                 185                 190

Ala Ser Cys Gly Ser Pro Pro Val Ala Gly His Arg Gln Ala Ser Pro
        195                 200                 205

Ala Ala Val Ala Ser His Gly Leu Asp Pro Ser Thr Ser Pro Val Pro
    210                 215                 220

Gln Pro Ala Ala Pro Thr Pro His Tyr Gln Gln Pro Leu Arg Arg Ser
225                 230                 235                 240

Ala Val Pro Ala Val Thr Tyr Ala Thr Pro Ser Pro Ala Ser Ala Ala
                245                 250                 255

Ala Gln Gln Leu Arg Ala Gln Gln Ala Ala Ala Arg Gln Ala
            260                 265                 270

Ala Gln Glu Pro Gln Ala Gln Arg Gln Gln Gln Ala Thr Ala Gln
        275                 280                 285

Pro Gly Ser Phe Ser Arg Ala Ser Ser Leu Gly Ser Ser Ala Gly Ser
    290                 295                 300

Ser Ser Leu Pro Ser Ser Ser Gly Asp Tyr Gly Ser Ser Ser Ser Gln
305                 310                 315                 320

Gly Ala Ala Pro Ala Ala Ile Met His Gln Asn Pro Leu Phe Ala Gly
                325                 330                 335

Gly Ser Glu Asn Ala Ser Phe Ala Ala Ser Arg Gln Gln Gly Ala Gln
            340                 345                 350

Pro Gln Thr Arg Pro Pro Pro Val Arg Val Ala Pro Pro Ala
        355                 360                 365

-continued

Ala Thr Pro Ala Thr Pro Pro Gly Gly Val Leu Ala Gly Thr Ala Gly
    370             375             380

Val Ser Pro Cys Pro Thr Pro Met Ser Asn Leu His Ala Ala Ser Asn
385             390             395             400

Leu Thr Met Leu Thr Asp Ser Arg Pro Val Ser Pro Gly Pro Phe Leu
            405             410             415

Ser Thr Leu Pro Ser Gly Ser Glu Arg Gly Ser Arg Pro Val Ser Pro
        420             425             430

Gln Cys Ile Asp Ser Val Pro Thr Pro Gly Ser Phe Ala Pro Pro
    435             440             445

Gly Leu Ala Ala Ala Ala Ala Ala Ser Arg Gly Met Leu Ser
    450             455             460

Pro Ile Arg Thr Ala Ser Ser Ala Gly Val Ala Gly Ser Gln His Ser
465             470             475             480

Arg Ser Leu Pro Thr Ser Pro Ala Pro Pro Ala Ala Ser Leu Pro
                485             490             495

Val Ala Gly Gly Ser Pro Ser Ala Cys Pro Ala Gly Met Pro Ser Gly
            500             505             510

Thr Ala Ala Phe Arg Val Pro Ile Phe Asn Gln Asp Gly Arg Leu Val
            515             520             525

Gly Tyr Lys Gln Asn Ser Asn Leu Ile Pro Arg Ala Gly Ala Cys Ile
    530             535             540

Ser Ser Ala Pro Ser Ser Pro Ser Arg Ser Ala Phe Leu Ala Asp Pro
545             550             555             560

Ile Thr Phe Gln Thr Thr Ser Phe Ser Ala Ala Ala Gly Ala Val Glu
                565             570             575

Gly Ala Ser Pro Gln Pro Lys Pro Pro Val Val Arg Pro Pro Val Ser
            580             585             590

Asp Ser Gly Asp Phe Ala Glu Ser Leu Ala Asp Pro Cys Lys Gly Phe
        595             600             605

Pro Asp Ala Asp Asn Met Val Pro Gly Tyr Val Leu Gly Pro Val Leu
    610             615             620

Gly Lys Gly Gly Phe Cys Ser Val Arg Lys Ala Leu His Glu Val Thr
625             630             635             640

Gly Gln Ala Val Ala Cys Lys Ile Ile Glu Lys Gly Lys Leu Lys Asp
            645             650             655

Pro Lys Asp Arg Asp Arg Val Asp Arg Glu Cys Arg Val Met Arg Asn
        660             665             670

Leu Ser Asn His Cys Ala Val Ile Lys Leu Tyr Glu Tyr Val Glu Thr
    675             680             685

Arg Asp Cys Val Tyr Ile Met Met Glu Ala Ala Lys Arg Gly Ser Leu
690             695             700

Leu Asp Tyr Val Arg Glu Arg Lys Arg Leu Pro Glu Ala Glu Ala Val
705             710             715             720

Leu Ile Phe Gln Gln Leu Leu His Ala Leu Gln Phe Cys His Arg Lys
            725             730             735

Asp Val Val His Arg Asp Ile Lys Leu Glu Asn Ile Leu Ile Asp Gly
            740             745             750

Ala Gly His Met Lys Leu Ile Asp Phe Gly Leu Cys Gly Tyr Tyr Val
            755             760             765

Ala Gly Lys Arg Leu Arg Cys His Cys Gly Ser Pro Ser Tyr Ala Ala
    770             775             780

Pro Glu Ile Val Ala Arg Lys Asp Tyr Leu Gly Pro Pro Val Asp Val

```
                785                 790                 795                 800
Trp Ser Leu Gly Ile Val Leu Phe Ala Met Leu Ala Gly Tyr Leu Pro
                    805                 810                 815

Phe His Ala Lys Glu Lys Lys Gln Leu Ser Glu Lys Ile Leu Ala Gly
                    820                 825                 830

Val Tyr Lys Pro Ala Ala Trp Met Ser Ala Asp Ala Gln Asp Leu Leu
                    835                 840                 845

Ser Arg Met Leu Cys Leu Asp Pro Gln Arg Ile Ser Leu Glu Ala
850                 855                 860

Val Trp Ala His Pro Trp Val Gly Ala Pro Arg Trp Glu Pro Pro
865                 870                 875                 880

Gly Val Gly Ala Asp Arg Leu Tyr Arg Cys Leu Thr Asp Pro Thr Ser
                    885                 890                 895

Gly Ala Val Leu Pro Asp Glu Ala Val Met Ala Gln Leu Glu Ala Leu
                    900                 905                 910

Gly Ala Asp Thr Gly Ala Ile Arg Arg Ala Leu Arg Ser Arg Glu Cys
                    915                 920                 925

Asn Pro Leu Thr Ala Thr Tyr His Leu Gln Leu Glu Ala His Val Glu
930                 935                 940

Ala Gln Arg Ala Ala Ala Ala Arg Glu Arg Glu Ala Ala Glu Arg
945                 950                 955                 960

Ala Ala Val Lys Arg Ala Val Glu Gln Arg Gly Ala Ser Ser Ser
                    965                 970                 975

Ala Asp Trp Gln Trp Asp Phe Ala Ala Ile Ser Ala His Ala Thr Ala
                    980                 985                 990

Ala Asp Arg Ser Gln Ala Ala Pro Ala Ser Ser Gln Ala Gly Ala Ala
                    995                 1000                1005

Gly Ser Gly Ala Pro Ser Ser Pro Ala Ala Gly Ser Ser Gly Leu
            1010                1015                1020

Arg Gly Gly Gly Ser Pro Ala Arg Leu Arg Val Ala Ala Ala Pro
            1025                1030                1035

Pro Ala Gly Ser Pro Thr Arg Phe Gly Met Glu Ala Ala Ala Ala
            1040                1045                1050

Gly Tyr Val Ala Ser Pro Arg Arg Pro Ala Thr Ser Gly Ala Ala
            1055                1060                1065

Thr Pro Thr Leu His Phe Gly Gly Thr Pro Phe Ser Ser Pro Pro
            1070                1075                1080

Pro Ala Gln Ala Pro Pro Ala Ala Gln Arg Pro Asp Ala Val Pro
            1085                1090                1095

Leu Ala Phe Ala Ala Ala Glu Gln Gln Gln Pro Arg Pro Val Pro
            1100                1105                1110

Ser Glu Pro Phe Thr Ile Lys Ala Leu Arg Ala Pro Pro Gly Ser
            1115                1120                1125

Gly Glu Pro Ser Val Ser Thr Pro Val Ala Ala Ala Ala Ala
            1130                1135                1140

Ala Glu Leu Ala Ala Thr Pro Gly Leu Ile Thr Ala Ser Ala Val
            1145                1150                1155

Thr Thr Thr Thr Ala Val Val Glu Gly Glu Gly Pro Thr Ser Pro
            1160                1165                1170

Ser Lys Ser Pro Arg Leu Ala Pro Leu Pro Ala Val Leu Ser Pro
            1175                1180                1185

Lys Gln Leu Ala Gly Val Gly Ala Pro Gly Thr Thr Ser Gly Gly
            1190                1195                1200
```

Asp His Ser Pro Pro Leu Ala Gln Ala Val
    1205            1210

<210> SEQ ID NO 16
<211> LENGTH: 3642
<212> TYPE: DNA
<213> ORGANISM: Chlorella sorokiniana

<400> SEQUENCE: 16

| | | | | | |
|---|---|---|---|---|---|
| atggccgaca | gggggctccg | caggcgcgat | atttcttgcc | gccggcgcct | gcgctgtacc | 60 |
| cgcctgccga | gtcgcccacc | ggccgctcac | ccgcacgttg | ctgcctgccc | accccgccca | 120 |
| cccacagatg | cgccgcccac | ctgggactta | ggcgcagccg | cgcaaggcgg | cgcagccacc | 180 |
| agccagcggc | cggtgacgcc | ggggcttgga | gccctcggcg | acggcggcag | ccggcactcg | 240 |
| cggcagccgg | cggcgcgggc | ggccactgcc | gcgccgacct | cgcagaagca | gcccggattc | 300 |
| ttcagggcag | ccatgcgcac | cacctccggc | tccctgagcg | gcctgctcaa | gcggtcgggc | 360 |
| acggcggcgc | ccgcgccggc | cggctcctcg | cctctctttg | aggtgcgcgg | cgcggcgatg | 420 |
| ctgccgcccg | atccccaac | gcggccagcc | actgcggcac | ctgccggacc | gccgagccgc | 480 |
| accagcgcac | accagcagca | gcagcagcag | cacaaggcgg | cggcgccgcc | cacgtacaat | 540 |
| gtgcacgccc | gggcggcgca | cagccggccg | gccaccgcca | gctgcgggag | cccgcctgtt | 600 |
| gcgggacacc | ggcaggcctc | cccggcagcg | gttgcatcgc | acgggctgga | cccatccacc | 660 |
| agcccagtgc | cgcagccggc | agcacccacg | ccgcactacc | agcagccgtt | cggcgatcg | 720 |
| gctgtgcccg | cagtgacgta | cgccacgccc | agcccggcca | gcgcggcagc | ccagcagctg | 780 |
| cgggctcagc | agcaggcggc | cgcgcagcgg | caggcagccc | aggagccgca | agctcagcgg | 840 |
| cagcagcagc | aggcgacggc | gcagccgggc | tccttcagcc | gagcctcttc | cctgggcagc | 900 |
| agcgcaggca | gcagctcgct | gccctccagc | tcaggtgact | acggctccag | cagcagccag | 960 |
| ggcgccgccc | cagccgccat | catgcaccag | aacccgctgt | ttgcaggtgg | cagcgagaac | 1020 |
| gccagctttg | cagcctcgcg | gcagcagggg | gcgcagccgc | agacacggcc | accgccgccg | 1080 |
| gtgcgtgtgg | cgccgccgcc | tgcagccacg | cccgccacgc | caccaggcgg | cgtgcttgcg | 1140 |
| ggcacggcag | gcgtctcgcc | ctgccccaca | cccatgagca | acctgcacgc | tgcctccaac | 1200 |
| ctgacgatgt | tgactgacag | ccggcccgtc | agcccgggcc | ccttcctgtc | caccctgccc | 1260 |
| agcggcagtg | aacgcggcag | ccgcccgtc | agcccgcagt | gcatcgatag | cgtgccgccc | 1320 |
| acgcccggct | cgtttgcgcc | gccaggcctg | cggcagcgg | cagcagcggc | cgcctcgcgg | 1380 |
| ggcatgctgt | cccccattcg | cacagcctcg | tcagcaggcg | ttgctggcag | ccagcattcg | 1440 |
| cggtcgctgc | ccacctcgcc | ggcgccgcct | gccgctgcct | ccttgccggt | tgcgggcggc | 1500 |
| tcgccgtcgg | cttgccctgc | gggcatgccc | tctggcaccg | ccgctttccg | ggtgccatt | 1560 |
| ttcaaccagg | acggccgcct | ggtgggctac | aagcagaaca | gcaacctcat | cccgcgggcc | 1620 |
| ggcgcctgca | tcagctcggc | accctcctcg | ccctcgcgct | ccgccttcct | ggcggacccc | 1680 |
| atcaccttcc | agaccaccctc | cttctctgct | gccgctgggg | cggtggaggg | cgcgtcgccg | 1740 |
| cagccaaagc | cgccggtggt | gcgcccgccc | gtgagcgaca | cggcgacttt | tgccgagtcc | 1800 |
| ctggccgacc | cgtgcaaggg | cttccctgac | gccgacaaca | tggtgccggg | ctacgtgctg | 1860 |
| gggccggtgc | tggcaagggg | cggcttctgc | agcgtgcgca | aggcgctgca | cgaggtgacg | 1920 |
| ggccaggcg | tggcctgcaa | gatcatcgag | aagggcaagc | tcaaggaccc | caaggaccgg | 1980 |
| gaccgcgtgg | accgcgagtg | ccgcgtgatg | cgcaacctgt | ccaaccactg | cgccgtgatc | 2040 |

-continued

```
aagctgtacg agtacgtgga gacgcgcgac tgcgtgtaca tcatgatgga ggcagccaag    2100
cgcggctcgc tgctggacta tgtgcgcgag cgcaagcgcc tgcccgaggc cgaggcggtg    2160
ctcatcttcc agcagcttct gcacgccctg cagttctgcc accgcaagga cgtggtgcac    2220
cgggacatca agctggagaa catcctgatt gacggcgcgg ccacatgaa gctgatcgac     2280
tttgggctgt gcggctacta cgtggcgggc aagcggctgc gctgccactg cggctccccc    2340
tcctacgccg cccccgagat tgtggcccgc aaggactacc tgggcccgcc cgtggatgtg    2400
tggtcgctgg gcatcgtgct gtttgccatg ctggcgggct acctgccctt ccacgccaag    2460
gagaagaagc agctgagcga gaagatcctg gcgggcgtgt acaagccggc ggcctggatg    2520
agcgcggacg cccaggacct gctgtcccgt atgctgtgcc tggaccccga gcagcgcatc    2580
agcctggagg ctgtgtgggc caccccctgg gtggcgggcg cgccgcgctg ggagccgccc    2640
ggcgtgggcg ccgaccgcct ctaccgctgc ctcaccgacc ccacctcagg ggcggtgctg    2700
cccgacgaag cagtcatggc gcagctggag gcgctgggtg ccgacacggg cgccatccgc    2760
cgcgcgctgc gctcgcgcga gtgcaacccc ctcacagcca cgtaccacct ccagctggag    2820
gcgcatgtgg aggcgcagcg tgcggcgcct gctcgggagc gcgaggcggc cgccgagcgt    2880
gccgccgtca agcgcgcggt ggagcagcag cgcggcgcct cctcctctgc cgactggcag    2940
tgggactttg ccgccatcag cgcgcacgcc accgcagcag accgctccca ggctgcgcct    3000
gccagcagcc aggccggcgc agccggcagc ggtgccccct cctctcctgc cgccggcagc    3060
agcggcctgc ggggcggcgg atcgccagcg cggctgcgcg tggccgctgc accgccagca    3120
ggcagccccca cccggttcgg catggaggca gctgccgctg gctacgtggc gtcgccgcgg    3180
cggcccgcca ccagcggcgc agccacgccc acgctgcact ttggcggcac gcccttctcc    3240
tcgccacccc ctgcccaggc gccgccggca gcgcagcggc cggacgccgt gccgctcgcc    3300
tttgcagctg cagagcagca gcagccgcgg ccggtgccca gcgagccctt cacaatcaag    3360
gcgttgcgtg cgccacctgg cagcggcgag cccagcgtca gcacgccggt ggcggcggct    3420
gccgcggccg ccgagctggc ggccaccccc ggcctcatca ccgcgtcggc ggtcaccacg    3480
accacggcgg tggtggaggg ggaggggccc acctcccct ccaagtcgcc gcgcctggcg    3540
cccctgccag ccgtgctctc gcccaagcag ctggcaggcg tgggcgcccc tggcaccacc    3600
agcggcggcg accacagccc gccgctggcg caggcggtgt ga                      3642
```

<210> SEQ ID NO 17
<211> LENGTH: 555
<212> TYPE: PRT
<213> ORGANISM: Chlorella sorokiniana

<400> SEQUENCE: 17

Met Thr Ser Val Ser Pro Gly Asp Ala Ala Ala Ala Gly His Ala
1               5                   10                  15

Gly Gln Pro Gly Ala Gln Gly Phe Ala Thr Thr Ser Ala Glu Phe Phe
            20                  25                  30

Leu Gln Asn Tyr Arg Leu Gly Lys Thr Leu Gly Ile Gly Ser Phe Gly
        35                  40                  45

Lys Val Lys Val Ala Glu His Ile Leu Thr Gly His Lys Val Ala Ile
    50                  55                  60

Lys Ile Leu Asn Arg Lys Lys Ile Lys Gln Met Asp Met Glu Glu Lys
65                  70                  75                  80

Val Arg Arg Glu Ile Lys Ile Leu Arg Leu Phe Met His Pro His Ile

```
            85                  90                  95
Ile Arg Leu Tyr Glu Val Val Glu Thr Ser Asn Asp Ile Tyr Val Val
            100                 105                 110
Met Glu Tyr Ala Gly Glu Leu Phe Asp Tyr Ile Val Glu Lys Gly Arg
            115                 120                 125
Leu Leu Glu Asp Glu Ala Arg His Phe Phe Gln Gln Ala Arg Ala Lys
            130                 135                 140
Thr Thr Ile Ile Ser Gly Val Glu Tyr Cys His Arg Asn Met Val Val
145                 150                 155                 160
His Arg Asp Leu Lys Pro Glu Asn Leu Leu Leu Asp Ser Lys Met Asn
                165                 170                 175
Ile Lys Ile Ala Asp Phe Gly Leu Ser Asn Val Met Arg Asp Gly His
                180                 185                 190
Phe Leu Lys Thr Ser Cys Gly Ser Pro Asn Tyr Ala Ala Pro Glu Val
                195                 200                 205
Ile Ser Gly Arg Leu Tyr Ala Gly Pro Glu Val Asp Val Trp Ser Cys
            210                 215                 220
Gly Val Ile Leu Tyr Ala Leu Leu Cys Gly Ser Leu Pro Phe Asp Asp
225                 230                 235                 240
Glu Asn Ile Pro Asn Leu Phe Lys Lys Ile Lys Gly Gly Ile Tyr Thr
                245                 250                 255
Leu Pro Ser His Leu Ser Pro Gly Ala Arg Asp Leu Ile Pro Arg Met
                260                 265                 270
Leu Leu Val Asp Pro Leu Lys Arg Ile Thr Ile Pro Glu Ile Arg Gln
                275                 280                 285
His Pro Trp Phe Thr Val His Leu Pro Arg Tyr Leu Ala Val Met Gln
            290                 295                 300
Ala Asp Pro Val Ala Ala Gly Met His Val Asp Glu Asp Ile Val Arg
305                 310                 315                 320
Asp Val Val Arg Leu Gly Phe Thr Arg Asp Phe Val Val Asp Ser Leu
                325                 330                 335
Arg Ala Arg Gln Gln Asn Lys Ala Ser Val Ala Tyr Tyr Leu Met Ala
                340                 345                 350
Asp Asn Arg Arg Arg Met Pro Ser Ser Ala Tyr Leu Lys Glu Glu Met
                355                 360                 365
Thr Glu Ala Thr Asp Pro Gly Leu Ala Ala Phe Pro Ser Gly Val Met
            370                 375                 380
Ala Thr Ser Arg Ser Ser Thr Ser Leu Gln Pro Ala Pro Arg Leu Val
385                 390                 395                 400
Glu Leu Tyr Arg Thr Leu Gln Tyr Cys Gly Val Phe Trp Lys Lys Asn
                405                 410                 415
Gly Pro Tyr Asn Leu Lys Cys Arg Ala Val Leu His Leu Ala Pro Pro
                420                 425                 430
Ala Ala Glu Asp Glu Ala Gly Gly Ala Ala Pro Asn Gly Gln Ala
                435                 440                 445
Gly Ala Gly Gly Glu Leu Thr Arg Asp His Ser Asp Ser Met Gly
            450                 455                 460
Gly Ser Met Glu Ala Ser Pro Ala Val Ala Val Gln Gln Gln Gln Gly
465                 470                 475                 480
Gly Leu Ala Ala Ala Leu Ala Ala Glu Asp Ala Arg Met Ala Glu Ala
                485                 490                 495
Ala Ala Ala Val Thr Gly Ala Gly Gly Gly Ala Ala Ala Met Glu Arg
            500                 505                 510
```

Glu Val Lys Phe Glu Ala Gln Leu Tyr Lys Met Arg Asp Gly Glu Tyr
          515                 520                 525

Ala Leu Asp Phe Gln Arg Leu Ser Gly Asp Leu Phe Leu Phe Met Asp
          530                 535                 540

Thr Cys Ser Ser Leu Leu Ser Val Leu Arg Leu
545                 550                 555

<210> SEQ ID NO 18
<211> LENGTH: 1668
<212> TYPE: DNA
<213> ORGANISM: Chlorella sorokiniana

<400> SEQUENCE: 18

| | |
|---|---|
| atgacctcgg tgtcaccggg ggatgccgcc gcggccgctg ccacgccgg gcagccaggg | 60 |
| gcacagggct tcgccaccac cagcgccgag ttcttcctgc agaactaccg gctgggcaag | 120 |
| acgctgggca tcggatcgtt cggcaaggtc aaggtggcag agcacattct gacggggcac | 180 |
| aaggtggcca tcaagatcct gaaccgcaag aagatcaagc agatggacat ggaggagaaa | 240 |
| gtgcggcgcg agatcaagat tctccggctc ttcatgcacc gcacatcat ccggctgtat | 300 |
| gaggtggtgg agacgtccaa cgacatctac gtggtcatgg agtatgcggg cgagctgttt | 360 |
| gactacattg tggagaaggg gcggctgctg gaggacgagg cgcgccactt cttccagcag | 420 |
| gcgcgtgcta agaccacaat catctcgggc gtggagtact gtcaccgcaa catggtggtg | 480 |
| caccgagacc tgaagcccga gaacctgctg ctggacagca agatgaacat caagattgcg | 540 |
| gactttggcc tctccaacgt gatgcgggac ggccacttcc tcaaaacctc ctgcggctcc | 600 |
| cccaactatg cggctccaga ggtcatctcc ggccggctgt atgcgggccc agaggtggat | 660 |
| gtctggtcct gcggcgtcat cctgtacgcc ctgctctgcg gctcgctgcc ctttgacgac | 720 |
| gaaaacatcc ccaacctgtt caagaagatt aagggcggca tctacaccct gcccagccac | 780 |
| ctgagccccg gcgcgcgaga cttgatcccc gcatgctgc tggtggaccc gctcaagcgc | 840 |
| atcaccattc cggagatcag gcagcacccc tggttcacgg tccacctacc taggtacctg | 900 |
| gcagtcatgc aggcggaccc agtggcagca ggcatgcacg ttgatgagga cattgtgagg | 960 |
| gacgtggtcc gactaggctt caccgcgat tttgtggtgg actcgttgcg ggcgcggcag | 1020 |
| cagaacaagg cctcggtggc ttactacctg atggccgaca accggcggcg catgccctcc | 1080 |
| agcgcttacc tgaaagagga gatgacggaa gcaacagatc cggggctggc tgcttttccg | 1140 |
| tcaggtgtca tggccaccag ccgcagcagc acgagcctgc agccggcgcc gcgtctggtg | 1200 |
| gagctgtacc gcacgctgca gtactgcggc gtgttctgga agaagaacgg tccttacaac | 1260 |
| ctcaagtgcc gggcggtcct gcacctggcc ccgcccgctg cggaggacga ggccggcggc | 1320 |
| gcagcagcac ccaacggcca ggccggggca ggcggagagc tcactaggga ccactcggat | 1380 |
| gatagcatgg gcgggtctat ggaggcctcg ccagcggtgg cagtgcagca gcagcagggc | 1440 |
| ggcttggcgg cggcgctggc ggcagaggat gcgcgcatgg cggaggcggc ggcggcggtc | 1500 |
| acgggcgcag gcggcggcgc ggccgccatg gagcgtgagg tcaagtttga ggcgcagctg | 1560 |
| tacaagatgc gggacggcga atatgcgctc gacttccagc gcctgtcggg cgacctgttc | 1620 |
| ctgttcatgg acacctgcag cagcctgctg agcgtgctgc gcctctag | 1668 |

<210> SEQ ID NO 19
<211> LENGTH: 1192
<212> TYPE: PRT
<213> ORGANISM: Chlorella sorokiniana -continued

<400> SEQUENCE: 19

```
Met Ala Glu Gly Arg Pro Thr Arg Thr Gln Asp Leu His Pro His Ala
1               5                   10                  15

Arg Ser Ser Ala Asp Ala Pro Pro Leu Trp Glu Phe Gly Ala Ala Ala
            20                  25                  30

His Arg Gly Ala Ala Ser Gln Arg Pro Val Thr Pro Ala Val Gly Ala
        35                  40                  45

Leu Gly Asp Gly Gly Ser Arg Gln Ala Arg Gln Pro Ala Ala Arg Ala
    50                  55                  60

Ala Thr Ala Ala Pro Pro Ala Ser Leu Lys Gln Pro Gly Phe Phe Arg
65                  70                  75                  80

Ala Ala Met Arg Thr Thr Ser Asp Ser Leu Ser Gly Leu Leu Lys Arg
                85                  90                  95

Pro Gly Thr Ala Ala Pro Ala Pro Ala Ala Gly Ala Ser Pro Leu
            100                 105                 110

Phe Glu Val Arg Gly Ala Ala Met Leu Ala Pro Glu Pro Ala Gln
            115                 120                 125

Leu Ala Thr Val Ala Pro Ala Ala Ser His Gly Arg Ser Gly Val His
    130                 135                 140

Pro Gln Gln His Lys Pro Ala Pro Ala Tyr Asn Val His Ala Arg
145                 150                 155                 160

Ala Ala His Ser Arg Pro Ala Thr Ala Thr Cys Ala Ser Pro Pro Val
                165                 170                 175

Ala Pro Ser Pro Gln Arg Gln Ala Ser Pro Ala Ala Val Ala Ser His
            180                 185                 190

Gly Leu Asp Pro Ser Thr Ser Pro Ala Pro Gln Pro Ala Ala Thr
            195                 200                 205

Pro His Tyr Gln Gln Pro Leu Arg Arg Pro Ala Ala Val His Ala
    210                 215                 220

Thr Thr Asn Pro Thr Ala Ala Ser Ser Ala Ala Ala Ala Gln Gln
225                 230                 235                 240

Ala Ala Ala Gln Arg Gln Ala Ala Gln Glu Gln Gln Phe Gln Arg Gln
                245                 250                 255

Gln Gln Gln Thr Gln Ala Gln Gly Gly Thr Phe Ser Arg Ala Ser Ser
            260                 265                 270

Leu Gly Ser Ser Ala Gly Ser Ser Leu Pro Ser Ser Gly Asp
        275                 280                 285

Tyr Gly Ser Ser Gln Gly Pro Ala Pro Ala Val Met His Gln
    290                 295                 300

Asn Pro Leu Tyr Thr Gly Gly Ser Glu Ser Val Ser Phe Gly Leu Ser
305                 310                 315                 320

Arg Gln Gln Ala Ala Gln Pro Gln Ala Arg Pro Pro Val Arg Val
                325                 330                 335

Ala Pro Pro Ala Arg Ala Leu Pro Ala Thr Pro Ala Ser Met Val
            340                 345                 350

Ala Gly Thr Ala Gly Val Ser Pro Ser Pro Thr Pro Thr Ser Asn Leu
        355                 360                 365

Gln Ala Ala Ser Asn Leu Thr Met Leu Thr Asp Ser Arg Pro Ile Ser
    370                 375                 380

Pro Gly Pro Phe Met Ser Thr Leu Pro Ser Gly Ser Glu Arg Gly Ser
385                 390                 395                 400

Arg Pro Val Ser Pro Gln Cys Ile Asp Ser Val Pro Pro Thr Pro Gly
```

```
                405                 410                 415
Ser Phe Ala Pro Pro Gly Met Ala Ala Ala Ala Ala Ala Ala
            420                 425                 430

Ser Arg Gly Met Leu Ser Pro Thr Arg Thr Ala Ser Ser Ala Ala Val
            435                 440                 445

Thr Val Gly Gln Gln Ser Arg Ser Leu Pro Thr Ser Pro Ala Pro Pro
        450                 455                 460

Ala Ala Ala Ser Leu Pro Val Ala Gly Gly Ser Pro Ser Ala Cys Pro
465                 470                 475                 480

Ala Gly Met Pro Ser Gly Thr Ala Ala Phe Arg Val Pro Ile Phe Asn
            485                 490                 495

Gln Asp Gly Arg Leu Val Gly Tyr Lys Gln Asn Ser Asn Leu Ile Pro
            500                 505                 510

Arg Pro Gly Ala Cys Ile Ser Ser Ala Pro Ser Ser Pro Ser Arg Ser
            515                 520                 525

Ala Tyr Leu Ala Asp Pro Thr Thr Phe Gln Thr Ala Ser Phe Ser Ala
        530                 535                 540

Ala Gly Ala Ala Glu Gly Ala Ser Pro Gln Pro Lys Pro Pro Val Val
545                 550                 555                 560

Arg Pro Pro Ala Ser Asp Ser Gly Asp Phe Ala Asp Tyr Leu Ala Asp
                565                 570                 575

Pro Cys Lys Gly Phe Pro Asp Ala Asp Asn Met Val Pro Gly Tyr Val
        580                 585                 590

Leu Gly Pro Val Leu Gly Lys Gly Phe Cys Ser Val Arg Lys Ala
        595                 600                 605

Leu His Glu Leu Thr Gly Gln Ala Val Ala Cys Lys Ile Ile Glu Lys
        610                 615                 620

Gly Lys Leu Lys Asp Pro Lys Asp Arg Asp Arg Val Asp Arg Glu Cys
625                 630                 635                 640

Arg Val Met Arg Asn Leu Ser Asn His Cys Ala Val Ile Lys Leu Phe
                645                 650                 655

Glu Tyr Val Glu Thr Arg Asp Cys Val Tyr Ile Met Met Glu Ala Ala
                660                 665                 670

Lys Arg Gly Ser Leu Leu Asp Tyr Val Arg Glu Arg Lys Arg Leu Pro
        675                 680                 685

Glu Pro Glu Ala Val Leu Ile Phe Gln Gln Leu Leu Ser Leu Gln
        690                 695                 700

Phe Cys His Arg Lys Asp Val Val His Arg Asp Ile Lys Leu Glu Asn
705                 710                 715                 720

Ile Leu Ile Asp Ala Ala Gly His Met Lys Leu Ile Asp Phe Gly Leu
                725                 730                 735

Cys Gly Tyr Tyr Val Ala Gly Lys Leu Arg Cys His Cys Gly Ser
            740                 745                 750

Pro Ser Tyr Ala Ala Pro Glu Ile Val Ala Arg Lys Asp Tyr Leu Gly
            755                 760                 765

Pro Pro Val Asp Val Trp Ser Leu Gly Ile Val Leu Phe Ala Met Leu
770                 775                 780

Ala Gly Tyr Leu Pro Phe His Ala Lys Glu Lys Lys Gln Leu Ser Glu
785                 790                 795                 800

Lys Ile Leu Ala Gly Val Tyr Lys Pro Ala Ala Trp Met Ser Ala Glu
                805                 810                 815

Ala Gln Asp Leu Leu Ser Arg Met Leu Cys Leu Asp Pro Glu Gln Arg
            820                 825                 830
```

Ile Thr Leu Glu Ala Val Trp Ala His Pro Trp Ala Gly Ala Pro
    835                 840                 845

Arg Trp Glu Pro Pro Gly Val Gly Ala Gly Arg Val Tyr Arg Cys Leu
    850                 855                 860

Thr Asp Pro Thr Thr Gly Ala Val Leu Pro Asp Glu Ala Val Met Ala
865                 870                 875                 880

Gln Leu Glu Ala Leu Gly Ala Asp Thr Ala Ala Ile Arg Arg Ala Leu
                885                 890                 895

Arg Ser Arg Glu Cys Asn Ser Leu Thr Ala Ser Tyr His Leu Gln Leu
            900                 905                 910

Glu Ala His Leu Glu Ala Gln Arg Ala Ala Ser Arg Glu Arg Glu
        915                 920                 925

Ala Ala Ala Glu Arg Ala Ala Lys Arg Leu Ala Glu Gln Gln Arg
    930                 935                 940

Gly Ala Ser Cys Ser Ala Asp Trp Gln Trp Asp Phe Ala Ala Ile Ser
945                 950                 955                 960

Ala His Ala Ala Ala Ala Glu Arg Cys Gln Ala Ala Ala Ala Gly
                965                 970                 975

Ser Gln Ala Ala Ala Gly Gly Ser Gly Ala Pro Leu Ser Pro Ala Ala
            980                 985                 990

Ala Ala Ala Gly Ser Gly Gly Leu Arg Gly Ser Gly Ser Pro Ala Arg
        995                 1000                1005

Leu Arg Leu Ala Val Ala Pro Pro Ala Gly Ser Pro Thr Arg Phe
    1010                1015                1020

Gly Val Glu Ala Ala Ala Gly Tyr Val Ser Ser Pro Arg Arg
    1025                1030                1035

Pro Ala Thr Ser Gly Ala Ala Thr Pro Thr Leu His Phe Gly Gly
    1040                1045                1050

Thr Pro Phe Ser Ser Pro Leu Ala Gln Ala Pro Pro Ala Ala
    1055                1060                1065

Gln Gln Pro Glu Ala Val Pro Ala Met Pro Ala Ala Phe Val Ser
    1070                1075                1080

Ala Glu Ala Arg Pro Arg Pro Ala Asp Ser Glu Pro Phe Thr Ile
    1085                1090                1095

Lys Ala Leu His Ala Pro Pro Gly Ser Gly Glu Pro Ser Val Ser
    1100                1105                1110

Thr Pro Val Ala Ala Ala Ala Ala Ala Glu Leu Ala Ala Thr
    1115                1120                1125

Pro Ala Leu Ile Thr Ala Ala Ala Ala Thr Thr Thr Thr Ala Val
    1130                1135                1140

Val Glu Gly Glu Gly Pro Thr Ser Pro Ser Lys Ser Pro Arg Leu
    1145                1150                1155

Ala Pro Leu Pro Ala Val Leu Ser Pro Lys Gln Leu Ala Gly Met
    1160                1165                1170

Gly Ala Pro Gly Thr Thr Ser Ala Gly Asp His Ser Pro Pro Met
    1175                1180                1185

Ala Gln Ala Val
    1190

<210> SEQ ID NO 20
<211> LENGTH: 3582
<212> TYPE: DNA
<213> ORGANISM: Chlorella sorokiniana

```
<400> SEQUENCE: 20
atggctgaag gccggccaac cagaacgcag gacctccacc cgcacgcccg tagctccgca      60
gatgcgccgc ccttgtggga gtttggcgca gccgcacaca ggggcgccgc cagccagcgg     120
ccggtgacgc cggcagtcgg cgccttgggc gatggcggca gccggcaggc gcggcagccg     180
gcggcgcggg cggccaccgc tgcgccgccc gcctcgctca agcagcccgg cttcttcagg     240
gcagccatgc gcaccacctc cgactcactc agcggcctgc tgaagcggcc aggcactgcg     300
gcgcctgcac ctgcagctgc cggcgcctcg ccgctgtttg aggtgcgcgg tgccgcaatg     360
ctggcgcctg agcctccggc acagctagcc accgtagcgc cagccgcctc gcacggccgc     420
tctggcgtgc atccgcagca gcacaagccg gcgccgccgg cgtacaatgt gcacgcccgg     480
gcggcgcaca gcaggccggc caccgccacc tgcgccagcc cgcccgtggc gccgtcccca     540
caacggcagg catcccagc agcagtggcg tcgcatgggc tggacccatc caccagccct     600
gcgccgcaac cagcagcagc cacgccgcac taccagcagc cgctgcgccg gccagctgca     660
gcggtgcatg ccacgaccaa ccccaccgca gccagctctg ccgccgctgc ggcccagcag     720
gcagcggcgc agcggcaggc ggcccaggag cagcagttcc agcggcagca gcagcaaacg     780
caggcacagg gaggcacgtt cagccgcgcc tcctcgctgg gcagcagcgc cggcagcagc     840
tcgctgccct ccagctcggg cgactacggc agcagcagcc agggcccagc ccgcccgct      900 gtgatgcacc aaaaccctct gtacacgggc ggcagcgaga gcgtcagctt ggggctgtcg     960
cggcagcagg cggcgcagcc gcaggcgcgg ccgccgccag tgcgggtggc gccgcctgcc    1020
agggcgctgc ctgccacgcc gccggccagc atggttgcgg gcacggctgg cgtctcgccc    1080
agccccacac ccactagcaa cttgcaggcg gcctccaacc tgacgatgct gaccgatagc    1140
cggcccatca gccggggccc cttcatgtcc accctgccaa gcggcagtga gcgcggcagc    1200
cgccccgtca gcccgcagtg catcgatagc gtgcctccca ctcccggctc gtttgcgcca    1260
ccaggcatgg ctgcggcagc ggcagctgcg ccgcctcccc gtggcatgct gtcccccact    1320
cggacagcat cctcagcagc ggtcacagtt ggccagcagt cacgctcgct gcccacgtct    1380
ccggcgccgc ctgcagctgc ctccctgccg gtggcaggcg gctcgccctc agcctgcccg    1440
gcgggcatgc cctccggcac agcggctttc cgggtgccca tcttcaatca ggatggccgc    1500
ctggtgggct acaagcagaa cagcaacctc atccccggc ccggagcctg catcagctcg    1560
gcgccatcct cgccctcgcg ctccgcctat ctggcagacc ccaccacctt ccagaccgcc    1620
tccttctccg ccgctggagc ggctgagggc cgtcgcccc aacccaagcc gccggtggtg    1680
cgcccgcccg ccagcgacag cggcgacttt gccgactacc ttgccgaccc gtgcaagggc    1740
ttccccgatg cagacaacat ggtgccgggc tacgtgctgg gccgggtgct gggcaagggc    1800
ggcttctgca gcgtgcgcaa ggcgctgcat gagctgacgg ggcaggcggt ggcctgcaag    1860
atcatcgaga agggcaagct caaggacccc aaggaccgcg accgcgttga ccgcgagtgc    1920
cgcgtgatgc gcaacctgtc caaccactgc gccgtgatca agctgtttga gtacgtggag    1980
acgcgcgact gcgtgtacat catgatggag gcggccaagc gcggctcgct gctggactat    2040
gtgcgggagc gcaagcgcct gccggagccc gaggcggtgt catcttcca gcagctgctg    2100 cactccctgc agttctgcca ccgcaaggac gtggtgcacc gcgacatcaa gctggagaac    2160
atcctgattg acgccgcggg gcacatgaag ctgatcgact ttggcctgtg cggctactac    2220
gtggccggca gcggctgcg ctgccactgc ggctcgccct cgtatgccgc ccccgagatt    2280
gtggcccgca aggactacct gggcccgccg gtggacgtgt ggtcgctggg catcgtgctg    2340
```

```
tttgccatgc tggcgggcta cctgcccttc cacgccaagg agaagaagca gctgagcgag    2400
aagatcctgg cgggcgtgta caagcccgcg gcctggatga gcgccgaagc ccaggacctg    2460
ctgtcccgca tgctgtgctt ggaccccgag cagcgcatta cactagaagc cgtgtgggca    2520 caccccctggg tggcgggcgc gccccgttgg gagccgcccg gagtgggcgc cggccgcgtc    2580
taccgctgcc tcaccgaccc caccacgggg gcggtgctgc ccgacaaagc ggtcatggcc    2640
cagctggagg cgctgggcgc cgacacagcc gccatccggc gcgcgctgcg ctcgcgggaa    2700
tgcaactccc tgaccgccag ctaccacctg cagctggagg cgcacctgga ggcgcagcgg    2760
gcggctgcct cccgagagcg cgaggcggca gccgagcggg ccgccgccaa gcgtttggcg    2820
gagcagcagc gcggcgcctc ctgctccgcc gactggcagt gggatttcgc ggccatcagc    2880
gcgcacgccg cggcagcgga cgctgccag cggcggcag cagctggcag ccaggcggca    2940
gcaggaggca gcggagcccc cttgtctccc gctgccgcgg ctgccggcag cggtggcctg    3000
cggggcagcg gctcgccggc gcggctgcgc ctggcagttg cgccacctgc gggtagcccc    3060
actcgatttg gcgtggaggc tgcggctgct ggctatgtct cgtcgccacg gcggcccgcg    3120
accagcggag cagccacgcc cacgctgcac tttggcggca cccccttctc ctcgccgccg    3180
ctggcccagg caccgcccgc agcgcagcag ccagaggccg tgcccgccat gccggcggcc    3240
tttgtctctg ccgaggcgcg gccacggccg gcagacagcg agccgttcac aatcaaggcg    3300
ctgcatgcgc ctcccggcag cggcgagccc agcgtgagca cgcctgtggc ggcagctgcg    3360
gcggccgctg agctagcggc cacccctgcc ctcatcaccg cggctgcagc tgtcaccacc    3420
acgacagcgg ttgtggaggg agaggggccc acctctcccct ccaagtcgcc cgcgcctggcg   3480 cctctcccag ccgtgctgtc gcccaagcag ctggcgggga tgggcgcccc aggcacaacc    3540
agcgccggcg accacagccc gccgatggcg caggccgtct ga                         3582
```

<210> SEQ ID NO 21
<211> LENGTH: 580
<212> TYPE: PRT
<213> ORGANISM: Chlorella sorokiniana

<400> SEQUENCE: 21

```
Met Thr Ser Val Ser Pro Gly Asp Gly Ala Ala Gly His Ala
1               5                   10                  15

Gly Gln Pro Gly Ala Gln Gly Phe Val Ser Ser Ala Glu Phe Phe
                20                  25                  30

Leu Gln Asn Tyr Arg Leu Gly Lys Thr Leu Gly Ile Gly Ser Phe Gly
            35                  40                  45

Lys Val Lys Val Ala Glu His Ile Leu Thr Gly His Lys Val Ala Ile
        50                  55                  60

Lys Ile Leu Asn Arg Lys Lys Ile Lys Gln Met Asp Met Glu Glu Lys
65                  70                  75                  80

Val Arg Arg Glu Ile Lys Ile Leu Arg Leu Phe Met His Pro His Ile
                85                  90                  95

Ile Arg Leu Tyr Glu Val Val Glu Thr Thr Asn Asp Ile Tyr Val Val
            100                 105                 110

Met Glu Tyr Val Lys Ala Gly Glu Leu Phe Asp Tyr Ile Val Glu Lys
        115                 120                 125

Gly Arg Leu Leu Glu Asp Glu Ala Arg His Phe Phe Gln Gln Ile Ile
    130                 135                 140

Ser Gly Val Glu Tyr Cys His Arg Asn Met Val Val His Arg Asp Leu
```

-continued

```
            145                 150                 155                 160
        Lys Pro Glu Asn Leu Leu Leu Asp Ser Lys Met Asn Val Lys Ile Ala
                        165                 170                 175

Asp Phe Gly Leu Ser Asn Val Met Arg Asp Gly His Phe Leu Lys Thr
                        180                 185                 190

Ser Cys Gly Ser Pro Asn Tyr Ala Ala Pro Glu Val Ile Ser Gly Arg
                        195                 200                 205

Leu Tyr Ala Gly Pro Glu Val Asp Val Trp Ser Cys Gly Val Ile Leu
                        210                 215                 220

Tyr Ala Leu Leu Cys Gly Ser Leu Pro Phe Asp Asp Glu Asn Ile Pro
        225                 230                 235                 240

Asn Leu Phe Lys Lys Ile Lys Gly Gly Ile Tyr Thr Leu Pro Ser His
                        245                 250                 255

Leu Ser Pro Gly Ala Arg Asp Leu Ile Pro Arg Met Leu Leu Val Asp
                        260                 265                 270

Pro Leu Lys Arg Ile Thr Ile Pro Glu Ile Arg Gln His Pro Trp Phe
                        275                 280                 285

Thr Val His Leu Pro Arg Tyr Leu Ala Val Met Gln Ala Ser Gly Leu
                        290                 295                 300

Val Gln Ala Asp Pro Val Ala Ala Gly Thr His Val Asp Glu Glu Ile
        305                 310                 315                 320

Val Arg Asp Val Val Arg Leu Gly Phe Thr Arg Asp Phe Val Val Asp
                        325                 330                 335

Ser Leu Arg Ala Arg Gln Gln Asn Lys Ala Ser Val Ala Tyr Tyr Leu
                        340                 345                 350

Met Ala Asp Asn Arg Arg Met Pro Ser Ser Ala Tyr Leu Lys Glu
                        355                 360                 365

Glu Met Thr Glu Ala Thr Asp Pro Gly Leu Ala Ala Phe Pro Ser Gly
                        370                 375                 380

Met Met Ala Thr Ser Arg Ser Asn Thr Ser Leu Gln Pro Ala Pro Arg
        385                 390                 395                 400

Leu Val Val Glu Arg Arg Trp Arg Leu Gly Leu Cys Ser Arg Ala His
                        405                 410                 415

Pro Ser Ser Ile Met Gln Ala Ser Glu Leu Tyr Arg Thr Leu Gln Tyr
                        420                 425                 430

Cys Gly Val Ser Trp Lys Lys Asn Gly Pro Tyr Asn Leu Lys Cys Arg
                        435                 440                 445

Ala Val Leu His Leu Thr Pro Leu Ala Gly Ala Gly Glu Ala Gly
        450                 455                 460

Gly Asp Ala Ala Pro Asn Gly Gln Ala Gly Val Gly Gly Leu Pro
        465                 470                 475                 480

Arg Asp Ala Ser Asp Asp Ser Met Gly Val Ala Met Glu Ala Ser Pro
                        485                 490                 495

Ala Ala Ala Ala Gln Gln Gln Gln Gly Gly Leu Ala Ala Ala Leu Ala
                        500                 505                 510

Ala Glu Asp Ala Arg Met Ala Glu Ala Ala Ala Val Val Gly Ser
                        515                 520                 525

Gly Gly Gly Ala Gly Thr Leu Glu Arg Glu Val Lys Phe Glu Ala Gln
        530                 535                 540

Leu Tyr Lys Met Arg Asp Gly Glu Tyr Ser Leu Asp Phe Gln Arg Leu
        545                 550                 555                 560

Ser Gly Asp Leu Phe Leu Phe Met Asp Thr Cys Ser Ser Leu Leu Ser
                        565                 570                 575
```

Val Leu Arg Leu
        580

<210> SEQ ID NO 22
<211> LENGTH: 1855
<212> TYPE: DNA
<213> ORGANISM: Chlorella sorokiniana

<400> SEQUENCE: 22

```
atagcacagt cgcgttccaa cgccccgcca gcccgctccg acatcgcctg gcccgctcgc      60
agctctccgg tcgccgcagg gtcgcttatc gccgcagctg acgggaccaa caatgacctc     120
agtgtcgcct ggagacggtg gcgcggccgc aggccacgca gggcagccag gggcgcaggg     180
cttcgtctcc tccagcgccg agttcttcct gcagaactac cggctgggca agacgctggg     240
catcggctct ttcggcaagg tcaaggtggc ggagcacatc ctgacggggc acaaggtggc     300
catcaagatt ctgaaccgca agaagatcaa gcagatggac atggaggaga aggtgcggcg     360
cgagatcaag attctgcggc tgttcatgca cccgcacatt atccggctct acgaggtggt     420
ggagacgacc aacgacatct acgtggtcat ggagtacgtc aaggcgggcg agctgtttga     480
ctacatcgtg gagaaggggc ggctgctgga ggacgaggcg cgccacttct tccagcagat     540
catctcgggc gtggagtact gccaccgcaa catggtggtg caccgtgacc tgaagcccga     600
gaacctgctt ctggacagca agatgaacgt gaagattgcg gacttcgggc tgtccaacgt     660
gatgcgcgat gggcacttcc tcaaaacgtc ctgcggctcc ccaactatg cggcgccaga     720
agtcatttct gggcggctgt acgcgggccc cgaggtggat gtctggtcct gcggcgtcat     780
cctgtacgcc ctgctctgcg gctcgctgcc ctttgacgac gaaaacatcc ccaacctgtt     840
caagaagatc aagggcggca tctacacgct gcccagccac ctgagcccgg agcgcgcga     900
cctcatcccc gcatgctgc tggtcgaccc gctcaaacgc atcaccatcc cggagatcag     960
gcagcatccc tggttcacgg tgcacctgcc tcgctaccta gcggtcatgc aggcgagtgg    1020
gctggtgcag gcggacccgg tggcggcggg cacgcatgtg gacgaagaga ttgtgcgaga    1080
cgtggtgcgg ctaggcttca cgcgcgactt tgtggtggac tcgctgcgtg cacggcagca    1140
gaacaaggcc tcagtagcgt actacctcat ggctgacaac cggcgccgca tgccttctag    1200
cgcatacttg aaggaggaga tgacggaggc gacagacccg gggctggctg cgttcccctc    1260
aggcatgatg gccaccagcc gcagcaacac gagcctgcag ccggcgcctc gctggtggt    1320
ggagcgacgc tggcgcctgg gcctgtgctc gcgtgcgcac ccctcctcca tcatgcaggc    1380
gagtgagctg taccgcacgc tgcagtactg cggtgtgtcc tggaagaaga atggtcctta    1440
caacctcaag tgccgggcgg tcctgcacct cacgccgctc gccggcgcgg caggcgaggc    1500
tggcggcgat gcagcaccca acggccaggc agggtgggc ggaggcctgc ctcgtgacgc    1560
ctcggatgat agcatgggtg tcgcgatgga ggcatcgccc gcggcagcag cgcagcagca    1620
gcagggcggc ttggcggcgg cgctggcggc agaagatgcg cgcatggcgg aagcggcggc    1680
ggcggtagtg ggcagcggcg gcggcgcagg cacccctgga gcgggaggtca agtttgaggc    1740
gcagctgtac aagatgcggg acggggagta ttcgctcgac ttccagcgcc tctctggaga    1800
cctgttcttg ttcatggaca cctgcagcag cctgctgagc gtgctgcgcc tctag        1855
```

<210> SEQ ID NO 23
<211> LENGTH: 441
<212> TYPE: PRT
<213> ORGANISM: Chlorella sorokiniana

<400> SEQUENCE: 23

```
Ser Ala Pro Ser Ser Pro Ser Arg Ser Ala Tyr Leu Ala Asp Pro Thr
1               5                   10                  15

Thr Phe Gln Thr Thr Ser Phe Ser Ala Ala Gly Gly Val Glu Gly Ala
            20                  25                  30

Ser Pro Gln Pro Arg Ala Pro Val Ala Arg Pro Pro Val Ser Asp Ser
            35                  40                  45

Gly Asp Phe Ala Glu Tyr Leu Ala Asp Pro Cys Lys Gly Phe Pro Asp
    50                  55                  60

Ala Asp Asn Met Val Pro Gly Tyr Val Leu Gly Pro Val Leu Gly Lys
65                  70                  75                  80

Gly Gly Phe Cys Ser Val Arg Lys Ala Leu His Glu Val Thr Gly Gln
                85                  90                  95

Ala Val Ala Cys Lys Ile Ile Glu Lys Gly Lys Leu Lys Asp Pro Lys
            100                 105                 110

Asp Arg Asp Arg Val Asp Arg Glu Cys Arg Val Met Arg Asn Leu Ser
            115                 120                 125

Asn His Cys Ala Val Ile Lys Leu Phe Glu Tyr Val Glu Thr Arg Asp
130                 135                 140

Cys Val Tyr Ile Met Met Glu Ala Ala Lys Arg Gly Ser Leu Leu Asp
145                 150                 155                 160

Tyr Val Arg Glu Arg Lys Arg Leu Pro Glu His Glu Ala Val Thr Ile
                165                 170                 175

Phe Gln Gln Leu Leu His Ala Leu Gln Phe Cys His Arg Lys Asp Val
            180                 185                 190

Val His Arg Asp Ile Lys Leu Glu Asn Ile Leu Ile Asp Ala Ala Gly
            195                 200                 205

His Met Lys Leu Ile Asp Phe Gly Leu Cys Gly Tyr Tyr Val Ala Gly
    210                 215                 220

Lys Arg Leu Arg Cys His Cys Gly Ser Pro Ser Tyr Ala Ala Pro Glu
225                 230                 235                 240

Ile Val Ala Arg Lys Asp Tyr Leu Gly Pro Pro Val Asp Val Trp Ser
                245                 250                 255

Leu Gly Ile Val Leu Phe Ala Met Leu Ala Gly Tyr Leu Pro Phe His
            260                 265                 270

Ala Lys Glu Lys Lys Gln Leu Ser Glu Lys Ile Leu Ala Gly Val Tyr
            275                 280                 285

Lys Pro Ala Ala Trp Met Ser Gly Asp Ala Gln Asp Leu Leu Ser Arg
    290                 295                 300

Met Leu Cys Leu Asp Pro Glu Gln Arg Ile Thr Leu Glu Gly Val Trp
305                 310                 315                 320

Ala His Pro Trp Val Ala Ala Pro Arg Trp Glu Pro Pro Gly Val
                325                 330                 335

Gly Ala Gly Arg Leu Tyr Arg Cys Leu Thr Asp Pro Thr Gly Ala
            340                 345                 350

Val Leu Pro Asp Glu Ala Val Met Ala Gln Leu Glu Ala Leu Gly Ala
            355                 360                 365

Asp Thr Ala Ala Ile Arg Arg Ala Leu Arg Ser Arg Glu Cys Asn Ser
    370                 375                 380

Leu Thr Ala Thr Tyr His Leu Gln Leu Glu Ala His Leu Asp Ala Gln
385                 390                 395                 400

Arg Ala Ala Thr Ala Arg Glu Arg Glu Ala Glu Arg Ala Thr Ala Ala
```

```
                    405                 410                 415
Ala Ala Ala Lys Arg Ala Ala Glu Gln Gln Arg Gly Ala Cys Ser Ser
            420                 425                 430

Ala Asp Trp Gln Trp Asp Phe Ala Ala
        435                 440

<210> SEQ ID NO 24
<211> LENGTH: 1323
<212> TYPE: DNA
<213> ORGANISM: Chlorella sorokiniana

<400> SEQUENCE: 24
tccgcgccct cctcgccctc gcgctccgcc tacctggcgg accccaccac cttccagact      60
acctccttct ccgccgccgg cggagtggag ggcgcgtcgc cgcagcccag ggcgccagtg     120
gcacgcccgc ctgtcagcga cagcggcgac tttgccgagt acctggccga cccgtgcaag     180
ggcttccctg atgcagacaa catggtgccg gctacgtgc tgggcccggt gctgggcaag      240
ggcggcttct gcagcgtgcg caaggcgctg acgaggtga cggggcaggc ggtggcctgc     300
aagatcatcg agaagggcaa gctcaaggac cccaaggacc gcgaccgcgt ggaccgcgag     360
tgccgcgtga tgcgcaacct gtccaaccac tgcgccgtga tcaagctgtt cgagtacgtg     420
gagacgcgcg actgcgtgta catcatgatg gaggccgcca agcgcggctc gctgctggac     480
tatgtgcggg agcgcaagcg cctgccggag cacgaggcgg tgaccatctt ccagcagctg     540
ctgcatgctc tgcagttctg ccaccgcaag gacgtggtgc accgcgacat caagctggag     600
aatatcctga ttgacgccgc ggggcacatg aagctgatcg actttgggct gtgcggctac     660
tacgtggccg gcaaacggct gcgctgccac tgcggctccc cctcctacgc cgccccgag     720
atcgtggcgc gcaaggacta cctgggcccg ccggtgacg tgtggtccct gggcatcgtg     780
ctgtttgcca tgctggccgg ctacctgccc ttccacgcca aggaaaagaa gcagctgagc     840
gagaagatcc tggcgggcgt gtacaagccc gcggcatgga tgagcggcga tgctcaggac     900
ttgctgtccc gcatgctgtg cctggaccct gagcagcgca tcacgctgga gggcgtgtgg     960
gcacacccct gggtggcggc cgcgccgcgc tgggagccac cggagtgggg cgccggccgc    1020
ttgtaccgct gcctcaccga tcccaccacc ggggcggtgc tgcctgacga agcagtcatg    1080
gctcagctgg aggcgctggg cgccgacacc gctgccatcc gaaggcgct gcgctcgcga    1140
gagtgcaact ccctgaccgc cacgtaccac ctgcagctgg aggcgcactt agatgcccag    1200
cgggcagcga ctgcccgcga gcgcgaggcg gagcgcgcca ccgccgcagc ggcagccaag    1260
cgggcagcgg agcagcagcg cggcgcctgc tcctctgctg actggcagtg ggactttgct    1320
gcc                                                                 1323

<210> SEQ ID NO 25
<211> LENGTH: 572
<212> TYPE: PRT
<213> ORGANISM: Chlorella sorokiniana

<400> SEQUENCE: 25

Met Thr Ser Val Ser Pro Gly Asp Ala Gly Ala Ala Pro Gly His Ala
1               5                   10                  15

Gly Gln Pro Gly Ala Gln Gly Phe Ala Ser Ser Ser Ala Glu Phe Phe
            20                  25                  30

Leu Gln Asn Tyr Arg Leu Gly Lys Thr Leu Gly Ile Gly Ser Phe Gly
        35                  40                  45
```

```
Lys Val Lys Val Ala Glu His Ile Leu Thr Gly His Lys Val Ala Ile
 50                  55                  60
Lys Ile Leu Asn Arg Lys Ile Lys Gln Met Asp Met Glu Glu Lys
 65                  70                  75                  80
Val Arg Arg Glu Ile Lys Ile Leu Arg Leu Phe Met His Pro His Ile
                 85                  90                  95
Ile Arg Leu Tyr Glu Val Val Glu Thr Thr Asn Asp Ile Tyr Val Ala
                100                 105                 110
Gly Glu Leu Phe Asp Tyr Ile Val Glu Lys Gly Arg Leu Leu Glu Asp
                115                 120                 125
Glu Ala Arg His Phe Phe Gln Gln Ile Ile Ser Gly Val Glu Tyr Cys
            130                 135                 140
His Arg Asn Met Val Val His Arg Asp Leu Lys Pro Glu Asn Leu Leu
145                 150                 155                 160
Leu Asp Ser Lys Met Asn Val Lys Ile Ala Asp Phe Gly Leu Ser Asn
                165                 170                 175
Val Met Arg Asp Gly His Phe Leu Lys Thr Ser Cys Gly Ser Pro Asn
                180                 185                 190
Tyr Ala Ala Pro Glu Val Ile Ser Gly Arg Leu Tyr Ala Gly Pro Glu
                195                 200                 205
Val Asp Val Trp Ser Cys Gly Val Ile Leu Tyr Ala Leu Leu Cys Gly
210                 215                 220
Ser Leu Pro Phe Asp Asp Glu Asn Ile Pro Asn Leu Phe Lys Lys Ile
225                 230                 235                 240
Lys Gly Gly Ile Tyr Thr Leu Pro Ser His Leu Ser Pro Gly Ala Arg
                245                 250                 255
Asp Leu Ile Pro Arg Met Leu Val Asp Pro Leu Lys Arg Ile Thr
                260                 265                 270
Ile Pro Glu Ile Arg Val Ala Ser Ala Thr Phe Val Met Leu Val Asp
                275                 280                 285
Pro Leu Lys Arg Val Thr Ile Pro Glu Ile Arg Gln His Pro Trp Phe
                290                 295                 300
Thr Val His Leu Pro Arg Tyr Leu Ala Ala Asp Pro Val Ala Ala Gly
305                 310                 315                 320
Thr His Ile Asp Glu Asp Ile Ile Arg Asp Val Val Arg Leu Gly Phe
                325                 330                 335
Thr Arg Asp Phe Val Val Asp Ser Leu Arg Ala Arg Gln Gln Asn Lys
                340                 345                 350
Ala Ser Val Ala Tyr Tyr Leu Met Ala Asp Asn Arg Arg Met Pro
                355                 360                 365
Ser Ser Ala Tyr Leu Lys Glu Glu Met Thr Glu Ala Thr Asp Pro Gly
370                 375                 380
Leu Ala Ala Phe Pro Ser Gly Val Met Ala Thr Ser Arg Ser Asn Thr
385                 390                 395                 400
Ser Leu Gln Pro Ala Pro Arg Leu Val Val Glu Arg Arg Trp Arg Leu
                405                 410                 415
Gly Leu Cys Ser Arg Ala His Pro Ser Ser Ile Met Gln Ala Arg Ala
                420                 425                 430
Gly Cys Val Cys Glu Arg Ala Cys Ala Val Lys Pro Ala Glu Leu Tyr
                435                 440                 445
Arg Thr Leu Gln Tyr Cys Gly Val Phe Trp Lys Lys Asn Gly Pro Tyr
450                 455                 460
Asn Leu Lys Cys Arg Ala Val Leu His Leu Thr Pro Pro Ala Asp Gly
```

```
                465                 470                 475                 480
            Gly Ser Gly Glu Gly Gly Gly Ala Ala Pro Asn Gly Gln Ala Gly
                        485                 490                 495

Ala Ser Gly Gln Leu Thr Arg Asp His Ser Asp Ser Met Gly Val
                        500                 505                 510

Ala Met Glu Ala Ser Pro Ala Ala Gly Gln Gln Gln Gly Ala
                        515                 520                 525

Leu Ala Ala Leu Ala Ala Glu Asp Ala Arg Met Ala Glu Ala Ala
                        530                 535                 540

Ala Ala Val Val Gly Ser Gly Gly Ser Asp Ser Ala Gly Ser Leu Glu
            545                 550                 555                 560

Arg Glu Val Lys Phe Glu Ala Gln Leu Tyr Lys Met
                        565                 570

<210> SEQ ID NO 26
<211> LENGTH: 1824
<212> TYPE: DNA
<213> ORGANISM: Chlorella sorokiniana

<400> SEQUENCE: 26
cttgtgtatc ccctaccagc ataccagcgc gctcccaggc ccctccgaca ccgctcgcaa      60
gcgcccggtc ccgcaggctc gctcatcgcc ccagctgcag cgttcagcat gacctcggtg     120
tcaccgggag acgctgggcc ggcgccaggc cacgccgggc agcccggggc gcagggcttc     180
gcctcctcca gcgcggagtt cttcctgcag aactaccggc tgggcaagac gctgggtatc     240
ggctctttcg gcaaggtcaa ggtggcggag cacatactga cagggcacaa ggtggccatc     300
aagatcctga accgcaagaa gatcaagcag atggacatgg aggaaaaggt gcggcgagag     360
atcaagatcc tgcgcctgtt catgcacccg cacatcatcc ggctgtatga ggtagtggag     420
accaccaatg atatctacgt ggcgggcgag ctgtttgact acattgtgga aggggcgg      480 ctgctggagg acgaggcgcg ccacttcttc cagcagatca tttcgggcgt ggagtactgc     540
caccgcaaca tggtggtgca ccgagacctc aagcccgaga acctgctgct ggacagcaag     600
atgaacgtca agattgcaga cttttgggctg tcaaacgtga tgcgggacgg ccacttcctc     660
aaaacctcct gcggctcccc caactatgcg gcgccagagg tcatctccgg ccggctgtac     720
gcggggcctg aggtggatgt gtggtcctgc ggcgtcatct tgtacgccct gctctgcggc     780
tcgctgccct cgacgacga gaacatcccc aacctgttca gaagatcaa gggcggcatt     840 tacacgctgc ccagccacct gagccccggg gcgcgcgacc tcatcccgcg catgctgctg     900
gtcgacccgc tcaagcgcat cacgatcccc gagatcagag tagccagcgc tactttgtg     960 atgctggttg acccactcaa gcgcgtcacc atccccgaga tcaggcagca ccctggttc    1020 acggtgcacc tgccgcggta cctggccgcg gacccagtag cagccggaac gcacatagac    1080
gaggacatca ttcgggacgt ggtgcggcta ggcttcaccc gcgattttgt ggtggactcc    1140
ctgcggggcg ggcagcagaa caaggcgtcc gtggcctact acctcatggc cgacaaccgg    1200
cggcgcatgc cctccagcgc ctatttgaaa gaagagatga cggaggccac ggatccgggg    1260
ctggccgcct ttccctcagg cgtcatggcc acgagccgca gcaacacgag cctgcagccg    1320
gcgccgcgcc tggtggtgga cggcgctgg cgcctggggc tgtgctcccg ggcgcacccc    1380
tcctccatca tgcaggcaag ggctggttgt gtgtgcgagc gagcgtgtgc tgtcaagcct    1440
gcggagctgt accgtacgct gcagtactgc ggggtgttct ggaagaaaaa cggcccttac    1500
aacctcaagt gccgagcggt cctgcacctc acgccgcccg ccgacggcgg cagcggagag    1560
```

```
ggcggcggcg gcgcggcgcc aacggccag gcgggcgcga gcgggcagct gaccagggac    1620
cactcagatg atagcatggg cgtggctatg gaggcttcgc ctgcggcagc agggcagcag    1680
cagcagggcg ccttggcagc ggcgctggca gcggaggatg cacgcatggc ggaagcggcg    1740
gcggcggtcg tgggcagcgg cggcagtgat agcgcaggct cccttgagcg tgaggtcaaa    1800
tttgaggcgc agctgtacaa gatg                                          1824
```

<210> SEQ ID NO 27
<211> LENGTH: 918
<212> TYPE: PRT
<213> ORGANISM: Chlamydomonas reinhardtii

<400> SEQUENCE: 27

| Met | Arg | Arg | Gln | Gly | Gln | Pro | Ser | Gly | Met | Asp | Cys | Asp | Leu | Leu | Glu |
|---|---|---|---|---|---|---|---|---|---|---|---|---|---|---|---|
| 1 | | | | 5 | | | | | 10 | | | | | 15 | |

| Leu | Gln | Gln | His | Thr | Ser | Arg | Ala | Arg | Leu | Leu | Lys | Ala | Lys | Glu | Arg |
| | | | 20 | | | | | 25 | | | | | 30 | | |

| His | Ile | Gly | His | Ser | Ser | Asn | Met | Gln | Asp | Cys | Asn | Asn | Gln | Lys | Ser |
| | | | 35 | | | | 40 | | | | | 45 | | | |

| Ser | Ala | Arg | Gly | Leu | Leu | Ser | Lys | Gly | Gly | Glu | His | Lys | Ala | Ala | Ala |
| | 50 | | | | | 55 | | | | | 60 | | | | |

| Lys | Pro | Ile | Asn | Pro | Thr | Gly | Gly | Phe | Arg | Ala | Lys | Leu | Leu | Ala | Ala |
| 65 | | | | | 70 | | | | 75 | | | | | | 80 |

| Lys | Arg | Arg | Ala | Ala | Phe | Gly | Gly | Ala | Ser | Thr | Thr | Ala | Lys | Ala |
| | | | | 85 | | | | 90 | | | | | 95 | |

| Gly | His | Val | Pro | Ala | Pro | Ser | Pro | Ser | Ser | Gly | Ser | Gly | Ser | Asp |
| | | | 100 | | | | | 105 | | | | | 110 | |

| Ala | Ala | Ser | Gly | Ser | Gly | Gly | Val | Ser | Asn | Gly | Ser | Ser | His | Gln | Gln |
| | | | 115 | | | | | 120 | | | | | 125 | | |

| Ala | Pro | Ser | Thr | Lys | Thr | Asn | Thr | Asn | Thr | Cys | Ser | Asn | Lys | Asn | Gly |
| | 130 | | | | | 135 | | | | | 140 | | | | |

| Gly | Ser | Asn | Lys | Thr | Ala | Gly | Thr | Ser | Thr | Thr | Ala | Ser | Val | Arg | Ile |
| 145 | | | | | 150 | | | | 155 | | | | | | 160 |

| Gly | Phe | Pro | Ser | Val | Arg | Arg | Pro | Ser | Ala | Ser | Ser | Thr | Ser | Ser |
| | | | | 165 | | | | 170 | | | | | 175 | |

| Arg | His | Ala | Leu | Pro | Ala | Ala | Thr | Gln | Pro | Thr | Ser | Cys | Val | Pro |
| | | | 180 | | | | | 185 | | | | | 190 | |

| Gly | Ala | Lys | Pro | Ala | Ala | Pro | Gln | Gln | Ser | Asn | Ala | Ala | Ala | Ala | Thr |
| | | | 195 | | | | | 200 | | | | | 205 | | |

| Thr | Val | Ala | Val | Ala | Pro | Ala | Thr | Ala | Gly | Ser | Ser | Ser | Gly | Ala | Arg |
| | 210 | | | | | 215 | | | | | 220 | | | | |

| Arg | Met | Glu | Gly | Arg | Cys | Arg | Pro | Tyr | Arg | Pro | Pro | Met | Arg | Val | Gln |
| 225 | | | | | 230 | | | | 235 | | | | | | 240 |

| Gly | Asp | Glu | Gly | Gly | Lys | Ala | Ala | Thr | Ala | Gly | Thr | Gly | Pro | Gly | Ser |
| | | | | 245 | | | | 250 | | | | | 255 | |

| Ser | Ser | Gly | Ser | Gly | Leu | Met | Leu | Arg | Ser | Leu | Val | Gly | Cys | Leu | Leu |
| | | | 260 | | | | | 265 | | | | | 270 | | |

| Pro | His | Leu | Ala | Thr | Ala | Ala | Ile | Glu | Lys | Ala | Ala | His | Val | Ala | Ala |
| | | | 275 | | | | | 280 | | | | | 285 | | |

| Ala | Val | Ala | Arg | Arg | Val | Met | Ala | Pro | Val | Ala | Ala | Ala | Ala | Ala |
| | | | 290 | | | | | 295 | | | | | 300 | |

| Val | Pro | Tyr | Arg | Arg | Met | Glu | Ala | Pro | Val | Ala | Ala | Ala | Ala | Ala | Ala |
| 305 | | | | | 310 | | | | 315 | | | | | | 320 |

```
Val Pro Cys Arg Val Met Val Ala Pro Val Ala Thr Ala Ala Ala Val
                325                 330                 335

Pro Cys Gly Met Val Ala Pro Val Ala Thr Ala Ala Ala Val Pro Cys
            340                 345                 350

Gly Met Val Ala Pro Val Ala Thr Ala Ala Ala Val Pro Cys Gly Met
                355                 360                 365

Val Ala Pro Val Ala Gly Ala Val Ala Pro Lys Leu Val Ala Phe Arg
370                 375                 380

Pro Pro Pro Pro Pro Ile Thr Pro Val His Gln His Gln His Gln His
385                 390                 395                 400

Gln Gln Ala Gly Pro Arg Tyr Val Ala Arg Pro Ala Val Gln Pro Met
                405                 410                 415

Met Gly Pro Pro Val Val Gln Ala Thr Ala Gly Ala Ala Ala Val Ala
            420                 425                 430

Ala Pro Arg Leu Leu Val Gly Ala Pro Val Lys Leu Leu Met Ala Pro
            435                 440                 445

Gln Leu Leu Gln Arg Gln Gln His Asn Ile Gln Leu Ala Asn Arg Val
450                 455                 460

Ala Cys Val Pro Tyr Pro His Pro His Pro Ala Val Gln Pro Gln Pro
465                 470                 475                 480

Val Leu Val His Gly Gly Met Pro Ala Pro Arg Gln Pro His Gln Gln
                485                 490                 495

Gln Asp Gln Ser Leu Gln Met Arg Met Gln Gln Leu Gln Gln Ala Gln
            500                 505                 510

Gln Met Trp Gln Ala Gln Lys Lys Val Gln Glu Ala Glu Ala Arg Asn
            515                 520                 525

Gln Arg Ile Gln Glu Ala Ile Gln Glu Glu Asp Ile Val Val Ala
530                 535                 540

Asn Val Arg Glu Leu Met Gln Arg Phe Thr Ser Gly Ala Ser Lys Pro
545                 550                 555                 560

Phe Glu Leu Ile Arg Leu Lys Arg His Leu Gly Gln Gly Ala Phe Gly
                565                 570                 575

Cys Val Asp Cys Trp Glu Val Thr Glu Arg Gln Ser Ala Thr Ala Ser
            580                 585                 590

Ser Ala Ala Ser Ser Ser Gly Leu Ala Ala Ala Ala Ser Cys Thr Ala
            595                 600                 605

Thr Ala Thr Ser Ser Ser His Thr Phe Glu Ala Ala Val Lys Thr Cys
            610                 615                 620

Ala Leu Asp Leu Glu Gly Leu Ala Ala Gly Gly Glu Thr Pro His Ser
625                 630                 635                 640

Val Glu Met His Ala Lys Glu Ala Ala Val Leu Ala Val Gln Ala
                645                 650                 655

Leu Asp Ser Arg His Leu Val Lys Val Leu Gly Ala Tyr Val Asp Val
                660                 665                 670

Leu Thr Pro Gly Glu Asp Val Pro Pro Arg Gly Cys Gly Ile Ala Asn
            675                 680                 685

Leu His Val Gly Arg Ile Val Met Glu Val Ala Arg Glu Ser Leu Thr
            690                 695                 700

Asp Val Val Thr Gly His Arg Val Leu Ala His Cys Ala Ala Gly Gly
705                 710                 715                 720

Ala Ala Ala Ala Phe Asp Ala Asp Ser Glu Asp Thr Ser Gly Tyr Arg
                725                 730                 735

Leu Pro Glu Thr Ala Val Arg Val Val Leu Ala Ser Val Leu Leu Gly
```

```
                    740                 745                 750
Leu Arg Asp Leu His Gly Arg Ala Arg Leu Ala His Arg Asp Leu Lys
            755                 760                 765

Leu Asp Asn Leu Leu Val Gly Thr Asp Arg Leu Val Lys Ile Thr Asp
        770                 775                 780

Phe Gly Leu Val Thr Pro Leu Asp Ser Gln Gly Arg Leu Val Ser Glu
785                 790                 795                 800

Val Gly Gly Arg Arg Gly Thr Lys Gly Tyr Gln Ala Pro Glu Thr Leu
                805                 810                 815

Ala Arg Arg Thr Phe Ala Ala Asn Glu Arg Asp Leu Pro Ser Trp Pro
            820                 825                 830

Ala Ala Lys Ser Asp Ile Tyr Ala Val Gly Val Ile Gly Ala Ala Leu
        835                 840                 845

Val Cys Gly Thr Glu Ser Gly Pro Glu Met Glu Ala Phe Arg Ala Ser
    850                 855                 860

Gly Glu Leu Pro Pro His Arg His Ala Ser Pro Ala Leu Arg Gln Leu
865                 870                 875                 880

Leu Lys Gly Met Ala Ala Asp Pro Ala Gln Arg Leu Gly Val Glu
                885                 890                 895

Glu Ala Leu Ala His Pro Ala Leu Arg Arg Ala Leu Ser Ser Glu Arg
            900                 905                 910

Ala Arg Arg Phe Ile Trp
        915

<210> SEQ ID NO 28
<211> LENGTH: 4314
<212> TYPE: DNA
<213> ORGANISM: Chlamydomonas reinhardtii

<400> SEQUENCE: 28
gatctggcat acgtttcctt gcgacgcctg cactcggccg ctgtcaagcc cgcggcaagg      60
caccgggcgc agcgcccaag cgcgggaaaa cgcatccggc tcagccctag ctcctcaaag     120
cgcttgctat gcaaattttg cagaatctct tgcattagcg catcagggct gctgggcgca     180
tggctgggct ggagcaagtc cgcgctgcgg gctcaaagcg cctgtgtacg ctttcagctc     240
tcttccagcg cttttatgc atgcacagaa ttcagctttt gcctttgcac ccgctttgca     300
gcaaccgcag cgcaggcgcg gccacggcac tacttgcagg cgcgctactg ggtgcgcttg     360
gctccaagcg ctgtcactta aggctggctt agcaaattaa ggtattcata tggagcagct     420
ttccagggca ttccgcgcgg gtcaacccac ggtcaagcgg gatggggctc ctttcgttt      480
gggggccatt ctttacttga gccacgcgcg gcgttctata gcaaaagctt tcagtgagct     540
catacacata catacaacta gctttcctct caagccccag agcctcgcct agctaactat     600
ttctgacttg cgtcttcttc ctcgcttttc ctatcaaagg ccctcaactt acagcatcgg     660
ctcactgtga cacttgttgc ttgtggcgac acgcatcgag tgggcggcac tgcaagaggc     720
gaacacgctt ccgacggacg gaaacgcgct cctggctctc ccgttctgta tgcggcggca     780
agggcagcct agcggtatgg attgcgacct gctggagctg cagcagcaca cttcgcgagc     840
gaggctgctg aaggccaagg agcggcacat agggcacagc agcaacatgc aggactgcaa     900
caaccagaag tccagcgccc gcggtctcct gtccaagggc ggcgagcaca aggccgcggc     960
caaacccatc aatccgaccg gcggtttccg tgccaagctt ctggcggcta agcgccgtgc    1020
cgcctttggc ggtggcgcct cgaccacggc taaggctggc catgtgcccg cgccctctcc    1080
```

```
tagcagcggc ggcagcgggt ctgacgcggc ctccggcagc ggtggggtct ccaacggctc    1140
atcgcaccag caggcgccct cgacaaaaac caacaccaac acctgcagca acaagaatgg    1200
tggcagcaac aagactgctg gcaccagcac gaccgcctca gtgaggattg gcttcccatc    1260
cgttcgccgt cgcccatccg cctcttccac cagcagcagg cacgcgctgc ctgctgccgc    1320
cacacaaccc acctcctgcg tgcccggtgc caagcctgct gcaccccagc agtccaacgc    1380
cgccgccgcc accaccgtcg ctgttgctcc tgcgactgct ggctcatcat caggagcccg    1440
ccgcatggag ggccgctgcc gccctaccg gccgcccatg cgggtgcagg gcgacgaggg    1500
cggcaaggcg gccaccgctg gcactggccc tggcagcagc agtggctcgg gcctgatgct    1560
ccgcagcttg gtagggtgcc tgctgcccca cctcgccact gccgccatcg agaaggcagc    1620
gcacgtcgcg gccgccgtcg cccgccgggt gatggcaccc gtcgccgccg ccgccgccgc    1680
cgtgccctac cgccggatgg aggcacccgt cgccgccgcc gccgccgccg tgccttgccg    1740
ggtgatggtg gcaccgtcg ccactgccgc cgccgtgccc tgcgggatgg tggccccgt    1800 cgccactgcc gccgccgtgc cctgcgggat ggtggccccc gtcgccactg ccgccgccgt    1860
gccctgcggg atggtggccc ccgtcgccgg cgcggtggcg cccaagctcg tggccttccg    1920
gccgccgccc ccgcccatca cgccagtgca ccagcaccag caccagcacc agcaggcggg    1980
gccgcggtac gtggcgcggc cggcggtgca accgatgatg gggccgcctg tggttcaggc    2040
taccgctggc gccgcggccg tggcggcgcc gcggctgctc gtgggggctc cggtcaagct    2100
cctgatggcg cctcagctgc ttcagcggca gcagcacaac atccagctgg ccaaccgcgt    2160
ggcttgcgtg ccgtacccgc acccgcaccc ggcggtgcag ccgcagccgg tcctggtgca    2220
cggcggcatg ccggctccgc gccagccgca ccagcagcaa gaccaaagcc tgcagatgcg    2280
gatgcagcag ctgcagcagg cgcagcagat gtggcaagcg cagaagaagg tgcaggaggc    2340
ggaggcccgg aatcagcgga tccaggaggc cattcaggag gaggaggaca ttgttgtcgc    2400
caacgtgcgc gagctcatgc agcgcttcac cagcggcgcc tccaagccct tcgagctcat    2460
ccgcctcaag cggcacctgg gccagggcgc cttcggctgc gtcgactgct gggaggtcac    2520
agagcgccag tccgccaccg cctcctccgc cgcctcctcc tctggcctgg cggcggcggc    2580
ctcctgcacc gccactgcca ccagcagcag ccacacgttt gaggcggcgg tgaagacctg    2640
cgctctggac ctggagggcc tggcggcggg cggcgaaacg ccgcattctg tggagatgca    2700
tgccaaggag gcggcggcgg tgctggcggt tcaggcgctg gactcgcggc acctggtcaa    2760
ggtgctgggg gcctacgtcg acgtgctgac acccggggag gacgtgccgc ccgaggctg    2820 cggcatcgcc aacctgcacg tcgggcgcat cgtgatggag gtggcgcggg agtcgctgac    2880
tgacgtggtg acgggccacc gcgtgctcgc gcactgcgcc gcggcggcg ccgccgccgc    2940 ctttgacgcc gactcggagg acacgtccgg ctaccggctg cccgagaccg cggtgcgcgt    3000
ggtgctggcc tcggtgctgc tgggcctgcg cgacctgcac ggccgcgcgc ggctggctca    3060
ccgtgacctg aagctggaca accttctggt tggcacggac cggcttgtta agatcaccga    3120
cttcggcctg gtgacgccac tagacagcca gggccgcctg gtctcggagg tcggggggcg    3180
gcggggcacg aagggctacc aggcccctga cgctggcg cgccgcacct tcgcggccaa    3240
cgagcgcgac ctgcccagct ggccagccgc caagagcgac atttacgcgg tgggcgtgat    3300
cggcgcggcg ctggtgtgcg gcaccgagtc ggggccggag atggaggcct tccgggccag    3360
tggcgagctg ccgccgcacc ggcacgcctc gccagcgctg cggcagctgc tcaagggcat    3420
ggcggcggcg gacccggcgc agcggctagg ggtggaggag gcactggcgc acccgcgct    3480
```

```
gcgcagggcg ctgagcagcg agcgggcgcg gcgcttcatc tggtgatggc ggcagggcca      3540
gatcgctcgg gcatgaggcg ggctagctac aggcgggcag tgcgtcagtg atgagcggcg      3600
gctgtcaaat gaataaagga gtgcttacat gtgtgtcaga gccagattgg cctgagggaa      3660
cattgattgg cctcaggata gaacccttag caagcaagcc gtggatggca gcgtgcatag      3720
tcgcggctgc taatccttgc tgcttcccct tgattgattg atgatagaca atagaacgcc      3780
gcgttgccgg cttgccgcaa gaggcagata ttgagacgaa tggatgcttg gccgtggcc      3840
caatggctcc ctgacgctgt gttctgaaac tgtagggtac catatgtgct ggcgcttgcg      3900
tgtgcgttag ttgtcggtcc ttcgggcgac ggatggcctg gtaggactac cttgattgag      3960
ccctgttttg actcctcctt acgtagtacg acgtgttgat ctctttccgt cctgtccgcg      4020
tgattgctcg ctgtatcccg gatatggacc ccagcagttt gagcacaggt ctacctggcg      4080
ttgagcttgc ttgacatgtc ttgtgtgacc gttttgcaac tgaatccatg tgttctgtcg      4140
ggcctatacg gtgcaagctt agctatgtag ccatgattgt gcacgcctct gaagagctgc      4200
aagctgctgg tcgttcctag gtgcgcagcg gcggtgtgca ctgaccgctc agagcgctga      4260
ctcctggaac atatacagcg ggttcgtgca catggtacga taacccgcct tgta           4314
```

<210> SEQ ID NO 29
<211> LENGTH: 913
<212> TYPE: PRT
<213> ORGANISM: Chlamydomonas reinhardtii

<400> SEQUENCE: 29

```
Met Asp Cys Asp Leu Leu Glu Leu Gln Gln His Thr Leu Arg Ala Arg
1               5                   10                  15

Leu Leu Lys Ala Lys Glu Arg Arg His Ile Gly His Ser Ser Asn Met
            20                  25                  30

Gln Asp Cys Asn Asn Gln Lys Ser Ser Ala Arg Ser Leu Leu Ser Lys
        35                  40                  45

Gly Gly Glu His Lys Ala Ala Ala Lys Pro Ile Lys Pro Thr Gly Gly
    50                  55                  60

Phe Arg Ala Lys Leu Leu Ala Ala Lys Arg Arg Ala Ala Phe Gly Gly
65                  70                  75                  80

Gly Ala Ser Thr Thr Ala Lys Ala Gly His Val Pro Ala Pro Ser Pro
                85                  90                  95

Ser Ser Gly Gly Ser Gly Ser Asp Ala Asp Cys Asn Asn Gln Lys Ser
            100                 105                 110

Ser Ala Arg Ser Leu Leu Ser Lys Gly Gly Glu His Lys Ala Ala Ala
        115                 120                 125

Lys Pro Thr Lys Pro Thr Gly Gly Phe Arg Ala Lys Leu Leu Ala Ala
    130                 135                 140

Lys Arg Arg Ala Ala Phe Gly Gly Gly Ala Ser Thr Thr Ala Lys Ala
145                 150                 155                 160

Gly His Val Pro Ala Pro Ser Pro Ser Ser Gly Ser Gly Ser Asp
                165                 170                 175

Ala Ala Pro Gly Ser Gly Gly Val Ser Asn Gly Ser Ser Arg Gln Gln
            180                 185                 190

Ala Pro Ser Ala Asn Thr Asn Thr Asn Thr Asn Ser Tyr Ser Thr Ser
        195                 200                 205

Ser Arg His Ala Leu Pro Ala Ala Thr Gln Pro Thr Pro Cys Val Pro
    210                 215                 220
```

```
Ser Ile Gln Pro Ala Ala Pro Arg Ser Ser Ala Ala Ala Ala Thr
225                 230                 235                 240

Thr Val Ala Ala Ala Thr Ala Ala Gly Ser Ser Gly Ala Arg Arg
            245                 250                 255

Met Glu Gly Arg Cys Arg Pro Tyr Arg Pro Met Arg Val Gln Gly
        260                 265                 270

Asp Glu Gly Gly Lys Ala Ala Thr Ala Gly Ser Gly Pro Gly Ser Ser
        275                 280                 285

Ser Gly Ser Gly Leu Met Leu Arg Ser Leu Val Gly Cys Leu Leu Pro
        290                 295                 300

His Leu Ala Thr Ala Ala Ile Gln Lys Thr Ala His Val Ala Ala Ala
305                 310                 315                 320

Val Ala Arg Arg Val Met Ala Pro Val Ala Ala Ala Thr Ala Val
            325                 330                 335

Pro Cys Arg Val Met Ala Pro Val Ala Thr Ala Ala Val Pro Cys
            340                 345                 350

Arg Val Val Ala Pro Val Ala Ala Ala Ala Asp Ala Gly Ala Val
            355                 360                 365

Ala Pro Lys Leu Val Ala Phe Arg Pro Pro Pro Pro Ile Met Pro
370                 375                 380

Val His Gln His Gln His Asp Gln His Gln Gln Ala Gly Pro Trp
385                 390                 395                 400

Tyr Val Ala Arg Pro Ala Val Gln Pro Met Met Gly Pro Pro Val Val
            405                 410                 415

Gln Ala Thr Ala Gly Ala Ala Val Ala Ala Pro Arg Leu Leu Val
            420                 425                 430

Gly Ala Pro Val Lys Leu Leu Met Ala Thr Gln Leu Leu Gln Gln Gln
            435                 440                 445

Gln His Ile Gln Leu Ala Asn Arg Val Ala Cys Val Pro Tyr Pro His
        450                 455                 460

Pro His Pro Ala Val Gln Pro Gln Pro Val Leu Val His Gly Gly Met
465                 470                 475                 480

Pro Ala Pro Arg Gln Pro His Gln Gln Gln Asp Gln Ser Leu Gln Met
            485                 490                 495

Arg Met Gln Arg Leu Gln Gln Ala Lys Gln Met Trp Gln Ala Gln Lys
            500                 505                 510

Lys Lys Val Gln Glu Ala Glu Ala Arg Gln Arg Ile Gln Glu Ala
            515                 520                 525

Ile Gln Glu Glu Glu Asp Ile Val Val Ala Asn Val Arg Glu Leu Met
530                 535                 540

Gln Arg Cys Thr Ser Gly Ala Ser Lys Pro Val Glu Leu Ile Arg Leu
545                 550                 555                 560

Lys Arg His Leu Gly Gln Gly Ala Phe Gly Cys Val Asp Cys Trp Glu
            565                 570                 575

Val Thr Glu Arg Gln Ser Pro Thr Ala Ser Ser Ala Ala Ser Ser Ser
            580                 585                 590

Gly Leu Ala Ala Ala Ala Ser Gly Thr Ala Thr Ala Thr Ser Ser
            595                 600                 605

Ser Arg Thr Phe Glu Ala Ala Val Lys Thr Cys Ala Leu Asp Leu Lys
            610                 615                 620

Gly Leu Ala Ala Gly Gly Ala Thr Pro His Ser Val Glu Met His Ala
625                 630                 635                 640

Lys Glu Ala Ala Ala Val Leu Ala Val Gln Ala Leu Asp Ser Arg His
```

```
                        645                 650                 655
Leu Val Lys Val Leu Gly Ala Tyr Val Asp Val Leu Thr Pro Gly Glu
                660                 665                 670

Asp Val Pro Arg Gly Cys Gly Ile Ala Asn Leu Arg Val Gly Arg
            675                 680                 685

Ile Val Met Glu Val Ala Arg Glu Ser Leu Thr Asp Val Val Thr Gly
        690                 695                 700

His Arg Val Leu Ala His Cys Ala Val Gly Ala Ala Ala Phe
705                 710                 715                 720

Asp Ala Asp Ser Glu Asp Thr Ser Gly Tyr Arg Leu Pro Glu Thr Ala
                725                 730                 735

Val Arg Val Val Leu Ala Ser Val Leu Gly Leu Arg Asp Leu His
                740                 745                 750

Gly Arg Ala Arg Leu Ala His Arg Asp Leu Lys Leu Asp Asn Leu Leu
                755                 760                 765

Val Gly Thr Asp Arg Leu Val Lys Ile Thr Asp Phe Gly Leu Val Thr
            770                 775                 780

Pro Leu Asp Ser Gln Gly Arg Leu Val Ser Glu Val Gly Gly Arg Arg
785                 790                 795                 800

Gly Thr Lys Gly Tyr Gln Ala Pro Glu Thr Leu Ala Arg Arg Thr Phe
                805                 810                 815

Ala Ala Asn Glu Arg Asp Leu Pro Ser Trp Pro Ala Ala Lys Ser Asp
                820                 825                 830

Val Phe Ala Val Gly Val Ile Gly Ala Ala Leu Val Cys Gly Thr Glu
            835                 840                 845

Ser Gly Pro Glu Met Glu Ala Phe Arg Gly Ser Gly Glu Leu Pro Pro
850                 855                 860

His Arg His Ala Ser Pro Ala Leu Arg Gln Leu Leu Lys Gly Met Ala
                870                 875                 880

Ala Ala Asp Pro Ala Gln Arg Leu Gly Val Glu Glu Ala Leu Ala His
                885                 890                 895

Pro Ala Leu Arg Arg Ala Leu Ser Ser Glu Arg Ala Arg Phe Ile
                900                 905                 910

Trp

<210> SEQ ID NO 30
<211> LENGTH: 4486
<212> TYPE: DNA
<213> ORGANISM: Chlamydomonas reinhardtii

<400> SEQUENCE: 30
ctacctggca cacatttcgt tgcgacgcct gcactccggc cgccttcaag cccgcggtaa      60
ggcaccgggc gcagcgccca agcgcgggaa aacgcatccg gctcagccct agctcctcaa     120
agcgcctgct atgcaaactt tgcagaatct cttgcattag cgcatcagca gcagggctgc     180
tgggcgcatg gctgggctgg agcaagtccg cgctgcgggc tcaaagcgcc tgtgtacgct     240
ttcagctctc ttccagcgct ttttttcatg cacagaattc agcttttgcc tttgcacccg     300
ctttgcagca accgcagcgc aggcgcggcc acgcacttg caggcgcgct actgggtgcg      360
cctggctcca agcgctggca cttaaggctg cttagcaaa ttaaggtatt catatggagc      420
agctttccag gcattccgc gcgggtcaac ccacggtcaa gcgggatggg gcttcttttc      480
gtttgcaggc cattctttac ttgggccacg cgcggcgttc tatagcaaaa gctttcagtg     540
agctcatacg cgcacacaca tacatacaac tagcttttcct ctcaagcccc agagcctcgc     600
```

```
ctagctaact atttccgact tgcgtcttct tcctcgcttt tcctatcaaa ggccctcaac      660
ttgcagcatc ggctcactgt ggcacttgtt gcttgtggcg acaagcatcg agtgggcggc      720
actgcaagag gcgcacacgc ttccgacgga cggaaacgcg ctcctggctc tcccgtgctg      780
tttgcggcgg caagggcagc ctagcggtat ggattgcgac ctgctggagc tgcagcagca      840
cactttgcga gcgaggctgc tcaaggccaa ggagcggcgg cacatcggcc acagcagcaa      900
catgcaggac tgcaacaacc agaagtccag cgcccgcagt ctcctgtcca agggcggcga      960
gcacaaggcc gcggccaaac ccatcaaacc gaccggcggt ttccgtgcca agcttctggc     1020
ggcgaagcgc cgtgccgcct ttggcggtgg cgcctcgacc acggctaagg ctggccatgt     1080
gcccgcgccc tctcctagca gcggcggcag cgggtctgac gcggactgca caaccagaa      1140 gtccagcgcc cgcagtctcc tgtccaaggg cggcgagcac aaggccgcgg ccaaacccac     1200
caaaccgacc ggcggtttcc gtgccaagct tctggcggcg aagcgccgtg ccgcctttgg     1260
cggtggcgcg tcgactacgg ctaaggctgg ccatgtgccc gcgcctctc ctagcagcgg      1320 cggcagcggg tctgacgcgg cccccggcag cggtggggtc tccaacggct catcgcgcca     1380
gcaggcgccc tcggccaaca ccaacaccaa caccaactcg tactccacca gcagcaggca     1440
cgcgctgccc gccgccacac aacccacccc ctgcgtgccc agtattcagc ctgctgcacc     1500
ccggtccagt gccgccgccg ccgccaccac cgtcgctgct gctacggctg ctggctcatc     1560
atcaggagcc cgccgcatgg agggccgctg ccgcccctac cggccgccca tgcgggtgca     1620
gggcgacgag ggcggcaagg cggccaccgc tggcagtggc cctggcagca gcagtggctc     1680
aggcctgatg ctccgcagct tggtagggtg cctgctgccc cacctcgcca ctgccgccat     1740
ccagaagaca gcgcacgtcg cggccgccgt cgcccgccgg gtgatggcac ccgtcgccgc     1800
cgccgccacc gccgtgccct gccgggtgat ggcacccgtc gccactgccg ccgccgtgcc     1860
ctgccgggtg gtggcacccg tcgccgctgc cgcggccgac gccggcgcgg tggcgcccaa     1920
gctcgtggcc ttccggcctc cgccgccgcc catcatgcca gtgcaccagc accagcacca     1980
ggaccagcac cagcaggcgg ggccgtggta cgtggcgcgg ccggcggtgc aaccgatgat     2040
ggggccgcct gtggttcagg ctaccgctgg cgccgcggcc gtggcggcgc gcggctgct     2100 cgtggggct ccggtcaagc tcctgatggc aactcagctg cttcagcagc agcagcacat     2160
ccagctggcc aaccgcgtgg cttgcgtgcc gtacccgcac ccgcacccgg cggtgcagcc     2220
gcagccggtc ctggtgcacg gcggcatgcc ggctccgcgc cagccgcacc agcagcaaga     2280
ccaaagcctg cagatgcgga tgcagcggct gcagcaggcg aagcagatgt ggcaagcgca     2340
gaagaagaag gtgcaggagg cggaggcccg gcagcagagg atccaggagg ccattcagga     2400
ggaggaggac attgttgtcg ccaacgtgcg cgagctcatg cagcgctgca ccagcggcgc     2460
ctccaagccc gtcgagctca tccgcctcaa gcggcacctg gccagggcg cttcggctg     2520 cgtcgactgc tgggaggtca cagagcgcca gtccccacc gcctcctccg cggcctcctc     2580
ctctggcctg gcggcggcgg cggcctccgg caccgccact gccaccagca gcagccgcac     2640
ctttgaggcg gcggtgaaga cctgcgctct ggacctgaag ggcctggcgg cgggcggcgc     2700
aacgccgcat tctgtggaga tgcatgccaa ggaggcggcg gcggtgctgg cggttcaggc     2760
gctggactcg cggcacctgg tcaaggtgct gggggcctac gtcgacgtgc tgacacccgg     2820
ggaggacgtg ccgccccgcg gctgcggcat cgccaacctg cgcgtcgggc gcatagtgat     2880
ggaggtggcg cgggagtcgc tgactgacgt ggtgacgggc caccgcgtgc tcgcgcactg     2940
```

-continued

| | |
|---|---|
| cgccgtgggc ggcgccgccg ccgcctttga cgccgactcg gaggacacgt ccggctaccg | 3000 |
| gctgcccgag accgcggtgc gcgtggtgct ggcctcggtg ctgctgggcc tgcgcgacct | 3060 |
| gcacggccgc gcgcggctgg cgcaccggga cctgaagctg acaaccttc tggttggcac | 3120 |
| ggaccggctt gttaagatca ccgacttcgg cctggtgacg cctctggaca gccagggccg | 3180 |
| cctggtctcg gaggtcgggg ggcggcgggg cacgaagggc taccaagccc ctgagacgct | 3240 |
| ggcgcgccgc accttcgcgg ccaacgagcg cgacctgccc agctggccgg ccgccaagag | 3300 |
| cgatgtgttc gcggtgggcg tgatcggcgc ggcgctggtg tgcggcaccg agtcggggcc | 3360 |
| ggagatggag gccttccggg gcagtggtga gctgccgccg caccggcacg cctcgccggc | 3420 |
| gctgcggcag ctgctcaagg gcatggcggc ggcggacccg gcgcagcggc tgggggtgga | 3480 |
| ggaggcactg gcgcacccg cgctgcgcag ggcgctgagc agcgagcggg cgcggcgctt | 3540 |
| catctggtga aggcggcaag gccagatcgc tcgggcatga ggcgggctat atgcggacag | 3600 |
| tgcgtcagtg atgagcggcg gctgtcaaat gaataaagga gtgcgtacgt gtgtgtgcca | 3660 |
| gagcttactt gcttgagagc tgggtgtttt taagtataaa gacacagcat gcgcagtgtt | 3720 |
| gaggaccgca cagaggttca taggacatag attggcctga gggaacgttg attggcctca | 3780 |
| gggtagaacc cttagcaagc aagccgtgga tggcagcatg catagttgcg gctgctgatc | 3840 |
| cttgctgctt cccttgatt gattgatgat acggtaggcc tagacattag aatgccgcgt | 3900 |
| tgattgcttg ccggcttgcc gcaagaggca gatagaacg aatggatgct gggccgtgg | 3960 |
| cccaatggct ccatgacgct gtgttctgaa actcaagggt accacatgtg ctggcgcttg | 4020 |
| cgtgtgcgtt gtcggtcctt cgatcaacac gtcttactac gtacgaaaat tcgggcaacg | 4080 |
| gactgcggta gggctacctt tactaccttg agccctattt tgactcctct gcacgtagta | 4140 |
| cgacgtgttg atctatttcc gtcctttccg cgtgattgct gtatcccggc ggacatgacc | 4200 |
| ccagcagttt gagcacaggt ctacctggcg ttgagcttgc ttgacatgtc ttgtgtgacc | 4260 |
| gttcgcaact gaatccatgt gttctgtcgg gtgtatacgg tgcaagctta gctatgtagc | 4320 |
| catggttgtg cacgcctgtg atgaagagcc gcaagctgct ggtcgtctcc taggcgcgca | 4380 |
| gcggtaggtg cgcactgacc gctcagagcg ctgactcctg aacatatac agcaggttcg | 4440 |
| tgcacatggt acggtaaccc gccttgtagt gcaaagggac actcca | 4486 |

<210> SEQ ID NO 31
<211> LENGTH: 834
<212> TYPE: PRT
<213> ORGANISM: Chlamydomonas reinhardtii

<400> SEQUENCE: 31

Met Asp Cys Asp Leu Leu Ser Glu Leu Gln Gln His Thr Leu Arg Ala
1               5                   10                  15

Arg Leu Leu Lys Ala Lys Glu Arg His Ile Gly His Ser Ser Asn Met
            20                  25                  30

Gln Asp Tyr Asn Asn Lys Ser Ser Ala Arg Gly Leu Leu Ser Lys
        35                  40                  45

Gly Gly Glu His Lys Ala Ala Ala Lys Pro Lys Ser Thr Gly Gly Phe
    50                  55                  60

Arg Ala Lys Leu Leu Ala Ala Lys Arg Arg Ala Phe Gly Gly Gly
65                  70                  75                  80

Ala Ser Thr Thr Ala Met Ala Gly His Val Pro Ala Pro Ser Pro Ser
                85                  90                  95

Ser Gly Gly Ser Gly Ser Asp Ala Ala Pro Gly Ser Gly Gly Val Ser

```
                100             105             110
Asn Gly Ser Ser Arg Gln Gln Ala Pro Ser Ala Asn Ala Asn Thr Asp
            115                 120             125

Thr Asn Thr Asn Thr Gly Ser Asn Lys Thr Gly Gly Thr Asn Thr Thr
        130                 135             140

Ala Ser Pro Ala Ala Pro Gln Gln Ser Asn Ala Ala Ala Ala Thr Thr
145                 150                 155                 160

Val Ala Val Ala Pro Ala Thr Ala Gly Ser Ile Ser Gly Ala Arg Arg
                165                 170                 175

Met Glu Gly Arg Cys Arg Pro Tyr Arg Pro Met Arg Val Gln Gly
            180                 185             190

Asp Glu Gly Gly Lys Ala Ala Thr Ala Gly Thr Gly Pro Ala Gly Ser
        195                 200             205

Ser Ser Ser Gly Ser Gly Leu Met Leu Arg Ser Leu Val Gly Cys Leu
        210                 215             220

Leu Pro His Leu Ala Thr Ala Ala Ile Glu Lys Ala Ala His Val Ala
225                 230                 235                 240

Ala Ala Val Ala Pro Arg Val Met Ala Pro Val Ala Ala Ala Ala Ala
                245                 250                 255

Ala Val His Tyr Arg Arg Met Glu Ala Pro Val Ala Ala Ala Ala Ala
            260                 265                 270

Val Pro Cys Arg Met Val Ala Pro Val Ala Gly Ala Val Ala Pro Lys
        275                 280                 285

Leu Val Ala Phe Arg Pro Pro Pro Pro Ile Met Pro Val His Gln
        290                 295                 300

His Gln His Gln Asp Gln His Gln Gln Ala Gly Pro Arg Tyr Val Ala
305                 310                 315                 320

Arg Pro Ala Val Gln Pro Met Met Gly Pro Pro Val Val Gln Ala Thr
                325                 330                 335

Ala Gly Ala Ala Ala Val Ala Ala Pro Arg Leu Leu Val Gly Ala Pro
            340                 345                 350

Val Lys Leu Leu Met Ala Pro Gln Val Leu Gln Gln Gln His Ile
        355                 360                 365

Gln Gln Leu Ala Asn Arg Val Ala Cys Val Pro Tyr Pro His Pro His
370                 375                 380

Pro Ala Val Gln Pro Gln Pro Val Leu Val His Gly Gly Gly Met Pro
385                 390                 395                 400

Ala Ala Arg Gln Pro His Gln Gln Gln Asp Gln Ser Leu Gln Met Arg
            405                 410                 415

Leu Glu Gln Arg Leu Gln Gln Ala Lys Gln Met Trp Gln Ala Thr Lys
        420                 425                 430

Lys Arg Val Gln Glu Ala Lys Ala Arg Arg Lys Gln Arg Ile Gln Glu
        435                 440                 445

Ala Ile Gln Glu Glu Glu Asp Ile Val Val Ala Asn Val Arg Glu Leu
        450                 455                 460

Met Gln Arg Val Thr Ser Gly Ala Pro Lys Pro Phe Glu Leu Ile Arg
465                 470                 475                 480

Leu Lys Arg His Leu Gly Gln Gly Ala Phe Gly Cys Val Asp Cys Trp
            485                 490                 495

Glu Val Thr Glu Arg Gln Ser Ala Thr Ala Ser Ser Ala Ala Ser Ser
            500                 505                 510

Ser Gly Leu Ala Ala Ala Ala Ser Gly Thr Ala Thr Ala Thr Ser
        515                 520                 525
```

-continued

```
Ser Ser Arg Thr Phe Glu Ala Ala Val Lys Thr Cys Ala Leu Asp Leu
        530                 535                 540

Glu Gly Leu Ala Ala Gly Gly Glu Thr Pro His Thr Val Glu Met His
545                 550                 555                 560

Ala Lys Glu Ala Ala Ala Val Leu Ala Val Gln Ala Leu Asp Ser Arg
                565                 570                 575

His Leu Val Lys Val Leu Gly Ala Tyr Val Asp Val Leu Thr Pro Gly
                580                 585                 590

Glu Asp Val Pro Pro Arg Gly Cys Gly Ile Ala Asn Leu Arg Val Gly
                595                 600                 605

Arg Ile Val Met Glu Val Ala Arg Glu Ser Leu Thr Asp Val Val Thr
                610                 615                 620

Gly His Arg Val Leu Ala His Cys Ala Ala Gly Gly Ala Ala Ala Ala
625                 630                 635                 640

Phe Asp Ala Asp Ser Glu Asp Thr Ser Gly Tyr Arg Leu Pro Glu Thr
                645                 650                 655

Ala Val Arg Val Val Leu Ala Ser Val Leu Gly Leu Arg Asp Leu
                660                 665                 670

His Gly Arg Ala Arg Leu Ala His Arg Asp Leu Lys Leu Asp Asn Leu
                675                 680                 685

Leu Val Gly Thr Asp Arg Leu Ile Lys Ile Thr Asp Phe Gly Leu Val
690                 695                 700

Thr Pro Leu Asp Ser Gln Gly Arg Leu Val Ser Glu Val Gly Gly Arg
705                 710                 715                 720

Arg Gly Thr Lys Gly Tyr Gln Ala Pro Glu Thr Leu Ala Arg Arg Thr
                725                 730                 735

Phe Ala Ala Asn Glu Arg Glu Leu Pro Ser Trp Pro Ala Ala Lys Ser
                740                 745                 750

Asp Val Phe Ala Val Gly Val Ile Gly Ala Ala Leu Val Cys Gly Thr
                755                 760                 765

Glu Ser Gly Pro Glu Met Glu Ala Phe Arg Ala Ser Gly Glu Leu Pro
770                 775                 780

Pro His Arg His Ala Ser Pro Ala Leu Arg Gln Leu Leu Lys Gly Met
785                 790                 795                 800

Ala Ala Ala Asp Pro Ala Arg Arg Leu Gly Val Glu Glu Ala Leu Ala
                805                 810                 815

His Pro Ala Leu Arg Arg Ala Leu Ser Ser Glu Arg Ala Arg Arg Phe
                820                 825                 830

Ile Trp

<210> SEQ ID NO 32
<211> LENGTH: 3849
<212> TYPE: DNA
<213> ORGANISM: Chlamydomonas reinhardtii

<400> SEQUENCE: 32
gttacacata caactagctt tcctctcaag ccccagagcc tcgcctagct aactatttcc      60
gacttgcgtc ttcttcctcg cgctcgcttt tcctatcaaa ggccctcaac ttgcagcatc     120
ggctcactgt ggcacttgtt gcttgtggcg acaagcatcg agtgggcggc actgcgagag     180
gcgcacacgc ttccgacgga cggaaacgcg ctcctggctc tcccgtgctg tttgcggcgg     240
caagggcagc ctagcggtat ggattgcgac ctgctgtctg agctgcagca gcacactttg     300
cgagcgaggc tgctgaaggc caaggagcgg cacataggcc acagcagcaa catgcaggac     360
```

```
tacaacaacc agaagtccag cgcccgcggt ctcctgtcca agggcggcga gcacaaggcc      420
gcggccaaac ccaaatcgac cggcggtttc cgtgccaagc ttctggcggc caagcgccgt      480
gccgcctttg gcggtggcgc ctcgaccacg gctatggctg ccatgtgcc cgcgccctct       540
cctagcagcg gcggcagcgg gtctgacgcg gcccccggca gcggtggggt ctccaacggc      600
tcatcgcgcc agcaggcgcc ctcggccaac gccaacaccg acaccaacac caacaccggc      660
agcaacaaga ctggtggcac gaacacgacc gcctcgcctg ctgcacccca gcagtccaac      720
gccgccgctg ccaccaccgt cgctgttgct cctgcgactg ctggctcaat atcaggagcc      780
cgccgcatgg agggccgctg ccgccctac cggccgccca tgcgggtgca gggcgacgag       840
ggcggcaagg cggccaccgc tggcactggc cctgctggca gcagcagcag tggctcgggc      900
ctgatgctcc gcagcttggt aggtgcctg ctgccccacc tcgccactgc cgccatcgag       960
aaggcagcgc acgtcgcggc cgccgtcgcc cccgggtga tggcacccgt cgccgccgcc      1020
gccgccgccg tgcactaccg ccggatggag gcacccgtcg ccgctgccgc cgccgtgccc     1080
tgccggatgg tggcacccgt cgccggcgcg gtggcgccca agctcgtggc cttccggcct     1140
ccgccgccgc ccatcatgcc agtgcaccag caccagcacc aggaccagca ccagcaggcg     1200
gggccgcggt acgtggcgcg gccggcggtg caaccgatga tggggccgcc tgtggttcag     1260
gctaccgctg gcgccgcggc cgtggcggcg ccgcggctgc tcgtggggc tccggtcaag      1320
ctcctgatgg cacctcaggt gcttcagcag cagcagcaca tccagcagct ggccaaccgc     1380
gtggcttgcg tgccgtaccc gcacccgcac ccggcggtgc agccgcagcc ggtcctggtg     1440
cacggcggcg gcatgccggc tgcgcgccag ccgcaccagc agcaagacca aagcctgcag     1500
atgcggctgg agcagcggct gcagcaggcg aagcagatgt ggcaagcgac gaagaagagg     1560
gtgcaggagg cgaaggcccg gcggaagcag cggatccagg aggctattca ggaggaggag     1620
gacattgttg tggccaacgt gcgcgagctc atgcagcgcg tcaccagcgg cgcccccaag     1680
cccttcgagc tcatccgcct caagcggcac ctgggccagg gtgccttcgg ctgcgtcgac     1740
tgctgggagg tcacagagcg ccagtccgcc accgcctcct ccgcggcctc ctcctctggc     1800
ctggcggcgg cggcggcctc cggcaccgcc actgccacca gcagcagccg cacctttgag     1860
gcggcggtga agacctgcgc tctggacctg gagggcctgg cagcgggcgg cgaaacgccg     1920
catacggtgg agatgcatgc caaggaggcg gcggcggtgc tggcggttca ggcgctggac     1980
tcgcggcacc tggtcaaggt gctgggggcc tacgtcgacg tgctgacacc cggggaggac     2040
gtgccgcccc gcgctgcgg catcgccaac ctgcgcgtcg ggcgcatcgt gatggaggtg      2100
gcgcgggagt cgctgactga cgtggtgacg ggccaccgcg tgctcgcgca ctgcgccgcg     2160
gcggcgccc ccgccgcctt tgacgccgac tcggaggaca cgtccggcta ccggctgccc      2220
gagaccgcgg tgcgcgtggt gctggcctcg gtgctgctgg gcctgcgcga cctgcacggc     2280
cgcgcgcggc tggcgcaccg ggacctgaag ctggacaacc ttctggttgg cacggaccgt     2340
ctgattaaga tcaccgactt cggcctggtc acgccgcttg acagccaggg ccgcctggtc     2400
tcggaggtcg gggggcggcg gggcacgaag ggctaccagg cccctgagac gttggcgcgc     2460
cgcaccttcg cggccaacga gcgcgaactg cccagctggc cagccgccaa gagcgatgta     2520
ttcgcggtgg gcgtgatcgg cgcggcgctg gtgtgcggca ccgagtcggg gccggagatg     2580
gaggccttcc gggccagtgg cgagctgccg ccgcaccggc acgcctcgcc agcgctgcgg     2640
cagctgctca agggcatggc ggcggcggac ccggcgcggc ggctgggggt ggaggaggca     2700
```

```
ctggcgcacc ccgcgctacg cagggcgctg agcagcgagc gggcgcggcg cttcatctgg    2760
tgatggcggc aaggccagat cgctcgggca tgaggcgggc tataggcagg cagtgcgtta    2820
gtgatgagcg gcggctgtca aatgaataaa agagtgcgta cgtgtgtgtc agagcttact    2880
tgcttgaggg ctgggtattc ataagtataa agacacagcg tgcgcagtgt tgaggaccgt    2940
atggaggttc atactataac acatagattg gcggcctgag ggaaaattga ttggcctcag    3000
gatagaaccc ttagcacgca agccgtggat ggcagcgtgc atagttgcgg ctgctaatcc    3060
ttgctgcttc cccttgattg attgatgata ggcctagaca ctagaacgcc gcgcgtgctg    3120
ctgtcttgcc gcacttggca gatacgcatg gataggccgt ggcctaatgg ctccttatgc    3180
ttgttccgaa acggaagggt accatctgct tgtgcttgcg tgtgcattgt cggtactttg    3240
ggcaacggac tgaggccgga ctaccttgag ccgtattttg actcatccgt gttgatcttt    3300
ttccgtcctg tccgcgtgat tgctgacatg catggacccc ccgcagtttg agtacaggtc    3360
tcgcgtagag cttgacatgt cgtgtgtgac cgttttgcga tccacgtgtt ccgtcaggcc    3420
tatacggtcc atgcttgcga gctgtgtata gccaggattg tgcgagcctc tgaagagccg    3480
taagctgctg gtcttttcct aggcgcgcag cggagtgcac tgacgtgcgc aaggtaaccc    3540
gccttgtagt gcaaagggac actcgacaaa taaatggttg tgcacgcctg tgatgaagag    3600
ccgcaagctg ctggtcgtct cctaggcgcg cagcggtagg tgcgcactga ccgctcagag    3660
cgctgactcc tggaacatat acagcaggtt cgtgcacatg gtacggtaac ccgccttgta    3720
gtgcaaaggg acactccaca caaccaagcg tgtgagcttg ggtgctaggc attgacatgc    3780
cttacaggga gataagtatg acacgcgagc ttgattgagc cgcccttcga attgtaataa    3840
gtgtttgct                                                            3849
```

<210> SEQ ID NO 33
<211> LENGTH: 595
<212> TYPE: PRT
<213> ORGANISM: Chlamydomonas reinhardtii

<400> SEQUENCE: 33

```
Met Ala Gly Gln Ala Leu Asp Pro Ala Ala Gly Phe Asn Asn Ala
1               5                   10                  15

Ala Gln Val Gln Gly Tyr Asn Gln Ser Ala Glu Phe Phe Leu Ser Asn
            20                  25                  30

Tyr Arg Leu Gly Lys Thr Leu Gly Ile Gly Ser Phe Gly Lys Val Lys
        35                  40                  45

Val Ala Glu His Val Leu Thr Gly His Lys Val Ala Ile Lys Ile Leu
    50                  55                  60

Asn Arg Arg Lys Ile Gln Gln Met Glu Met Glu Glu Lys Val Arg Arg
65                  70                  75                  80

Glu Ile Lys Ile Leu Arg Leu Phe Met His Pro His Ile Ile Arg Leu
                85                  90                  95

Tyr Glu Val Ile Glu Thr Pro Ser Asp Ile Tyr Val Val Met Glu Tyr
            100                 105                 110

Val Lys Thr Gly Glu Leu Phe Asp Tyr Ile Val Glu Lys Gly Arg Leu
        115                 120                 125

Gly Glu Asp Glu Ala Arg His Phe Phe Gln Gln Ile Ile Ser Gly Val
    130                 135                 140

Glu Tyr Cys His Arg Asn Met Val Val His Arg Asp Leu Lys Pro Glu
145                 150                 155                 160

Asn Leu Leu Leu Asp Ala Lys Met Asn Val Lys Ile Ala Asp Phe Gly
```

```
                165                 170                 175
Leu Ser Asn Ile Met Arg Asp Gly His Phe Leu Lys Thr Ser Cys Gly
            180                 185                 190

Ser Pro Asn Tyr Ala Ala Pro Glu Val Ile Ser Gly Lys Leu Tyr Ala
            195                 200                 205

Gly Pro Glu Val Asp Val Trp Ser Cys Gly Val Ile Leu Tyr Ala Leu
210                 215                 220

Leu Cys Gly Ser Leu Pro Phe Asp Asp Glu Asn Ile Pro Asn Leu Phe
225                 230                 235                 240

Lys Lys Ile Lys Gly Gly Ile Tyr Asn Leu Pro Ser His Leu Ser Pro
            245                 250                 255

Gly Ala Arg Asp Leu Ile Pro Arg Met Leu Leu Val Asp Pro Leu Lys
            260                 265                 270

Arg Ile Thr Ile Pro Glu Ile Arg Gln His Pro Trp Phe Asn Met His
            275                 280                 285

Leu Pro Arg Tyr Leu Ala Val Met Gln Ala Glu Pro Val Val Gly Val
            290                 295                 300

Pro Arg Ile Asp Glu Glu Ile Leu Glu Glu Val Val Arg Leu Gly Phe
305                 310                 315                 320

Asp Arg Asp Gly Leu Leu Asp Ser Leu Arg Ser Arg Ala Ala Asn Lys
            325                 330                 335

Ala Thr Val Thr Tyr Tyr Leu Met Thr Asp Asn Arg Arg Lys Met Pro
            340                 345                 350

Ser Ser Gly Tyr Leu Ser Ala Asp Met Ala Glu Gly Ser Thr Gly Ala
            355                 360                 365

Ala Met Ala Ala Ala Gly Met Ser Leu Leu Pro Ser Pro Gly Ala Thr
            370                 375                 380

Ala Ser Ala Ser Val Ala Ala Val Gly Gly Gly Gly Gly Gly Gly Gly
385                 390                 395                 400

Gly Thr Pro Gln Gln Arg Leu Val Ala Glu Arg Arg Trp Arg Leu Gly
            405                 410                 415

Val His Ala Arg Gly His Pro Ser Ala Leu Met Ala Glu Leu Tyr Arg
            420                 425                 430

Val Leu Gln Leu Asn Gly Val Ala Trp Lys Lys Val Ala Pro Tyr Ala
            435                 440                 445

Leu Lys Cys Arg Ala Ala Val Arg Lys Pro Pro Gln Glu Leu Arg
            450                 455                 460

Arg Arg Ser Ser Ala Gly Gly Ser Gly Ser Gly Ala Ala Gly Gly Pro
465                 470                 475                 480

Ala Arg Met Ser Asp Asp Leu Asp Asp His Ile Glu Leu Asp Gly Ala
            485                 490                 495

Gly Ser Gly Pro Pro Gly Gly Ala Val Thr Pro Gly Gly Gly Val
            500                 505                 510

Ala Gly Val Gly Leu Ile Thr Ser Gly Ser Arg Arg Gly Leu Gly Gly
            515                 520                 525

Gly Ala Ser Gly Ser Asp Val Ala Gly Ala Ala Gly Val Pro Pro Gly
            530                 535                 540

Thr Gly Asp Ala Glu Thr His Tyr Val Thr Arg Phe Glu Cys Gln Met
545                 550                 555                 560

Tyr Lys Val Arg Asp Asp Glu Tyr Val Ile Asp Ile Gln Arg Val Asp
            565                 570                 575

Gly Glu Leu Phe Leu Phe Met Asp Val Val Gly Arg Val Leu Thr Asp
            580                 585                 590
```

Leu Arg Met
    595

<210> SEQ ID NO 34
<211> LENGTH: 4405
<212> TYPE: DNA
<213> ORGANISM: Chlamydomonas reinhardtii

<400> SEQUENCE: 34

| | | | | | |
|---|---|---|---|---|---|
| cctaagctgt | gcaggcagca | atccggtttg | ggactggtat | tatgaatggt | catgtggaag | 60 |
| gaaggaaagg | cgcgtccggg | tggttggaca | tggcacacag | tcgcagtctg | atttgtggca | 120 |
| gctctagtca | tgggggctta | ctctagtagc | ggtgcacatc | tagtaacgct | acgagctcta | 180 |
| ggtagcttgg | agcaccgtcc | ccatgtgccc | ttgctgacat | cagcccgcgc | tggccaccaa | 240 |
| gaatttgcag | tcttcacca | agttcgactt | cgctatagac | tggagatatt | tgtcatttta | 300 |
| ccacaagcat | tcgccaaagg | ccccaccagc | aacactgcaa | gcgaattcct | tgtcaaaaca | 360 |
| caatacgcac | atatcatttt | cgccccgctt | aatgtgacgt | cttaaagagc | attgcaaata | 420 |
| accattaacg | ttaggaagcc | ggccagggca | gcggaagagg | aggagcgggg | tcgcccaagg | 480 |
| gcgaggacgg | ctgcgaaggc | cacgcactct | ccggtgtaag | gccaggcagc | tgtgccatgg | 540 |
| cagaagcagc | tcccatggcg | ggccaagcgc | tggatccggc | agcggcgggc | ttcaataacg | 600 |
| cagcgcaagt | gcaggatac | aaccagagtg | cggagttctt | cctcagcaat | taccggctag | 660 |
| ggaaaacact | cggcatggtt | cctttggcaa | ggtcaaggtc | gcggagcatg | tgctcacggg | 720 |
| gcacaaggtg | gcgattaaga | tcctcaaccg | gcgtaaaatc | cagcagatgg | agatggagga | 780 |
| gaaagtccgt | cgtgagatca | agatcctgcg | gctgttcatg | caccccgcaca | tcatccggct | 840 |
| gtatgaggtg | atcgagacgc | cgtctgatat | ctacgtggtc | atggagtacg | tcaagaccgg | 900 |
| cgagctgttt | gactacattg | tggagaaggg | gcggctgggg | gaggacgagg | cacgccactt | 960 |
| cttccagcag | atcatatccg | gagtggagta | ctgccaccgc | aacatggtgg | tccaccgcga | 1020 |
| cctcaagccc | gagaacctgc | tgctggacgc | caagatgaac | gtcaagatcg | cggactttgg | 1080 |
| cctgtccaac | atcatgcgcg | acggccactt | cctcaaaacc | agctgcggct | cgcccaacta | 1140 |
| cgccgcgccc | gaggtgatta | gcggcaagct | gtatgcgggc | ccggaggtgg | acgtgtggag | 1200 |
| ctgcggcgtc | attctgtacg | cgctgttgtg | tggatcactg | cccttgacg | acgagaacat | 1260 |
| ccccaacctg | ttcaagaaga | tcaagggcgg | catctacaac | ctgccctcac | acctcagccc | 1320 |
| gggcgcgcgc | gacctgatcc | gcgcatgct | gctggtggac | ccgctcaagc | gcatcaccat | 1380 |
| ccccgagatc | cggcagcacc | cctggttcaa | catgcacctg | ccgcgatacc | tggccgtcat | 1440 |
| gcaggccgag | ccggtggtgg | gcgtgccgcg | cattgatgag | gagatcctgg | aggaggtggt | 1500 |
| gcggctgggc | tttgaccggg | acgggcttct | ggactcgctg | cgcagccgcg | ccgccaacaa | 1560 |
| ggccaccgtc | acctactacc | tcatgactga | aacaggagg | aagatgccca | gcagcggcta | 1620 |
| cctgtctgct | gacatggcgg | agggcagtac | ggggcggcc | atggcggcgg | cgggcatgag | 1680 |
| cctactgccc | tcgccaggcg | cgaccgcgtc | agcaagcgtg | gcgcggcgcg | tgggcggcgg | 1740 |
| cggcggcggc | ggcggcacgc | tcagcagcgc | gctggtggcg | gagcggcggt | ggcggctggg | 1800 |
| cgtgcacgcg | cgaggccacc | cctcggctct | catggcggag | ctatacaggg | tgctgcagct | 1860 |
| caacggcgtc | gcctggaaga | aggtggcgcc | ctacgcgctc | aagtgccggg | ccgccgtgcg | 1920 |
| caagccgccg | ccgcaggagc | tgcggcgccg | cagcagcgcc | ggcggcagcg | gcagcggcgc | 1980 |
| ggcgggcggg | ccggcgcgca | tgagcgacga | cctggatgac | cacatagagc | tggatggggc | 2040 |

```
gggcagtggc ccgccgggcg gcgcagtgac ccctggtggc ggcggcgtcg caggtgttgg    2100
cctgatcacc agcggcagcc ggagagggct gggcggcggc gccagcgggt ctgacgtggc    2160
gggggcggcg ggcgtgccgc ccggcaccgg cgacgcggag acgcactacg tgacacgttt    2220
cgagtgccag atgtacaagg tccgggacga cgagtacgtg atagacattc agcgtgtgga    2280
cggcgagctg tttctgttca tggacgtggt ggggcgcgtg ctcactgacc tgcgcatgtg    2340 aggggggggtg ttggcagcag tggaggcagc actggaggcc gcgtgctcac agacctgcgc    2400
atgtgagggg gggtgttggc agcagtggag gcagcactgg aggcggcgtg ctcaccgatt    2460
tgcgcatgtg aggggggcggc ggcagcagtg gaggcagcac tggaggccgc gtgctcacag    2520
acctgcgcat gtgaagggag ggcggcagca gtggaggctg cactggaggc cgcgtgctca    2580
ccgacctgcg catgtgaggg ggcggcggca gcagtggagg cagcactgga ggccgcgtgc    2640
tcacagacct gcgcatgtga agggagggcg gcagcagtgg aggctgcact ggaggccgcg    2700
tgctcaccga cctgcgcatg tgaggggcgc ggcggcagcag tggaggcagc actggaggcc    2760
gcgtgctcac agacctgcgc atgtgacaag caggcaggag gcgatggggg cgagcctggc    2820
tgcgcatacg agcagtcaag gaagcaggca gttggtgcga ggagcgagga agcggcggtg    2880
gaggctgcga cggcgtgcaa ttgttgttgt gaaggggcag cacgcacatg ggcagtcgca    2940
gcagctgtca gccgcgcccc agggctcacc acagcgctaa gtgcgagaca gcccgtggga    3000
gaaggagcgt gagccatcag cggaggcggc aaagcaggag cagggggggag caggaggcag    3060 tcacttcagc cactgtccat tatcaggagg ctgtggttgg ctgtggtcgg cggtgtgtgt    3120
gttcggtgtg gtgtgggtgt gtgtgtgtgt gtgtgtgtgt gtgtgtgtgt gtgtgtatgt    3180
gtgtgtatgt gtgcgtgcgt gtgtgtgtgt gtgtgtgtgt gtgtctttgt tttgcatgca    3240
tgcacgcgcg aatagcgttg aatggttggg ccatgctttc aaaggcttgc cgaggaggtc    3300
gcgacacacc ggggccgggg cacagccgtc cagacggagg tggaacaatt ttgtagggtt    3360
gaagctggtg cgggtgggga agaggggggct gctgtgattt gcgtggatga ggtaggcggg    3420
tggttggagg aaggcgggga gggcagcagg cgcagcaggg tggggaagga tcgaaggagg    3480
ttggtgaggc gacctggtgc accatgaacg gatgagatat agactcgccg gttttacggc    3540
aggcatgtga attgtgggtg ctgatagtgc gtctttgctg caaggtgttc agttaggtga    3600
tcaaaggtgc cgcgttcatt attagcggct aggcaccgcg acttgcacgc ggagctggac    3660
aacctgatta ctcgtgatgc cttgccactc gccagcttgg ctgccagggc tctaacaatc    3720
gctgttgcat gcgtgattg cggtccttgc atgcaccacg tgctgtgtgt gatgcgctca    3780
agaaggcgac ggtgtgcacg ccctgctgtg cactgtgcga tgtggtgcgc agtgccgtgc    3840
tttgtgatgc gaagaagtgc gcagcggatg gcgtgtaggg tgagtggctg acaaaagtgg    3900
atgcatgccg tttgtagatg ttgctcgcgg aggtggttgc gagggtggtg tggggcgca    3960 ttggctgctg cgagcatcaa gcctcagtcg tgcggttgag ccagcagtac atgctgcatg    4020
acagcatgac tgcatgatag catgacagca tgagttgggc agacggacat tcctggcacc    4080
acgctcccgt ggcgcagcgg acctggctag cctgctgggc gagggacggt tggtgttcgt    4140
tgtagcgccg ctaaaccttg tgtccagtat gtttgtgtgc gggtcggctg attgcagccg    4200
ttgccaaagc actttgcagg aagagacagt ccgttcgggc cctcatcccg agcggcccag    4260
ccggagagaa gagaacccct ctacttggca gccggcctcc cgaaacttac gcaacatgag    4320
tgacttccct cgggcgagat agattgggca cttctggggg tgcattctcg ccgcgtgggg    4380
```

```
ttgcatacgg tccccaaatc tcgcc                                          4405
```

<210> SEQ ID NO 35
<211> LENGTH: 927
<212> TYPE: DNA
<213> ORGANISM: Chlorella sorokiniana

<400> SEQUENCE: 35

```
atgacggtgg agcagctgcg gacaaaggtg tgcatcattg gctccggccc cgccggccac    60
acagccgcca tctatgcggc gcgtgcggag ctgcagccgg tgatgctgga ggggtggatg   120
gcgaacggca ttgccgcagg cggccagctg accaccacgc acgaggttga gaacttcccc   180
ggcttccccg agggcatcct gggcggcgag atctgcgagc gcttccgggc gcagagcctg   240
cggtttggca ccaagatctt ttcggagacg gtcaccaagg tcgacttctc caagcggccc   300
ttccacatct tcaccgacga gaaggaggtg gtggctgatg ccgtcatcat tgccacgggt   360
gctgtggccc ccgcctgcc cttcaagggt ccgatgaag acaacggttt ctggaacaag   420
ggcatttcag cctgcgcgt gtgcgacggc gcggctccca tgttccgcaa ccagcccatt   480
gcagtgattg gcggcggcga ctctgccatg aagaggccc actttctgac caagtacggc   540
agcaagaagc gggccatgga ccaccccaag atcgaaatcc tgtggaacag cgtggtggag   600
gaggcgtacg gcaatgcaaa gggggctgctg gcggcgtca aggtcaagaa cgtcaagacc   660
ggcgagatca cggatctgcc gctggcgggc ctgttcttcg caatcggcca cgagcccgcc   720
accgcgttcc ttggcggcca ggtggagctt gacgaggaca agtacattgt caccgcggcc   780
gactccaccg cgaccagcgt gccgggcgtg tttgcagcgg gcgatgtgca ggacaagaag   840
taccggcagg ccatcaccgc ggcaggctcg ggctgcatgg ctgcgcttga ggtcgagcac   900
ttccttgagg cacagggcga ggcctga                                       927
```

<210> SEQ ID NO 36
<211> LENGTH: 308
<212> TYPE: PRT
<213> ORGANISM: Chlorella sorokiniana

<400> SEQUENCE: 36

```
Met Thr Val Glu Gln Leu Arg Thr Lys Val Cys Ile Ile Gly Ser Gly
1               5                   10                  15

Pro Ala Gly His Thr Ala Ala Ile Tyr Ala Ala Arg Ala Glu Leu Gln
            20                  25                  30

Pro Val Met Leu Glu Gly Trp Met Ala Asn Gly Ile Ala Ala Gly Gly
        35                  40                  45

Gln Leu Thr Thr Thr His Glu Val Glu Asn Phe Pro Gly Phe Pro Glu
    50                  55                  60

Gly Ile Leu Gly Gly Glu Ile Cys Glu Arg Phe Arg Ala Gln Ser Leu
65                  70                  75                  80

Arg Phe Gly Thr Lys Ile Phe Ser Glu Thr Val Thr Lys Val Asp Phe
                85                  90                  95

Ser Lys Arg Pro Phe His Ile Phe Thr Asp Glu Lys Glu Val Val Ala
            100                 105                 110

Asp Ala Val Ile Ile Ala Thr Gly Ala Val Ala Arg Arg Leu Pro Phe
        115                 120                 125

Lys Gly Ser Asp Glu Asp Asn Gly Phe Trp Asn Lys Gly Ile Ser Ala
    130                 135                 140

Cys Ala Val Cys Asp Gly Ala Ala Pro Met Phe Arg Asn Gln Pro Ile
145                 150                 155                 160
```

```
Ala Val Ile Gly Gly Gly Asp Ser Ala Met Glu Glu Ala His Phe Leu
                165                 170                 175
Thr Lys Tyr Gly Ser Lys Lys Arg Ala Met Asp His Pro Lys Ile Glu
            180                 185                 190
Ile Leu Trp Asn Ser Val Val Glu Glu Ala Tyr Gly Asn Ala Lys Gly
        195                 200                 205
Leu Leu Gly Gly Val Lys Val Lys Asn Val Lys Thr Gly Glu Ile Thr
    210                 215                 220
Asp Leu Pro Leu Ala Gly Leu Phe Phe Ala Ile Gly His Glu Pro Ala
225                 230                 235                 240
Thr Ala Phe Leu Gly Gly Gln Val Glu Leu Asp Glu Asp Lys Tyr Ile
                245                 250                 255
Val Thr Ala Ala Asp Ser Thr Ala Thr Ser Val Pro Gly Val Phe Ala
            260                 265                 270
Ala Gly Asp Val Gln Asp Lys Lys Tyr Arg Gln Ala Ile Thr Ala Ala
        275                 280                 285
Gly Ser Gly Cys Met Ala Ala Leu Glu Val Glu His Phe Leu Glu Ala
    290                 295                 300
Gln Gly Glu Ala
305

<210> SEQ ID NO 37
<211> LENGTH: 1255
<212> TYPE: DNA
<213> ORGANISM: Chlorella sorokiniana

<400> SEQUENCE: 37
agcggccatg acggtggagc agctgcggac aaaggtgtgc atcatcggct ccggccccgc       60
cggccacaca gccgccatct atgcggcgcg tgcggagctg cagccggtga tgctggaggg      120
atggatggca acggcattg ccgcaggcgg ccagctgacc accacccacg aggttgagaa       180
cttccccggc ttccccgagg gcatcctggg cggcgagatc tgcgagcggc tccgggcgca      240
gagcctgctg tggttgggcg cgagatttg cgagcggttc cgggcgcaga gcctgcggtt       300
tggcaccaag atcttctcag agacggtcgc caaggtggac ctctccaagc ggcccttcca      360
catctggacg gatgagaagg aggtgattgc ggatgcggtg atcatcgcca ccggcgccgt      420
ggcccgccgc ctgcccttca agggctccga tgaggacaac ggcttctgga caagggcat       480 ctccgcctgc gcgggcagcg ggttctggaa caagggcatc tccgcgcgcg cggtgtgcga      540
cggcgcggcg cccatgttcc gcaaccagcc cattgcagtc attggcggcg cgactcggc       600 catggaggag gcgcacttcc ttaccacgta cggcagcagt gcagaatacc ctctttcact      660
gaatgaggac ctgttgatct ccatggagga agctcacttc ctcaccaagt acggcagcaa      720
ggtgtacatc atccaccgcc gcgacgagct gcgcgcatcc aagatcatgc aggcaaggct      780
gttgtgctac cgaccccttg ctgttgctgt tggtgtgaag ctgctggtga gcgggcgct       840 ggagcacccc aagattgaga tcctgtggaa cagcgtggtg gaggaggcat acggcaacgc      900 aaagggggctt ctgggcggcg tcaaggtcaa gaacgtcaag actggcgagg tcaacgacct     960
gctgctggcg ggctgcgagg tcaccgatgt gccgctggcg ggcctgttct ttgccatcgg     1020
ccacgagcca gccaccgcct tctgggcgg ccaggtggag ctggatgagg acaagtacat      1080
cgtgactgcg gccgactcca ctgcaaccag cgtgccgggc gtgtttgcgg cgggcgtgtt     1140
tgcggcaggc gatgtgcagg acaagaagta ccggcaggcc atcaccgcgg caggctcagg     1200
```

```
ctgcatggct gcgctggagg ttgagcggtt cctggaggac catggacagg cttga            1255
```

<210> SEQ ID NO 38
<211> LENGTH: 415
<212> TYPE: PRT
<213> ORGANISM: Chlorella sorokiniana

<400> SEQUENCE: 38

| Met | Thr | Val | Glu | Gln | Leu | Arg | Thr | Lys | Val | Cys | Ile | Ile | Gly | Ser | Gly |
|---|---|---|---|---|---|---|---|---|---|---|---|---|---|---|---|
| 1 | | | | 5 | | | | | 10 | | | | | 15 | |

| Pro | Ala | Gly | His | Thr | Ala | Ala | Ile | Tyr | Ala | Ala | Arg | Ala | Glu | Leu | Gln |
|---|---|---|---|---|---|---|---|---|---|---|---|---|---|---|---|
| | | | 20 | | | | | 25 | | | | | 30 | | |

| Pro | Val | Met | Leu | Glu | Gly | Trp | Met | Ala | Asn | Gly | Ile | Ala | Ala | Gly | Gly |
|---|---|---|---|---|---|---|---|---|---|---|---|---|---|---|---|
| | | 35 | | | | | 40 | | | | | 45 | | | |

| Gln | Leu | Thr | Thr | Thr | His | Glu | Val | Glu | Asn | Phe | Pro | Gly | Phe | Pro | Glu |
|---|---|---|---|---|---|---|---|---|---|---|---|---|---|---|---|
| | 50 | | | | | 55 | | | | | 60 | | | | |

| Gly | Ile | Leu | Gly | Gly | Glu | Ile | Cys | Glu | Arg | Leu | Arg | Ala | Gln | Ser | Leu |
|---|---|---|---|---|---|---|---|---|---|---|---|---|---|---|---|
| 65 | | | | | 70 | | | | | 75 | | | | | 80 |

| Leu | Trp | Leu | Gly | Gly | Glu | Ile | Cys | Glu | Arg | Phe | Arg | Ala | Gln | Ser | Leu |
|---|---|---|---|---|---|---|---|---|---|---|---|---|---|---|---|
| | | | | 85 | | | | | 90 | | | | | 95 | |

| Arg | Phe | Gly | Thr | Lys | Ile | Phe | Ser | Glu | Thr | Val | Ala | Lys | Val | Asp | Leu |
|---|---|---|---|---|---|---|---|---|---|---|---|---|---|---|---|
| | | | | 100 | | | | | 105 | | | | | 110 | |

| Ser | Lys | Arg | Pro | Phe | His | Ile | Trp | Thr | Asp | Glu | Lys | Glu | Val | Ile | Ala |
|---|---|---|---|---|---|---|---|---|---|---|---|---|---|---|---|
| | | 115 | | | | | 120 | | | | | 125 | | | |

| Asp | Ala | Val | Ile | Ile | Ala | Thr | Gly | Ala | Val | Ala | Arg | Arg | Leu | Pro | Phe |
|---|---|---|---|---|---|---|---|---|---|---|---|---|---|---|---|
| | 130 | | | | | 135 | | | | | 140 | | | | |

| Lys | Gly | Ser | Asp | Glu | Asp | Asn | Gly | Phe | Trp | Asn | Lys | Gly | Ile | Ser | Ala |
|---|---|---|---|---|---|---|---|---|---|---|---|---|---|---|---|
| 145 | | | | | 150 | | | | | 155 | | | | | 160 |

| Cys | Ala | Gly | Ser | Gly | Phe | Trp | Asn | Lys | Gly | Ile | Ser | Ala | Arg | Ala | Val |
|---|---|---|---|---|---|---|---|---|---|---|---|---|---|---|---|
| | | | | 165 | | | | | 170 | | | | | 175 | |

| Cys | Asp | Gly | Ala | Ala | Pro | Met | Phe | Arg | Asn | Gln | Pro | Ile | Ala | Val | Ile |
|---|---|---|---|---|---|---|---|---|---|---|---|---|---|---|---|
| | | | 180 | | | | | 185 | | | | | 190 | | |

| Gly | Gly | Gly | Asp | Ser | Ala | Met | Glu | Glu | Ala | His | Phe | Leu | Thr | Thr | Tyr |
|---|---|---|---|---|---|---|---|---|---|---|---|---|---|---|---|
| | | 195 | | | | | 200 | | | | | 205 | | | |

| Gly | Ser | Ser | Ala | Glu | Tyr | Pro | Leu | Ser | Leu | Asn | Glu | Asp | Leu | Leu | Ile |
|---|---|---|---|---|---|---|---|---|---|---|---|---|---|---|---|
| | 210 | | | | | 215 | | | | | 220 | | | | |

| Ser | Met | Glu | Glu | Ala | His | Phe | Leu | Thr | Lys | Tyr | Gly | Ser | Lys | Val | Tyr |
|---|---|---|---|---|---|---|---|---|---|---|---|---|---|---|---|
| 225 | | | | | 230 | | | | | 235 | | | | | 240 |

| Ile | Ile | His | Arg | Arg | Asp | Glu | Leu | Arg | Ala | Ser | Lys | Ile | Met | Gln | Ala |
|---|---|---|---|---|---|---|---|---|---|---|---|---|---|---|---|
| | | | | 245 | | | | | 250 | | | | | 255 | |

| Arg | Leu | Leu | Cys | Tyr | Pro | Thr | Leu | Ala | Val | Ala | Val | Gly | Val | Lys | Leu |
|---|---|---|---|---|---|---|---|---|---|---|---|---|---|---|---|
| | | | 260 | | | | | 265 | | | | | 270 | | |

| Leu | Val | Lys | Arg | Ala | Leu | Glu | His | Pro | Lys | Ile | Glu | Ile | Leu | Trp | Asn |
|---|---|---|---|---|---|---|---|---|---|---|---|---|---|---|---|
| | | 275 | | | | | 280 | | | | | 285 | | | |

| Ser | Val | Val | Glu | Glu | Ala | Tyr | Gly | Asn | Ala | Lys | Gly | Leu | Leu | Gly | Gly |
|---|---|---|---|---|---|---|---|---|---|---|---|---|---|---|---|
| | 290 | | | | | 295 | | | | | 300 | | | | |

| Val | Lys | Val | Lys | Asn | Val | Lys | Thr | Gly | Glu | Val | Asn | Asp | Leu | Leu | Leu |
|---|---|---|---|---|---|---|---|---|---|---|---|---|---|---|---|
| 305 | | | | | 310 | | | | | 315 | | | | | 320 |

| Ala | Gly | Cys | Glu | Val | Thr | Asp | Val | Pro | Leu | Ala | Gly | Leu | Phe | Phe | Ala |
|---|---|---|---|---|---|---|---|---|---|---|---|---|---|---|---|
| | | | | 325 | | | | | 330 | | | | | 335 | |

| Ile | Gly | His | Glu | Pro | Ala | Thr | Ala | Phe | Leu | Gly | Gly | Gln | Val | Glu | Leu |
|---|---|---|---|---|---|---|---|---|---|---|---|---|---|---|---|
| | | | 340 | | | | | 345 | | | | | 350 | | |

| Asp | Glu | Asp | Lys | Tyr | Ile | Val | Thr | Ala | Ala | Asp | Ser | Thr | Ala | Thr | Ser |
|---|---|---|---|---|---|---|---|---|---|---|---|---|---|---|---|
| | | 355 | | | | | 360 | | | | | 365 | | | |

Val Pro Gly Val Phe Ala Ala Gly Val Phe Ala Ala Gly Asp Val Gln
    370             375                 380

Asp Lys Lys Tyr Arg Gln Ala Ile Thr Ala Ala Gly Ser Gly Cys Met
385             390                 395                 400

Ala Ala Leu Glu Val Glu Arg Phe Leu Glu Asp His Gly Gln Ala
            405                 410                 415

<210> SEQ ID NO 39
<211> LENGTH: 1329
<212> TYPE: DNA
<213> ORGANISM: Chlorella sorokiniana

<400> SEQUENCE: 39

| | | | | | | |
|---|---|---|---|---|---|---|
| atggcatccg | tagcagtatc | ctcggcgagc | gctgtcgtgc | cgggcaccgc | tcacctgcgg | 60 |
| cagcagcagc | cgcggccatg | cacggggcgg | gcggcatggg | tgccgcagca | ccgcctccgg | 120 |
| ctgtggcgcc | gggcgctgag | cgtgcacgcg | agcagcagca | acggcaatgg | caacggcaat | 180 |
| ggggcagccg | tcgacaagcg | cgagcgcatg | accaccagcg | tggcgattgt | gggcagcggc | 240 |
| cccgccgcgc | acaccgctgc | catctacctg | gcacgtgcgg | agctggagcc | catcctgttt | 300 |
| gagggggtgga | tggccaacgg | cctggccccc | ggcggccagc | tcaccaccac | cacgtacgtg | 360 |
| gagaacttcc | ccggcttccc | cgagcccatc | ctgggagcag | acctgtgcga | ccgcttccgc | 420 |
| cagcagtcaa | agaactacgg | cacccgcatc | tacaccgaga | ctgtggacaa | gctggatctg | 480 |
| ctgaatggcc | cgcccttccg | gctggagacc | gacagccgcg | tggtggaggc | ggatgcagtc | 540 |
| atcattgcca | cggggcggc | cgctcgcaag | ctgcccatca | agggctgga | gcagtactgg | 600 |
| aacaatggca | tctccgccctg | cgcagtctgc | gacggctcgt | cgccgctctt | ccgcaacaag | 660 |
| ccggtggcgg | tggttggggg | cggtgacgtg | cgtgcgaag | aggcgctctt | cctggccccgc | 720 |
| tacgcctcaa | aggtgtacat | cgtgcagcgc | tacgactacc | tggagtcgtc | caaggtgatg | 780 |
| gctcggcgcg | cggtgagcca | ccccaaggtg | gaagtcctgt | tcagccacga | gtgccaggag | 840 |
| gcgtacggcg | gcgaggacgg | caccctgagc | ggcattgtgc | tgcgcaacaa | ccagacgcag | 900 |
| gaggtcacgt | acctgcccgt | gggcggcctc | ttcttcgcca | ttggccacgc | ccccgccacc | 960 |
| gccttcctgg | ggggacagct | ggagctggac | agccacggcc | acatcgtgac | gccaccagga | 1020 |
| ggcaccacca | ccagcgtgcc | cggcgtgttt | gctgcgggcg | acgtgcagga | ctggcaatgg | 1080 |
| cggcaggcca | tcactgccgc | tggctcaggc | tgcatggcgg | ccaaggaggc | ggaggactac | 1140 |
| ctgtcccagc | tggcgctgga | ggcggagaag | ggcggcgatg | gcgtggtgca | gctcaacgcc | 1200 |
| gcctgggtgg | cggaggtgcg | ccaggaggag | cgcaagctgc | gcaaggagcg | caaggcagcg | 1260 |
| gaagcagcag | cggcggcggc | agcagccgct | gccgagagcg | ccacgcctga | gcccacgcct | 1320 |
| gctgcgtga | | | | | | 1329 |

<210> SEQ ID NO 40
<211> LENGTH: 442
<212> TYPE: PRT
<213> ORGANISM: Chlorella sorokiniana

<400> SEQUENCE: 40

Met Ala Ser Val Ala Val Ser Ser Ala Ser Ala Val Val Pro Gly Thr
1               5                   10                  15

Ala His Leu Arg Gln Gln Gln Pro Arg Pro Cys Thr Gly Arg Ala Ala
            20                  25                  30

Trp Val Pro Gln His Arg Leu Arg Leu Trp Arg Arg Ala Leu Ser Val
        35                  40                  45

His Ala Ser Ser Ser Asn Gly Asn Gly Asn Gly Ala Ala Val
        50                  55                  60

Asp Lys Arg Glu Arg Met Thr Thr Ser Val Ala Ile Val Gly Ser Gly
65                  70                  75                  80

Pro Ala Ala His Thr Ala Ala Ile Tyr Leu Ala Arg Ala Glu Leu Glu
                85                  90                  95

Pro Ile Leu Phe Glu Gly Trp Met Ala Asn Gly Leu Ala Pro Gly Gly
            100                 105                 110

Gln Leu Thr Thr Thr Thr Tyr Val Glu Asn Phe Pro Gly Phe Pro Glu
            115                 120                 125

Pro Ile Leu Gly Ala Asp Leu Cys Asp Arg Phe Arg Gln Gln Ser Lys
        130                 135                 140

Asn Tyr Gly Thr Arg Ile Tyr Thr Glu Thr Val Asp Lys Leu Asp Leu
145                 150                 155                 160

Leu Asn Gly Pro Pro Phe Arg Leu Glu Thr Asp Ser Arg Val Val Glu
                165                 170                 175

Ala Asp Ala Val Ile Ile Ala Thr Gly Ala Ala Ala Arg Lys Leu Pro
            180                 185                 190

Ile Lys Gly Leu Glu Gln Tyr Trp Asn Asn Gly Ile Ser Ala Cys Ala
        195                 200                 205

Val Cys Asp Gly Ser Ser Pro Leu Phe Arg Asn Lys Pro Val Ala Val
210                 215                 220

Val Gly Gly Gly Asp Val Ala Cys Glu Glu Ala Leu Phe Leu Ala Arg
225                 230                 235                 240

Tyr Ala Ser Lys Val Tyr Ile Val Gln Arg Tyr Asp Tyr Leu Glu Ser
                245                 250                 255

Ser Lys Val Met Ala Arg Arg Ala Val Ser His Pro Lys Val Glu Val
            260                 265                 270

Leu Phe Ser His Glu Cys Gln Glu Ala Tyr Gly Gly Glu Asp Gly Thr
        275                 280                 285

Leu Ser Gly Ile Val Leu Arg Asn Asn Gln Thr Gln Glu Val Thr Tyr
        290                 295                 300

Leu Pro Val Gly Gly Leu Phe Phe Ala Ile Gly His Ala Pro Ala Thr
305                 310                 315                 320

Ala Phe Leu Gly Gly Gln Leu Glu Leu Asp Ser His Gly Tyr Ile Val
                325                 330                 335

Thr Pro Pro Gly Gly Thr Thr Thr Ser Val Pro Gly Val Phe Ala Ala
            340                 345                 350

Gly Asp Val Gln Asp Trp Gln Trp Arg Gln Ala Ile Thr Ala Ala Gly
        355                 360                 365

Ser Gly Cys Met Ala Ala Lys Glu Ala Glu Asp Tyr Leu Ser Gln Leu
        370                 375                 380

Ala Leu Glu Ala Glu Lys Gly Gly Asp Gly Val Val Gln Leu Asn Ala
385                 390                 395                 400

Ala Trp Val Ala Glu Val Arg Gln Glu Arg Lys Leu Arg Lys Glu
                405                 410                 415

Arg Lys Ala Ala Glu Ala Ala Ala Ala Ala Ala Ala Ala Glu
            420                 425                 430

Ser Ala Thr Pro Glu Pro Thr Pro Ala Ala
        435                 440

<210> SEQ ID NO 41
<211> LENGTH: 1081

<212> TYPE: DNA
<213> ORGANISM: Picochlorum soloecismus

<400> SEQUENCE: 41

```
atgactggcg gaacgaaaga gcaactgaag acccaagttt gcatcatagg gagcgggcct    60
gctggtcata ctgctgcgat ttatgctgcg agagcgggta tgtcaccta ggagtgtgca    120
atacgtgtgg atagatttag acataagtgt ggtagtatag gtatgtgaac ctttggatca   180
tgttgtcgca gaactgaaac cagtcatgct ggaaggtgg ctggcgaacg gtattgcagc    240
gggtgggcag ctgacaacga cttcggatgt ggaaaatttc ccaggatttc ccgaggggat   300
tatgggggt gaaatctgcg ataagtttcg tgcccaaagt gctcgtttcg ggacagatat    360
tttctctgag actgtgacgt ctgtggactt tcagaacgg cctttaaag tggtgacgga     420
tgagaaggag gttattgccg atactgtaat tatttctaca ggagcggtgg ctcgtaagct   480
gtctttcca ggatccgacg aggagaatgg gtattggaat aagggaatca gtgcatgcgc    540
agtatgtgat ggtgctgcac caatgttcag aaacaaacca attgctgtga ttggaggtgg   600
agattctgct tgcgaggagg caacttttt aacaaaatac gggtccaaag tttacttgat    660
tcatcgtcgt gatgagttgc gtgcgtccaa gattatgcag aagagggtga ttgatcatga   720
gaaggtggag attttgtggg atagtgttgt ggattctgca tatgggaatg aaaaaggttt   780
actcggggga ttgaaagttc gcaacgtcaa gactggagaa ataaccgatc ttcctgtggc   840
tgggctgttc tttgcgattg ccacgagcc tgcaaccaag tttttggacg gtcaaatcaa    900
tcttgatgaa gagggataca tacaaacaga gcctggcacc acaaagacaa atattcctgg   960
cgtgtttgca gcaggtgatg tgcaagataa aaaatatagg caagcgatta ctgctgccgg   1020
tacaggatgc atggctgcat tggaagcaga acacttcctt gaggcgttgc atgattcatg   1080
a                                                                   1081
```

<210> SEQ ID NO 42
<211> LENGTH: 328
<212> TYPE: PRT
<213> ORGANISM: Picochlorum soloecismus

<400> SEQUENCE: 42

```
Met Thr Gly Gly Thr Lys Glu Gln Leu Lys Thr Gln Val Cys Ile Ile
1               5                  10                  15

Gly Ser Gly Pro Ala Gly His Thr Ala Ala Ile Tyr Ala Ala Arg Ala
                20                  25                  30

Glu Leu Lys Pro Val Met Leu Glu Gly Trp Leu Ala Asn Gly Ile Ala
            35                  40                  45

Ala Gly Gly Gln Leu Thr Thr Thr Ser Asp Val Glu Asn Phe Pro Gly
        50                  55                  60

Phe Pro Glu Gly Ile Met Gly Gly Glu Ile Cys Asp Lys Phe Arg Ala
65                  70                  75                  80

Gln Ser Ala Arg Phe Gly Thr Asp Ile Phe Ser Glu Thr Val Thr Ser
                85                  90                  95

Val Asp Phe Ser Glu Arg Pro Phe Lys Val Val Thr Asp Glu Lys Glu
                100                 105                 110

Val Ile Ala Asp Thr Val Ile Ser Thr Gly Ala Val Ala Arg Lys
            115                 120                 125

Leu Ser Phe Pro Gly Ser Asp Glu Glu Asn Gly Tyr Trp Asn Lys Gly
        130                 135                 140

Ile Ser Ala Cys Ala Val Cys Asp Gly Ala Ala Pro Met Phe Arg Asn
```

|   |   |   | 145 |   |   |   | 150 |   |   |   | 155 |   |   |   | 160 |
|---|---|---|---|---|---|---|---|---|---|---|---|---|---|---|---|

Lys Pro Ile Ala Val Ile Gly Gly Asp Ser Ala Cys Glu Glu Ala
                      165                 170                 175

Thr Phe Leu Thr Lys Tyr Gly Ser Lys Val Tyr Leu Ile His Arg Arg
              180                 185                 190

Asp Glu Leu Arg Ala Ser Lys Ile Met Gln Lys Arg Val Ile Asp His
        195                 200                 205

Glu Lys Val Glu Ile Leu Trp Asp Ser Val Val Asp Ser Ala Tyr Gly
    210                 215                 220

Asn Glu Lys Gly Leu Leu Gly Gly Leu Lys Val Arg Asn Val Lys Thr
225               230                 235              240

Gly Glu Ile Thr Asp Leu Pro Val Ala Gly Leu Phe Phe Ala Ile Gly
              245                 250                 255

His Glu Pro Ala Thr Lys Phe Leu Asp Gly Gln Ile Asn Leu Asp Glu
        260                 265                 270

Glu Gly Tyr Ile Gln Thr Glu Pro Gly Thr Thr Lys Thr Asn Ile Pro
    275                 280                 285

Gly Val Phe Ala Ala Gly Asp Val Gln Asp Lys Lys Tyr Arg Gln Ala
              290                 295              300

Ile Thr Ala Ala Gly Thr Gly Cys Met Ala Ala Leu Glu Ala Glu His
305               310                 315              320

Phe Leu Glu Ala Leu His Asp Ser
              325

<210> SEQ ID NO 43
<211> LENGTH: 1641
<212> TYPE: DNA
<213> ORGANISM: Chlorella sorokiniana

<400> SEQUENCE: 43

```
atggcagctg tggcggcagt ctcggtggca gcggcgcccg ctcgctgcgc ggcgaccegc      60
caggcgcgat cggcggcttg ccccgccctg cagcatggca atgcgcgcag ctgcagccgc     120
agccggcgct cgctggcagg gaccgccgct gctgcgggcc agctcgcgt gcagcggcgc     180
ctggggctgc gcctgagggc gcaggccagc ggcaacggcg cccccgaggt ggagaacatg     240
gtcatcattg gcagtggccc tgccggctac accgccgcca tctacgcggc ccgtgccaac     300
ctgcggcccct ttgtgtttga gggcctgtcc gcaggcggcg tgcgcggcgg ccagctgatg     360
accacgaccg aagtcgagaa cttcccgggc ttccccgagg gcatcaccgg ccggacctg     420
atggaccgca tgcgcgcgca ggccgagcgc tggggcgccc gctgagac tgaggatgtg     480
gtgtcggtgg acctctccac ccgcccttc accgtgcgcg gcactgagaa caccgtcaag     540
gcgcactccg tgattgtggc cacgggcgcc accgccaaga agctgaacct gcccagcgag     600
cagcgcttct ggtctaacgg catctccgcc tgcgccatct gcgacggcgc ctcaaccatc     660
ttcaagcagc aggcgagagg gggcggcttc atgcgtacca cggagctggc tgtggtgggc     720
ggcggcgaca ccgccaccga ggaggccgtg tacctcacca gtacgcctc ccacgtgcac     780
ctgctggtgc gtggcgacaa gatgcgggcc agcaaggcga tgcaggaccg cgtgctggcc     840
aaccccaaga tcacggtgca catgaacacg gaggtggatg atgcctacgg cgacgacagc     900
gccatgaagg gcctgcacct cgcgacgcc aagaccggcg agaagcgcga cctgccggtg     960
cgcggcctgt ctacggcat cggccacaag cccaactcgg acttcctggc gggccagctg    1020
gagctggacc aggagggta cgtggtggtg aagcatggcg gcaagacgag cgtggagggt    1080
```

-continued

```
gtgtttgcgg cgggagacct gcacgacgtg gagtggcgcc aggccatcac cgcggcgggc    1140
agcggctgcc aggcggccct ggctgcggag cgctacctca cgccaacgg gctggcccag     1200 gagttcagcc aggcggtgac cgaggagaag tacggctcga cgcctgagac gcaggcggcc    1260
agcagcagcg cgccgacac ggaggagacc tttgaccccg cagccgacaa gcacaagggc     1320
cagtttgcgc tgcgcaagct gtaccacgag agcagccgcc cgctcattgt gctgtacacg    1380
gcgcccacgt gcggcccctg ccgcacgctc aagcccatcc tgggcaaggt ggtggacgag    1440
tttgcgggca aggtgcactt tgtggagatt gacattgagc aggacgcggc gctggcggag    1500
ggtgcgggcg tcaacggcac gcccaccgtg cagatcttca aggacaaggc catggtggag    1560
acgatggtgg gcgtgaagca aagagccag taccgggcag tggtggagaa ggcgctgggc     1620
gcggccaccg tcagtgcgtg a                                               1641
```

<210> SEQ ID NO 44
<211> LENGTH: 546
<212> TYPE: PRT
<213> ORGANISM: Chlorella sorokiniana

<400> SEQUENCE: 44

```
Met Ala Ala Val Ala Ala Val Ser Val Ala Ala Pro Ala Arg Cys
1               5                  10                  15

Ala Ala Thr Arg Gln Ala Arg Ser Ala Ala Cys Pro Ala Leu Gln His
            20                  25                  30

Gly Asn Ala Arg Ser Cys Ser Arg Ser Arg Arg Ser Leu Ala Gly Thr
        35                  40                  45

Ala Ala Ala Gly Pro Ala Arg Val Gln Arg Arg Leu Gly Leu Arg
    50                  55                  60

Leu Arg Ala Gln Ala Ser Gly Asn Gly Ala Pro Glu Val Glu Asn Met
65                  70                  75                  80

Val Ile Ile Gly Ser Gly Pro Ala Gly Tyr Thr Ala Ala Ile Tyr Ala
                85                  90                  95

Ala Arg Ala Asn Leu Arg Pro Phe Val Phe Glu Gly Leu Ser Ala Gly
            100                 105                 110

Gly Val Arg Gly Gly Gln Leu Met Thr Thr Thr Glu Val Glu Asn Phe
        115                 120                 125

Pro Gly Phe Pro Glu Gly Ile Thr Gly Pro Asp Leu Met Asp Arg Met
    130                 135                 140

Arg Ala Gln Ala Glu Arg Trp Gly Ala Arg Leu Glu Thr Glu Asp Val
145                 150                 155                 160

Val Ser Val Asp Leu Ser Thr Arg Pro Phe Thr Val Arg Gly Thr Glu
                165                 170                 175

Asn Thr Val Lys Ala His Ser Val Ile Val Ala Thr Gly Ala Thr Ala
            180                 185                 190

Lys Lys Leu Asn Leu Pro Ser Glu Gln Arg Phe Trp Ser Asn Gly Ile
        195                 200                 205

Ser Ala Cys Ala Ile Cys Asp Gly Ala Ser Thr Ile Phe Lys Gln Gln
    210                 215                 220

Ala Arg Gly Gly Gly Phe Met Arg Thr Thr Glu Leu Ala Val Val Gly
225                 230                 235                 240

Gly Gly Asp Thr Ala Thr Glu Glu Ala Val Tyr Leu Thr Lys Tyr Ala
                245                 250                 255

Ser His Val His Leu Leu Val Arg Gly Asp Lys Met Arg Ala Ser Lys
            260                 265                 270
```

Ala Met Gln Asp Arg Val Leu Ala Asn Pro Lys Ile Thr Val His Met
            275                 280                 285

Asn Thr Glu Val Asp Asp Ala Tyr Gly Asp Ser Ala Met Lys Gly
        290                 295                 300

Leu His Leu Arg Asp Ala Lys Thr Gly Glu Lys Arg Asp Leu Pro Val
305                 310                 315                 320

Arg Gly Leu Phe Tyr Gly Ile Gly His Lys Pro Asn Ser Asp Phe Leu
                325                 330                 335

Ala Gly Gln Leu Glu Leu Asp Gln Glu Gly Tyr Val Val Lys His
            340                 345                 350

Gly Gly Lys Thr Ser Val Glu Gly Val Phe Ala Ala Gly Asp Leu His
        355                 360                 365

Asp Val Glu Trp Arg Gln Ala Ile Thr Ala Ala Gly Ser Gly Cys Gln
370                 375                 380

Ala Ala Leu Ala Ala Glu Arg Tyr Leu Ser Ala Asn Gly Leu Ala Gln
385                 390                 395                 400

Glu Phe Ser Gln Ala Val Thr Glu Glu Lys Tyr Gly Ser Thr Pro Glu
                405                 410                 415

Thr Gln Ala Ala Ser Ser Ser Gly Ala Asp Thr Glu Glu Thr Phe Asp
            420                 425                 430

Pro Ala Ala Asp Lys His Lys Gly Gln Phe Ala Leu Arg Lys Leu Tyr
435                 440                 445

His Glu Ser Ser Arg Pro Leu Ile Val Leu Tyr Thr Ala Pro Thr Cys
            450                 455                 460

Gly Pro Cys Arg Thr Leu Lys Pro Ile Leu Gly Lys Val Val Asp Glu
465                 470                 475                 480

Phe Ala Gly Lys Val His Phe Val Glu Ile Asp Ile Glu Gln Asp Ala
                485                 490                 495

Ala Leu Ala Glu Gly Ala Gly Val Asn Gly Thr Pro Thr Val Gln Ile
            500                 505                 510

Phe Lys Asp Lys Ala Met Val Glu Thr Met Val Gly Val Lys Gln Lys
        515                 520                 525

Ser Gln Tyr Arg Ala Val Val Glu Lys Ala Leu Gly Ala Ala Thr Val
530                 535                 540

Ser Ala
545

<210> SEQ ID NO 45
<211> LENGTH: 1679
<212> TYPE: DNA
<213> ORGANISM: Picochlorum soloecismus

<400> SEQUENCE: 45
atgaatcgtg ggagggcatt ggggtctact cggagattgt cgggcagtgt aggtcttgtc      60
cgaccacaag ttatcaatct ggacctttct tcaaagattt ctgcaaaagg gaatggagcg     120
ctgagcagat gtaagcgaga tgtaaaaatg ctcgttagtg cttctgcagc ggaagggact     180
gggtcgaatg agaaggttga aaatttggtg ataatcggga gtggtccagc aggatacact     240
gcggccatct acgcctcaag agcgagtctc cggcctctcg tgttcgaagg gtatcaggct     300
ggtggggttc gaggtggaca attaatgaca acgacagagg tggagaactt ccggggtttt     360
cctgaaggta ttactggccc agatttgatg gataggatga ggcaacaggt gagttacctg     420
cagactgtga atctggttc gagggtcgtt ttgcatttac agaccagtga aaatgaaagc     480
atttattttc tatgatctga atatgttgtt cactgcaggc ggagcgatgg ggtagcaatt     540

```
tgctgttgga agatgtagaa tcagttgact tgtctcagag gccattcgtt atcaagggaa      600
gtgaaaccac tgtcaaagcc aatagtttga tcattgcgac tggggcaacc gcgaaaaggc      660
ttagtattcc atctgaacat accttctgga gtagaggtat tagtgcatgc gcaatttgtg      720
atggagcatc gccaatcttt aaggatcagg aattggctgt tgttggagga ggggatactg      780
caacggaaga ggcagtgtat ttgacgaaat atgggaggca cgttcatctc ttggttcgtg      840
gacctacgat gcgtgcaagc aaagctatgc aggagcgtgt cctcaagaat cccaagataa      900
cagtgcactt tagtactgca attgaagatg catacggaga caagaagggg caatggcag       960 gtttgcacct tgtcaataat gacaccggtg aaaagaaaga cttgcaagtt cgagggctgt     1020
tttatggcat tggccattcc ccaaacagtg gtttcttga tgggcaagta gaactagact       1080
cttctggtta tgtgaaggtg aaggaaggag ggccctggac caatgtagaa ggcgtcttct     1140
cagcaggaga cctccatgat acagaatgga gacaggcgat tacagctgca ggcagtggct     1200
gcatggcagc actcgcagcc gagagatatc tcactgcaaa tgaactgatt gtggaggccc     1260
cagaagaaga agcacctgaa ccacagaaac aagcagaggc ccctagcaag aaggaagaag     1320
tgaagaaaga agtgtcgatg gaagaagagt caatctata tgccgataaa caccgcggac      1380
aatacgccct aagaaagttg tatcacgaaa gcgatagatt gctgactgtt ctgtacactt     1440
ctcctacctg cggtccatgt agatcattga aacctatatt gaacaaagtt cttgatgagt     1500
atgctgggaa atacacttg gtggaaatag atatcgctga ggacccagaa atcgcacagg      1560
ctgcgggagt gaacggtact ccaaccgtcc agatgtttaa gaacaaggac agggttgcaa     1620
atttgcctgg tgtcaaaatg aagaatgaat acaagaaaca cattgaaagc catttgtag     1679
```

<210> SEQ ID NO 46
<211> LENGTH: 522
<212> TYPE: PRT
<213> ORGANISM: Picochlorum soloecismus

<400> SEQUENCE: 46

```
Met Asn Arg Gly Arg Ala Leu Gly Ser Thr Arg Arg Leu Ser Gly Ser
1               5                   10                  15

Val Gly Leu Val Arg Pro Gln Val Ile Asn Leu Asp Leu Ser Ser Lys
            20                  25                  30

Ile Ser Ala Lys Gly Asn Gly Ala Leu Ser Arg Cys Lys Arg Asp Val
        35                  40                  45

Lys Met Leu Val Ser Ala Ser Ala Glu Gly Thr Gly Ser Asn Glu
    50                  55                  60

Lys Val Glu Asn Leu Val Ile Ile Gly Ser Gly Pro Ala Gly Tyr Thr
65                  70                  75                  80

Ala Ala Ile Tyr Ala Ser Arg Ala Ser Leu Arg Pro Leu Val Phe Glu
                85                  90                  95

Gly Tyr Gln Ala Gly Gly Val Arg Gly Gly Gln Leu Met Thr Thr Thr
            100                 105                 110

Glu Val Glu Asn Phe Pro Gly Phe Pro Glu Gly Ile Thr Gly Pro Asp
        115                 120                 125

Leu Met Asp Arg Met Arg Gln Gln Ala Glu Arg Trp Gly Ser Asn Leu
    130                 135                 140

Leu Leu Glu Asp Val Glu Ser Val Asp Leu Ser Gln Arg Pro Phe Val
145                 150                 155                 160

Ile Lys Gly Ser Glu Thr Thr Val Lys Ala Asn Ser Leu Ile Ile Ala
                165                 170                 175
```

```
Thr Gly Ala Thr Ala Lys Arg Leu Ser Ile Pro Ser Glu His Thr Phe
            180                 185                 190

Trp Ser Arg Gly Ile Ser Ala Cys Ala Ile Cys Asp Gly Ala Ser Pro
        195                 200                 205

Ile Phe Lys Asp Gln Glu Leu Ala Val Val Gly Gly Gly Asp Thr Ala
    210                 215                 220

Thr Glu Glu Ala Val Tyr Leu Thr Lys Tyr Gly Arg His Val His Leu
225                 230                 235                 240

Leu Val Arg Gly Pro Thr Met Arg Ala Ser Lys Ala Met Gln Glu Arg
                245                 250                 255

Val Leu Lys Asn Pro Lys Ile Thr Val His Phe Ser Thr Ala Ile Glu
            260                 265                 270

Asp Ala Tyr Gly Asp Lys Lys Gly Ala Met Ala Gly Leu His Leu Val
        275                 280                 285

Asn Asn Asp Thr Gly Glu Lys Lys Asp Leu Gln Val Arg Gly Leu Phe
    290                 295                 300

Tyr Gly Ile Gly His Ser Pro Asn Ser Gly Phe Leu Asp Gly Gln Val
305                 310                 315                 320

Glu Leu Asp Ser Ser Gly Tyr Val Lys Val Lys Glu Gly Gly Pro Trp
                325                 330                 335

Thr Asn Val Glu Gly Val Phe Ser Ala Gly Asp Leu His Asp Thr Glu
            340                 345                 350

Trp Arg Gln Ala Ile Thr Ala Ala Gly Ser Gly Cys Met Ala Ala Leu
        355                 360                 365

Ala Ala Glu Arg Tyr Leu Thr Ala Asn Glu Leu Ile Val Glu Ala Pro
    370                 375                 380

Glu Glu Glu Ala Pro Glu Pro Gln Lys Gln Ala Glu Ala Pro Ser Lys
385                 390                 395                 400

Lys Glu Glu Val Lys Lys Glu Val Ser Met Glu Glu Glu Phe Asn Leu
                405                 410                 415

Tyr Ala Asp Lys His Arg Gly Gln Tyr Ala Leu Arg Lys Leu Tyr His
            420                 425                 430

Glu Ser Asp Arg Leu Leu Thr Val Leu Tyr Thr Ser Pro Thr Cys Gly
        435                 440                 445

Pro Cys Arg Ser Leu Lys Pro Ile Leu Asn Lys Val Leu Asp Glu Tyr
    450                 455                 460

Ala Gly Lys Ile His Leu Val Glu Ile Asp Ile Ala Glu Asp Pro Glu
465                 470                 475                 480

Ile Ala Gln Ala Ala Gly Val Asn Gly Thr Pro Thr Val Gln Met Phe
                485                 490                 495

Lys Asn Lys Asp Arg Val Ala Asn Leu Pro Gly Val Lys Met Lys Asn
            500                 505                 510

Glu Tyr Lys Lys His Ile Glu Ser His Leu
        515                 520

<210> SEQ ID NO 47
<211> LENGTH: 1629
<212> TYPE: DNA
<213> ORGANISM: Chlorella sorokiniana,

<400> SEQUENCE: 47
atggcggccg tgacggcagt ctcccttccg gcggcgactg ctcgctgcgc ggcgacccgc      60
caggcgcgat cggcggcatg cccgcccctg cagaccggca atgcgcggcg cagccggcct     120
```

|  |  |
|---|---|
| agccgctcgc tggcagggac cgcggcttct gcgagccaga cccgtgtgca gcggcgcctg | 180 |
| gcgctgcgcc tgagggccga ggccgccggc aacggcgccc cgaggtgga gaacatggtc | 240 |
| atcattggca gcggccccgc cggctacacc gccgccatct acgccgcccg cgccaacctg | 300 |
| cggcccttg tgttcgaggg cgtgtcggca ggcggcgtgc gcggcgggca gctcatgacc | 360 |
| acgaccgagg tggagaactt ccccggcttc ccggagggta tcacgggccc ggacctgatg | 420 |
| gatcgcatgc gcgcgcaggc tgagcgctgg ggtgcccgcc tggagactga ggacgtggtg | 480 |
| tccgtggacc tgtccacccg ccccttcacc gtgcgcggca ccgacaccac cgtcaaggcg | 540 |
| cactcggtca ttgtggccac gggcgccacc gccaagaagc tcaacctgcc cagcgagcag | 600 |
| cgcttctggt ccaacggcat ctccgcctgc gccatctgcg acggagcctc caccatcttc | 660 |
| aagcagcagg cgagcgggcg cttgctgttt gagctggctg tggtgggcgg cggcgacacc | 720 |
| gccaccgagg aggccgtcta cctgaccaag tatgcctcgc acgtgcacct gctggtgcgc | 780 |
| ggcgacaaga tgcgggccag caaggcgatg caggaccgcg tgctgtccaa ccccaagatc | 840 |
| acggtgcaca tgaacacgga gattgatgat gcatatggcg acgacagcgc catgaagggc | 900 |
| ctgcacctgc gcgacgccaa gacaggcgag aagcgcgacc tgcccgtgcg cggcctgttc | 960 |
| tacggcatcg gccacaagcc caactcggac ttcctggccg ccagattgc gctggacaag | 1020 |
| gaggggtacg tggtggtgca gcacggcggg cgcaccagcg tggagggcgt gtttgcggcg | 1080 |
| ggagacctgc acgacgtgga gtggcgccag gccatcaccg cggcaggcag cggctgccag | 1140 |
| gcggcgctgg ctgctgagcg gtacctcagc gccaacgggc tggcgcagga gttcagccaa | 1200 |
| gctgtgaccg aggagaagta cggctcgacg ccggagacgc gggcggccag cagcagcggt | 1260 |
| gccgacactg aggagacatt cgaccccaac gccgacaagc acaagggcca gttcgcgctg | 1320 |
| cgcaagctgt accacgagag cagccgccca ctcatcgtgc tgtacacagc ccccacctgc | 1380 |
| gggccgtgcc gcacgctgaa gcccatcctg gcaaggtgg tggacgagtt cgctggcaag | 1440 |
| gtgcactttg tggagattga cattgagcag gacgcggcgc tggccgaggg cgcaggcgtg | 1500 |
| aatggcacgc ccaccgtgca gatcttcaag gacaaggcca tggtggagac gatggtgggc | 1560 |
| gtgaagcaga gagccagta ccgcgcggtg gtggagaagg cgatgggtgc ggccaccgtc | 1620 |
| agcgcgtaa | 1629 |

<210> SEQ ID NO 48
<211> LENGTH: 542
<212> TYPE: PRT
<213> ORGANISM: Chlorella sorokiniana

<400> SEQUENCE: 48

Met Ala Ala Val Thr Ala Val Ser Leu Pro Ala Ala Thr Ala Arg Cys
1               5                   10                  15

Ala Ala Thr Arg Gln Ala Arg Ser Ala Ala Cys Pro Pro Leu Gln Thr
            20                  25                  30

Gly Asn Ala Arg Arg Ser Arg Pro Ser Arg Ser Leu Ala Gly Thr Ala
        35                  40                  45

Ala Ser Ala Ser Gln Thr Arg Val Gln Arg Arg Leu Ala Leu Arg Leu
    50                  55                  60

Arg Ala Glu Ala Ala Gly Asn Gly Ala Pro Glu Val Glu Asn Met Val
65                  70                  75                  80

Ile Ile Gly Ser Gly Pro Ala Gly Tyr Thr Ala Ala Ile Tyr Ala Ala
                85                  90                  95

Arg Ala Asn Leu Arg Pro Phe Val Phe Glu Gly Val Ser Ala Gly Gly

```
                100                 105                 110
Val Arg Gly Gly Gln Leu Met Thr Thr Thr Glu Val Glu Asn Phe Pro
            115                 120                 125
Gly Phe Pro Glu Gly Ile Thr Gly Pro Asp Leu Met Asp Arg Met Arg
        130                 135                 140
Ala Gln Ala Glu Arg Trp Gly Ala Arg Leu Glu Thr Glu Asp Val Val
145                 150                 155                 160
Ser Val Asp Leu Ser Thr Arg Pro Phe Thr Val Arg Gly Thr Asp Thr
                165                 170                 175
Thr Val Lys Ala His Ser Val Ile Val Ala Thr Gly Ala Thr Ala Lys
            180                 185                 190
Lys Leu Asn Leu Pro Ser Glu Gln Arg Phe Trp Ser Asn Gly Ile Ser
        195                 200                 205
Ala Cys Ala Ile Cys Asp Gly Ala Ser Thr Ile Phe Lys Gln Gln Ala
        210                 215                 220
Ser Gly Arg Leu Leu Phe Glu Leu Ala Val Val Gly Gly Gly Asp Thr
225                 230                 235                 240
Ala Thr Glu Glu Ala Val Tyr Leu Thr Lys Tyr Ala Ser His Val His
                245                 250                 255
Leu Leu Val Arg Gly Asp Lys Met Arg Ala Ser Lys Ala Met Gln Asp
                260                 265                 270
Arg Val Leu Ser Asn Pro Lys Ile Thr Val His Met Asn Thr Glu Ile
            275                 280                 285
Asp Asp Ala Tyr Gly Asp Ser Ala Met Lys Gly Leu His Leu Arg
        290                 295                 300
Asp Ala Lys Thr Gly Glu Lys Arg Asp Leu Pro Val Arg Gly Leu Phe
305                 310                 315                 320
Tyr Gly Ile Gly His Lys Pro Asn Ser Asp Phe Leu Ala Gly Gln Ile
                325                 330                 335
Ala Leu Asp Lys Glu Gly Tyr Val Val Val Gln His Gly Gly Arg Thr
            340                 345                 350
Ser Val Glu Gly Val Phe Ala Ala Gly Asp Leu His Asp Val Glu Trp
        355                 360                 365
Arg Gln Ala Ile Thr Ala Ala Gly Ser Gly Cys Gln Ala Ala Leu Ala
    370                 375                 380
Ala Glu Arg Tyr Leu Ser Ala Asn Gly Leu Ala Gln Glu Phe Ser Gln
385                 390                 395                 400
Ala Val Thr Glu Glu Lys Tyr Gly Ser Thr Pro Glu Thr Arg Ala Ala
                405                 410                 415
Ser Ser Ser Gly Ala Asp Thr Glu Thr Phe Asp Pro Asn Ala Asp
            420                 425                 430
Lys His Lys Gly Gln Phe Ala Leu Arg Lys Leu Tyr His Glu Ser Ser
        435                 440                 445
Arg Pro Leu Ile Val Leu Tyr Thr Ala Pro Thr Cys Gly Pro Cys Arg
    450                 455                 460
Thr Leu Lys Pro Ile Leu Gly Lys Val Val Asp Glu Phe Ala Gly Lys
465                 470                 475                 480
Val His Phe Val Glu Ile Asp Ile Glu Gln Asp Ala Ala Leu Ala Glu
                485                 490                 495
Gly Ala Gly Val Asn Gly Thr Pro Thr Val Gln Ile Phe Lys Asp Lys
            500                 505                 510
Ala Met Val Glu Thr Met Val Gly Val Lys Gln Lys Ser Gln Tyr Arg
        515                 520                 525
```

```
Ala Val Val Glu Lys Ala Met Gly Ala Ala Thr Val Ser Ala
    530                 535                 540
```

<210> SEQ ID NO 49
<211> LENGTH: 2437
<212> TYPE: DNA
<213> ORGANISM: Chlorella sorokiniana, strain 1412; NTRC

<400> SEQUENCE: 49

| | | | | | |
|---|---|---|---|---|---|
| atgctcacca | gcgcggaagc | cggatcggcg | ctgcacagca | gcgcggcggc | gctgccgctg | 60 |
| ccgccaccgc | tgcacgtact | gccgggcgcc | tgggcgctcc | tggcagacct | ggccacggcg | 120 |
| ttgcagccct | cctgcttcga | cgccgagtgc | cagcgggaga | aagacatgct | gctggaggcc | 180 |
| agcctggcta | tcccggtgct | agtgctgttc | gcctcggtgg | cgttcctgct | cgcccgccg | 240 |
| ccgcagggca | gcatcgacga | ggggcggctg | tttgaggacc | ccaagacagg | catcctgttt | 300 |
| gaggcgccac | cggagcggc | gcctgagcgg | gaccgcaagg | gcgagcttgc | cttccgcccc | 360 |
| atctcctaca | cgccctggcc | tgtggaggag | ggggcagagg | gcgagcggat | cctgcgcag | 420 |
| cccagccagc | tggtgatggc | cacacttgag | cggccgctgg | ggattgaatt | tgaggaggcc | 480 |
| aagggcgcta | agcgcaccgt | ggtggccagc | ctcacgccag | gcgggcacgc | tgagcagctg | 540 |
| gccaagcggg | gcggctcaa | cacctcgctg | ctggcctcct | gcccgctgga | gggagatgtg | 600 |
| ctgcgcggct | gcacctgcac | caacatcacc | tggcccggcg | gcgacttccc | caagcgagag | 660 |
| attgtgcgcc | gcctggggct | gcgcctgagg | gcagaggccg | ccgggaacgg | cgccccgag | 720 |
| gtggagaaca | tggtcatcat | tggcagcggc | cccgccggct | acaccgccgc | catctacgcc | 780 |
| gcccgcgcca | acctgcggcc | ctttgtgttt | gagggcgtgt | ccgcaggcgg | cgtgcgcggt | 840 |
| gggcagctga | tgaccacaac | cgaggttgag | aacttccctg | gcttcccgga | gggcatcacg | 900 |
| gggccagacc | tgatggatcg | catgcgcgcg | caggctgagc | gctgggtgc | cgcctggag | 960 |
| actgaggatg | tggtgtctgt | ggacctgtcc | tcccgcccct | tcaccgtgcg | cggcactgac | 1020 |
| accactgtca | aggcgcacac | cgtcattgtg | gccacgggcg | ccaccgccaa | gaagctgaac | 1080 |
| ctgcccagcg | agcagcgctt | ctggtccaac | ggcatctccg | cctgcgccat | ctgcgacggc | 1140 |
| gcgtcaacca | tcttcaagca | gcaggcgagc | gggcagtgtg | gctgcctttt | ggctggccag | 1200 |
| gaatgttggc | tggcgcagga | atggctgcag | ggtatccaag | tgttggagct | ggctgtggtg | 1260 |
| ggcggcggcg | acaccgccac | cgaggaggcg | gtgtacctca | ccaagtatgc | ctcccatgtg | 1320 |
| cacctgctgg | tgcgtggcga | caagatgcgt | gccagcaagg | cgatgcagga | ccgcgtgctg | 1380 |
| gccaaccca | agatcacggt | gcatatgaac | actgagatcg | atgatgcctt | tggcgacgac | 1440 |
| agcggcatga | agggcctgca | cctgcgcgac | gccaagacgg | gcgagaagcg | ggacctgcct | 1500 |
| gtgcgcggcc | tgttctacgg | catcggccac | aagcccaact | cggacttcct | ggctggccag | 1560 |
| ctggagctgg | acaaggaggg | gtacgtggtg | gtggcgcacg | gcggcaggac | cagcctggag | 1620 |
| ggcgtgtttg | cagcgggaga | cctgcacgac | gtggagtggc | ccaggccat | caccgcagcg | 1680 |
| ggcagcggct | gccaggcggc | gctggcagcg | gagcggtacc | ttagcgccaa | cggcctggcg | 1740 |
| caggagttca | gccaggcagt | gactgaggag | aagtacggct | cgacgcctga | dacgcaggcc | 1800 |
| gccagcagca | gcggcgcgga | caccgaggag | accttgacc | ccaacgccga | caagcacaag | 1860 |
| ggccagtttg | cgctgcgcaa | gctgtaccac | gagagcagcc | gccgctcat | cgtgctgtac | 1920 |
| acggcgccca | cgtgcggccc | ctgccgcacg | ctgaagccca | tcctgggcaa | ggtggtggac | 1980 |
| gagtttgcgg | gcaaggtgca | ctatgtggag | attgacattg | agcaggacgc | ggcgctggcg | 2040 |

-continued

```
gagggcgcgg gcgtcaacgg cacgcccacc gtgcagatct tcaaggacaa ggccatggtg    2100
gaaacgatgg tgggcgtgaa gcagaagagc cagtaccgcg cggtggtgga aaggcgatt    2160 ggggccgcca ccgtcaacgc ttgagtgatg cagcgatgca tgcagcaccc catacgccgt    2220
gcatgccgga tagcagcaat tggacagcag gctggctaca ccgccgctgc aggcaacccc    2280
tccgtcccat gcccctgaa ccgctgctgg tgctgcactg cgatgcgtcc ctccctgcat    2340
tgtgcggagc gggcgctttt ccaatcaacc aaccctgcga gcgatgtgcc gaccctcga    2400 tgccatgaca ccctcaccgc aacacccacc ctgctgt                              2437
```

<210> SEQ ID NO 50
<211> LENGTH: 727
<212> TYPE: PRT
<213> ORGANISM: Chlorella sorokiniana

<400> SEQUENCE: 50

```
Met Leu Thr Ser Ala Glu Ala Gly Ser Ala Leu His Ser Ser Ala Ala
1               5                   10                  15

Ala Leu Pro Leu Pro Pro Leu His Val Leu Pro Gly Ala Trp Ala
                20                  25                  30

Leu Leu Ala Asp Leu Ala Thr Ala Leu Gln Pro Ser Cys Phe Asp Ala
            35                  40                  45

Glu Cys Gln Arg Glu Lys Asp Met Leu Leu Ala Ser Leu Ala Ile
    50                  55                  60

Pro Val Leu Val Leu Phe Ala Ser Val Ala Phe Leu Leu Arg Pro Pro
65                  70                  75                  80

Pro Gln Gly Ser Ile Asp Glu Gly Arg Leu Phe Glu Asp Pro Lys Thr
                85                  90                  95

Gly Ile Leu Phe Glu Ala Pro Pro Gly Ala Ala Pro Glu Arg Asp Arg
            100                 105                 110

Lys Gly Glu Leu Ala Phe Arg Pro Ile Ser Tyr Thr Pro Trp Pro Val
        115                 120                 125

Glu Glu Gly Ala Glu Gly Glu Arg Ile Leu Pro Gln Pro Ser Gln Leu
    130                 135                 140

Val Met Ala Thr Leu Glu Arg Pro Leu Gly Ile Glu Phe Glu Glu Ala
145                 150                 155                 160

Lys Gly Ala Lys Arg Thr Val Val Ala Ser Leu Thr Pro Gly Gly His
                165                 170                 175

Ala Glu Gln Leu Ala Lys Arg Gly Arg Leu Asn Thr Ser Leu Leu Ala
            180                 185                 190

Ser Cys Pro Leu Glu Gly Asp Val Leu Arg Gly Cys Thr Cys Thr Asn
        195                 200                 205

Ile Thr Trp Pro Gly Gly Asp Phe Pro Lys Arg Glu Ile Val Arg Arg
    210                 215                 220

Leu Gly Leu Arg Leu Arg Ala Glu Ala Ala Gly Asn Gly Ala Pro Glu
225                 230                 235                 240

Val Glu Asn Met Val Ile Ile Gly Ser Gly Pro Ala Gly Tyr Thr Ala
                245                 250                 255

Ala Ile Tyr Ala Ala Arg Ala Asn Leu Arg Pro Phe Val Phe Glu Gly
            260                 265                 270

Val Ser Ala Gly Gly Val Arg Gly Gly Gln Leu Met Thr Thr Thr Glu
        275                 280                 285

Val Glu Asn Phe Pro Gly Phe Pro Glu Gly Ile Thr Gly Pro Asp Leu
    290                 295                 300
```

```
Met Asp Arg Met Arg Ala Gln Ala Glu Arg Trp Gly Ala Arg Leu Glu
305                 310                 315                 320

Thr Glu Asp Val Val Ser Val Asp Leu Ser Ser Arg Pro Phe Thr Val
                325                 330                 335

Arg Gly Thr Asp Thr Thr Val Lys Ala His Thr Val Ile Val Ala Thr
                340                 345                 350

Gly Ala Thr Ala Lys Lys Leu Asn Leu Pro Ser Glu Gln Arg Phe Trp
                355                 360                 365

Ser Asn Gly Ile Ser Ala Cys Ala Ile Cys Asp Gly Ala Ser Thr Ile
370                 375                 380

Phe Lys Gln Gln Ala Ser Gly Gln Cys Gly Cys Leu Leu Ala Gly Gln
385                 390                 395                 400

Glu Cys Trp Leu Ala Gln Glu Trp Leu Gln Gly Ile Gln Val Leu Glu
                405                 410                 415

Leu Ala Val Val Gly Gly Asp Thr Ala Thr Glu Glu Ala Val Tyr
                420                 425                 430

Leu Thr Lys Tyr Ala Ser His Val His Leu Leu Val Arg Gly Asp Lys
                435                 440                 445

Met Arg Ala Ser Lys Ala Met Gln Asp Arg Val Leu Ala Asn Pro Lys
450                 455                 460

Ile Thr Val His Met Asn Thr Glu Ile Asp Asp Ala Phe Gly Asp Asp
465                 470                 475                 480

Ser Gly Met Lys Gly Leu His Leu Arg Asp Ala Lys Thr Gly Glu Lys
                485                 490                 495

Arg Asp Leu Pro Val Arg Gly Leu Phe Tyr Gly Ile Gly His Lys Pro
                500                 505                 510

Asn Ser Asp Phe Leu Ala Gly Gln Leu Glu Leu Asp Lys Glu Gly Tyr
                515                 520                 525

Val Val Val Ala His Gly Gly Arg Thr Ser Leu Glu Gly Val Phe Ala
                530                 535                 540

Ala Gly Asp Leu His Asp Val Glu Trp Arg Gln Ala Ile Thr Ala Ala
545                 550                 555                 560

Gly Ser Gly Cys Gln Ala Ala Leu Ala Ala Glu Arg Tyr Leu Ser Ala
                565                 570                 575

Asn Gly Leu Ala Gln Glu Phe Ser Gln Ala Val Thr Glu Glu Lys Tyr
                580                 585                 590

Gly Ser Thr Pro Glu Thr Gln Ala Ala Ser Ser Gly Ala Asp Thr
                595                 600                 605

Glu Glu Thr Phe Asp Pro Asn Ala Asp Lys His Lys Gly Gln Phe Ala
610                 615                 620

Leu Arg Lys Leu Tyr His Glu Ser Ser Arg Pro Leu Ile Val Leu Tyr
625                 630                 635                 640

Thr Ala Pro Thr Cys Gly Pro Cys Arg Thr Leu Lys Pro Ile Leu Gly
                645                 650                 655

Lys Val Val Asp Glu Phe Ala Gly Lys Val His Tyr Val Glu Ile Asp
                660                 665                 670

Ile Glu Gln Asp Ala Ala Leu Ala Glu Gly Ala Gly Val Asn Gly Thr
                675                 680                 685

Pro Thr Val Gln Ile Phe Lys Asp Lys Ala Met Val Glu Thr Met Val
                690                 695                 700

Gly Val Lys Gln Lys Ser Gln Tyr Arg Ala Val Val Glu Lys Ala Ile
705                 710                 715                 720
```

Gly Ala Ala Thr Val Asn Ala
            725

<210> SEQ ID NO 51
<211> LENGTH: 796
<212> TYPE: PRT
<213> ORGANISM: Chlorella variabilis; phototropin A

<400> SEQUENCE: 51

Met Ala Gly Ala Ala Gly Leu Ala Gly Met Val Val Ala Ala Val
1               5                   10                  15

Asp Glu Glu Gly Val Glu Val Pro Val Lys Ala Gln Leu Thr Ser Ala
            20                  25                  30

Leu Ala Gln Leu Arg His Thr Phe Val Val Ala Asp Ala Thr Leu Pro
            35                  40                  45

Asp Cys Pro Leu Ile Tyr Ala Ser Glu Gly Phe Val His Met Thr Gly
        50                  55                  60

Tyr Ser Met Glu Glu Val Leu Gly His Asn Cys Arg Phe Leu Gln Gly
65                  70                  75                  80

Glu Gly Thr Asp Pro Lys Asp Val Lys Lys Leu Arg Asp Ala Val Arg
                85                  90                  95

Asn Gly Thr Pro Val Cys Thr Arg Leu Leu Asn Tyr Arg Lys Asp Gly
            100                 105                 110

Thr Pro Phe Trp Asn Leu Leu Thr Met Thr Pro Ile Lys Asp Glu Met
            115                 120                 125

Gly Arg Val Ile Lys Phe Val Gly Val Gln Val Asp Val Thr Asn Lys
        130                 135                 140

Thr Glu Gly Arg Ala Tyr Thr Asp Ser Ala Gly Val Pro Met Leu Val
145                 150                 155                 160

His Tyr Asp Asp Arg Leu Lys Glu Thr Val Ala Lys Pro Ile Val Asp
                165                 170                 175

Asp Val Leu Thr Ala Val Gln Glu Ala Asp Gly Lys Val Pro Val Arg
            180                 185                 190

Leu Ser Arg Gly Ser Pro Ser Arg Ala Leu Pro Arg Val Ala Leu Asp
            195                 200                 205

Leu Ala Thr Thr Val Glu Arg Ile Gln Ser Asn Phe Val Ile Ala Asp
        210                 215                 220

Pro Thr Leu Pro Asp Cys Pro Ile Val Phe Ala Ser Asp Pro Phe Leu
225                 230                 235                 240

Lys Leu Thr Gly Tyr Arg Arg Glu Glu Val Leu Gly Arg Asn Cys Arg
                245                 250                 255

Phe Leu Gln Gly Arg Asp Thr Asp Arg Ala Thr Val Asn Glu Leu Lys
            260                 265                 270

Ala Ala Ile Arg Ala Gly Arg Glu Cys Thr Val Arg Met Leu Asn Tyr
        275                 280                 285

Thr Lys Ala Gly Lys Pro Phe Trp Asn Met Leu Thr Val Ala Pro Ile
        290                 295                 300

Lys Asp Ile Glu Glu Arg Pro Arg Phe Leu Val Gly Val Gln Val Asp
305                 310                 315                 320

Val Thr Glu His Ala Thr Ala Thr Asp Ala Ala Pro Val Gly Ala Gln
                325                 330                 335

Ala Ala Asn Ile Val Gly Gln Ala Leu Gln Asn Met Asn Trp Val Gly
            340                 345                 350

Val Asp Pro Trp Ala Thr Phe Pro Ser Gly Leu Val Glu Pro Lys Pro
            355                 360                 365

```
His Arg Arg Met Asp Pro Ala Ala Ala Leu Lys Glu Ala Val Gln
    370                 375                 380

Arg Asp Gly Lys Leu Arg Leu Arg His Phe Ala Arg Val Arg Gln Leu
385                 390                 395                 400

Gly Ser Gly Asp Val Gly Met Val Asp Leu Val Gln Leu Val Gly Gly
                405                 410                 415

Glu His Arg Phe Ala Leu Lys Ser Leu Glu Lys Arg Glu Met Leu Glu
                420                 425                 430

Arg Asn Lys Val Gly Arg Val Arg Thr Glu Glu Ser Ile Leu Ser Lys
            435                 440                 445

Val Asp His Pro Phe Leu Ala Thr Leu Tyr Gly Thr Leu Gln Thr Asp
    450                 455                 460

Thr His Leu His Phe Leu Leu Glu Phe Cys Ser Gly Gly Glu Leu Tyr
465                 470                 475                 480

Ala Leu Leu Asn Ala Gln Pro Asn Lys Arg Leu Lys Glu Asp Ala Val
                485                 490                 495

Lys Phe Tyr Ala Ser Glu Val Leu Leu Ala Leu Gln Tyr Leu His Leu
                500                 505                 510

Gln Gly Phe Val Tyr Arg Asp Leu Lys Pro Glu Asn Ile Leu Leu His
            515                 520                 525

Gly Ser Gly His Val Met Leu Thr Asp Phe Asp Leu Ser Tyr Cys Gln
    530                 535                 540

Gly Ser Ser Ser Pro Ser Leu Leu Val Leu Pro Ala Asp His Pro Ser
545                 550                 555                 560

Val Ala Pro Ala Gly Gly Ala Ala Ala Arg Pro Glu Gly Arg Glu
                565                 570                 575

Ser Arg Arg Gly Ser Lys Asp Ser Ala Arg Val Ser Lys Asp Gly Gly
            580                 585                 590

Arg Arg Pro Leu Ala Leu Ala Ser Gly Gln His Val Leu Leu Val Ala
    595                 600                 605

Gln Pro Asp Gly Arg Ala Asn Ser Phe Val Gly Thr Glu Glu Tyr Leu
610                 615                 620

Ala Pro Glu Val Ile Thr Gly Ser Gly His Thr Ser Met Val Asp Trp
625                 630                 635                 640

Trp Ser Phe Gly Ile Leu Ile Tyr Glu Leu Leu Tyr Gly Thr Thr Pro
                645                 650                 655

Phe Arg Gly Ser Arg Arg Asp Ala Thr Phe Glu Asn Val Leu Lys Lys
                660                 665                 670

Pro Leu Ala Phe Pro Asp Ser Val Pro Val Ser Ala Glu Cys Lys Asp
            675                 680                 685

Leu Ile Thr Gln Leu Leu Ala Lys Glu Ala Ser Lys Arg Val Gly Ser
    690                 695                 700

Arg Ala Gly Ala Asp Glu Ile Lys Arg His Ala Trp Phe Ala Gly Leu
705                 710                 715                 720

Asn Trp Ala Leu Val Arg Asn Gln Lys Pro Pro Phe Val Thr Pro Arg
                725                 730                 735

Lys Thr Ser Thr Ser Ser Asp Val Pro Asn Ser Pro Met Ser Asp Asn
                740                 745                 750

Ala Phe Arg Gly Lys Ser Ala Glu Ser Pro Leu Pro Ala Ala Ala
            755                 760                 765

Ala Val Leu Asp Ala Gln Leu His His Lys Ala Lys Ser Glu Ala Ala
    770                 775                 780
```

```
Ala Ala Pro Ala Gly Pro Gly His Ile Asp Gly Phe
785                 790                 795

<210> SEQ ID NO 52
<211> LENGTH: 749
<212> TYPE: PRT
<213> ORGANISM: Chlamydomonas reinhardtii

<400> SEQUENCE: 52

Met Ala Gly Val Pro Ala Pro Ala Ser Gln Leu Thr Lys Val Leu Ala
1               5                   10                  15

Gly Leu Arg His Thr Phe Val Val Ala Asp Ala Thr Leu Pro Asp Cys
            20                  25                  30

Pro Leu Val Tyr Ala Ser Glu Gly Phe Tyr Ala Met Thr Gly Tyr Gly
            35                  40                  45

Pro Asp Glu Val Leu Gly His Asn Cys Arg Phe Leu Gln Gly Glu Gly
    50                  55                  60

Thr Asp Pro Lys Glu Val Gln Lys Ile Arg Asp Ala Ile Lys Lys Gly
65                  70                  75                  80

Glu Ala Cys Ser Val Arg Leu Leu Asn Tyr Arg Lys Asp Gly Thr Pro
                85                  90                  95

Phe Trp Asn Leu Leu Thr Val Thr Pro Ile Lys Thr Pro Asp Gly Arg
            100                 105                 110

Val Ser Lys Phe Val Gly Val Gln Val Asp Val Thr Ser Lys Thr Glu
            115                 120                 125

Gly Lys Ala Leu Ala Asp Asn Ser Gly Val Pro Leu Leu Val Lys Tyr
    130                 135                 140

Asp His Arg Leu Arg Asp Asn Val Ala Arg Thr Ile Val Asp Asp Val
145                 150                 155                 160

Thr Ile Ala Val Glu Lys Ala Glu Gly Val Glu Pro Gly Gln Ala Ser
                165                 170                 175

Ala Val Ala Ala Ala Ala Pro Leu Gly Ala Lys Gly Pro Arg Gly Thr
            180                 185                 190

Ala Pro Lys Ser Phe Pro Arg Val Ala Leu Asp Leu Ala Thr Thr Val
            195                 200                 205

Glu Arg Ile Gln Gln Asn Phe Cys Ile Ser Asp Pro Thr Leu Pro Asp
    210                 215                 220

Cys Pro Ile Val Phe Ala Ser Asp Ala Phe Leu Glu Leu Thr Gly Tyr
225                 230                 235                 240

Ser Arg Glu Glu Val Leu Gly Arg Asn Cys Arg Phe Leu Gln Gly Ala
                245                 250                 255

Gly Thr Asp Arg Gly Thr Val Asp Gln Ile Arg Ala Ala Ile Lys Glu
            260                 265                 270

Gly Ser Glu Leu Thr Val Arg Ile Leu Asn Tyr Thr Lys Ala Gly Lys
            275                 280                 285

Ala Phe Trp Asn Met Phe Thr Leu Ala Pro Met Arg Asp Gln Asp Gly
    290                 295                 300

His Ala Arg Phe Phe Val Gly Val Gln Val Asp Val Thr Ala Gln Ser
305                 310                 315                 320

Thr Ser Pro Asp Lys Ala Pro Val Trp Asn Lys Thr Pro Glu Glu Glu
                325                 330                 335

Val Ala Lys Ala Lys Met Gly Ala Glu Ala Ala Ser Leu Ile Ser Ser
            340                 345                 350

Ala Leu Gln Gly Met Ala Ala Pro Thr Thr Ala Asn Pro Trp Ala Ala
            355                 360                 365
```

Ile Ser Gly Val Ile Met Arg Arg Lys Pro His Lys Ala Asp Asp Lys
    370                 375                 380

Ala Tyr Gln Ala Leu Leu Gln Leu Gln Glu Arg Asp Gly Lys Met Lys
385                 390                 395                 400

Leu Met His Phe Arg Arg Val Lys Gln Leu Gly Ala Gly Asp Val Gly
                405                 410                 415

Leu Val Asp Leu Val Gln Leu Gln Gly Ser Glu Leu Lys Phe Ala Met
            420                 425                 430

Lys Thr Leu Asp Lys Phe Glu Met Gln Glu Arg Asn Lys Val Ala Arg
        435                 440                 445

Val Leu Thr Glu Ser Ala Ile Leu Ala Ala Val Asp His Pro Phe Leu
    450                 455                 460

Ala Thr Leu Tyr Cys Thr Ile Gln Thr Asp Thr His Leu His Phe Val
465                 470                 475                 480

Met Glu Tyr Cys Asp Gly Gly Glu Leu Tyr Gly Leu Leu Asn Ser Gln
                485                 490                 495

Pro Lys Lys Arg Leu Lys Glu Glu His Val Arg Phe Tyr Ala Ser Glu
            500                 505                 510

Val Leu Thr Ala Leu Gln Tyr Leu His Leu Leu Gly Tyr Val Tyr Arg
        515                 520                 525

Asp Leu Lys Pro Glu Asn Ile Leu Leu His His Thr Gly His Val Leu
    530                 535                 540

Leu Thr Asp Phe Asp Leu Ser Tyr Ser Lys Gly Ser Thr Thr Pro Arg
545                 550                 555                 560

Ile Glu Lys Ile Gly Gly Ala Gly Ala Ala Gly Ser Ala Pro Lys
                565                 570                 575

Ser Pro Lys Lys Ser Ser Ser Lys Ser Gly Gly Ser Ser Gly Ser
            580                 585                 590

Ala Leu Gln Leu Glu Asn Tyr Leu Leu Leu Ala Glu Pro Ser Ala Arg
        595                 600                 605

Ala Asn Ser Phe Val Gly Thr Glu Glu Tyr Leu Ala Pro Glu Val Ile
    610                 615                 620

Asn Ala Ala Gly His Gly Pro Ala Val Asp Trp Trp Ser Leu Gly Ile
625                 630                 635                 640

Leu Ile Phe Glu Leu Leu Tyr Gly Thr Thr Pro Phe Arg Gly Ala Arg
                645                 650                 655

Arg Asp Glu Thr Phe Glu Asn Ile Ile Lys Ser Pro Leu Lys Phe Pro
            660                 665                 670

Ser Lys Pro Ala Val Ser Glu Glu Cys Arg Asp Leu Ile Glu Lys Leu
        675                 680                 685

Leu Val Lys Asp Val Gly Ala Arg Leu Gly Ser Arg Thr Gly Ala Asn
    690                 695                 700

Glu Ile Lys Ser His Pro Trp Phe Lys Gly Ile Asn Trp Ala Leu Leu
705                 710                 715                 720

Arg His Gln Gln Pro Pro Tyr Val Pro Arg Arg Ala Ser Lys Ala Ala
                725                 730                 735

Gly Gly Ser Ser Thr Gly Gly Ala Ala Phe Asp Asn Tyr
            740                 745

<210> SEQ ID NO 53
<211> LENGTH: 714
<212> TYPE: PRT
<213> ORGANISM: Botryococcus terribilis -continued

```
<400> SEQUENCE: 53

Met Ala Ala His Leu His Pro Glu Leu Gln Arg Pro Gly Gln Ser Val
1               5                   10                  15

Pro Pro Pro Ala Gly Gln Leu Thr Lys Val Leu Ala Ser Leu Arg His
            20                  25                  30

Thr Phe Val Val Ala Asp Ala Thr Leu Pro Asp Cys Pro Leu Val Tyr
        35                  40                  45

Ala Ser Glu Gly Phe Leu Gln Met Thr Gly Tyr Ser Ala Asp Glu Val
    50                  55                  60

Leu Gly His Asn Cys Arg Phe Leu Gln Gly Glu Gly Thr Asp Pro Lys
65                  70                  75                  80

Glu Val Ala Val Ile Arg Glu Ala Val Arg Lys Gly Glu Gly Cys Ser
                85                  90                  95

Val Arg Leu Leu Asn Tyr Arg Lys Asp Gly Thr Pro Phe Trp Asn Leu
            100                 105                 110

Leu Thr Met Thr Pro Ile Lys Thr Glu Asp Gly Arg Val Ser Lys Tyr
        115                 120                 125

Val Gly Val Gln Val Asp Val Thr Ser Lys Thr Glu Gly Lys Ala Phe
    130                 135                 140

Ser Asp Ala Thr Gly Val Pro Leu Leu Val Lys Tyr Asp Thr Arg Leu
145                 150                 155                 160

Arg Glu Gly Val Ala Lys Gly Ile Val Gln Glu Val Thr Ser Asn Ile
                165                 170                 175

Gln Asp Ala Glu Leu Glu Thr Arg Leu Gly Lys Lys Met Thr Ala Pro
            180                 185                 190

Lys Ser Phe Pro Arg Val Ala Leu Asp Leu Ala Thr Thr Val Glu Arg
        195                 200                 205

Ile Gln Gln Asn Phe Cys Ile Cys Asp Pro Asn Leu Pro Asp Cys Pro
    210                 215                 220

Ile Val Phe Ala Ser Asp Gly Phe Leu Glu Met Thr Glu Phe Gly Arg
225                 230                 235                 240

Phe Glu Val Leu Gly Arg Asn Cys Arg Phe Leu Gln Gly Pro Glu Thr
                245                 250                 255

Asp Pro Lys Ala Ile Ala Glu Ile Lys Glu Ala Ile Lys Asn Arg Ser
            260                 265                 270

Glu Thr Thr Val Arg Ile Leu Asn Tyr Lys Lys Ser Gly Lys Pro Phe
        275                 280                 285

Trp Asn Met Phe Thr Leu Ala Pro Met Ala Asp Val Asp Gly Thr Pro
    290                 295                 300

Arg Phe Leu Ile Gly Val Gln Val Asp Val Thr Ala Ala Glu Ala Ala
305                 310                 315                 320

Gly Leu Thr Ser Val Glu Pro Ala Val Asp Thr Val Lys Ser Val Ala
                325                 330                 335

Met Gln Gln Leu Gly Ala Gly Trp Gly Arg Ala Asp Pro Trp Gln Asn
            340                 345                 350

Val His Ala Gly Leu Ser Val Ile Lys Pro His Lys Ala Gln Glu Lys
        355                 360                 365

Ala Tyr Val Ala Leu Ala Glu Val Glu Lys Ala Gln Lys Lys Leu Ala
    370                 375                 380

Leu Tyr Gln Phe Arg Arg Leu Lys Gln Leu Gly Thr Gly Asp Val Gly
385                 390                 395                 400

Leu Val Asp Leu Val Glu Leu Gln Gly Thr Asp Ser Lys Phe Ala Met
                405                 410                 415
```

```
Lys Thr Leu Glu Lys Asn Glu Met Leu Glu Arg Asn Lys Val Met Arg
                420                 425                 430

Val Leu Thr Glu Ala Lys Ile Leu Ser Ala Val Asp His Pro Phe Leu
            435                 440                 445

Ala Thr Leu Tyr Ala Thr Leu Ala Thr Asp Thr His Leu His Phe Leu
        450                 455                 460

Met Glu Tyr Cys Glu Gly Gly Glu Leu Tyr Gly Leu Leu Thr Arg Gln
465                 470                 475                 480

Pro Ala Lys Arg Phe Lys Glu Ser His Met Arg Phe Tyr Ala Ala Glu
                485                 490                 495

Gly Leu Ile Ala Leu Gln Tyr Leu His Leu Leu Gly Phe Val Tyr Arg
            500                 505                 510

Asp Leu Lys Pro Glu Asn Ile Leu Leu His His Thr Gly His Val Leu
        515                 520                 525

Leu Thr Asp Phe Asp Leu Ser Tyr Cys Gln Gly Lys Thr Gln Pro Thr
    530                 535                 540

Ile Glu Met Lys Ala Pro Arg Asn Pro Ala Thr Gly Thr Val Asp Pro
545                 550                 555                 560

Ala Asp Val Leu Leu Val Ala Glu Pro Glu Gly Arg Ala Asn Ser Phe
                565                 570                 575

Val Gly Thr Glu Glu Tyr Leu Ala Pro Glu Val Ile Asn Gly Thr Gly
            580                 585                 590

His Thr Ala Ala Val Asp Trp Trp Ser Phe Gly Ile Leu Met Tyr Glu
        595                 600                 605

Leu Val Tyr Gly Phe Thr Pro Phe Arg Gly Ser Lys Arg Glu Ala Thr
    610                 615                 620

Phe Glu Ser Ile Leu Lys Arg Pro Leu Ala Phe Pro Ser Lys Pro Val
625                 630                 635                 640

Val Ser Pro Ala Cys Gln Asp Leu Ile Ser Gln Leu Leu Ile Arg Asp
                645                 650                 655

Ala Ser Lys Arg Leu Gly Ser Lys Ala Gly Ala Glu Glu Ile Lys Ala
            660                 665                 670

His Pro Phe Phe Lys Gly Ile Asn Trp Ala Leu Leu Arg Asn Thr Val
        675                 680                 685

Pro Pro Tyr Val Pro Arg Val Ser Glu Ser Asp Arg Pro Asn Pro Pro
    690                 695                 700

Ala Ala Ala Gln Ala Ile Phe Asp Ala Phe
705                 710

<210> SEQ ID NO 54
<211> LENGTH: 719
<212> TYPE: PRT
<213> ORGANISM: Tetraselmis striata

<400> SEQUENCE: 54

Met Ala Ser Asp Glu Val Pro Ala Ala Asn Asn Leu Thr Ser Val
1               5                   10                  15

Leu Ser Gly Leu Lys His Thr Phe Val Val Ala Asp Ala Thr Leu Pro
            20                  25                  30

Asp Cys Pro Leu Val Phe Ala Ser Glu Ser Phe Tyr Thr Met Thr Gly
        35                  40                  45

Tyr Ser Lys Asp Glu Val Leu Gly His Asn Cys Arg Phe Leu Gln Gly
    50                  55                  60

Glu Gly Thr Ser Pro Lys Glu Ile Gln Lys Ile Arg Asp Ala Val Lys
```

-continued

```
                65                  70                  75                  80
        Thr Gly Glu Ile Cys Ser Val Arg Leu Leu Asn Tyr Arg Lys Asp Gly
                            85                  90                  95

Thr Pro Phe Trp Asn Leu Leu Thr Val Thr Pro Val Lys Thr Ser Thr
                        100                 105                 110

Gly Gln Val Thr Lys Phe Val Gly Val Gln Val Asp Val Thr Ser Arg
                    115                 120                 125

Thr Glu Gly Lys Ala Phe Ala Glu Thr Gly Gly Ala Pro Leu Leu Lys
                130                 135                 140

Tyr Asp Gly Arg Leu Arg Glu Asn Val Ala Lys Asn Ile Val Ala Glu
        145                 150                 155                 160

Val Val Asp Thr Val Glu Ser Val Glu Ser Asn Gly Lys Arg Ala Thr
                        165                 170                 175

Ala Pro Lys Ala Phe Pro Arg Val Ala Leu Asp Leu Ala Thr Thr Val
                    180                 185                 190

Glu Arg Ile Gln Gln Asn Phe Cys Ile Cys Asp Pro Thr Leu Pro Asp
                195                 200                 205

Val Pro Ile Val Phe Thr Ser Asp Ala Phe Leu Glu Leu Thr Glu Tyr
            210                 215                 220

Ser Arg Glu Glu Val Leu Gly Lys Asn Cys Arg Phe Leu Gln Gly Pro
        225                 230                 235                 240

Lys Thr Asp Pro Asp Thr Val Ala Thr Ile Arg Lys Ala Val Ile Asp
                        245                 250                 255

Lys Glu Glu Ile Thr Val Arg Ile Leu Asn Tyr Lys Lys Ser Gly Lys
                    260                 265                 270

Pro Phe Trp Asn Met Phe Thr Leu Ala Pro Ile Lys Asp Val Asp Gly
                275                 280                 285

Thr Cys Arg Phe Met Val Gly Val Gln Val Asp Val Thr Ala Ala Asp
            290                 295                 300

Ala Ser Ala Ser Pro Asp Ala Ile Pro Gln Met Gln Asn Asp Ala Gln
        305                 310                 315                 320

Leu Lys Ala Lys Gly His Asp Ala Ser Ala Val Ile Gly Ser Ala Leu
                        325                 330                 335

Gln Asn Leu Gly Met Gly Gly Lys Asp Glu Asp Pro Trp Lys Ser Ile
                    340                 345                 350

Val Thr Gly Val Leu Tyr Gln Lys Pro His Met Ser Asp Ser Pro Ala
                355                 360                 365

Val Val Ala Leu Arg Ala Ala Val Glu Gln His Gly Ala Leu Asn Ile
            370                 375                 380

Asp Ser Phe Lys Arg Gln Lys Gln Leu Gly Ser Gly Asp Val Gly Leu
        385                 390                 395                 400

Val Asp Leu Val Thr Leu Ala Gly Thr Asn His Glu Phe Ala Met Lys
                        405                 410                 415

Ser Leu Asp Lys Lys Glu Met Ile Glu Arg Asn Lys Ile Gly Arg Val
                    420                 425                 430

Gln Thr Glu Gln Ala Ile Leu Ala Ser Val Asp His Pro Phe Leu Ala
                435                 440                 445

Thr Leu Tyr Cys Thr Leu Asp Thr Pro Ser His Leu His Phe Ile Leu
            450                 455                 460

Gln Ile Cys Ala Gly Gly Glu Leu Tyr Gly Leu Leu Asn Ala Gln Pro
        465                 470                 475                 480

Lys Lys Arg Leu Arg Glu Ala His Val Arg Phe Tyr Ile Ala Glu Val
                        485                 490                 495
```

```
Leu Leu Ala Leu Gln Tyr Leu His Leu Gly Tyr Ile Tyr Arg Asp
                500                 505                 510

Leu Lys Pro Glu Asn Ile Leu His Gly Ser Gly His Val Met Leu
                515                 520                 525

Thr Asp Phe Asp Leu Ser Phe Gly Lys Gly Met Thr Glu Pro Lys Met
                530                 535                 540

Gln Lys Thr Val Thr Pro Val Glu Ala Ala Gly Cys Ser Gly Asn
545                 550                 555                 560

Pro Pro Lys Ala Lys Lys Pro Asn Glu Asn Tyr Ile Leu Leu Ala Glu
                565                 570                 575

Pro Ser Ala Lys Ser Asn Ser Phe Val Gly Thr Glu Glu Tyr Leu Ala
                580                 585                 590

Pro Glu Val Ile Asn Gly Thr Gly His Gly Ala Glu Val Asp Trp Trp
                595                 600                 605

Ala Leu Gly Ile Leu Thr His Glu Leu Leu Tyr Gly Val Thr Pro Phe
                610                 615                 620

Arg Gly Gln Arg Arg Asp Glu Thr Phe Glu Asn Val Leu Arg Val Pro
625                 630                 635                 640

Leu Asn Leu Pro Thr Lys Pro Thr Val Ser Pro Glu Cys Arg Asp Phe
                645                 650                 655

Ile Ser Gln Leu Leu Val Lys Asn Pro Glu Lys Arg Leu Gly Ala Lys
                660                 665                 670

Arg Gly Ala Glu Asp Ile Lys Ala His Pro Trp Phe Lys Asp Leu Asp
                675                 680                 685

Phe Asn Met Leu Arg His Glu Pro Pro Phe Val Pro Gln Ala Ser
                690                 695                 700

Gly Asp Ser Gly Ala Pro Pro Pro Asn Ala Ala Phe Lys Asn Phe
705                 710                 715

<210> SEQ ID NO 55
<211> LENGTH: 819
<212> TYPE: PRT
<213> ORGANISM: Micromonas pusilla, strain CCMP 1545; phototropin A

<400> SEQUENCE: 55

Met Ala Ala Met Ser Gly Gln Val Pro Pro Asp Lys Met Pro Gln Gly
1               5                   10                  15

Val Ser Tyr Thr Val Asp Glu Ser Gly Gly Ile Ala Ala Pro Glu Ala
                20                  25                  30

Ser Lys Gly Leu Thr Met Ala Leu Ala Ser Val Arg His Thr Phe Thr
            35                  40                  45

Val Ser Asp Pro Thr Leu Pro Asp Cys Pro Ile Val Tyr Ala Ser Asp
        50                  55                  60

Gly Phe Leu Lys Met Thr Gly Tyr Ser Ala Glu Glu Val Ile Asn Arg
65                  70                  75                  80

Asn Cys Arg Phe Leu Gln Gly Glu Asp Thr Asp Arg Asp Asp Val Gln
                85                  90                  95

Lys Ile Arg Asp Ala Val Gln Lys Gly Glu Arg Leu Thr Ile Arg Leu
            100                 105                 110

Gln Asn Tyr Lys Lys Asp Gly Thr Pro Phe Trp Asn Leu Leu Thr Ile
        115                 120                 125

Ala Pro Val Lys Met Glu Asp Gly Thr Val Ala Lys Phe Ile Gly Val
    130                 135                 140

Gln Val Asp Val Thr Asp Arg Thr Glu Gly Glu Val Gly Arg Thr Val
```

```
            145                 150                 155                 160
        Gly Asp Gly Gly Val Val Gly Ala Lys Asp Glu Lys Gly Leu Pro Leu
                        165                 170                 175

Leu Val Arg Tyr Asp Gln Arg Leu Lys Asp Gln Asn Tyr Pro Gly Val
                        180                 185                 190

Glu Asp Val Glu Lys Ala Val Met Lys Gly Glu Gly Ile Asp Ala Asp
                        195                 200                 205

Ala Thr Arg Asn Ser Arg Ala Arg Glu Gly Leu Asp Met Ala Thr Thr
                        210                 215                 220

Met Glu Arg Ile Gln Gln Ser Phe Leu Ile Ser Asp Pro Ser Leu Pro
        225                 230                 235                 240

Asp Cys Pro Ile Val Phe Ala Ser Asp Gly Phe Leu Asp Phe Thr Gly
                        245                 250                 255

Tyr Gly Arg Glu Glu Ile Leu Gly Arg Asn Cys Arg Phe Leu Gln Gly
                        260                 265                 270

Ala Gly Thr Asp Arg Asp Ala Val Lys Glu Ile Arg Asn Ala Ile Lys
                        275                 280                 285

Asp Asn Arg Glu Cys Thr Val Arg Leu Leu Asn Tyr Thr Lys Gln Gly
                        290                 295                 300

Lys Pro Phe Trp Asn Met Phe Thr Leu Ala Pro Val Arg Asp His Ala
        305                 310                 315                 320

Gly Glu Val Arg Phe Phe Ala Gly Val Gln Val Asp Val Thr Val Tyr
                        325                 330                 335

Thr Asp Ala Asp Gly Arg Arg Leu Asp Ser Val Glu Leu Leu Arg Gln
                        340                 345                 350

Thr Lys Ala Pro Thr Pro Arg His Ser Gly Asp Asp Glu Gly Lys Ser
                        355                 360                 365

Lys Ser Lys Ala Ala Thr Lys Lys Val Leu Glu Ala Ile Gly Gly Leu
                        370                 375                 380

Thr Ala Ala Asp Gly Glu Leu Pro Trp Ala Arg Met Val Gly Arg Leu
        385                 390                 395                 400

Gly Ala Pro Lys Pro His Gln Ala Gly Asp Ala Asn Trp Ala Ala Leu
                        405                 410                 415

Arg Lys Ile Val Ala Ala His Lys Ala Ala Gly Arg Pro Glu Arg Leu
                        420                 425                 430

Ala Pro Glu Asp Phe Thr Pro Leu Thr Arg Leu Gly His Gly Asp Val
                        435                 440                 445

Gly Ala Val His Leu Val Ser Leu Arg Asp Ala Pro Ser Ala Lys Phe
                        450                 455                 460

Ala Met Lys Val Leu Val Lys Gln Glu Met Val Asp Arg Asn Lys Leu
        465                 470                 475                 480

His Arg Val Arg Thr Glu Gly Arg Ile Leu Glu Ala Val Asp His Pro
                        485                 490                 495

Phe Val Ala Thr Leu Tyr Ser Ala Phe Gln Thr Asp Thr His Leu Tyr
                        500                 505                 510

Phe Leu Met Glu Tyr Cys Glu Gly Gly Glu Leu Tyr Glu Thr Leu Gln
                        515                 520                 525

Lys Gln Pro Gly Lys Arg Phe Thr Glu Ala Thr Lys Phe Tyr Ala
                        530                 535                 540

Ala Glu Val Leu Cys Ala Leu Gln Tyr Leu His Leu Met Gly Phe Ile
        545                 550                 555                 560

Tyr Arg Asp Leu Lys Pro Glu Asn Ile Leu Leu Arg Arg Asn Gly His
                        565                 570                 575
```

```
Val Ile Val Thr Asp Phe Asp Leu Ser Tyr Cys Ala Ser Ser Arg Ala
            580                 585                 590

His Val Val Met Ile Asp Gly Lys Gly Glu Asp Val Ala Gly Gly
            595                 600                 605

Gly Ser Ala Thr Thr Ser Gly Ser Gly Arg Gly Ser Gly Gly Gly
610                 615                 620

Gly Ser Gly Gly Gly Lys Lys Glu Arg Arg Pro Ser Asp Ala Gly
625                 630                 635                 640

Ser Glu Ser Ser Ser Ser Arg Gly Gly Gly Phe Cys Gly Lys Gly
                645                 650                 655

Gly Gly Gly Gly Ser Asn Pro Ala Thr Arg Arg Asp Thr Pro Arg Leu
            660                 665                 670

Val Ala Glu Pro Phe Ala Phe Thr Asn Ser Phe Val Gly Thr Glu Glu
            675                 680                 685

Tyr Leu Ala Pro Glu Val Leu Asn Ser Thr Gly His Thr Ser Ser Ile
            690                 695                 700

Asp Trp Trp Glu Leu Gly Ile Phe Ile His Glu Cys Val Phe Gly Leu
705                 710                 715                 720

Thr Pro Phe Arg Ala Ser Lys Arg Glu Gln Thr Phe Gln Asn Ile Ile
                725                 730                 735

Ser Gln Pro Leu Ser Phe Pro Ser Asn Pro Pro Thr Ser Pro Glu Leu
            740                 745                 750

Lys Asp Leu Leu Ser Gln Leu Leu Arg Arg Asp Pro Ser Glu Arg Leu
            755                 760                 765

Gly Thr Arg Gly Gly Ala Glu Val Lys Ala His Pro Phe Phe Lys
770                 775                 780

Gly Val Asp Trp Ala Leu Leu Arg Trp Lys Asp Ala Pro Leu Ala Lys
785                 790                 795                 800

Lys Pro Asp Pro Pro Arg Ala Asp Gly Gly Gly Asp Glu Val Phe Glu
                805                 810                 815

Ile Glu Val

<210> SEQ ID NO 56
<211> LENGTH: 691
<212> TYPE: PRT
<213> ORGANISM: Dunaliella salina; phototropin A

<400> SEQUENCE: 56

Met Phe Pro Ala Asp Pro Lys Cys Ser Met Phe Leu Ala Asp Pro Val
1               5                   10                  15

Thr Trp Arg Ile Ser Tyr Phe Ser Glu Ser Phe Gln Ala Gln Met Gly
            20                  25                  30

His Thr Lys Glu Glu Leu Ala Gln His Asp Phe Lys Leu Ile Glu
        35                  40                  45

Gly Ser Pro Asp Thr Pro Ser Cys Trp Arg Asp Ile Ser Glu Ile Arg
    50                  55                  60

Asp Ala Thr Arg Glu Glu Arg Pro Cys Ser Val Cys Leu Leu Leu His
65                  70                  75                  80

Lys Lys Asp Cys Thr Pro Phe Leu Ala Gln Phe Ala Leu Thr Pro Leu
                85                  90                  95

Arg Asp Asp Gln Gly Arg Leu Val His Phe Met Gly Ile Leu Val Asp
            100                 105                 110

Val Thr His Leu Ile Gly Ser Thr Asp Pro Ala Ala Leu Gln Asp Ala
        115                 120                 125
```

```
Asp Thr Glu Gln Arg Leu Gly Val Ala Glu Gly Val Glu Leu Asp
130                 135                 140

Thr Arg Lys Leu Ala Ala Glu Leu Lys Leu Glu Pro His Leu Asp Pro
145                 150                 155                 160

Glu His Leu Glu Ala His Pro Ser Val Pro Cys Ser Leu Lys His Ala
                165                 170                 175

Leu Ser Thr Ile Ile Ser Ala Phe Val Leu Ser Asp Pro Asn Leu Pro
                180                 185                 190

Asp Cys Pro Ile Val Phe Val Ser Glu Pro Phe Leu Lys Leu Thr Gly
                195                 200                 205

Tyr Pro Arg Glu Gln Val Ile Gly Arg Asn Cys Arg Phe Leu Gln Gly
                210                 215                 220

Pro Asp Thr Asp Pro Lys Thr Val Asp Ala Ile Arg Glu Ala Val Arg
225                 230                 235                 240

Asn Gln Lys Glu Ile Thr Val Arg Ile Leu Asn Tyr Thr Lys Ser Gly
                245                 250                 255

Arg Pro Phe Trp Asn Met Phe Thr Leu Ala Pro Met Ser Asp Ser Asp
                260                 265                 270

Cys Ala Thr Arg Phe Phe Val Gly Val Gln Val Asp Val Thr Ala Ser
                275                 280                 285

Gly Met Val Gly Gly Pro Thr Pro Ala Trp Thr Lys Thr Val Ser Gln
290                 295                 300

Glu Asn Ala Val Leu Lys Gln Gly His Leu Thr Ala Thr Gln Ile Asn
305                 310                 315                 320

Ser Ala Leu Gln Gly Met Ala Met Gln Asn Pro Trp Met Ala Ile Asn
                325                 330                 335

Gly Thr Val Met Lys Leu Lys Pro His Lys Cys Gln Asp Gln Ala Tyr
                340                 345                 350

Gln Glu Leu Leu Ala Leu Gln Gln Arg Glu Gly Arg Leu Lys Leu Met
                355                 360                 365

His Phe Arg Arg Val Lys Gln Leu Gly Ala Gly Asp Val Gly Leu Val
                370                 375                 380

Asp Leu Val Gln Leu Gln Gly Thr Asp Lys Lys Phe Ala Met Lys Thr
385                 390                 395                 400

Leu Asp Lys Phe Glu Met Gln Glu Arg Asn Lys Val Gln Arg Val Leu
                405                 410                 415

Thr Glu Glu Leu Ile Leu Thr Ala Val Asp His Pro Phe Leu Pro Thr
                420                 425                 430

Leu Tyr Cys Thr Ile Gln Thr Asp Thr His Leu His Phe Val Met Glu
                435                 440                 445

Tyr Cys Asp Gly Gly Glu Leu Tyr Gly Leu Leu Asn Ala Gln Pro Lys
450                 455                 460

Lys Arg Leu Arg Glu Glu His Val Arg Phe Tyr Val Ala Glu Val Leu
465                 470                 475                 480

Leu Ala Leu Gln Tyr Leu His Leu Leu Gly Tyr Val Tyr Arg Asp Leu
                485                 490                 495

Lys Pro Glu Asn Ile Leu Leu His His Thr Gly His Val Leu Leu Thr
                500                 505                 510

Asp Phe Asp Leu Ser Tyr Ser Lys Gly Val Thr Arg Pro Arg Leu Glu
                515                 520                 525

Lys Arg Pro Asn Gly Arg Val Val Lys Val Lys Asn Gly Lys Gln Tyr
530                 535                 540
```

```
Ala Val Asp Asp Tyr Val Leu Val Ala Glu Pro Glu Ala Arg Ala Asn
545                 550                 555                 560

Ser Phe Val Gly Thr Glu Glu Tyr Leu Ala Pro Glu Val Ile Asn Ala
                565                 570                 575

Ser Gly His Ser Ala Pro Val Asp Trp Trp Ser Phe Gly Ile Leu Ile
            580                 585                 590

Tyr Glu Leu Val Tyr Gly Val Thr Pro Phe Arg Gly Val Arg Arg Asp
        595                 600                 605

Glu Thr Phe Asp Asn Val Ile Lys Ala Pro Leu Arg Phe Pro Ala Lys
    610                 615                 620

Pro Gln Ile Ser Pro Glu Cys Gln Asp Leu Ile Ser Lys Leu Leu Ile
625                 630                 635                 640

Lys Asp Pro Ala Gln Arg Leu Gly Thr Lys Tyr Gly Ala Glu Val
                645                 650                 655

Lys Ala His Pro Phe Phe His Gly Leu Asn Phe Ala Leu Gln Arg Asn
            660                 665                 670

Glu Arg Pro Pro Tyr Val Pro Arg Arg Glu Ser Arg Pro Ala Pro Ala
        675                 680                 685

Gly Ser Ser
    690

<210> SEQ ID NO 57
<211> LENGTH: 730
<212> TYPE: PRT
<213> ORGANISM: Chlorella variabilis

<400> SEQUENCE: 57

Val Pro Ala Pro Gln Ala Gln Leu Thr Ser Ala Leu Ala Lys Leu Arg
1               5                   10                  15

Gln Thr Phe Val Val Ala Asp Ala Thr His Pro Asp Cys Pro Leu Ile
                20                  25                  30

Tyr Ala Ser Glu Gly Phe Tyr His Met Thr Gly Tyr Ser Gln Glu Glu
            35                  40                  45

Leu Val Gly Lys Asn Trp Tyr Ser Phe Leu Gln Gly Pro Asp Thr Asp
        50                  55                  60

Pro Gln Ala Val Arg Gln Leu Asp Glu Ala Val Glu Ala Gly Arg Pro
65                  70                  75                  80

Leu Thr Leu Arg Leu Leu Cys Tyr Arg Lys Ser Gly Lys Ala Phe Trp
                85                  90                  95

Asn Met Leu Thr Met Thr Pro Ile His Asp Asp Glu Gly Asn Val Val
                100                 105                 110

Lys Ile Val Gly Val Gln Val Asp Val Ser Arg Thr Glu Gly Arg
            115                 120                 125

Ala Val Gln Cys Cys Ala Gln Gly Leu Pro Leu Leu Val His Tyr Asp
            130                 135                 140

Glu Arg Leu Lys Glu Arg Val Ala Trp Pro Ala Thr Glu Glu Val Met
145                 150                 155                 160

Ala Ala Val Ser Pro Arg Ala Ser Arg Leu Ser Arg Ala Ser His His
                165                 170                 175

Gly Pro Arg Ser Phe Ser Leu Ser Met Gly Gly Ala Gly Gly Glu Glu
            180                 185                 190

Glu Ala Cys Pro His Arg Ala Ala Leu Asp Leu Ala Thr Thr Ile Glu
        195                 200                 205

Arg Ile Gln Thr Asn Phe Val Ile Ser Asp Pro Ser Leu Pro Asp Cys
    210                 215                 220
```

```
Pro Ile Val Phe Ala Ser Asp Ser Phe Leu Gln Leu Thr Gly Tyr Ala
225                 230                 235                 240

Arg Glu Asp Ile Leu Gly Arg Asn Cys Arg Phe Leu Gln Gly Pro Gly
            245                 250                 255

Thr Asp Arg Ala Thr Val Asn Glu Leu Arg Ala Ala Ile Leu Ala Gly
            260                 265                 270

Arg Glu Cys Thr Val Arg Met Leu Asn Tyr Thr Lys Ala Gly Lys Pro
            275                 280                 285

Phe Trp Asn Leu Leu Thr Val Ala Pro Ile Arg Asp Gly Leu Gly Val
290                 295                 300

Leu Arg Phe Ile Val Gly Ile Gln Val Asp Val Thr Glu Gln Pro Gln
305                 310                 315                 320

Pro Glu Gly Ala Ala Ala Leu Gly Gly Ala Ala Pro Arg Gly Leu Arg
            325                 330                 335

Asp Ala Lys Ala Val Gly Arg Ala Leu Gln Ser Met Gly Tyr Glu Gly
            340                 345                 350

Gly Gly Gly Gly Gly Glu Asp Leu Trp Ala Gly Phe Gly Gly Gln
            355                 360                 365

Val Ala Pro Val Lys Pro His Lys Ala Ala Asp Gly Ala Trp Ala Ala
370                 375                 380

Leu Arg Ala Ala Ala Gln Ala Glu Gly Arg Leu Thr Glu Gln His Phe
385                 390                 395                 400

Thr Arg Val Arg Gln Leu Gly Ala Gly Asn Val Gly Lys Val Glu Leu
            405                 410                 415

Val Glu Leu Ala Gly Ser Cys His Arg Phe Ala Leu Lys Ser Leu Asp
            420                 425                 430

Lys Arg Glu Met Val Glu Arg Asn Lys Val Gly Arg Val His Thr Glu
            435                 440                 445

Arg Arg Val Leu Ser Ala Leu Asp His Pro Phe Leu Val Thr Leu Tyr
450                 455                 460

Ala Thr Met Met Glu Thr Asp Thr Ala Val Gln Phe Leu Leu Glu Tyr
465                 470                 475                 480

Cys Pro Gly Ser Asp Leu His Ala Val Leu His Arg Ala Pro Tyr Arg
            485                 490                 495

Arg Leu Pro Glu Ala Ala Val Arg Arg Tyr Ala Thr Glu Val Val Ser
            500                 505                 510

Ala Leu Gln Tyr Leu His Leu Gln Gly Phe Ala Tyr Arg Asp Leu Asn
            515                 520                 525

Pro Glu Asn Ile Met Val His Glu Glu Ser Gly His Cys Met Leu Thr
            530                 535                 540

Asp Phe Asn Leu Ser Tyr Trp Gln Ala Gly Val Glu Pro Glu Leu Val
545                 550                 555                 560

Leu Pro Pro Pro Pro Pro Arg Gln Gln Arg Ala Ala Gly Gly
            565                 570                 575

Gly Ala Pro Ala Ala Ala Met Ala Thr Ala Ser Ser Leu Gly Gly
            580                 585                 590

Ala Pro Ser Gly Ser Pro Arg Ala Gly Gly Trp Leu Leu Ala Ala Ala
            595                 600                 605

Pro Ser Gly Gly Arg Ala Asn Ser Phe Val Gly Thr Glu Glu Tyr Leu
            610                 615                 620

Ala Pro Glu Val Val Lys Gly Thr Gly His Asp Ser Gly Val Asp Trp
625                 630                 635                 640
```

```
Trp Ser Phe Gly Ile Leu Leu Phe Glu Leu Phe Gly Tyr Thr Pro
            645                 650                 655

Phe Lys Gly Leu Arg Arg Asp Glu Thr Phe Asp Asn Ile Val Lys Met
        660                 665                 670

Glu Leu Ala Phe Pro Lys Gly Gly Ala His Val Ser Pro Gln Ala Lys
            675                 680                 685

Asp Leu Ile Thr Arg Leu Leu Ala Lys Asp Pro Arg Gln Arg Leu Gly
        690                 695                 700

Ala His Ala Gly Ala Asp Glu Val Lys Gln His Pro Trp Phe Asp Gly
705                 710                 715                 720

Val Asn Trp Ala Leu Gly Arg Ala Asp Gln
            725                 730
```

<210> SEQ ID NO 58
<211> LENGTH: 712
<212> TYPE: PRT
<213> ORGANISM: Haematococcus lacustris

<400> SEQUENCE: 58

```
Met Ala Gly Val Gln Leu Pro Ser Ala Ala Ser Gln Leu Thr Lys Val
1               5                   10                  15

Leu Ala Gly Leu Arg His Thr Phe Val Val Ala Asp Ala Thr Leu Pro
            20                  25                  30

Asp Met Pro Leu Ile Tyr Ala Ser Asp Gly Phe Tyr Ala Met Thr Gly
        35                  40                  45

Tyr Gly Pro Asp Glu Val Leu Gly His Asn Cys Arg Phe Leu Gln Gly
    50                  55                  60

Glu Gly Thr Asp Pro Lys Glu Val Leu Lys Ile Arg Asp Ala Ile Lys
65                  70                  75                  80

Lys Gly Glu Gly Val Ser Val Arg Leu Leu Asn Tyr Arg Lys Asp Gly
            85                  90                  95

Thr Pro Phe Trp Asn Leu Leu Thr Val Thr Pro Ile Lys Thr Pro Asp
        100                 105                 110

Gly Lys Val Ser Lys Phe Val Gly Val Gln Val Asp Val Thr Ser Lys
    115                 120                 125

Thr Glu Gly Lys Ala Val Thr Asp Asn Gly Gly Val Pro Leu Leu Val
130                 135                 140

Lys Tyr Asp Thr Arg Leu Arg Glu Asn Val Ala Lys Arg Ile Val Asp
145                 150                 155                 160

Glu Val Thr Thr Thr Val Glu Ser Ala Glu Pro Gly Arg Ala Gln Gly
            165                 170                 175

Ala Lys Gly Ser Ala Pro Lys Ser Phe Pro Arg Val Ala Leu Asp Leu
        180                 185                 190

Ala Thr Thr Val Glu Arg Ile Gln Gln Asn Phe Cys Ile Ser Asp Pro
    195                 200                 205

Thr Leu Pro Asp Cys Pro Ile Val Phe Ala Ser Asp Ala Phe Leu Asp
    210                 215                 220

Leu Thr Glu Tyr Lys Arg Glu Glu Val Leu Gly Arg Asn Cys Arg Phe
225                 230                 235                 240

Leu Gln Gly Pro Gly Thr Asp Gln Asn Thr Val Gln Met Ile Arg Asp
            245                 250                 255

Ala Ile Arg Thr Gly Ala Glu Ile Thr Val Arg Ile Leu Asn Tyr Thr
        260                 265                 270

Lys Ser Gly Arg Pro Phe Trp Asn Met Phe Thr Leu Ala Pro Met Ser
    275                 280                 285
```

```
Asp Ser Asp Gly Thr Thr Arg Phe Phe Val Gly Val Gln Val Asp Val
    290                 295                 300

Thr Ala Val Gln Pro Gly Ala Pro Leu Ala Ser Ser Lys Pro Thr Ala
305                 310                 315                 320

Ala Asp Glu Ala Asn Val Lys Arg Gly Val Gln Ala Ala Asn Met Ile
                325                 330                 335

Gly Thr Ala Leu Gln Gly Met Gly Tyr Ala Glu Ala Asn Pro Trp Ala
                340                 345                 350

Ser Leu Pro Ser Ala Val Met Lys Arg Lys Pro His Lys Thr Glu Asp
            355                 360                 365

Lys Ala Phe Leu Ala Leu Leu Ala Val Gln Ala Arg Asp Gly Lys Leu
370                 375                 380

Lys Leu Met His Phe Arg Arg Val Lys Gln Leu Gly Ala Gly Asp Val
385                 390                 395                 400

Gly Leu Val Asp Leu Val Gln Leu Gln Gly Thr Glu His Lys Phe Ala
                405                 410                 415

Met Lys Thr Leu Asp Lys Tyr Glu Met Gln Asp Arg Asn Lys Val Gln
                420                 425                 430

Arg Val Leu Thr Glu Glu Arg Ile Leu Thr Ala Val Asp His Pro Phe
            435                 440                 445

Leu Pro Thr Leu Tyr Cys Thr Ile Gln Thr Asp Thr His Leu His Phe
450                 455                 460

Val Met Glu Phe Cys Asp Gly Gly Glu Leu Tyr Gly Leu Leu Asn Ser
465                 470                 475                 480

Gln Pro Lys Lys Arg Leu Arg Glu Ala His Val Arg Phe Tyr Val Ala
                485                 490                 495

Glu Val Leu Leu Ala Leu Gln Tyr Leu His Leu Leu Gly Tyr Val Tyr
            500                 505                 510

Arg Asp Leu Lys Pro Glu Asn Ile Leu Leu Gln His Ser Gly His Val
            515                 520                 525

Leu Leu Thr Asp Phe Asp Leu Ser Tyr Gly Lys Gly Val Thr Thr Pro
530                 535                 540

Gln Val Glu Arg Arg Pro Asp Ala Arg Val Thr Lys Asn Lys Asn Gly
545                 550                 555                 560

Lys Ile Val Leu Met Asp Asp Phe Val Leu Leu Ala Glu Pro Val Ala
                565                 570                 575

Arg Ala Asn Ser Phe Val Gly Thr Glu Glu Tyr Leu Ala Pro Glu Val
            580                 585                 590

Ile Ser Ala Ala Gly His Ser Ala Pro Val Asp Trp Trp Ser Tyr Gly
            595                 600                 605

Ile Leu Ile Tyr Glu Leu Val Tyr Gly Thr Thr Pro Phe Arg Gly Ala
            610                 615                 620

Arg Arg Asp Glu Thr Phe Asp Asn Val Val Lys Ala Pro Leu Arg Phe
625                 630                 635                 640

Pro Ala Lys Pro Val Ser Pro Glu Cys Gln Asp Leu Ile Thr Gln
                645                 650                 655

Leu Leu Val Lys Asp Pro Ala Lys Arg Leu Gly Thr Arg Thr Gly Ala
                660                 665                 670

Glu Glu Ile Lys Ala His Pro Phe Phe Lys Gly Ile Thr Trp Ser Leu
            675                 680                 685

Leu Arg His Glu Ala Pro Pro Tyr Ile Pro His Arg Gln Ser Lys Thr
            690                 695                 700
```

Met Thr Ala Ser Gly Thr Asp Ala
705                710

<210> SEQ ID NO 59
<211> LENGTH: 719
<212> TYPE: PRT
<213> ORGANISM: Tetraselmis striata

<400> SEQUENCE: 59

Met Ala Ser Asp Glu Val Pro Ala Ala Asn Asn Leu Thr Ser Val
1               5                   10                  15

Leu Ser Gly Leu Lys His Thr Phe Val Val Ala Asp Ala Thr Leu Pro
            20                  25                  30

Asp Cys Pro Leu Val Phe Ala Ser Glu Ser Phe Tyr Thr Met Thr Gly
                35                  40                  45

Tyr Ser Lys Asp Glu Val Leu Gly His Asn Cys Arg Phe Leu Gln Gly
    50                  55                  60

Glu Gly Thr Ser Pro Lys Glu Ile Gln Lys Ile Arg Asp Ala Val Lys
65                  70                  75                  80

Thr Gly Glu Ile Cys Ser Val Arg Leu Leu Asn Tyr Arg Lys Asp Gly
                85                  90                  95

Thr Pro Phe Trp Asn Leu Leu Thr Val Thr Pro Val Lys Thr Ser Thr
                100                 105                 110

Gly Gln Val Thr Lys Phe Val Gly Val Gln Val Asp Val Thr Ser Arg
            115                 120                 125

Thr Glu Gly Lys Ala Phe Ala Glu Thr Gly Gly Ala Pro Leu Leu Lys
130                 135                 140

Tyr Asp Gly Arg Leu Arg Glu Asn Val Ala Lys Asn Ile Val Ala Glu
145                 150                 155                 160

Val Val Asp Thr Val Glu Ser Val Glu Ser Asn Gly Lys Arg Ala Thr
                165                 170                 175

Ala Pro Lys Ala Phe Pro Arg Val Ala Leu Asp Leu Ala Thr Thr Val
            180                 185                 190

Glu Arg Ile Gln Gln Asn Phe Cys Ile Cys Asp Pro Thr Leu Pro Asp
        195                 200                 205

Val Pro Ile Val Phe Thr Ser Asp Ala Phe Leu Glu Leu Thr Glu Tyr
    210                 215                 220

Ser Arg Glu Glu Val Leu Gly Lys Asn Cys Arg Phe Leu Gln Gly Pro
225                 230                 235                 240

Lys Thr Asp Pro Asp Thr Val Ala Thr Ile Arg Lys Ala Val Ile Asp
                245                 250                 255

Lys Glu Glu Ile Thr Val Arg Ile Leu Asn Tyr Lys Lys Ser Gly Lys
                260                 265                 270

Pro Phe Trp Asn Met Phe Thr Leu Ala Pro Ile Lys Asp Val Asp Gly
            275                 280                 285

Thr Cys Arg Phe Met Val Gly Val Gln Val Asp Val Thr Ala Ala Asp
            290                 295                 300

Ala Ser Ala Ser Pro Asp Ala Ile Pro Gln Met Gln Asn Asp Ala Gln
305                 310                 315                 320

Leu Lys Ala Lys Gly His Asp Ala Ser Ala Val Ile Gly Ser Ala Leu
                325                 330                 335

Gln Asn Leu Gly Met Gly Gly Lys Asp Glu Asp Pro Trp Lys Ser Ile
            340                 345                 350

Val Thr Gly Val Leu Tyr Gln Lys Pro His Met Ser Asp Ser Pro Ala
        355                 360                 365

Val Val Ala Leu Arg Ala Ala Val Glu Gln His Gly Ala Leu Asn Ile
    370                 375                 380

Asp Ser Phe Lys Arg Gln Lys Gln Leu Gly Ser Gly Asp Val Gly Leu
385                 390                 395                 400

Val Asp Leu Val Thr Leu Ala Gly Thr Asn His Glu Phe Ala Met Lys
                405                 410                 415

Ser Leu Asp Lys Lys Glu Met Ile Glu Arg Asn Lys Ile Gly Arg Val
            420                 425                 430

Gln Thr Glu Gln Ala Ile Leu Ala Ser Val Asp His Pro Phe Leu Ala
            435                 440                 445

Thr Leu Tyr Cys Thr Leu Asp Thr Pro Ser His Leu His Phe Ile Leu
    450                 455                 460

Gln Ile Cys Ala Gly Gly Glu Leu Tyr Gly Leu Leu Asn Ala Gln Pro
465                 470                 475                 480

Lys Lys Arg Leu Arg Glu Ala His Val Arg Phe Tyr Ile Ala Glu Val
                485                 490                 495

Leu Leu Ala Leu Gln Tyr Leu His Leu Leu Gly Tyr Ile Tyr Arg Asp
            500                 505                 510

Leu Lys Pro Glu Asn Ile Leu Leu His Gly Ser Gly His Val Met Leu
            515                 520                 525

Thr Asp Phe Asp Leu Ser Phe Gly Lys Gly Met Thr Glu Pro Lys Met
    530                 535                 540

Gln Lys Thr Val Thr Pro Val Glu Ala Ala Gly Cys Ser Gly Asn
545                 550                 555                 560

Pro Pro Lys Ala Lys Lys Pro Asn Glu Asn Tyr Ile Leu Leu Ala Glu
                565                 570                 575

Pro Ser Ala Lys Ser Asn Ser Phe Val Gly Thr Glu Glu Tyr Leu Ala
            580                 585                 590

Pro Glu Val Ile Asn Gly Thr Gly His Gly Ala Glu Val Asp Trp Trp
            595                 600                 605

Ala Leu Gly Ile Leu Thr His Glu Leu Leu Tyr Gly Val Thr Pro Phe
    610                 615                 620

Arg Gly Gln Arg Arg Asp Glu Thr Phe Glu Asn Val Leu Arg Val Pro
625                 630                 635                 640

Leu Asn Leu Pro Thr Lys Pro Thr Val Ser Pro Glu Cys Arg Asp Phe
                645                 650                 655

Ile Ser Gln Leu Leu Val Lys Asn Pro Glu Lys Arg Leu Gly Ala Lys
            660                 665                 670

Arg Gly Ala Glu Asp Ile Lys Ala His Pro Trp Phe Lys Asp Leu Asp
            675                 680                 685

Phe Asn Met Leu Arg His Glu Pro Pro Phe Val Pro Gln Ala Ser
    690                 695                 700

Gly Asp Ser Gly Ala Pro Pro Asn Ala Ala Phe Lys Asn Phe
705                 710                 715

<210> SEQ ID NO 60
<211> LENGTH: 803
<212> TYPE: PRT
<213> ORGANISM: Coccomyxa subellipsoidea

<400> SEQUENCE: 60

Met Pro Ala Gln Thr Gly Gln Ala Glu Lys Gln Gln Lys Asp Val Gln
1               5                   10                  15

Leu His Pro Glu Leu Gln Arg Pro Gly Gln Lys Val Pro Gly Pro Ala

```
            20                  25                  30
Pro Gln Leu Thr Lys Val Leu Ala Gly Leu Arg His Thr Phe Val Val
        35                  40                  45
Ala Asp Ala Thr Leu Pro Asp Cys Pro Leu Val Phe Ala Ser Glu Gly
50                  55                  60
Phe Leu Ser Met Thr Gly Tyr Ser Ala Glu Val Leu Gly His Asn
65                  70                  75                  80
Cys Arg Phe Leu Gln Gly Glu Gly Thr Asp Pro Lys Glu Val Ala Ile
                85                  90                  95
Ile Arg Asp Ala Val Lys Lys Gly Glu Gly Cys Ser Val Arg Leu Leu
                100                 105                 110
Asn Tyr Arg Arg Asp Gly Thr Pro Phe Trp Asn Leu Leu Thr Met Thr
                115                 120                 125
Pro Ile Lys Thr Glu Asp Gly Lys Val Ser Lys Phe Val Gly Val Gln
                130                 135                 140
Val Asp Val Thr Ser Lys Thr Glu Gly Arg Ala Phe Ser Asp Ala Thr
145                 150                 155                 160
Gly Val Pro Leu Leu Val Lys Tyr Asp Thr Arg Leu Arg Glu Asn Val
                165                 170                 175
Ala Lys Asn Ile Val Gln Asp Val Thr Leu Gln Val Gln Glu Ala Glu
                180                 185                 190
Glu Glu Asp Ser Gly Ala Ala Ser Glu Ala Ala Arg Val Ser Ser Leu
                195                 200                 205
Lys Gly Phe Asn Lys Leu Trp His Lys Met Gly Asn Lys Val Thr Arg
                210                 215                 220
Pro Gln Cys Leu Gly Gly Pro Pro Ser Ala Pro Leu Gly Asp Pro Lys
225                 230                 235                 240
Ala Gln Ala Ser Ala His Asp Pro Gln Leu Gln Lys Gln Gly Glu Arg
                245                 250                 255
Val Gly Lys Lys Met Thr Ala Pro Lys Thr Phe Pro Arg Val Ala Met
                260                 265                 270
Asp Leu Ala Thr Thr Val Glu Arg Ile Gln Gln Asn Phe Cys Ile Cys
                275                 280                 285
Asp Pro Asn Leu Pro Asp Asn Pro Ile Val Phe Ala Ser Asp Gly Phe
                290                 295                 300
Leu Glu Met Ser Gln Tyr Asp Arg Phe Glu Val Leu Gly Arg Asn Cys
305                 310                 315                 320
Arg Phe Leu Gln Gly Pro Asp Thr Asp Pro Lys Ala Ile Ser Ile Ile
                325                 330                 335
Arg Asp Ala Ile Lys Ser Gln Ser Glu Ala Thr Val Arg Ile Leu Asn
                340                 345                 350
Tyr Arg Lys Ser Gly Gln Pro Phe Trp Asn Met Leu Thr Ile Ala Pro
                355                 360                 365
Met Ala Asp Val Asp Gly Thr Ser Arg Phe Phe Ile Gly Val Gln Val
                370                 375                 380
Asp Val Thr Ala Glu Asp Val Pro Met Thr Gly Gly Ile Pro Gln Val
385                 390                 395                 400
Asp Ala Lys Ala Val Lys Ala Ala Asp Pro Met Gly Ser Val Leu Gly
                405                 410                 415
Met Ala Gln Arg Gln Met Gly Ala Gly Trp Ala Val His Asp Pro Trp
                420                 425                 430
Ala Ala Ile His Ala Gly Val Ala Ser Leu Lys Pro His Lys Ala Gln
                435                 440                 445
```

Glu Lys Val Trp Ala Ala Leu Arg Glu Asn Asp Arg Lys Asn Gly Arg
    450                 455                 460

Leu Ala Leu Ser Gln Phe Arg Arg Leu Lys Gln Leu Gly Thr Gly Asp
465                 470                 475                 480

Val Gly Leu Val Asp Met Val Glu Leu Gln Asp Gly Ser Gly Arg Tyr
                485                 490                 495

Ala Met Lys Thr Leu Glu Lys Ala Glu Met Leu Glu Arg Asn Lys Val
                500                 505                 510

Met Arg Val Leu Thr Glu Ala Lys Ile Leu Ser Val Val Asp His Pro
        515                 520                 525

Phe Leu Ala Ser Leu Tyr Gly Thr Ile Val Thr Asp Thr His Leu His
530                 535                 540

Phe Leu Met Gln Ile Cys Glu Gly Gly Glu Leu Tyr Ala Leu Leu Thr
545                 550                 555                 560

Ser Gln Pro Ser Lys Arg Phe Lys Glu Ser His Val Arg Phe Tyr Thr
                565                 570                 575

Ala Glu Val Leu Ile Ala Leu Gln Tyr Leu His Leu Met Gly Phe Val
                580                 585                 590

Tyr Arg Asp Leu Lys Pro Glu Asn Ile Leu Leu His Ser Ser Gly His
        595                 600                 605

Ile Leu Leu Thr Asp Phe Asp Leu Ser Phe Cys Gln Gly Ser Thr Lys
        610                 615                 620

Val Lys Phe Glu Lys Lys Asn Gly His Ala Asn Ser Ser Gln Pro
625                 630                 635                 640

Gly Ala Thr Gln Val Ser Pro Ala Glu Glu Ile Met Met Ile Ala Val
                645                 650                 655

Pro Glu Ala Arg Ala Asn Ser Phe Val Gly Thr Glu Glu Tyr Leu Ala
                660                 665                 670

Pro Glu Val Ile Asn Gly Val Gly His Gly Ala Gly Val Asp Trp Trp
            675                 680                 685

Ser Phe Gly Ile Leu Ile Tyr Glu Leu Leu Tyr Gly Phe Thr Pro Phe
        690                 695                 700

Arg Gly Lys Lys Arg Asp Glu Thr Phe Asn Asn Ile Leu Lys Arg Pro
705                 710                 715                 720

Leu Ser Phe Pro Glu Leu Pro Glu Val Ser Asp Glu Cys Lys Asp Leu
                725                 730                 735

Ile Ser Gln Leu Leu Glu Arg Asp Pro Ala Lys Arg Leu Gly Ala His
                740                 745                 750

Ala Gly Ala Glu Glu Ile Lys Ala His Pro Phe Tyr Glu Ser Ile Asn
        755                 760                 765

Trp Ala Leu Leu Arg Asn Thr Arg Pro Pro Tyr Ile Pro Arg Arg Ser
770                 775                 780

Ala Leu Arg Lys Ala Asn Lys Pro Ser Pro Ala Ala Gln Ala Gln Phe
785                 790                 795                 800

Asp Asp Phe

<210> SEQ ID NO 61
<211> LENGTH: 819
<212> TYPE: PRT
<213> ORGANISM: Micromonas pusilla

<400> SEQUENCE: 61

Met Ala Ala Met Ser Gly Gln Val Pro Pro Asp Lys Met Pro Gln Gly
1               5                   10                  15

```
Val Ser Tyr Thr Val Asp Glu Ser Gly Gly Ile Ala Ala Pro Glu Ala
             20                  25                  30

Ser Lys Gly Leu Thr Met Ala Leu Ala Ser Val Arg His Thr Phe Thr
         35                  40                  45

Val Ser Asp Pro Thr Leu Pro Asp Cys Pro Ile Val Tyr Ala Ser Asp
     50                  55                  60

Gly Phe Leu Lys Met Thr Gly Tyr Ser Ala Glu Val Ile Asn Arg
 65                  70                  75                  80

Asn Cys Arg Phe Leu Gln Gly Glu Asp Thr Asp Arg Asp Val Gln
                 85                  90                  95

Lys Ile Arg Asp Ala Val Gln Lys Gly Glu Arg Leu Thr Ile Arg Leu
                100                 105                 110

Gln Asn Tyr Lys Lys Asp Gly Thr Pro Phe Trp Asn Leu Leu Thr Ile
             115                 120                 125

Ala Pro Val Lys Met Glu Asp Gly Thr Val Ala Lys Phe Ile Gly Val
130                 135                 140

Gln Val Asp Val Thr Asp Arg Thr Glu Gly Glu Val Gly Arg Thr Val
145                 150                 155                 160

Gly Asp Gly Gly Val Val Gly Ala Lys Asp Glu Lys Gly Leu Pro Leu
                165                 170                 175

Leu Val Arg Tyr Asp Gln Arg Leu Lys Asp Gln Asn Tyr Pro Gly Val
             180                 185                 190

Glu Asp Val Glu Lys Ala Val Met Lys Gly Glu Gly Ile Asp Ala Asp
         195                 200                 205

Ala Thr Arg Asn Ser Arg Ala Arg Glu Gly Leu Asp Met Ala Thr Thr
         210                 215                 220

Met Glu Arg Ile Gln Gln Ser Phe Leu Ile Ser Asp Pro Ser Leu Pro
225                 230                 235                 240

Asp Cys Pro Ile Val Phe Ala Ser Asp Gly Phe Leu Asp Phe Thr Gly
                245                 250                 255

Tyr Gly Arg Glu Glu Ile Leu Gly Arg Asn Cys Arg Phe Leu Gln Gly
             260                 265                 270

Ala Gly Thr Asp Arg Asp Ala Val Lys Glu Ile Arg Asn Ala Ile Lys
         275                 280                 285

Asp Asn Arg Glu Cys Thr Val Arg Leu Leu Asn Tyr Thr Lys Gln Gly
290                 295                 300

Lys Pro Phe Trp Asn Met Phe Thr Leu Ala Pro Val Arg Asp His Ala
305                 310                 315                 320

Gly Glu Val Arg Phe Phe Ala Gly Val Gln Val Asp Val Thr Val Tyr
                325                 330                 335

Thr Asp Ala Asp Gly Arg Arg Leu Asp Ser Val Glu Leu Leu Arg Gln
         340                 345                 350

Thr Lys Ala Pro Thr Pro Arg His Ser Gly Asp Glu Gly Lys Ser
         355                 360                 365

Lys Ser Lys Ala Ala Thr Lys Lys Val Leu Glu Ala Ile Gly Gly Leu
         370                 375                 380

Thr Ala Ala Asp Gly Glu Leu Pro Trp Ala Arg Met Val Gly Arg Leu
385                 390                 395                 400

Gly Ala Pro Lys Pro His Gln Ala Gly Asp Ala Asn Trp Ala Ala Leu
                405                 410                 415

Arg Lys Ile Val Ala Ala His Lys Ala Ala Gly Arg Pro Glu Arg Leu
             420                 425                 430
```

Ala Pro Glu Asp Phe Thr Pro Leu Thr Arg Leu Gly His Gly Asp Val
435                 440                 445

Gly Ala Val His Leu Val Ser Leu Arg Asp Ala Pro Ser Ala Lys Phe
450                 455                 460

Ala Met Lys Val Leu Val Lys Gln Glu Met Val Asp Arg Asn Lys Leu
465                 470                 475                 480

His Arg Val Arg Thr Glu Gly Arg Ile Leu Glu Ala Val Asp His Pro
                485                 490                 495

Phe Val Ala Thr Leu Tyr Ser Ala Phe Gln Thr Asp Thr His Leu Tyr
                500                 505                 510

Phe Leu Met Glu Tyr Cys Glu Gly Gly Glu Leu Tyr Glu Thr Leu Gln
            515                 520                 525

Lys Gln Pro Gly Lys Arg Phe Thr Glu Ala Thr Thr Lys Phe Tyr Ala
            530                 535                 540

Ala Glu Val Leu Cys Ala Leu Gln Tyr Leu His Leu Met Gly Phe Ile
545                 550                 555                 560

Tyr Arg Asp Leu Lys Pro Glu Asn Ile Leu Leu Arg Arg Asn Gly His
                565                 570                 575

Val Ile Val Thr Asp Phe Asp Leu Ser Tyr Cys Ala Ser Ser Arg Ala
                580                 585                 590

His Val Val Met Ile Asp Gly Lys Gly Glu Asp Val Val Ala Gly Gly
            595                 600                 605

Gly Ser Ala Thr Thr Ser Gly Ser Arg Gly Ser Gly Gly Gly Gly
            610                 615                 620

Gly Ser Gly Gly Gly Lys Lys Glu Arg Arg Pro Ser Asp Ala Gly
625                 630                 635                 640

Ser Glu Ser Ser Ser Arg Gly Gly Gly Phe Cys Gly Lys Gly
                645                 650                 655

Gly Gly Gly Gly Ser Asn Pro Ala Thr Arg Arg Asp Thr Pro Arg Leu
                660                 665                 670

Val Ala Glu Pro Phe Ala Phe Thr Asn Ser Phe Val Gly Thr Glu Glu
                675                 680                 685

Tyr Leu Ala Pro Glu Val Leu Asn Ser Thr Gly His Thr Ser Ser Ile
            690                 695                 700

Asp Trp Trp Glu Leu Gly Ile Phe Ile His Glu Cys Val Phe Gly Leu
705                 710                 715                 720

Thr Pro Phe Arg Ala Ser Lys Arg Glu Gln Thr Phe Gln Asn Ile Ile
                725                 730                 735

Ser Gln Pro Leu Ser Phe Pro Ser Asn Pro Pro Thr Ser Pro Glu Leu
                740                 745                 750

Lys Asp Leu Leu Ser Gln Leu Leu Arg Arg Asp Pro Ser Glu Arg Leu
            755                 760                 765

Gly Thr Arg Gly Gly Ala Glu Glu Val Lys Ala His Pro Phe Phe Lys
            770                 775                 780

Gly Val Asp Trp Ala Leu Leu Arg Trp Lys Asp Ala Pro Leu Ala Lys
785                 790                 795                 800

Lys Pro Asp Pro Pro Arg Ala Asp Gly Gly Asp Glu Val Phe Glu
                805                 810                 815

Ile Glu Val

<210> SEQ ID NO 62
<211> LENGTH: 348
<212> TYPE: PRT
<213> ORGANISM: Vaucheria frigida

<400> SEQUENCE: 62

```
Met Asn Gly Leu Thr Pro Pro Leu Met Phe Cys Ser Arg Ser Asp Asp
1               5                   10                  15

Pro Ser Ser Thr Ser Asn Ile Asn Leu Asp Asp Val Phe Ala Asp Val
            20                  25                  30

Phe Phe Asn Ser Asn Gly Glu Leu Leu Asp Ile Asp Glu Ile Asp Asp
        35                  40                  45

Phe Gly Asp Asn Thr Cys Pro Lys Ser Ser Met Ser Val Asp Asp Asp
    50                  55                  60

Ala Ser Ser Gln Val Phe Gln Gly His Leu Phe Gly Asn Ala Leu Ser
65                  70                  75                  80

Ser Ile Ala Leu Ser Asp Ser Gly Asp Leu Ser Thr Gly Ile Tyr Glu
                85                  90                  95

Ser Gln Gly Asn Ala Ser Arg Gly Lys Ser Leu Arg Thr Lys Ser Ser
            100                 105                 110

Gly Ser Ile Ser Ser Glu Leu Thr Glu Ala Gln Lys Val Glu Arg Arg
        115                 120                 125

Glu Arg Asn Arg Glu His Ala Lys Arg Ser Arg Val Arg Lys Lys Phe
    130                 135                 140

Leu Leu Glu Ser Leu Gln Gln Ser Val Asn Glu Leu Asn His Glu Asn
145                 150                 155                 160

Asn Cys Leu Lys Glu Ser Ile Arg Glu His Leu Gly Pro Arg Gly Asp
                165                 170                 175

Ser Leu Ile Ala Gln Cys Ser Pro Glu Ala Asp Thr Leu Leu Thr Asp
            180                 185                 190

Asn Pro Ser Lys Ala Asn Arg Ile Leu Glu Asp Pro Asp Tyr Ser Leu
        195                 200                 205

Val Lys Ala Leu Gln Met Ala Gln Gln Asn Phe Val Ile Thr Asp Ala
    210                 215                 220

Ser Leu Pro Asp Asn Pro Ile Val Tyr Ala Ser Arg Gly Phe Leu Thr
225                 230                 235                 240

Leu Thr Gly Tyr Ser Leu Asp Gln Ile Leu Gly Arg Asn Cys Arg Phe
                245                 250                 255

Leu Gln Gly Pro Glu Thr Asp Pro Arg Ala Val Asp Lys Ile Arg Asn
            260                 265                 270

Ala Ile Thr Lys Gly Val Asp Thr Ser Val Cys Leu Leu Asn Tyr Arg
        275                 280                 285

Gln Asp Gly Thr Thr Phe Trp Asn Leu Phe Phe Val Ala Gly Leu Arg
    290                 295                 300

Asp Ser Lys Gly Asn Ile Val Asn Tyr Val Gly Val Gln Ser Lys Val
305                 310                 315                 320

Ser Glu Asp Tyr Ala Lys Leu Leu Val Asn Glu Gln Asn Ile Glu Tyr
                325                 330                 335

Lys Gly Val Arg Thr Ser Asn Met Leu Arg Arg Lys
            340                 345
```

<210> SEQ ID NO 63
<211> LENGTH: 183
<212> TYPE: PRT
<213> ORGANISM: Fucus distichus

<400> SEQUENCE: 63

```
Gly Val Thr Arg Arg Ser Ser Lys Glu Glu Gln Ala Lys Lys
1               5                   10                  15
```

-continued

Arg Arg Glu Arg Asn Arg Val Leu Ala Arg Arg Thr Arg Leu Arg Lys
            20                  25                  30

Lys Phe Phe Phe Gln Ser Leu Gln Gln Val Asn Asp Leu Gln Tyr
        35                  40                  45

Val Asn Glu Arg Leu Lys Gly Ile Ile Asn Thr Arg Cys Ala Asn Asn
50                  55                  60

Ser Ala Glu Ile Ile Arg Ser Cys Val Ser Arg Val Pro Ser Met Val
65                  70                  75                  80

Ala Asp Cys Ala Asn Gln Ala Thr Ala Leu Leu Glu Gln Ser Asp Phe
                85                  90                  95

Leu Leu Val Lys Ala Leu Gln Ser Ser Gln Pro Ser Phe Cys Val Thr
            100                 105                 110

Asp Pro Gln Leu Pro Asp Asn Pro Ile Val Tyr Ala Ser Asn Thr Phe
        115                 120                 125

Ile Glu Leu Thr Gly Tyr Asp Arg Ser Gln Val Leu Gly Arg Asn Cys
130                 135                 140

Arg Phe Leu Gln Gly Pro Asp Thr Asp Pro Asp Ala Val Ala Lys Ile
145                 150                 155                 160

Arg Lys Gly Ile Glu Glu Gly Lys Asp Thr Ser Val Phe Leu Arg Gln
                165                 170                 175

Tyr Lys Ala Asp Gly Thr Val
            180

<210> SEQ ID NO 64
<211> LENGTH: 360
<212> TYPE: PRT
<213> ORGANISM: Nannochloropsis gaditana

<400> SEQUENCE: 64

Met Ala Ala Ile Met Leu Gln Gln Pro Gln Cys Lys Val Pro Thr Ser
1               5                   10                  15

Leu Leu Pro Val Tyr Ser Arg Ala Gln Gly Gly Gln Ser Gly Asp Leu
            20                  25                  30

Asp Leu Asn Met Glu Gln Leu Leu Glu Ala Tyr Val Leu Asp Glu Gly
        35                  40                  45

Met Asp Leu Asp Phe Leu Asp Gly Thr Asn Ile Ser Asp Thr Ser Lys
50                  55                  60

Asp Thr Ala Pro Asn Asn Ile Ser Asp Leu Asp Leu Asp Glu Met
65                  70                  75                  80

Ala Asp Gly Val Gly Ile Asp Ser Glu Gly Asp Ile Val Lys Thr Gly
                85                  90                  95

Gly Lys Ser Lys Lys Arg Lys Thr Ser Gly Trp Ser Gly Ser Gly Ser
            100                 105                 110

Ser Ile Pro Arg Lys Lys Ser His Glu Gln Met Glu Arg Arg Arg Glu
        115                 120                 125

Arg Asn Arg Ile Leu Ala Arg Thr Arg Leu Arg Lys Lys Phe Ile
130                 135                 140

Phe Glu Ser Leu Gln Lys Gln Val Met Asp Leu Lys Arg Gln Asn Ser
145                 150                 155                 160

Arg Leu Lys Ser Ile Val Lys Asp Lys Met Ala Asp Gln Ala Ser Glu
                165                 170                 175

Val Leu Gly Ala Cys Thr Met Arg Leu Pro Ser Ile Val Thr Glu Ser
            180                 185                 190

Met Ala Glu Ala Ser Thr Val Leu Asp Arg Gly Asp Phe Asn Leu Ile

```
                195                 200                 205
Lys Ala Leu Gln Thr Thr Gln Gln Ser Phe Val Val Thr Asp Pro Ser
    210                 215                 220

Leu Pro Asp Asn Pro Ile Val Phe Ala Ser Gln Gly Phe Leu Glu Met
225                 230                 235                 240

Thr Gly Tyr Ser Met Ser Gln Val Leu Gly Arg Asn Cys Arg Phe Leu
                245                 250                 255

Gln Gly Pro Arg Thr Asp Gln Ala Thr Val Ala Gln Ile Arg Lys Gly
            260                 265                 270

Ile Ala Glu Gly Ala Asp Thr Ser Val Ala Leu Leu Asn Tyr Lys Val
        275                 280                 285

Asp Gly Thr Pro Phe Trp Asn Gln Phe Phe Val Ala Pro Leu Arg Asp
    290                 295                 300

Leu Asn Gly Glu Val Val Tyr Phe Val Gly Ala Gln Ser Lys Ile Asp
305                 310                 315                 320

Arg Pro Leu Glu Glu Ile Glu Lys Asp Ala Ala Glu Arg Ala Arg Gln
                325                 330                 335

Glu Ala Glu Glu Arg Asn Val Ala Gly Leu Ala Ser Gly Glu Gly Glu
            340                 345                 350

Glu Glu Glu Asp Glu Glu Asp
            355                 360

<210> SEQ ID NO 65
<211> LENGTH: 465
<212> TYPE: PRT
<213> ORGANISM: Nannochloropsis gaditana

<400> SEQUENCE: 65

Met Ala Ala Ile Gln Gln Pro Thr Ser Trp Gly Ile Leu Ser Arg Asn
1               5                   10                  15

Asn Ser Ser Thr Asp Leu Ala Gly Glu Ala Gly Gly Leu Glu Ala Pro
            20                  25                  30

Asp Gln Ile Lys Gln Glu Ala Ala Pro Leu Trp Thr Ala Pro Leu
        35                  40                  45

Tyr Ala Ser Ala Asn Asn Ser Asn Pro Met Ala Asp Thr Val Asp Leu
    50                  55                  60

Asp Glu Ile Phe Ala Asp Asp Phe Leu Leu Pro Gly Met Gly Met Val
65                  70                  75                  80

Pro Phe Gly Thr Glu Gly Asp Met Gly Pro Glu Asp Met Phe Pro Gly
                85                  90                  95

Gly Leu Ser Cys Asp Thr Ser Val Ala Thr Asn Asp Asn Asp Ser
            100                 105                 110

Ala Val Ala Ser Gly Met His Gly Lys Gly Lys Gly Ala Gln Phe Ala
        115                 120                 125

Asn Ala Ala Pro Gln Gly Glu Thr Glu Asp Lys Thr Asn Val Arg Ala
    130                 135                 140

Ala Ala Val Val Arg Ser Ala Ala Ser Arg Thr Arg Ser Gly Ile Thr
145                 150                 155                 160

Thr Arg Leu Gly Leu Asn Lys Gly Gln Gly Arg Ala Val Thr Gly Ala
                165                 170                 175

Ser Ser Met Leu Pro Ser Ala Val Pro Ser Arg Ala Arg Val Pro Thr
            180                 185                 190

Arg Lys Gly Ser Leu Pro Val Glu Glu Glu Asp Val Glu Glu Glu
        195                 200                 205
```

```
Glu Glu Glu Tyr Glu Thr Gly Ser Glu Glu Gly Gly Gly Asp
    210             215             220

Gly Arg Gly Ala Arg Arg Lys Lys Ala Lys Leu Thr Leu Lys Pro
225             230             235             240

Leu Thr Glu Ala Gln Arg Val Glu Arg Glu Arg Asn Arg Glu His
            245             250             255

Ala Lys Arg Ser Arg Met Arg Lys Lys Phe Met Leu Glu Ser Leu Gln
            260             265             270

Ala Gln Met Leu Ala Leu Arg Lys Glu Asn Leu Arg Leu Arg Gln Leu
        275             280             285

Val Ala Thr Lys Leu Pro Asp Lys Ala Asp Thr Ile Leu Arg Gly Cys
290             295             300

Ser Ser Ile Lys Thr Gln Asn Leu Leu Ser Ser Val Glu Leu Gly His
305             310             315             320

His Arg Ala Leu Ala Asp His Asp Gly Arg Leu Val Ser Ala Leu Gln
            325             330             335

Phe Ala Gln Gln Asn Phe Thr Val Ser Asp Pro Ser Leu Pro Asp Asn
        340             345             350

Pro Ile Ile Tyr Ala Ser Gln Gly Phe Leu Asp Leu Thr Gly Tyr Thr
        355             360             365

Ser Asp Gln Ile Val Gly Arg Asn Cys Arg Phe Leu Gln Gly Pro Gly
370             375             380

Thr Asp Pro Ala Ala Val Asp Ile Ile Arg Arg Gly Val Ala Leu Gly
385             390             395             400

Glu Asp Thr Ser Val Cys Leu Leu Asn Tyr Arg Ala Asp Gly Thr Pro
            405             410             415

Phe Trp Asn Gln Phe Phe Val Ala Ala Leu Arg Asp Met Glu Gly Asn
        420             425             430

Ile Val Asn Tyr Val Gly Val Gln Cys Lys Val Glu Glu Ala Pro Met
            435             440             445

Glu Glu Glu Leu Lys Glu Arg Val Lys Thr Ile Asn Phe Asp Glu Glu
    450             455             460

Glu
465

<210> SEQ ID NO 66
<211> LENGTH: 338
<212> TYPE: PRT
<213> ORGANISM: Sargassum fusiforme

<400> SEQUENCE: 66

Met Arg Thr Ser Leu Ser Gln Gly Ile Gly Ile Gly Ser Gly Gly Pro
1               5                   10                  15

Gly Gly Val Gly Ile Arg Gly Ile Thr Ser Val Ala Pro Pro Ser Gly
            20                  25                  30

Tyr Arg Gly Arg Gly Ser Tyr Ala Gly Ser Leu Pro Arg Arg Gln Arg
        35                  40                  45

His Lys Val Ser Ser Lys Asp Leu Thr Glu Glu Gln Arg Asn Glu Arg
    50                  55                  60

Arg Glu Arg Asn Arg Glu His Ala Lys Arg Ser Arg Val Arg Lys Lys
65                  70                  75                  80

Phe Leu Leu Asp Ser Leu Gln Arg Ser Val Asp Ala Leu Gln Ala Glu
                85                  90                  95

Asn Glu Ser Leu Lys Gly Ser Ile Ile Gly Ser Leu Gly Gln His Gly
            100                 105                 110
```

Arg Glu Leu Val Ala Lys Cys Ser Pro Glu Ala Glu Ser Thr Leu
            115                 120                 125

Val Thr Ala Asn Pro Thr Gln Ala Thr Lys Ile Leu Asp Asp Pro Asp
    130                 135                 140

Tyr Ser Leu Val Lys Ala Leu Gln Thr Ala Gln Gln Asn Phe Val Ile
145                 150                 155                 160

Thr Asp Ala Ser Pro Pro Asp Asn Pro Ile Val Phe Ala Ser Asn Gly
                165                 170                 175

Phe Leu Glu Leu Thr Arg Tyr Lys Leu Asn Glu Val Leu Gly Arg Asn
            180                 185                 190

Cys Arg Phe Leu Gln Gly Pro Glu Thr Asp Pro Arg Ala Val Asp Lys
            195                 200                 205

Ile Arg Thr Ala Ile Asp Glu Gly Tyr Asp Thr Ser Val Cys Leu Leu
    210                 215                 220

Asn Tyr Arg Ala Asp Asp Thr Thr Phe Trp Asn Gln Phe Phe Val Ala
225                 230                 235                 240

Ala Leu Arg Asp Gly Glu Gly Asn Thr Val Asn Tyr Val Gly Val Gln
                245                 250                 255

Cys Lys Val Gly Asp Asp Tyr Ala Arg Ile Val Val Asn Ala Gln Lys
            260                 265                 270

Lys Gln Leu Ala Arg Ser Gly Ser Ala Ala Gly Ser Thr Arg Arg Gly
            275                 280                 285

Pro Gln Thr Gln Arg Glu Gln Pro Val Leu Arg Pro Ser Thr Ser Gly
    290                 295                 300

Thr Ala Ala Ile Leu Thr Val Asp Ala Phe Ser Gly Ala Ser Ala Ala
305                 310                 315                 320

Phe Ala Ala Glu Ser Arg Gln Gly Gln Gly Gln Gly Gln Gly Gly Ala
                325                 330                 335

Asp Ile

<210> SEQ ID NO 67
<211> LENGTH: 346
<212> TYPE: PRT
<213> ORGANISM: Chlamydomonas reinhardtii

<400> SEQUENCE: 67

Met Val Glu Lys Met His Thr Lys Val Cys Ile Ile Gly Ser Gly Pro
1               5                   10                  15

Ala Ala His Thr Ala Ala Val Tyr Thr Ala Arg Ala Glu Leu Gln Pro
                20                  25                  30

Ile Leu Phe Glu Gly Phe Met Ala Asn Gly Ile Ala Ala Gly Gly Gln
            35                  40                  45

Leu Thr Thr Thr Thr Asp Val Glu Asn Phe Pro Gly Phe Pro Glu Gly
    50                  55                  60

Ile Leu Gly Ala Glu Leu Thr Thr Arg Phe Arg Glu Gln Ser Glu Arg
65                  70                  75                  80

Phe Gly Thr Arg Ile Tyr Ser Glu Thr Val Asp Ser Ile Asp Thr Ser
                85                  90                  95

Arg Arg Pro Phe Thr Val Arg Thr Ala Asp Lys Glu Val Thr Ala Asp
                100                 105                 110

Ser Leu Ile Ile Ala Thr Gly Ala Val Ala Arg Leu Glu Phe Pro
            115                 120                 125

Gly Ser Gly Glu Glu Gly Gly Phe Trp Asn Arg Gly Ile Ser Ala Cys
            130                 135                 140

```
Ala Val Cys Asp Gly Ala Ala Pro Ile Phe Arg Asn Lys Pro Ile Ala
145                 150                 155                 160

Val Ile Gly Gly Gly Asp Ser Ala Met Glu Glu Ala Thr Phe Leu Thr
                165                 170                 175

Lys Tyr Gly Ser Lys Val Tyr Ile Ile His Arg Arg Asp Ser Phe Arg
            180                 185                 190

Ala Ser Lys Ile Met Ala Lys Arg Ala Leu Glu His Pro Lys Ile Glu
        195                 200                 205

Val Leu Trp Asn Ser Val Val Glu Glu Ala Tyr Gly Asn Glu Lys Gly
    210                 215                 220

Leu Leu Gly Gly Val Lys Val Lys Asp Val Val Thr Gly Glu Leu His
225                 230                 235                 240

Asp Leu Pro Val Ser Gly Leu Phe Phe Ala Ile Gly His Gln Pro Ala
                245                 250                 255

Thr Ala Phe Leu Asn Gly Gln Leu Ala Leu Asp Ala Glu Gly Tyr Ile
                260                 265                 270

Val Thr Ala Pro Asp Ser Thr Ala Thr Ser Val Pro Gly Val Phe Ala
            275                 280                 285

Ala Gly Asp Val Gln Asp Lys Lys Trp Arg Gln Ala Ile Thr Ala Ala
        290                 295                 300

Gly Thr Gly Cys Met Ala Ala Leu Glu Ala Glu His Phe Ile Ser Ala
305                 310                 315                 320

His Glu Ala Glu Pro Glu Ala Asp Gly Ala Lys Glu Pro Ala Ala Ala
                325                 330                 335

Ala Ala Ala Pro Val Ala Asp Gly Asn Leu
                340                 345

<210> SEQ ID NO 68
<211> LENGTH: 536
<212> TYPE: PRT
<213> ORGANISM: Chlamydomonas reinhardtii

<400> SEQUENCE: 68

Met Ile Gln Leu Pro Ala Thr Val Val Gln Arg Arg Ala Pro Ile Gly
1               5                   10                  15

Ala Pro Ser Ala Val Gly Ala Cys Asn Pro Val Ala Gly Arg His Arg
            20                  25                  30

Ala Ala Pro Ala Leu Ala Ser Arg Thr Arg Thr Val Ala Thr Pro Ala
        35                  40                  45

Thr Ala Ala Pro Ala Ala Thr Ser Thr Gln Gln Val Ala Asp Val Glu
    50                  55                  60

Asn Val Val Ile Ile Gly Ser Gly Pro Ala Gly Tyr Thr Ala Ala Ile
65                  70                  75                  80

Tyr Ala Ala Arg Ala Asn Leu Lys Pro Val Val Phe Glu Gly Phe Arg
                85                  90                  95

Asn Gly Arg Gly Gly Gln Leu Met Thr Thr Thr Glu Val Glu Asn Phe
            100                 105                 110

Pro Gly Phe Pro Glu Gly Ile Thr Gly Pro Asp Leu Met Asp Arg Met
        115                 120                 125

Arg Lys Gln Ala Glu Arg Trp Gly Ser Glu Leu Tyr Thr Glu Asp Val
    130                 135                 140

Glu Gln Val Asp Leu Ser Val Arg Pro Phe Val Ile Arg Ser Ser Asp
145                 150                 155                 160

Arg Glu Leu Arg Ala His Ser Val Ile Ile Ala Thr Gly Ala Thr Ala
```

165                 170                 175

Lys Arg Leu Gly Leu Pro Ser Glu Asn Thr Phe Trp Ser Arg Gly Ile
            180                 185                 190

Ser Ala Cys Ala Ile Cys Asp Gly Ala Ser Pro Leu Phe Lys Asn Ala
            195                 200                 205

Glu Val Ala Val Val Gly Gly Asp Ser Ala Thr Glu Glu Ala Val
210                 215                 220

Tyr Val Thr Lys Tyr Ala Lys His Val His Leu Leu Val Arg Gly Glu
225                 230                 235                 240

Arg Met Arg Ala Ser Lys Ala Met Gln Asp Arg Val Leu Ala Asn Pro
                245                 250                 255

Arg Ile Thr Val His Phe Asn Thr Gly Ile Glu Asp Ala Phe Gly Gly
            260                 265                 270

Glu Val Leu Gln Gly Leu Arg Leu Phe Asp Thr Arg Thr Gly Glu Lys
            275                 280                 285

Arg Ser Leu Asp Val Gln Gly Met Phe Tyr Gly Ile Gly His Thr Pro
            290                 295                 300

Asn Ser Lys Leu Val Ala Gly Gln Val Glu Leu Asp Glu Ala Gly Tyr
305                 310                 315                 320

Val Lys Val Ala His Gly Ala Ala Thr Ser Val Pro Gly Val Phe Ser
                325                 330                 335

Ala Gly Asp Leu His Asp Thr Glu Trp Arg Gln Ala Ile Thr Ala Ala
            340                 345                 350

Gly Ser Gly Cys Met Ala Ala Leu Ser Ala Glu Arg Tyr Leu Thr Ala
            355                 360                 365

Asn Asn Leu Val Arg Glu Phe Lys Gln Lys Asp Glu Pro Ala Ala His
            370                 375                 380

Gly His Ala Ala Ala Gly Gly Asn Gly Asn Gly His Ala
385                 390                 395                 400

Ala Ala Ala Ala Asn Gly Gly Ser Glu Ala Lys Ala Thr Ser Ser Ile
                405                 410                 415

Asp Thr Pro Glu Thr Phe Asp Leu Ser Ala Asp Lys His Lys Gly Gln
            420                 425                 430

Tyr Ala Leu Arg Lys Leu Tyr His Glu Ser Asp Arg Leu Ile Cys Val
            435                 440                 445

Leu Tyr Thr Ser Pro Thr Cys Gly Pro Cys Arg Thr Leu Lys Pro Ile
450                 455                 460

Phe Asn Gly Val Val Asp Glu Tyr Thr Gly Lys Val His Tyr Val Glu
465                 470                 475                 480

Ile Asp Ile Glu Gln Asp Pro Glu Ile Ala Glu Ala Gly Val Met
                485                 490                 495

Gly Thr Pro Thr Val Gln Met Phe Lys Asp Lys Ala Arg Val Glu Gln
            500                 505                 510

Leu Ser Gly Val Lys Met Lys Lys Asp Tyr Arg Ala Ile Ile Glu Lys
            515                 520                 525

Tyr Val Pro Ala Ala Val Ser Ala
530                 535

<210> SEQ ID NO 69
<211> LENGTH: 59
<212> TYPE: PRT
<213> ORGANISM: Artificial sequence
<220> FEATURE:
<223> OTHER INFORMATION: artificial sequence
<220> FEATURE:

```
<221> NAME/KEY: Xaa
<222> LOCATION: (1)..(1)
<223> OTHER INFORMATION: selected from Leu, Ise, Val
<220> FEATURE:
<221> NAME/KEY: Xaa
<222> LOCATION: (3)..(3)
<223> OTHER INFORMATION: selected from any amino acid
<220> FEATURE:
<221> NAME/KEY: Xaa
<222> LOCATION: (5)..(6)
<223> OTHER INFORMATION: selected from any amino acid
<220> FEATURE:
<221> NAME/KEY: Xaa
<222> LOCATION: (7)..(7)
<223> OTHER INFORMATION: selected from Gly, Ser, Ala
<220> FEATURE:
<221> NAME/KEY: Xaa
<222> LOCATION: (8)..(8)
<223> OTHER INFORMATION: selected from any amino acid
<220> FEATURE:
<221> NAME/KEY: Xaa
<222> LOCATION: (9)..(9)
<223> OTHER INFORMATION: selected from Val, Ise, Ala, Leu
<220> FEATURE:
<221> NAME/KEY: Xaa
<222> LOCATION: (10)..(16)
<223> OTHER INFORMATION: selected from any amino acid
<220> FEATURE:
<221> NAME/KEY: Xaa
<222> LOCATION: (18)..(20)
<223> OTHER INFORMATION: selected from any amino acid
<220> FEATURE:
<221> NAME/KEY: Xaa
<222> LOCATION: (23)..(23)
<223> OTHER INFORMATION: selected from any amino acid
<220> FEATURE:
<221> NAME/KEY: Xaa
<222> LOCATION: (24)..(24)
<223> OTHER INFORMATION: selected from Lys, Arg
<220> FEATURE:
<221> NAME/KEY: Xaa
<222> LOCATION: (25)..(25)
<223> OTHER INFORMATION: selected from any amino acid
<220> FEATURE:
<221> NAME/KEY: Xaa
<222> LOCATION: (26)..(26)
<223> OTHER INFORMATION: selected from Ile, leu, Val
<220> FEATURE:
<221> NAME/KEY: Xaa
<222> LOCATION: (27)..(42)
<223> OTHER INFORMATION: selected from any amino acid
<220> FEATURE:
<221> NAME/KEY: Xaa
<222> LOCATION: (43)..(43)
<223> OTHER INFORMATION: selected from Asp, Glu
<220> FEATURE:
<221> NAME/KEY: Xaa
<222> LOCATION: (44)..(51)
<223> OTHER INFORMATION: selected from any amino acid
<220> FEATURE:
<221> NAME/KEY: Xaa
<222> LOCATION: (52)..(52)
<223> OTHER INFORMATION: selected from His, Ser
<220> FEATURE:
<221> NAME/KEY: Xaa
<222> LOCATION: (53)..(54)
<223> OTHER INFORMATION: selected from any amino acid
<220> FEATURE:
<221> NAME/KEY: Xaa
<222> LOCATION: (55)..(56)
<223> OTHER INFORMATION: selected from Ile, Val, Leu
<220> FEATURE:
<221> NAME/KEY: Xaa
<222> LOCATION: (57)..(57)
<223> OTHER INFORMATION: selected from Val, Ile, Leu
<220> FEATURE:
<221> NAME/KEY: Xaa
<222> LOCATION: (58)..(58)
<223> OTHER INFORMATION: selected from any amino acid
```

-continued

```
<220> FEATURE:
<221> NAME/KEY: Xaa
<222> LOCATION: (59)..(59)
<223> OTHER INFORMATION: selected from Leu, Ile, Val, Gln

<400> SEQUENCE: 69

Xaa Gly Xaa Gly Xaa Xaa Xaa Xaa Xaa Xaa Xaa Xaa Xaa Xaa Xaa
1               5                   10                  15

Thr Xaa Xaa Xaa Val Ala Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55

<210> SEQ ID NO 70
<211> LENGTH: 30
<212> TYPE: PRT
<213> ORGANISM: artificial sequence
<220> FEATURE:
<223> OTHER INFORMATION: artificial sequence
<220> FEATURE:
<221> NAME/KEY: Xaa
<222> LOCATION: (1)..(1)
<223> OTHER INFORMATION: Xaa is selected from His, Tyr, Phe
<220> FEATURE:
<221> NAME/KEY: Xaa
<222> LOCATION: (2)..(4)
<223> OTHER INFORMATION: Xaa is selected from any amino acid
<220> FEATURE:
<221> NAME/KEY: Xaa
<222> LOCATION: (5)..(5)
<223> OTHER INFORMATION: Xaa is selected from Leu, Ise, Val
<220> FEATURE:
<221> NAME/KEY: Xaa
<222> LOCATION: (6)..(6)
<223> OTHER INFORMATION: Xaa is selected from any amino acid
<220> FEATURE:
<221> NAME/KEY: Xaa
<222> LOCATION: (7)..(7)
<223> OTHER INFORMATION: Xaa is selected from His, Tyr, Phe
<220> FEATURE:
<221> NAME/KEY: Xaa
<222> LOCATION: (8)..(8)
<223> OTHER INFORMATION: Xaa is selected from any amino acid
<220> FEATURE:
<221> NAME/KEY: Xaa
<222> LOCATION: (10)..(10)
<223> OTHER INFORMATION: Xaa is selected from Leu, Ise, Val
<220> FEATURE:
<221> NAME/KEY: Xaa
<222> LOCATION: (11)..(11)
<223> OTHER INFORMATION: Xaa is selected from Lys, Arg
<220> FEATURE:
<221> NAME/KEY: Xaa
<222> LOCATION: (12)..(13)
<223> OTHER INFORMATION: Xaa is selected from any amino acid
<220> FEATURE:
<221> NAME/KEY: Xaa
<222> LOCATION: (14)..(14)
<223> OTHER INFORMATION: Xaa is selected from Asn, Asp, Glu
<220> FEATURE:
<221> NAME/KEY: Xaa
<222> LOCATION: (15)..(15)
<223> OTHER INFORMATION: Xaa is selected from Ile, Leu, Val
<220> FEATURE:
<221> NAME/KEY: Xaa
<222> LOCATION: (16)..(16)
<223> OTHER INFORMATION: Xaa is selected from Leu, Phe, Ile, Val
<220> FEATURE:
<221> NAME/KEY: Xaa
<222> LOCATION: (17)..(17)
<223> OTHER INFORMATION: Xaa is selected from Ile, Leu, Val, Phe
<220> FEATURE:
```

```
<221> NAME/KEY: Xaa
<222> LOCATION: (18)..(26)
<223> OTHER INFORMATION: Xaa is selected from any amino acid
<220> FEATURE:
<221> NAME/KEY: Xaa
<222> LOCATION: (28)..(28)
<223> OTHER INFORMATION: Xaa is selected from Phe, Leu, Tyr
<220> FEATURE:
<221> NAME/KEY: misc_feature
<222> LOCATION: (29)..(29)
<223> OTHER INFORMATION: Xaa can be any naturally occurring amino acid

<400> SEQUENCE: 70

Xaa Xaa Xaa Xaa Xaa Xaa Xaa Xaa Asp Xaa Xaa Xaa Xaa Xaa Xaa
1               5                   10                  15

Xaa Xaa Xaa Xaa Xaa Xaa Xaa Xaa Xaa Xaa Asp Xaa Xaa Gly
            20                  25                  30

<210> SEQ ID NO 71
<211> LENGTH: 10
<212> TYPE: PRT
<213> ORGANISM: artificial sequence KA1 domain
<220> FEATURE:
<223> OTHER INFORMATION: KA1 domain artificial sequence
<220> FEATURE:
<221> NAME/KEY: Xaa
<222> LOCATION: (1)..(1)
<223> OTHER INFORMATION: selected from Val, Ile, Leu, Met
<220> FEATURE:
<221> NAME/KEY: Xaa
<222> LOCATION: (2)..(2)
<223> OTHER INFORMATION: selected from Tyr, Arg
<220> FEATURE:
<221> NAME/KEY: Xaa
<222> LOCATION: (3)..(3)
<223> OTHER INFORMATION: selected from Phe, Trp, Leu
<220> FEATURE:
<221> NAME/KEY: Xaa
<222> LOCATION: (4)..(4)
<223> OTHER INFORMATION: selected from Asp, Glu
<220> FEATURE:
<221> NAME/KEY: Xaa
<222> LOCATION: (5)..(5)
<223> OTHER INFORMATION: selected from any amino acid
<220> FEATURE:
<221> NAME/KEY: Xaa
<222> LOCATION: (6)..(6)
<223> OTHER INFORMATION: selected from Glu, Gln
<220> FEATURE:
<221> NAME/KEY: Xaa
<222> LOCATION: (7)..(7)
<223> OTHER INFORMATION: selected from Val, Ile, Leu, Met
<220> FEATURE:
<221> NAME/KEY: Xaa
<222> LOCATION: (8)..(8)
<223> OTHER INFORMATION: selected from Cys, Val, Tyr
<220> FEATURE:
<221> NAME/KEY: Xaa
<222> LOCATION: (9)..(9)
<223> OTHER INFORMATION: selected from Tyr, Arg, Gln
<220> FEATURE:
<221> NAME/KEY: Xaa
<222> LOCATION: (9)..(9)
<223> OTHER INFORMATION: selected from Lys, Arg, Gln
<220> FEATURE:
<221> NAME/KEY: Xaa
<222> LOCATION: (10)..(10)
<223> OTHER INFORMATION: selected from Leu, Val, Ala, Met

<400> SEQUENCE: 71

Xaa Xaa Xaa Xaa Xaa Xaa Xaa Xaa Xaa Xaa
1               5                   10

<210> SEQ ID NO 72
```

```
<211> LENGTH: 26
<212> TYPE: PRT
<213> ORGANISM: artificial sequence KA1 domain
<220> FEATURE:
<223> OTHER INFORMATION: artificial sequence
<220> FEATURE:
<221> NAME/KEY: Xaa
<222> LOCATION: (1)..(1)
<223> OTHER INFORMATION: amino acid selected from Tyr, Asn, His
<220> FEATURE:
<221> NAME/KEY: Xaa
<222> LOCATION: (2)..(2)
<223> OTHER INFORMATION: amino acid selected from Gly, Val, Leu, Ser
<220> FEATURE:
<221> NAME/KEY: Xaa
<222> LOCATION: (3)..(3)
<223> OTHER INFORMATION: amino acid selected from Val, Leu, Ise
<220> FEATURE:
<221> NAME/KEY: Xaa
<222> LOCATION: (4)..(5)
<223> OTHER INFORMATION: amino acid selected from any amino acid
<220> FEATURE:
<221> NAME/KEY: Xaa
<222> LOCATION: (6)..(6)
<223> OTHER INFORMATION: amino acid selected from Lys, Arg, Gln
<220> FEATURE:
<221> NAME/KEY: Xaa
<222> LOCATION: (7)..(7)
<223> OTHER INFORMATION: amino acid selected from Arg, Lys
<220> FEATURE:
<221> NAME/KEY: Xaa
<222> LOCATION: (8)..(8)
<223> OTHER INFORMATION: amino acid selected from Leu, Ile, Val, Met
<220> FEATURE:
<221> NAME/KEY: Xaa
<222> LOCATION: (10)..(10)
<223> OTHER INFORMATION: amino acid selected from Asp, Phe, Glu
<220> FEATURE:
<221> NAME/KEY: Xaa
<222> LOCATION: (11)..(13)
<223> OTHER INFORMATION: amino acid selected from any amino acid
<220> FEATURE:
<221> NAME/KEY: Xaa
<222> LOCATION: (14)..(14)
<223> OTHER INFORMATION: amino acid selected from Tyr, Phe
<220> FEATURE:
<221> NAME/KEY: Xaa
<222> LOCATION: (15)..(16)
<223> OTHER INFORMATION: amino acid selected from any amino acid
<220> FEATURE:
<221> NAME/KEY: Xaa
<222> LOCATION: (17)..(17)
<223> OTHER INFORMATION: amino acid selected from Leu, Ise, Val, Thr
<220> FEATURE:
<221> NAME/KEY: Xaa
<222> LOCATION: (18)..(18)
<223> OTHER INFORMATION: amino acid selected from Ala, Cys, Val
<220> FEATURE:
<221> NAME/KEY: Xaa
<222> LOCATION: (19)..(20)
<223> OTHER INFORMATION: amino acid selected from any amino acid
<220> FEATURE:
<221> NAME/KEY: Xaa
<222> LOCATION: (21)..(21)
<223> OTHER INFORMATION: amino acid selected from  Ile, Leu, Val, Phe
<220> FEATURE:
<221> NAME/KEY: Xaa
<222> LOCATION: (22)..(24)
<223> OTHER INFORMATION: amino acid selected from Leu, Met, Ala
<220> FEATURE:
<221> NAME/KEY: Xaa
<222> LOCATION: (25)..(25)
<223> OTHER INFORMATION: amino acid selected from Lys, Arg, Glu, Asn
<220> FEATURE:
<221> NAME/KEY: Xaa
<222> LOCATION: (26)..(26)
<223> OTHER INFORMATION: amino acid selected from Leu, Ise, Val, Met

<400> SEQUENCE: 72
```

```
Xaa Xaa Xaa Xaa Xaa Xaa Xaa Xaa Gly Xaa Xaa Xaa Xaa Xaa Xaa Xaa
1               5                   10                  15

Xaa Xaa Xaa Xaa Xaa Xaa Xaa Xaa Xaa Xaa
            20                  25
```

<210> SEQ ID NO 73
<211> LENGTH: 32
<212> TYPE: PRT
<213> ORGANISM: artificial sequence ubiquitin associated domain
<220> FEATURE:
<223> OTHER INFORMATION: artificial sequence
<220> FEATURE:
<221> NAME/KEY: Xaa
<222> LOCATION: (1)..(1)
<223> OTHER INFORMATION: amino acid selected from Val, Ile, Leu, Thr
<220> FEATURE:
<221> NAME/KEY: Xaa
<222> LOCATION: (2)..(3)
<223> OTHER INFORMATION: amino acid selected from any amino acid
<220> FEATURE:
<221> NAME/KEY: Xaa
<222> LOCATION: (4)..(4)
<223> OTHER INFORMATION: amino acid selected from Leu, Ile, Met, Val
<220> FEATURE:
<221> NAME/KEY: Xaa
<222> LOCATION: (5)..(6)
<223> OTHER INFORMATION: amino acid selected from any amino acid
<220> FEATURE:
<221> NAME/KEY: Xaa
<222> LOCATION: (7)..(7)
<223> OTHER INFORMATION: amino acid selected from Met, Leu
<220> FEATURE:
<221> NAME/KEY: Xaa
<222> LOCATION: (8)..(8)
<223> OTHER INFORMATION: amino acid selected from Gly, Ser, Asn
<220> FEATURE:
<221> NAME/KEY: Xaa
<222> LOCATION: (9)..(9)
<223> OTHER INFORMATION: amino acid selected from Tyr, Phe, Val
<220> FEATURE:
<221> NAME/KEY: Xaa
<222> LOCATION: (10)..(10)
<223> OTHER INFORMATION: amino acid selected from Asp, Phe, Glu, Thr
<220> FEATURE:
<221> NAME/KEY: Xaa
<222> LOCATION: (11)..(11)
<223> OTHER INFORMATION: amino acid selected from Lys, Arg, Glu
<220> FEATURE:
<221> NAME/KEY: Xaa
<222> LOCATION: (12)..(12)
<223> OTHER INFORMATION: amino acid selected from  Asp, Glu, Asn
<220> FEATURE:
<221> NAME/KEY: Xaa
<222> LOCATION: (13)..(13)
<223> OTHER INFORMATION: amino acid selected from any amino acid
<220> FEATURE:
<221> NAME/KEY: Xaa
<222> LOCATION: (14)..(14)
<223> OTHER INFORMATION: amino acid selected from Cys, Ile, Val, Leu
<220> FEATURE:
<221> NAME/KEY: Xaa
<222> LOCATION: (15)..(15)
<223> OTHER INFORMATION: amino acid selected from any amino acid
<220> FEATURE:
<221> NAME/KEY: Xaa
<222> LOCATION: (16)..(16)
<223> OTHER INFORMATION: amino acid selected from Glu, Asn, Asp
<220> FEATURE:
<221> NAME/KEY: Xaa
<222> LOCATION: (17)..(17)
<223> OTHER INFORMATION: amino acid selected from Ala, Val, Ser
<220> FEATURE:
<221> NAME/KEY: Xaa
<222> LOCATION: (18)..(18)
<223> OTHER INFORMATION: amino acid selected from Leu, Tyr, Val
<220> FEATURE:

```
<221> NAME/KEY: Xaa
<222> LOCATION: (19)..(23)
<223> OTHER INFORMATION: amino acid selected from any amino acid
<220> FEATURE:
<221> NAME/KEY: Xaa
<222> LOCATION: (24)..(24)
<223> OTHER INFORMATION: amino acid selected from Arg, Gly, Asp, Ser
<220> FEATURE:
<221> NAME/KEY: Xaa
<222> LOCATION: (25)..(27)
<223> OTHER INFORMATION: amino acid selected from any amino acid
<220> FEATURE:
<221> NAME/KEY: Xaa
<222> LOCATION: (28)..(28)
<223> OTHER INFORMATION: amino acid selected from Ala, Val, Ser
<220> FEATURE:
<221> NAME/KEY: Xaa
<222> LOCATION: (29)..(31)
<223> OTHER INFORMATION: amino acid selected from any amino acid
<220> FEATURE:
<221> NAME/KEY: Xaa
<222> LOCATION: (32)..(32)
<223> OTHER INFORMATION: amino acid selected from a Leu, Ile, Val

<400> SEQUENCE: 73

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

PRODUCTIVITY AND BIOPRODUCT FORMATION IN PHOTOTROPIN KNOCK/OUT MUTANTS IN MICROALGAE

CROSS-REFERENCE TO RELATED APPLICATIONS

This application is a continuation of International Patent Application No. PCT/IB2016/054466, entitled "Improved Productivity and Bioproduct Formation in Phototropin Knock/Out Mutants in Microalgae", filed on Jul. 26, 2016, which claims priority to and benefit of the filing of U.S. Provisional Patent Application No. 62/171,176 entitled "Improved Productivity and Bioproduct Formation in Phototropin Knock/out Mutants in Microalgae" filed on Jun. 4, 2015, and the specification and claims thereof are incorporated herein by reference.

STATEMENT REGARDING FEDERALLY SPONSORED RESEARCH

This invention was made with government support under grants Nos. Prime Contract No. DE-AC52-06NA25396 and NMC subcontract No. 277529. The U.S. government has certain rights in the invention.

SEQUENCE LISTING

The instant application contains a Sequence Listing which has been submitted electronically in ASCII format and is hereby incorporated by reference in its entirety. Said ASCII copy, created on Dec. 4, 2017, is named PHOT_US_Sequences_120417_ST25.txt and is 316 Kbytes in size.

TECHNICAL FIELD

Disclosed embodiments of the present invention are in the field of improved performance of microalgae in the production of biological products such as but not limited to biofuels, biomass, pigments, starch, oils and the like through selection, mutagenesis or engineering to reduce expression or knockout the phototropin gene for example.

BACKGROUND

Phototropin is a blue light receptor, which mediates a variety of blue-light elicited physiological processes in plants and algae. In higher plants these processes include phototropism, chloroplast movement and stomatal opening. In the unicellular green alga *Chlamydomonas reinhardtii*, phototropin (PHOT) plays a vital role in the progression of the sexual life cycle and in the control of the eye spot size and light sensitivity. Phototropin is also involved in blue-light mediated changes in the synthesis of chlorophylls, carotenoids, and chlorophyll binding proteins. The UV-A/blue light sensing phototropins mediate a variety of light responses and are responsible in higher plants for optimization of photosynthetic yields (Chen, Chory et al. 2004).

Phototropins are commonly composed of two domains, an amine terminal photosensory domain and a carboxy terminal serine/threonine protein kinase domain. The photosensory domain is a flavin mononucleotide binding domain, the LOV domain. Plants and green algae contain two of these domains in the phototropin regulatory sequence, LOV1 and LOV2 (Chen, Chory et al. 2004).

Phototropin knock-out mutants (PHOT K/O) have been made previously in plants (Suetsugu and Wada 2007, Moni, Lee et al. 2015) and algae (Zorin, Lu et al. 2009; Trippens, Greiner et al. 2012). However, all the PHOT K/O mutant prior art that has been located to date did not show improved productivity of the plant or alga.

In plants two phototropins have been reported, phot1 and phot2, these phototropins share sequence homology and have overlapping functions. These blue-light-sensitive receptors consist of two parts: a C-terminal serine-threonine kinase and two LOV domains that bind flavin mononucleotide as chromophores at the N-terminus. Recently, in the unicellular green alga, *Chlamydomonas reinhardtii*, a phototropin homolog was identified. It exhibits photochemical properties similar to those of higher plant phototropins and is also functional in *Arabidopsis*. Studies show that the basic mechanism of phototropin action is highly conserved, even though its apparent physiological functions are quite diverse.

Phototropin in Higher Plants:

Plants utilize several families of photoreceptors to better react to their environment, allowing them to fine tune pathways controlled by the photoreceptors—phototropin, phytochrome, and cryptochrome (Chen, Chory et al. 2004).

In higher plants phototropin mediates a variety of blue-light elicited physiological processes (Sullivan, Thomson et al. 2008). Phototropins are UV-A/blue light sensing photoreceptors that are known to optimize photosynthetic yields (Chen, Chory et al. 2004). The involvement of phototropin in photomovement in higher plants is well documented (Suetsugu and Wada 2007, Kagawa, Kimura et al. 2009). Studies involving *Arabidopsis* mutants lacking the phot1 and phot2 genes have revealed that in addition to regulating hypocotyl curvature of seedlings towards blue light, phototropins also regulate a diverse range of responses in flowering plants. These responses include chloroplast movements, nuclear positioning, stomatal opening, leaf expansion, leaf movements and leaf photomorphogenesis.

Phototropin knock-out mutants (PHOT K/O) have been made previously in plants (Suetsugu and Wada 2007, Moni, Lee et al. 2015). For instance in *Physcomitrella patens* (a moss) there are three PHOT genes and they have all been knocked out in different mutants (Suetsugu and Wada 2007). The focus of the *P. patens* study was the effect of PHOT K/O on phototropism (movement toward light) and the phenotypes they observed allowed them to determine which of the genes were necessary for phototropism (Suetsugu and Wada 2007).

PHOT expression was higher in darkness than in light, and phot1 *Arabidopsis* mutants was shown to increase the number of lateral roots produced (Moni, Lee et al. 2015). phot was also demonstrated to mediate phototropism, chloroplast relocation and leaf expansion (Matsuoka, Iwata et al. 2007). Using phot deficient *Arabidopsis* mutants, phototropin 2 was linked to palisade parenchyma cell development of leaves (Kozuka, Kong et al. 2011).

Another study looked at the role of phototropin under low photosynthetically active radiation (Takemiya, Inoue et al. 2005). They found that the wild-type and the PHOT1 mutant both showed increased but similar growth in low radiance blue light super imposed on red light. In white light there was no increase in biomass in both phot1 and phot2 mutants as well as in the double phot mutant.

A study by Folta and colleagues investigated the relationship between phot1 and phototropism and growth inhibition in *Arabidopsis* (Folta, Lieg et al. 2003). They found that the onset of phototropism and the phot1-mediated growth inhibition coincided and postulated that both were due to phot1 expression.

There is a substantial amount of patent literature around phototropin in higher plants. However, the focus has been on the commercial utility of the upstream, light regulated areas rather than on the phototropin gene itself. These light control domains that regulate PHOT expression—the light-oxygen-voltage-sensing (LOV) domains—have been carefully evaluated for potential commercial application in higher plants.

Shu & Tsien application (US20130330718) focused on using the LOV domain for control of proteins that generate singlet oxygen (SOGs). These fusion protein tags could be used for imaging under blue light for research purposes.

Other patents use light switchable regulatory sequences and contemplate the use of the phototropin LOV domain such as Yang and colleagues (EP2682469).

Hahn & Karginov (WO2011133493) focused on allosteric regulation of kinases using the light activated domains for control of expression in engineered fusion proteins (such as the LOV domains).

Hahn and colleagues (U.S. Pat. No. 8,859,232) demonstrated that the LOV domain of phototropin can be used as a light activated switch for the activation or inactivation of fusion proteins of interest. They contemplated using a LOV domain that could contain substantial portions of the phototropin molecule in addition to the LOV domain. They contemplated using the LOV domain isolated from algae and gave the specific example of *Vaucheria frigida*, a stramenopile or heterokont alga.

Kinoshita and colleagues (WO2014142334) demonstrated that overexpression of phototropin had no impact of stomatal opening in higher plants.

Bonger and colleagues (US20140249295) used the LOV domain as a fusion with another functional protein wherein the light switching ability of the LOV domain was used to control the stability and/or function of the fusion protein.

Folta and colleagues (WO2014085626) using mutants of phototropin 1 were able to show that the function of phot1 is mediation of the pathway in which green light reverses the effects of red and/or blue light on plant growth.

Schmidt & Boyden (US20130116165) describe a new group of fusion proteins with light regulatory regions derived from *Avena sativa* phototropin 1. These regulatory domains are used for altering channel function in membranes.

To date there is no disclosure of the use of PHOT knockout or knockdown (suppression) technology to improve or algae plant productivity.

Phototropin in Algae:

Phototropin has already been well studied in several different algae including *Chlamydomonas reinhardtii* (Briggs and Olney 2001). However, there are indications that phototropins have diverged significantly or that the genes that function as phototropin are not very homologous to plant phototropin genes. For instance it was reported that in *Thalassiosira pseudonana* (a diatom) and *Cyanidioschyzon merolae* (unicellular red alga) no genes were found encoding the phototropins (Grossman 2005). However putative genes with photosensory LOV domains, aurechromes, have been reported for these and other photosynthetic stramenopiles (Table 1). Most aureochromes contain a single LOV domain and function as transcription factors that regulate cell division, chloroplast movement, pigment production, and phototropism. (Takahashi. J Plant Res (2016) 129:189-197)

In *Chlamydomonas reinhardtii*, phototropin plays a vital role in progression of the sexual life cycle (Huang and Beck 2003), control of the eye spot size and light sensitivity (Trippens, Greiner et al. 2012). Phototropin is also involved in blue-light mediated changes in the synthesis of chlorophylls, carotenoids, chlorophyll binding proteins. Phototropin has been localized to the flagella of *Chlamydomonas reinhardtii* (Huang, Kunkel et al. 2004). Phototropin is also known to be involved in expression of genes encoding chlorophyll and carotenoid biosynthesis and LHC apoproteins in *Chlamydomonas reinhardtii* (Im, Eberhard et al. 2006). The *Chlamydomonas reinhardtii* phototropin gene has been cloned and shown to function when expressed in *Arabidopsis* (Onodera, Kong et al. 2005).

Phototropin has been shown to control multiple steps in the sexual life cycle of *Chlamydomonas reinhardtii* (Huang and Beck 2003). PHOT knockdowns using RNAi were generated (Huang and Beck 2003). The entire focus of this study was on sexual mating and no mention of improved biomass, starch accumulation or photosynthesis rate was observed. It is also involved in the chemotaxis that is the initial phase of the sexual cycle of *Chlamydomonas reinhardtii* (Ermilova, Zalutskaya et al. 2004). However, no cell cycle implications of phototropin knockout or knockdowns have been published.

Detailed studies have carefully analyzed the function of the LOV domain in several algal species. An example is the *Chlamydomonas reinhardtii* mutant LOV2-C250S where careful studies of the light activation and regulation of this domain were carried out to better understand the mechanism of action (Sethi, Prasad et al. 2009).

Phototropin knock-out mutants (PHOT K/O) have been made previously in algae (Zorin, Lu et al. 2009 Trippens, Greiner et al. 2012). PHOT minus strains had larger eyespots than the parental strain (Trippens, Greiner et al. 2012). This study focused on the impact of PHOT on eyespot structure function. These authors used a knock-out mutant of PHOT to reduce expression of phototropin (Trippens, Greiner et al. 2012).

Novel phototropins have been described in the green alga *Ostreococcus tauri* and with a focus on their LOV domain structure/function (Veetil, Mittal et al. 2011).

Abad and colleagues (WO2013056212) provide the sequence for phototropin from a green alga, *Auxenochlorella protothecoides*, and indicate that the gene would be important for photosynthetic efficiency. However, they do not discuss the impact of deletion or inhibition of this gene on the alga.

Definitions

Unless otherwise defined, all technical and scientific terms have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned are incorporated by reference in their entirety. In case of conflict, the present specification and definitions will control. In addition, the materials, methods, and examples are illustrative only and not intended to be limiting for the practice of this invention.

Unless specifically referred to in the specification singular forms such as "a," "an," and "the," include their plural forms. As an example, "an alga" includes its plural form "algae" and "a plant" includes the plural "plants."

The term "algae" will refer to all organisms commonly referred to as algae including the prokaryotic cyanophyta (commonly called blue-green algae and cyanobacteria), prochlorophyta, glaucophyta, rhodophyta, heterokontophyta, haptophyte, cryptophyta, dinophyta, euglenophyta, chloroaracniophyta, chlorophyta, and those organisms of indeterminate nomenclature normally referred to as algae. A full description of these is found in the book "*Algae An Introduction to Phycology*" by Van Den Hoek, Mann & Jahns (1995), which is included by reference.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence.

The term "overexpression" as used herein refers to excessive expression of a gene product (RNA or protein) in greater-than-normal amounts.

The term "homologous" refers to the relationship between two proteins that possess a "common evolutionary origin", including proteins from superfamilies (e.g., the immunoglobulin superfamily) in the same species, as well as homologous proteins from different species.

As used herein, "identity" means the percentage of identical nucleotide or amino acid residues at corresponding positions in two or more sequences when the sequences are aligned to maximize sequence matching, i.e., taking into account gaps and insertions.

The term "sequence similarity" refers to the degree of identity or correspondence between nucleic acid or amino acid sequences that may or may not share a common evolutionary origin (Reeck, de Haen et al. 1987). However, in common usage and in the current invention, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 75%, and more preferably at least 80%, and more preferably at least 85%, and more preferably at least about 90% or at least about 95% of the nucleotides (or any integer value in between) match over a defined length of the nucleic acid sequences, as determined by a sequence comparison algorithm such as BLAST, CLUSTAL, MUSCLE, etc. An example of such a sequence is an allelic or species variant of the specific phototropin gene of the present invention. Sequences that are substantially homologous may also be identified by hybridization, e.g., in a Southern hybridization experiment under stringency conditions as defined for that particular system. The homology may be as high as about 93-95%, 98%, or 99% (or any integer value in between). For example, the sequence to which homology is matched is a wild-type parental line and the length of the sequence is the full length of the sequence from wild-type parental line.

Similarly, in particular embodiments of the invention, two amino acid sequences are "substantially homologous" or "substantially similar" when greater than 75% of the amino acid residues are identical wherein identical contemplates a conservative substitution at a nucleic acid position. In a preferred embodiment there is at least 80%, and more preferably at least 85%, and more preferably at least about 90% and more preferably at least about 90-95% of the amino acid residues are identical (or any integer value in between). Two sequences are functionally identical when greater than about 95% of the amino acid residues are similar. Preferably the similar or homologous polypeptide sequences are identified by alignment using, for example, the GCG (Genetics Computer Group, Version 7, Madison, Wis.) pileup program, or using any of the programs and algorithms described above. Conservative amino acid substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants or algae of the invention are those proteins that differ from a disclosed protein as the result of deletion or insertion of one or more amino acids in a native sequence.

The term "knockout" or "gene knockout" refers herein to any organism and/or its corresponding genome where the gene of interest has been rendered unable to perform its function. This can be accomplished by both classical mutagenesis, natural mutation, specific or random inactivation, targeting in cis or trans, or any method wherein the normal expression of a protein is altered to reduce its effect. For example but not to limit the definition 1) one can use chemical mutagenesis to damage the gene and then select for organisms not expressing the gene, 2) one can target the gene and remove a portion or all of the gene by homologous recombination, 3) one can use RNAi methods to produce an inhibitor molecule for a particular protein and similar methods and 4) one can use genome editing tools (i.e. CRISPR-Cas) to specifically modify the gene.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature (Sambrook, Fritsch et al. 1989, Ausubel, Brent et al. 1997, Green and Sambrook 2012).

The term "transcriptome" refers to the set of RNA molecules present in a population of cells. It often reflects how an organism responds to particular situations and is looking at what genes are regulated under a particular condition. Examples of transcriptome analyses on algae are found in the following references (Hwang, Jung et al. 2008, Rismani-Yazdi, Haznedaroglu et al. 2011, Fu, Wang et al. 2014, Koid, Liu et al. 2014).

The term "biofuel" refers to any fuel made through the application of biological processes not on a geological timescale. Examples include but are not limited to conversion of algal biomass to biocrude through hydrothermal liquefaction, anaerobic digestion of spent algal biomass for conversion to methane, extraction of lipid from algal biomass to convert to biodiesel, and conversion of water to biohydrogen through biological processes.

The term "bioproduct" is any product produced from biological processes either in whole or in part.

The term biomass productivity or production as used herein refers to the rate of generation of biomass in an ecosystem. It is usually expressed in units of mass per unit surface (or volume) per unit time, for instance grams per square metre per day ($g\ m^{-2}\ d^{-1}$). The mass unit may relate to biologically produced dry matter generated.

The term "sink molecules", "sink compounds", sink materials" refers to molecules used by an organism to store captured carbon. These can be but are not limited to sugars, starch, glycogen, lipids, fats, waxes, and similar biomolecules.

The publications discussed above are provided solely for their disclosure before the filing date of the present application. Nothing herein is to be construed as an admission that the invention is not entitled to antedate such disclosures by virtue of prior invention.

SUMMARY OF THE INVENTION

This and other unmet needs of the prior art are met by exemplary compositions and methods as described in more detail below.

One embodiment of the present invention provides for a method for increasing a biomass productivity of an algal strain wherein the expression or function of a *Chlamydomonas reinhardtii* phototropin gene, a gene substantially similar to the *Chlamydomonas reinhardtii* phototropin gene or a sequence substantially similar to SEQ ID NO 1-14 and 51-66 is reduced or eliminated. In a preferred embodiment the gene substantially similar has greater than 75% homology, more preferably greater than 80% homology to the *Chlamydomonas reinhardtii* phototropin gene or the sequence identified in SEQ ID NO 1-14 and 51-66.

For example, the biomass productivity of the algal strain is increased by greater than around 2-fold. The biomass production of storage product(s) in the algal strain is increased by greater than around 2-fold, for example the storage product(s) is selected from starch, lipid, pigments and other sink molecules and for example the productivity of biomass is increased by greater than around 2-fold. Further, the biomass productivity may be increased for bioproducts chosen from lipids, waxes, polysaccharides (e.g., starch, glycogen, mannans, glycans, cellulose, hemicellulose), pigments (e.g., xanthophyll). In a preferred embodiment the expression of the *Chlamydomonas reinhardtii* phototropin gene, the gene substantially similar to the *Chlamydomonas reinhardtii* phototropin gene or the sequence substantially similar to SEQ ID NO 1-14 and 51-66 is reduced by example chemical mutagenesis and selection, genome editing, trans acting elements (e.g., RNAi), and/or an inducible basis through an inducible promoter.

Another embodiment of the present invention provides for an algal strain wherein relative to the wild-type parental line the expression of the phototropin gene or a substantially similar gene is reduced, the photosynthetic pigments making up the antenna complex are reduced, and/or the content of sink molecules is increased. In a preferred embodiment the phototropin gene or a substantially similar gene been rendered to be non-functional. In a preferred embodiment the non-functional gene has been substantially deleted or is rendered to be non-functional on an inducible basis through an inducible promoter. In a preferred embodiment the algal line having the phototropin gene deletion would generate sterile and stable diploid population of polyploid algae to avoid recombination of genetic material during sexual reproduction or in another embodiment would be used to generate stable transgene-stacking traits in polyploid algal strains. In a preferred embodiment the photogropin gene or a substantially similar gene is selected from SEQ ID NO 1-14 and 51-66. In another preferred embodiment the gene the gene substantially similar has greater than 75% homology, or more preferably greater than 80% homology to the *Chlamydomonas reinhardtii* phototropin gene or the sequence identified in SEQ ID NO 1-14 and 51-66.

In another embodiment a method for increasing a biomass productivity of an algal strain wherein the expression or function of a *Chlamydomonas reinhardtii* NTR2 or NTRC gene, a gene substantially similar to a *Arabidopsis* NTR2 or NTRC gene or a sequence substantially similar to SEQ ID NO 35-50 and 67-68 is over expressed in the algal strain is provided. In a preferred embodiment the gene substantially similar has greater than 75% homology, or preferably greater than 80% homology to the *Arabidopsis* NTR2 or NTRC gene or the sequence identified in SEQ ID NO 35-50 and 67-68.

For example, the biomass productivity of the algal strain is increased by greater than around 2-fold. The biomass production of storage product(s) in the algal strain is increased by greater than around 2-fold, for example the storage product(s) is selected from starch, lipid, pigments and other sink molecules and for example the productivity of biomass is increased by greater than around 2-fold. Further, the biomass productivity may be increased for bioproducts chosen from lipids, waxes, polysaccharides (e.g., starch, glycogen, mannans, glycans, cellulose, hemicellulose), pigments (e.g., xanthophyll).

In yet another embodiment a method for increasing a productivity of an algal strain wherein the expression or function of a *Chlamydomonas reinhardtii* KIN10 or KIN11 gene, a gene substantially similar to a *Arabidopsis* KIN10 or KIN11 gene or a sequence substantially similar to SEQ ID NO 15-34 is over expressed in the algal strain is provided. In a preferred embodiment the gene substantially similar has greater than 75% homology, or preferably greater than 80% homology to the *Arabidopsis* KIN10 or KIN11 gene or the sequence identified in SEQ ID NO 15-34. For example, the biomass productivity of the algal strain is increased by greater than around 2-fold. The biomass production of storage product(s) in the algal strain is increased by greater than around 2-fold, for example the storage product(s) is selected from starch, lipid, pigments and other sink molecules and for example the productivity of biomass is increased by greater than around 2-fold. Further, the biomass productivity may be increased for bioproducts chosen from lipids, waxes, polysaccharides (e.g., starch, glycogen, mannans, glycans, cellulose, hemicellulose), pigments (e.g., xanthophyll).

Exemplary embodiments of the compositions, systems, and methods disclosed herein wherein algae are treated so as to reduce or eliminate the expression of phototropin or a heterologous gene with the same function such that improved productivity is achieved.

In one aspect, embodiments of the present invention provide an organism and the method to use such organism where the phototropin gene is knocked out and the photosynthetic rate is improved and the biomass productivity improves.

In a further aspect, the mutant is produced from *Chlamydomonas reinhardtii* and the biomass productivity is doubled.

Another embodiment of the present invention provides an organism with reduced PHOT expression wherein the sexual cycle is arrested and the genetic stability of the algal cell culture line is improved.

In a further embodiment the organism is derived from *Chlamydomonas reinhardtii* and has reduced promiscuity resulting in a more stable genotype and phenotype.

In one aspect, embodiments of the present invention provide an organism with reduced phototropin gene expression and the method to use such organism which as improved non-photochemical quenching providing the ability for better response to high light levels.

In one aspect, embodiments of the present invention provide an organism with reduced phototropin expression and the method to use such organism that results in higher levels of sink molecules, such as but not limited to lipid and starch.

In a further embodiment the organism has enhanced cell division compared to wild-type.

In a further embodiment the organism is derived from *Chlamydomonas reinhardtii*.

In another embodiment of the method wherein the expression of the *Chlamydomonas reinhardtii* phototropin gene is reduced by genome editing (i.e. CRISPR/Cas).

In another embodiment of the method wherein the expression of the *Chlamydomonas reinhardtii* phototropin gene is reduced by trans acting elements (e.g., RNAi).

In a further embodiment the gene downstream of PHOT has substantial homology to the *Arabidopsis* KIN10 or KIN11 genes or a portion thereof (Snf1 related kinases, SNRK) and can be overexpressed to increase the productivity of an algal strain.

In yet a further embodiment the KIN10 and KIN11 genes or a portion thereof are chosen from genes substantially homologous to a nucleic acid sequence identified in SEQ ID NO 15 to 34 or a nucleic acid sequence encoding for an amino acid sequence identified in SEQ ID NO 15 to 34.

In a further embodiment the gene downstream of phot has substantial homology to the *Arabidopsis* NTRC and NTR2 gene(s) or a portion thereof and can be overexpressed to increase the productivity of an algal strain.

In yet a further embodiment the NTRC and NTR2 genes or a portion thereof are chosen from genes substantially homologous to a nucleic acid sequence identified in SEQ ID NO 35 to 50 or a nucleic acid sequence encoding for an amino acid sequence selected in SEQ ID NO 35 to 50.

BRIEF DESCRIPTION OF THE DRAWINGS

A better understanding of the exemplary embodiments of the invention will be had when reference is made to the accompanying drawings, and wherein.

DETAILED DESCRIPTION

While there have been numerous studies on algal phototropin (Huang and Beck 2003, Ermilova, Zalutskaya et al. 2004, Huang, Kunkel et al. 2004, Im, Eberhard et al. 2006, Sethi, Prasad et al. 2009, Veetil, Mittal et al. 2011, Trippens, Greiner et al. 2012) to date there has been no correlation of the reduction or knock-out of phototropin to higher levels of biomass production and increased production of sink molecules/products such as starch and lipid.

Figure 6:
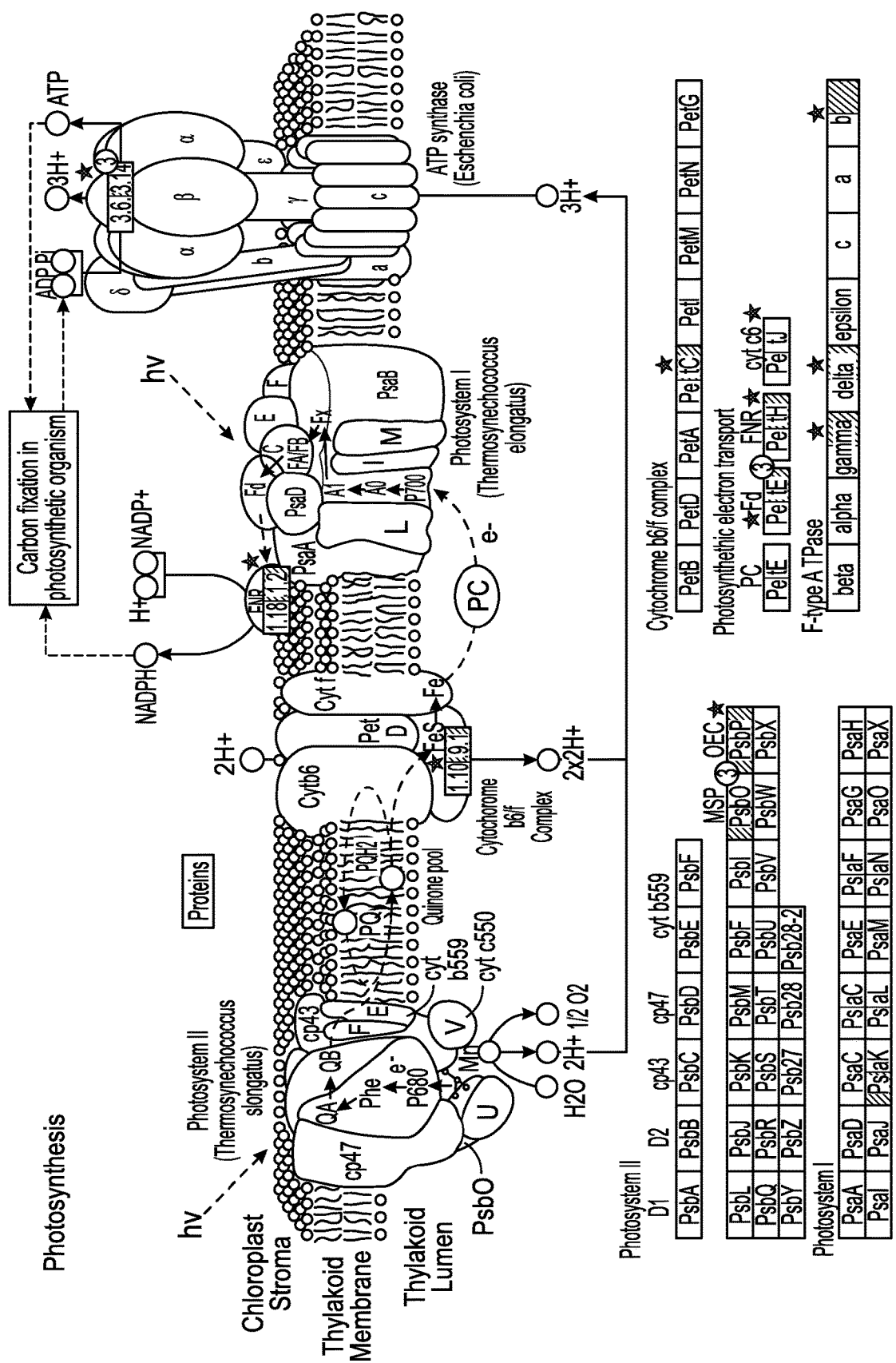
FIG. 6—KEGG pathway graphical data on photosynthetic electron transport chain related gene expression *Chlamydomonas reinhardtii* PHOT K/O lines and parent lines. Star indicates fold change in transcript abundance relative to parent line.

The transcriptome of a *Chlamydomonas reinhardtii* phototropin knock out (PHOT K/O) mutant and the wild-type parent were compared to analyze differences in gene expression in high light grown cultures (500 µmol photons $m^{-2}$ $s^{-1}$). An up-regulation of genes involved in photosynthetic electron transport chain, carbon fixation pathway, starch, lipid, and cell cycle control genes was observed in the PHOT K/O mutants. Referring now to FIG. 6, with respect to photosynthetic electron transport genes, genes encoding proteins of the cytochrome $b_6f$ and ATP synthase complex were up regulated potentially facilitating rate limitations in proton-coupled electron transfer. In addition genes involved in the rate limiting steps in the Calvin cycle, including Ribulose-1,5-bisphosphate carboxylase/oxygenase (RuBisCO), sidoheptulose 1,7 bisphosphatase (SBPase), glyceraldehyde-3-phosphate dehydrogenase (3PGDH) and that mediate cell-cycle control (CDK), were also up regulated in the PHOT K/O mutants as well as the starch synthase and fatty acid biosynthesis genes involved in starch and lipid synthesis. In addition, transmission electron micrographs show increased accumulation of starch granules in PHOT K/O mutant compared to wild-type, which is consistent with the higher expression of starch synthase genes. Collectively, the altered patterns of gene expression in the PHOT K/O mutants were associated with a two-fold increase in growth and biomass accumulation compared to wild-type when grown in environmental photobioreactors (PBR101 from Phenometrics, Inc., Lansing, Mich.) that simulate a pond environment as evidence of increase productivity of algae. These surprising results suggest that phototropin may be a master gene regulator that suppresses rapid cell growth and promotes gametogenesis and sexual recombination in wild-type strains. Therefore, down regulating expression or eliminating the phototropin genes (e.g., PHOTO K/O mutants) provides a valuable means to increase productivity of algae that has commercial applications.

Using a variety of methods exemplary embodiments of the invention are directed at improving the productivity of algal systems based on control of the phototropin gene and genes similar to phototropin in algal systems. This is particularly applicable to improving biomass productivity in algal mass culturing either for production of algal biofuels or bioproducts.

Productivity is a central issue in algae production and a doubling of the productivity could be very attractive to groups who hope to cross the threshold of commercial viability. However, one should note that widespread adoption of transgenic algae as a production system is not yet embraced. Several companies (for example Algenol, Ft. Meyers, Fla.) are using transgenic algae (cyanobacteria) in closed tube reactors outdoors and, presumably, have a track to (national) regulatory approval. Use of transgenic algae has been approved in Florida and approvals have recently been granted by the US EPA for GMO field trials for Sapphire Energy Company.

Production of bioproducts using this invention, owing to the observed doubling of productivity in biomass and sink molecules/compounds, could be pivotal in reaching commercial viability. The observed increase in starch production by this invention is especially important as it shows sink molecules/compounds are enhanced by the methods of this invention.

Alternative genome editing technologies such as CRISPR/Cas 9, Talen and Zinc finger nuclease approaches could also be used to inhibit expression of phototropin (Gaj, Gersbach et al. 2013, Sizova, Greiner et al. 2013).

It is possible to make PHOT knockouts using non-GMO approaches such as classical mutagenesis using chemical mutagens such as methylnitronitroso guanidine and ethyl methane sulfonate (Yan, Aruga et al. 2000).

Figure 1:
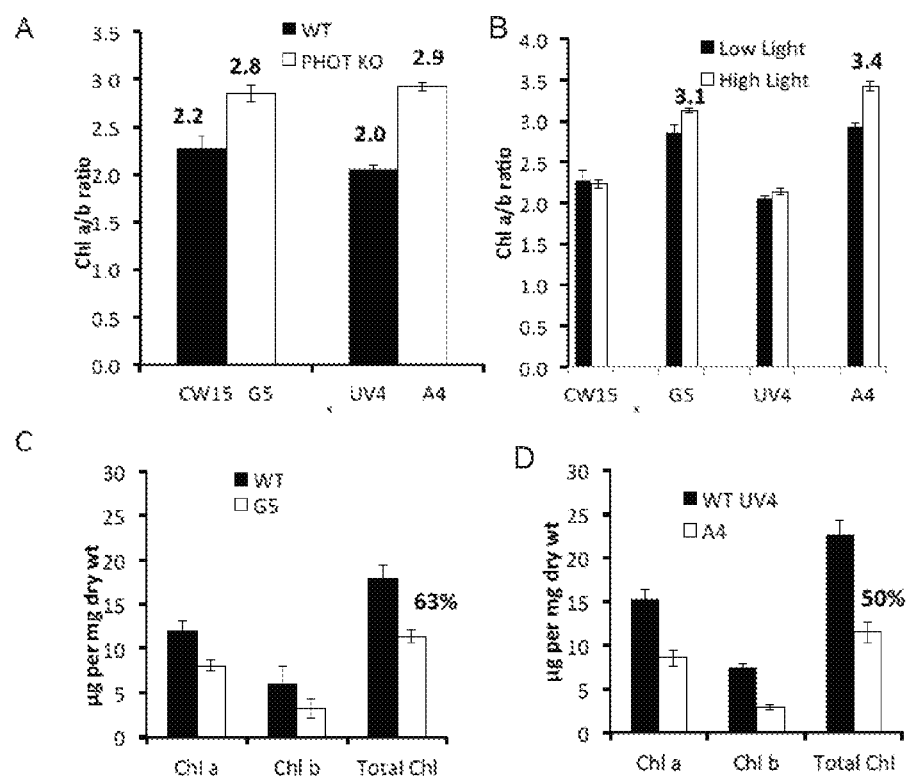
FIG. 1A-D Comparison of chlorophyll a/b ratios and chlorophyll content of PHOT K/O lines (PHOT K/O line G5 and parent cw15) and (PHOT K/O line A4 and parent UVM4): (A) chlorophyll a/b ratios in low light, (B) chlorophyll a/b ratios in low light and high light, (C) chlorophyll content in low light grown cells of cw15 parent and G5 mutant, and (D) chlorophyll content in low light grown cells of UV4 parent and A4 mutant.
Figure 5:
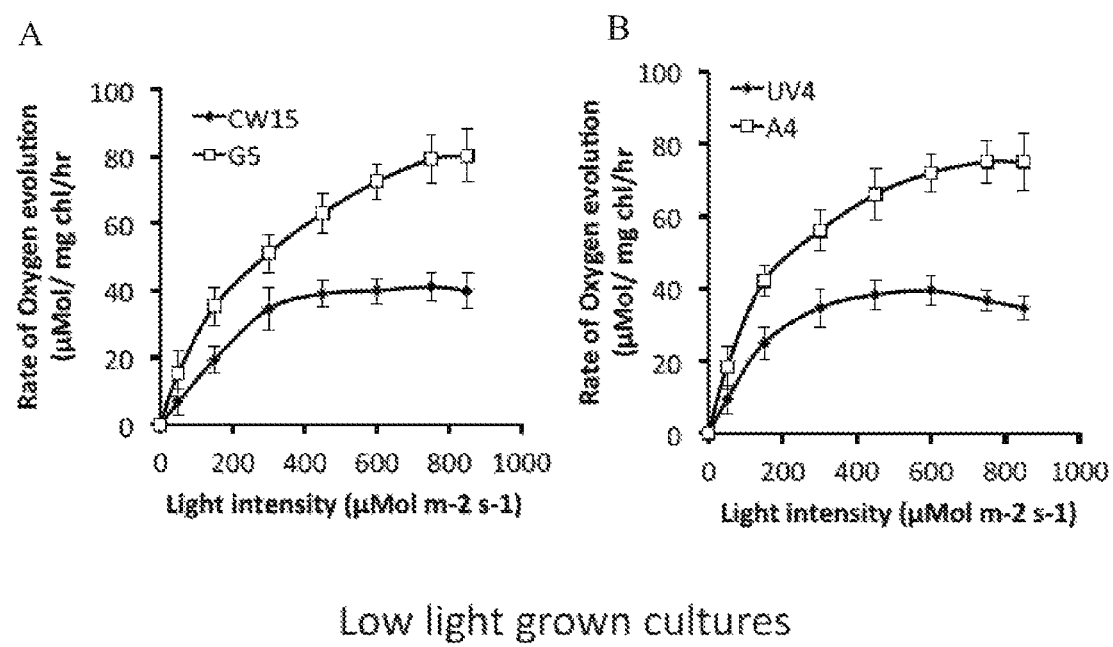
FIG. 5A-B— Photosynthetic rate comparison of *Chlamydomonas reinhardtii* PHOT K/O lines and parent lines under increasing light intensity. CW15 and UV4 are parental wild-type lines while G5 and A4 are the PHOT K/O lines.

To date, supporting data for this invention have been limited to the green alga, *Chlamydomonas reinhardtii*. Compared to wild-type *C. reinhardtii*, PHOT K/O mutants of the invention show:

1. Reduction in chlorophyll and carotenoid pigments (see FIG. 1).
2. Reduced light harvesting antenna size (see FIG. 1).
3. 2-fold increase in photosynthesis rate (see in FIG. 5).
4. Increased expression of genes that control rate limiting steps in photosynthetic electron transfer and Calvin Cycle activity (see FIG. 6 and FIG. 8).
5. 2-fold increase in growth and biomass (see in FIG. 7.)
6. Increased expression of starch synthesis genes (see in FIG. 10.)
7. Increased accumulation of xanthophyll cycle pigments (see in FIG. 12).
8. Higher accumulation of starch grains (see in FIG. 11B).
9. Increased expression of the chloroplast localized MEP terpenoid synthesis pathway but not the cytoplasmic MVA terpenoid synthesis pathway (see in FIG. 12)
10. Increased expression of cell cycle control genes potentially accelerating rates of cell division (see in FIG. 9).
11. Increased expression of glycolysis pathway genes.
12. Increased expression of Kin10/Kin11 (SNRK) genes.
13. Increased expression of NTR2 and NTRC genes.

Additionally, PHOT K/O mutants were unable to undergo sexual mating, which was attributed to an impact of the PHOT K/O on the cell cycle—effectively blocking meiosis while accelerating photosynthetic and cell division rates.

PHOT Knockout (K/O) Mutants of *Chlamydomonas reinhardtii*

*Chlamydomonas reinhardtii* PHOT knockout lines were generated in different parental backgrounds. PHOT K/O line G5 was made in cw15 parental background and A4 mutant line was made in UV4 background (Zorin, Lu et al. 2009).

Pigment Analysis of Phototropin Knock Out Lines

Chlorophyll (Chl) and carotenoids are the central pigments of the photosynthetic apparatus. These pigments are associated with light-harvesting complexes and reaction-center complexes in photosynthetic organisms. The light environment plays a major role in governing the pigment composition of pigment-protein complexes of the photosynthetic apparatus. Blue light is especially important in modulating the synthesis of Chl and carotenoids, as well as the biogenesis of the photosynthetic apparatus in microalgae and vascular plants. Consistent with phototropin regulation of pigment biosynthetic pathways *C. reinhardtii* PHOT K/O lines showed:

Chlorophyll Content:

Higher chlorophyll a/b (Chl a/b) ratios compared to their respective wild-types when grown under low light intensities. As shown in FIGS. 1A and 1B, the G5 mutant line has Chl a/b ratios of 2.8 and 3.1 in low and high light, respectively while its parent CW15 has a Chl a/b ratio of 2.2 in low light with no significant increase in high light. Similarly the mutant A4 line has Chl a/b ratios of 2.9 and 3.4 in low light and high light respectively, and its parent has a Chl a/b ratio of 2 in low light with no significant change in high light. Chl a/b ratios are also higher in PHOT K/O lines under high light grown cultures, which is consistent with a reduction in chlorophyll antenna size at high light. FIGS. 1C and 1D shows a 50-60% reduced chlorophyll content per gram dry weight in the PHOT mutants compared to parent wild-type.

Figure 2:
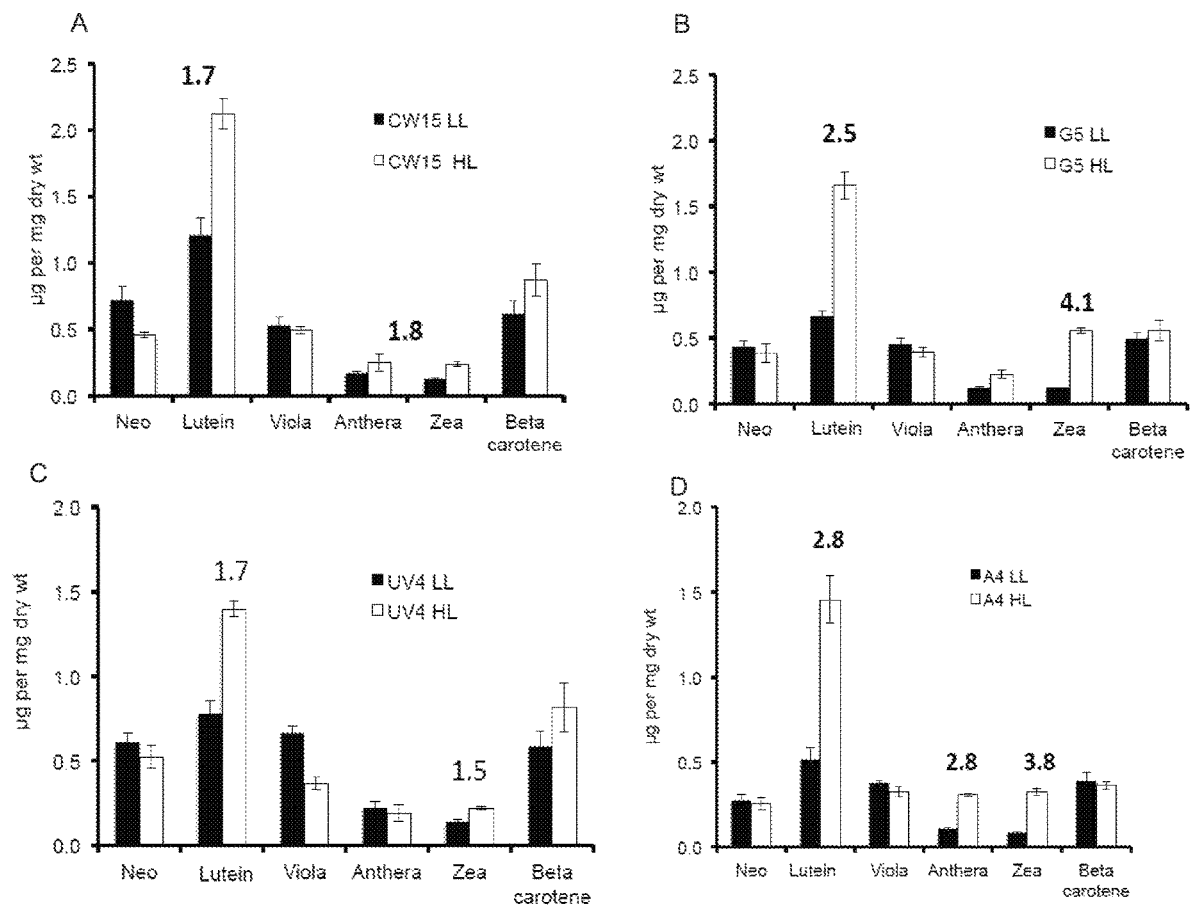
FIG. 2A-D—Carotenoid pigment comparison of low light (LL) and high light (HL) grown cultures of *Chlamydomonas reinhardtii* PHOT K/O lines compared to wild-type. LL=Low light, HL=high light, CW15=Parent for G5 PHOT K/O line, UV4=parent for A4 PHOT K/O line, Neo=neoxanthin, Lutein=lutein, Viola=violaxanthin, Anthera=antheraxanthin, and Zea=zeaxanthin.

Carotenoid Content:

When grown under low light intensities PHOT K/O lines showed a 30-40% reduction in carotenoid content compared to parent wild. The changes in xanthophyll cycle pigments were analyzed since the xanthophyll cycle pigments play an important role as antioxidants and for non-photochemical quenching of excess energy captured by the light harvesting complex. Both PHOT K/O lines show higher accumulation of photoprotective pigments in high light compared to their respective WT parents. Referring now to FIG. 2B, G5 PHOT accumulates 2.5 fold more lutein and 4.1 fold more zeaxanthin compared to the parental line as shown in FIG. 2A. Referring now to FIG. 2D, A4 PHOT K/O accumulates 2.8 lutein and 3.8 fold zeaxanthin as well as 2.8 fold antheraxanthin compared to its respective parent as shown in FIG. 2C. These results are consistent with the better photosynthetic performance of these lines when grown in high light intensities.

Figure 3:
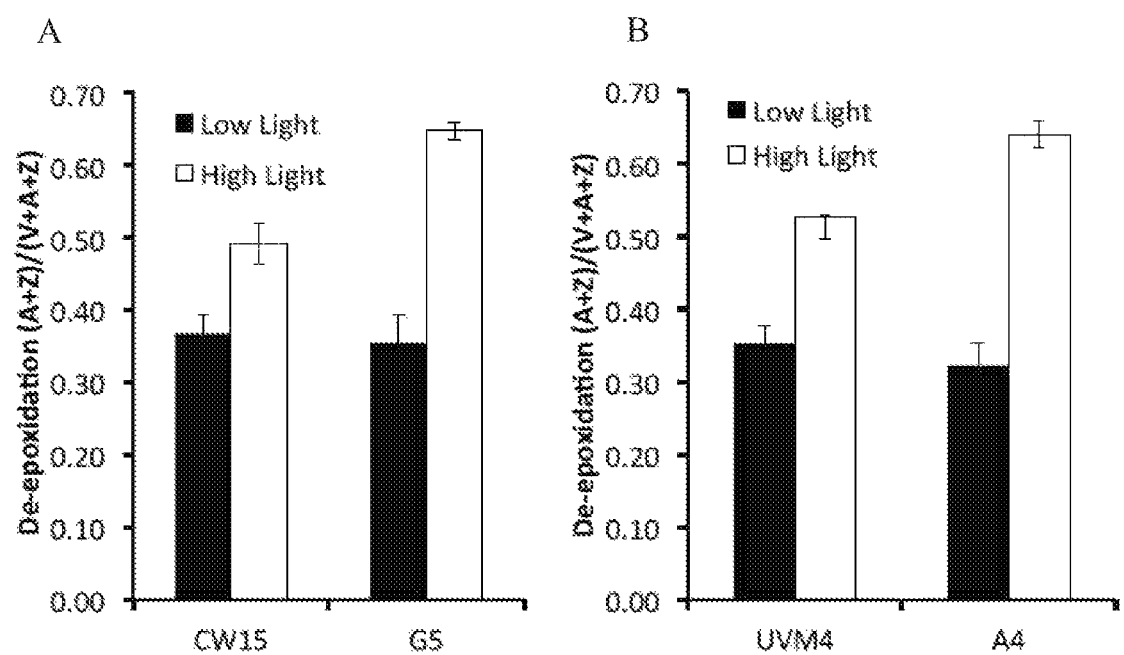
FIG. 3A-B—Xanthophyll cycle carotenoid de-epoxidation in *Chlamydomonas reinhardtii* PHOT K/O (lines G5 and A4) and their corresponding parental lines (CW15 and UVM4) grown at low and high light intensities.

De-Epoxidation Rates:

Consistent with the xanthophyll cycle pigment accumulation PHOT K/O lines show higher De-epoxidation in high light conditions as compared to their respective wild-type under high light (FIG. 3A-B). These data are consistent with the better performance of PHOT K/O lines in high light intensities as they have more robust photoprotection mechanisms.

Figure 4:
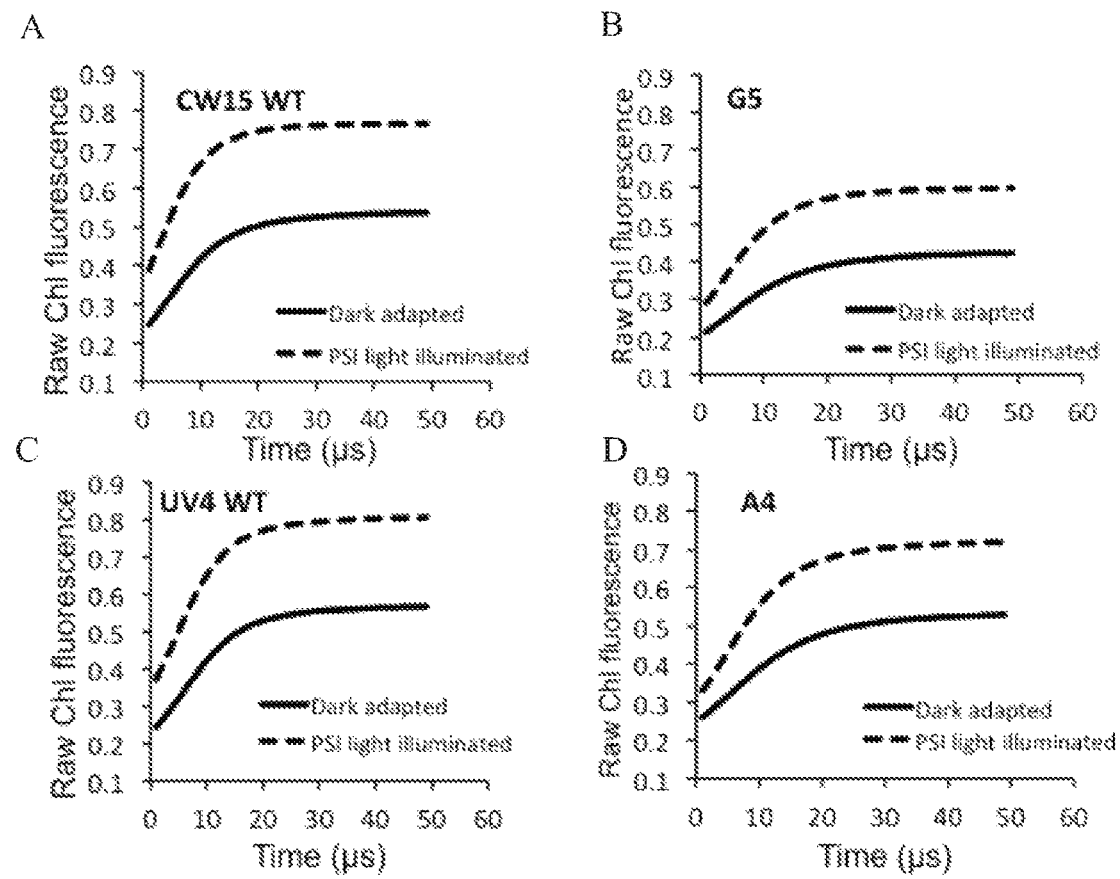
FIG. 4A-D—Chlorophyll fluorescence induction kinetics of low-light grown *Chlamydomonas reinhardtii* PHOT K/O lines and respective wild-type parental strains. Cultures were either dark adapted or pre-illuminated with 715 nm light (photosystem I (PSI) actinic light) prior to measurement. For Chl fluorescence induction measurements, Chl fluorescence was measured under continuous, non-saturating illumination every microsecond.

Photosynthetic State Transition Analysis in Parent and PHOT K/O Lines:

In *C. reinhardtii*, the peripheral PSII antenna is able to migrate laterally between PSII and PSI, in a process known as state transitions, to balance the excitation energy distribution between the two photosystems and to regulate the ratio of linear and cyclic electron flows. Linear electron transfer produces ATP and NADPH, while cyclic electron transfer driven by PSI produces only ATP. Increasing the antenna size of the PSI complex facilitates cyclic electron transfer and has been shown to enhance ATP production and support the optimal growth of *Chlamydomonas*. To assess the impact of reduced pigment content on the ability to carry out state transitions, chlorophyll (Chl) fluorescence induction kinetics were measured in low-light grown parent wild-type (FIGS. 4A and C) and PHOT K/O cells (FIGS. B and D), that were either dark adapted (sold line) or pre-illuminated with PSI (715 nm) actinic light (broken line). PSI actinic light pre-illumination promotes light harvesting complex II (LHCII) migration from PSI to PSII. An increase in the PSII antenna size would accelerate Chl fluorescence rise kinetics and increase the maximal Chl fluorescence level at sub-saturating light intensities. Wild-type strains (FIGS. 4A and C) and PHOT K/O lines (FIGS. 4B and D) all had faster Chl fluorescence rise kinetics and achieved greater maximum Chl fluorescence levels following pre-illumination with PSI light as compared to dark adapted cells consistent with robust state transitions.

Photosynthetic Rates in WILD-TYPE and PHOT K/O Lines:

Referring now to FIG. 5A_and FIG. 5B, the photosynthetic rates of the PHOT lines were determined under increasing light conditions and PHOT K/O lines (open boxes) show 2 fold higher photosynthetic rates compared to their respective parent strains (filled circles). Rate limiting genes in photosynthetic electron transport genes were up-regulated in high light grown cultures (FIG. 6). Up-regulation of these genes may play a role in higher photosynthetic efficiency of PHOT K/O mutants.

Photosynthetic Electron Transport Pathway Genes:

The transcriptomic analysis of the PHOT K/O mutants compared to wild-type parental strains provided information on the different genes impacted by the elimination of phototropin expression (FIG. 6). These data are reported in the KEGG (Kyoto Encyclopedia of Genes and Genome) pathway format (Kanehisa and Goto 2000, Kanehisa, Goto et al. 2014) found on the world wide web at genome.jp/kegg/mapper.html last visited May 25, 2016. Rate limiting genes in photosynthetic electron transport pathway were up-regulated in high light grown cultures. Up-regulation of these genes may play a role in higher photosynthetic efficiency of PHOT K/O mutants.

1. PetC: Is a nuclear gene encoding the Rieske protein of the cytochrome $b_6/f$ (cyt $b_6/f$) complex. The cytochrome $b_6f$ complex catalyzes the rate-limiting step in photosynthetic electron transport. Increases in its expression levels or stoichiometry relative to the PSI and PSII reaction centers would be predicted to increase rates of electron and proton transfer. A 2-fold increase on petC expression was observed for the PHOT K/O mutants (see FIG. 6).

AtpD: Encodes the delta subunit for ATPase. A 3-fold increase on AtpD expression was observed for the PHOT K/O mutants (see FIG. 6).

F type ATPase genes: The delta and gamma subunits of the F type ATPase gene were evaluated. Increases in expression of the ATPase complex would facilitate proton flux, increase ATP synthesis and reduce feedback inhibition on proton coupled electron transfer by accelerating dissipation of the delta pH gradient across the thylakoid membrane. A 3-fold increase was observed for the PHOT K/O mutants (see FIG. 6).

PGRL1: Is an important gene for efficient cyclic electron flow. A 2.2 fold increase was observed for PHOT K/O mutants PGR7: Is a gene necessary for efficient photosynthetic electron transport. A 6.4 fold increase was observed for PHOT K/O mutants.

Figure 7:
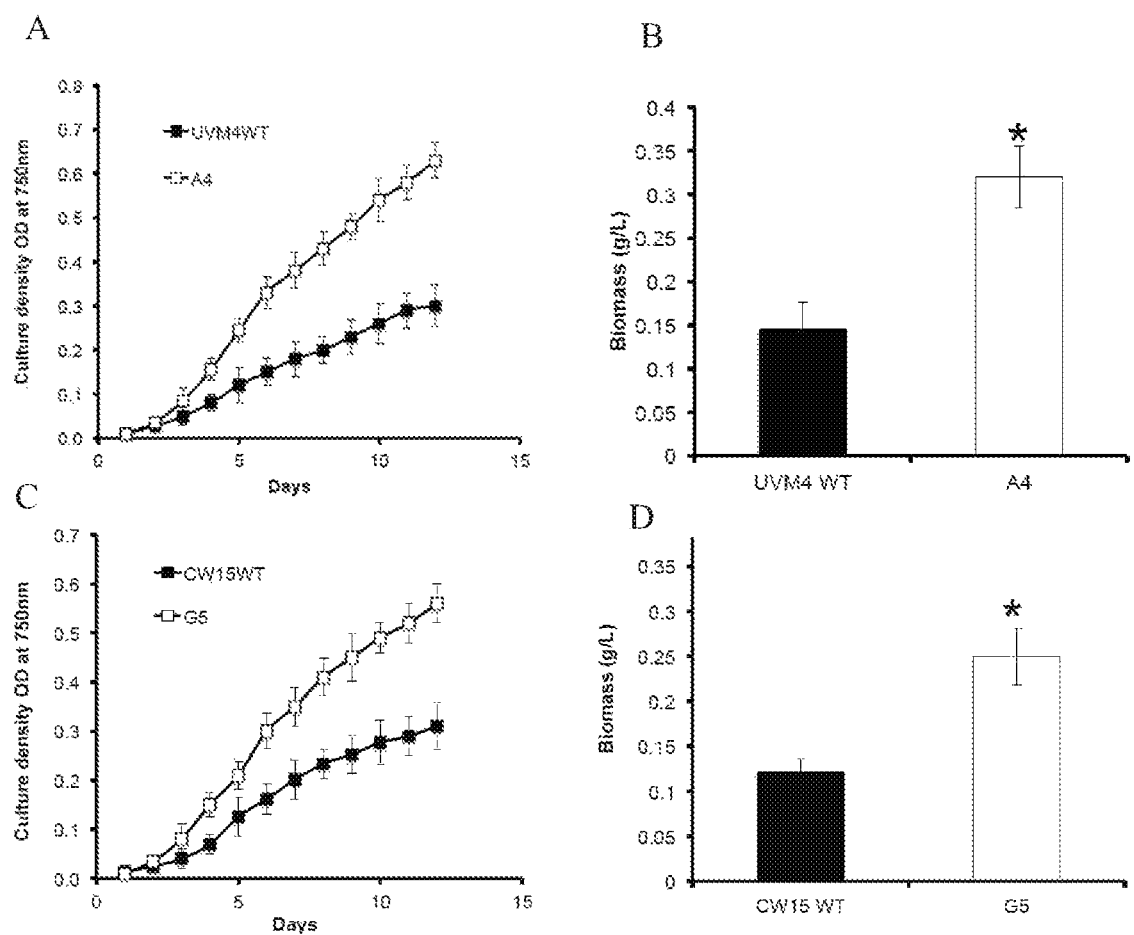
FIG. 7A-D—Growth and biomass comparison of *Chlamydomonas reinhardtii* PHOT K/O lines and parent lines in environmental photobioreactors from Phenometric (ePBRs).

Growth and Biomass Analysis in Parent and PHOT K/O Lines:

Most importantly, phototropin knock out lines (open boxes), had twice the cell density (FIGS. 7A and 7C) and accumulated twice the biomass (FIGS. 7B and 7D) of their respective parental wild-type strain (solid boxes) when approaching the stationary phase of growth (after 12 days) (FIG. 7). These results are consistent with higher photosynthetic rates in phototropin knock out lines also impact biomass yield of cells grown under conditions mimicking the pond simulating conditions (ePBRs). These results are in concert with up-regulation of the genes involved in carbon fixation and cell cycle as determined by transcriptomic analysis.

Figure 8:
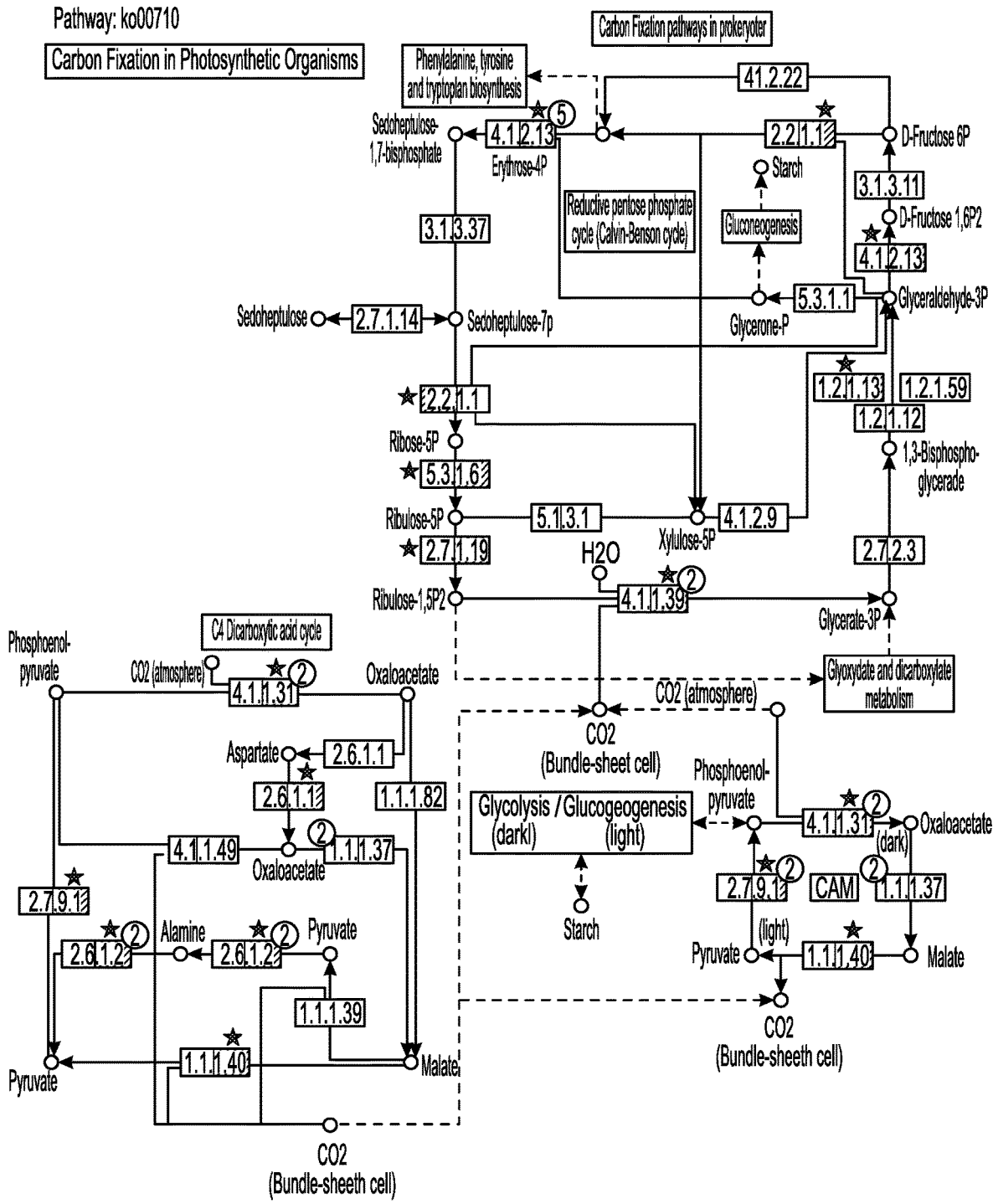
FIG. 8—KEGG pathway graphical data on carbon fixation related gene expression *Chlamydomonas reinhardtii* PHOT K/O lines and parent lines. Hatched line and/or star indicates fold change in transcript abundance relative to parent line.

Carbon Fixation Pathway Genes Upregulated:

Carbon fixation is the main pathway for storing energy and accumulating biomass in algae and plants. Many rate limiting genes were up-regulated in PHOT K/O lines (FIG. 8). SBPase and RuBisCO are limiting enzymes in the Calvin Cycle and their overexpression would increase carbon flux through the carbon reduction pathways. Carbonic anhydrase (CA), an enzyme active in the interconversion of bicarbonate and $CO_2$ facilitating $CO_2$ fixation.

1. Ribulose-1,5-bisphosphate carboxylase/oxygenase (RuBisCO) A 3-fold increase was observed for the PHOT K/O mutants (see FIG. 8).
2. Sidoheptulose 1,7 bisphosphatase (SBPase): A 3-fold increase was observed for the PHOT K/O mutants (see FIG. 8).
3. Glyceraldehyde-3-phosphate dehydrogenase (3PGDH): A 2-fold increase was observed for the PHOT K/O mutants (see FIG. 8).
4. α carbonic anhydrases: A 2.6 to 5 fold increase was observed for the PHOT K/O mutants.
5. β carbonic anhydrases: A 8 fold to 6 fold increase was observed for the PHOT K/O mutants.

Thioredoxin Reductase Genes are Up-Regulated in PHOT K/O Lines:

Thioredoxins are small ubiquitous redox proteins, which are crucial components of the regulatory redox networks in all living cells. Thioredoxins are reduced by different reductases, depending on their subcellular localization. Among these reductases, NADPH-dependent thioredoxin reductases (NTR) genes are known to regulate multiple gene targets involved in photosynthesis, non-photochemical quenching (NPQ), Calvin-Benson cycle, starch biosynthesis, cold stress tolerance and thermotolerance.

1. NADPH-dependent thioredoxin reductase C (NTRC): A 2.4 fold increase was observed for the PHOT K/O mutants
2. NADPH-dependent thioredoxin reductase 2 (NTR2): A 4 fold increase was observed for the PHOT K/O mutants Key Growth Regulatory Genes are Up-Regulated in PHOT K/O Lines:

KIN10 or KIN11 ((Snf1 related kinases, SNRK) are one of the very well-studied central regulators of energy and stress metabolism in plants. SNRK1 proteins play central roles in coordinating energy balance and nutrient metabolism in plants. A 10-fold increase was observed for the PHOT K/O mutants.

Figure 9:
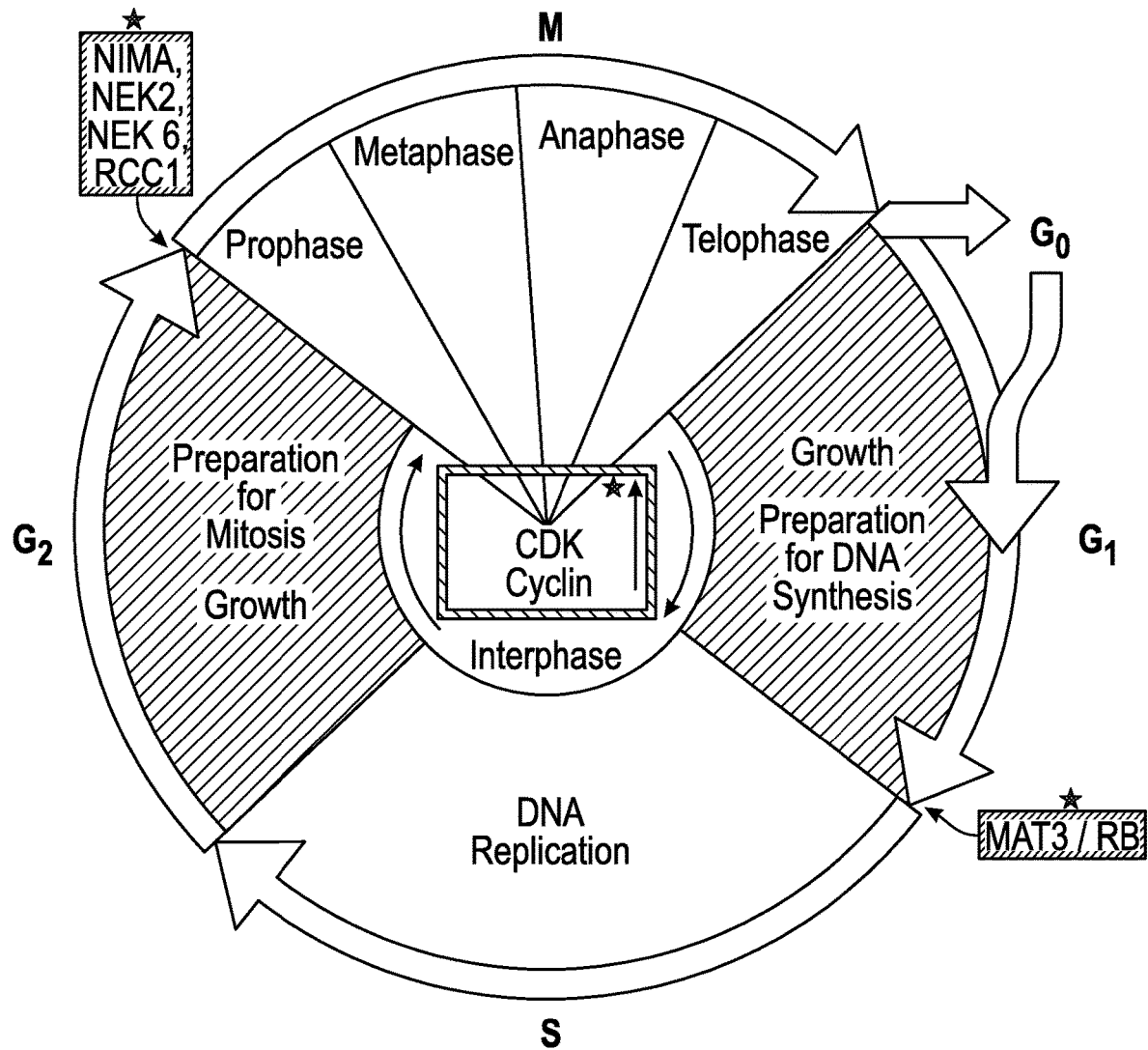
FIG. 9—Cell cycle pathway diagram. N/MA (Never in mitosis), NEK2, NEK6 (N/MA related kinases), Cyclin and CDK (Cyclin-dependent kinases), RB (retinoblastoma)/mat3 (mating type-linked) genes are up-regulated in cell cycle pathway.

Cell Cycle Pathway Genes Up Regulated:

Cell cycle genes are up regulated in *Chlamydomonas reinhardtii* PHOT K/O mutants may enhance cell division in these lines contributing to the higher biomass in these lines (FIG. 9).

1. NIMA (Never in mitosis), NEK2, NEK6 (NIMA related kinases): Cell cycle progression (G2/M progression) 15, 5 and 5 fold increase, respectively, was observed for the PHOT K/O mutants.

RCC1 (Regulator of chromosome condensation): A 16 fold increase was observed for the PHOT K/O mutants. Cyclin and cyclin-dependent kinases (CDK): Cyclin-dependent kinases are involved in overall regulation of cell cycle progression and demonstrated a 2-fold increase for the PHOT K/O mutants.

A 3-fold increase in MAT3 a homolog of retinoblastoma protein (MAT3/RB) was observed for the PHOT K/O mutants: These genes regulate the cell cycle at two key points: 1.) early/mid G1 control point, and 2) the size checkpoint for the dividing cell.

Glycolysis Pathway Genes are Up-Regulated in PHOT K/0 Lines:

Glycolysis is the first step in the breakdown of glucose to extract energy for cellular metabolism, which converts glucose to pyruvate and generates ATP (energy) and NADH (reducing power). Many important genes of this pathway show higher expression in PHOT K/O mutants.

1. Hexokinase: A 3.4 fold increase was observed for the PHOT K/O mutants.
2. Glyceraldehyde phosphate dehydrogenase: A 6 fold increase was observed for the PHOT K/O mutants
3. Fructose—bisphosphate Aldolase: A 4 fold increase was observed for the PHOT K/O mutants.
4. Pyruvate Kinase: A 16 fold increase was observed for the PHOT K/O mutants.

Thylakoid Membrane Structure and Starch Accumulation in Parent and PHOT K/O Lines:

We compared the chloroplast ultrastructure of the parental and PHOT K/O cells to determine whether there were changes in thylakoid membrane structure and starch accumulation. Starch represents the most widespread storage polysaccharide found in the plastids of both photosynthetic and non-photosynthetic cells of plants and algae. PHOT K/O lines exhibited higher accumulation of starch grains compared to their respective parent strains as well as up-regulation of starch synthesis genes (FIGS. 10 and 11B) (discussed below).

Figure 10:
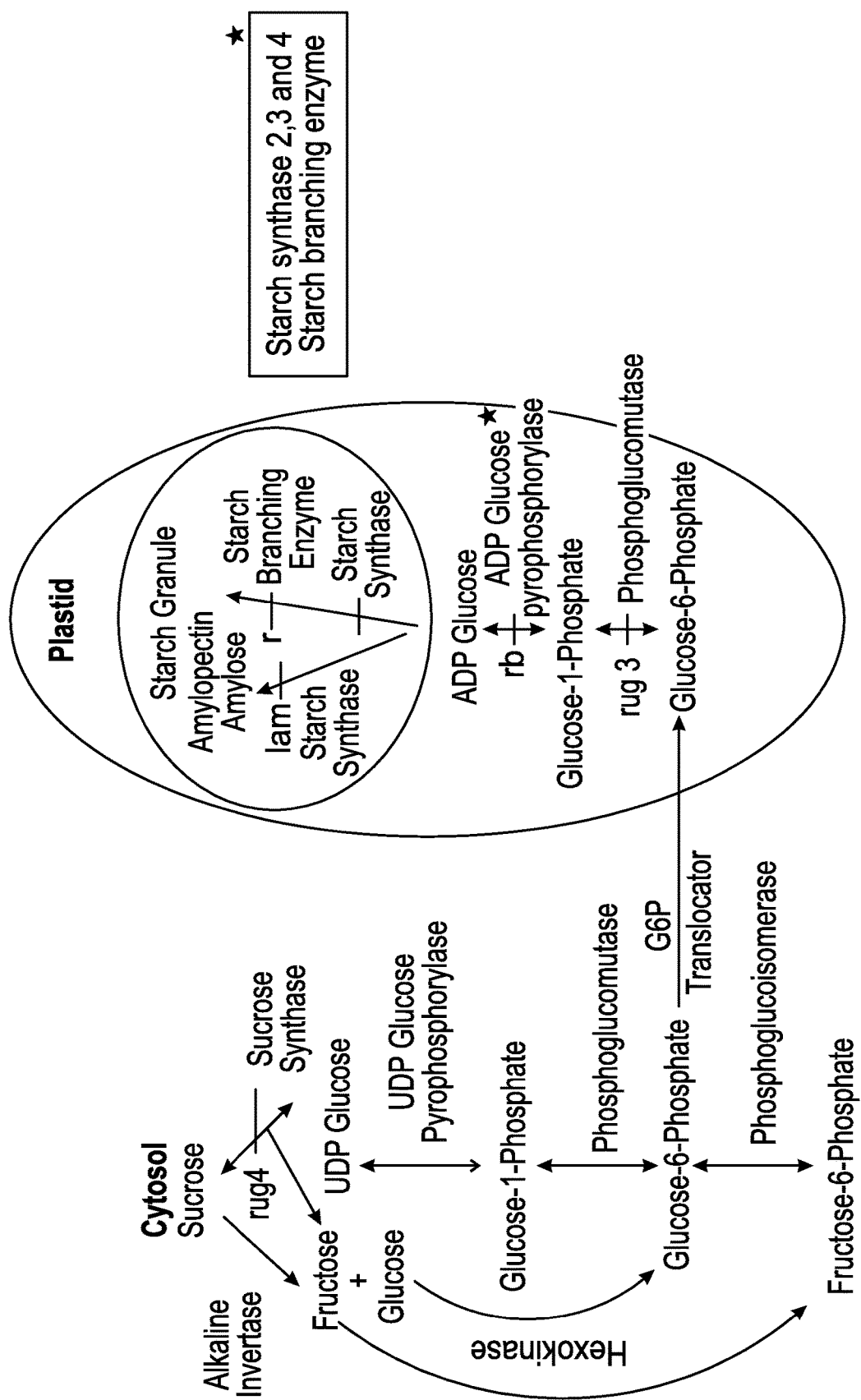
FIG. 10—Starch synthesis pathway.
Figure 11A:
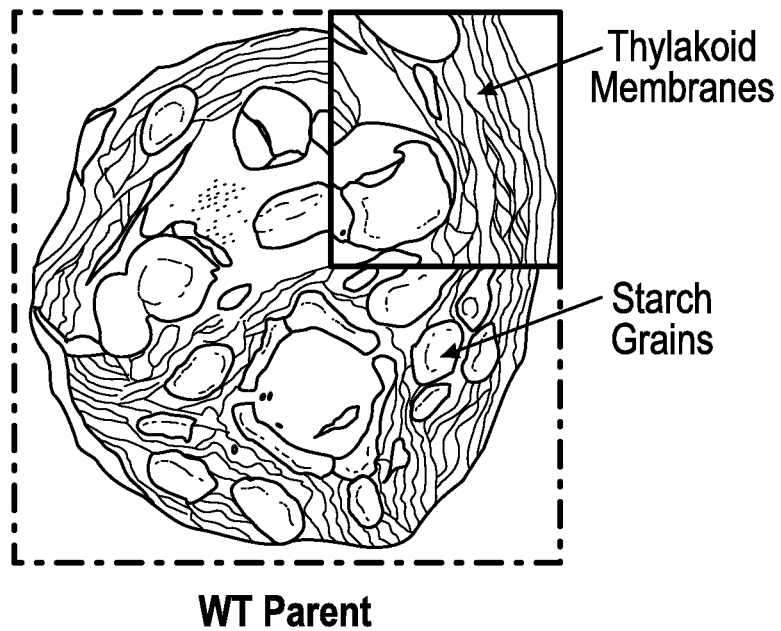
FIG. 11A-B—Thylakoid membrane structure and starch accumulation comparison of PHOT K/O line with parent line. Inserts are a magnification of the thylakoid grana stacks.
Figure 11B:
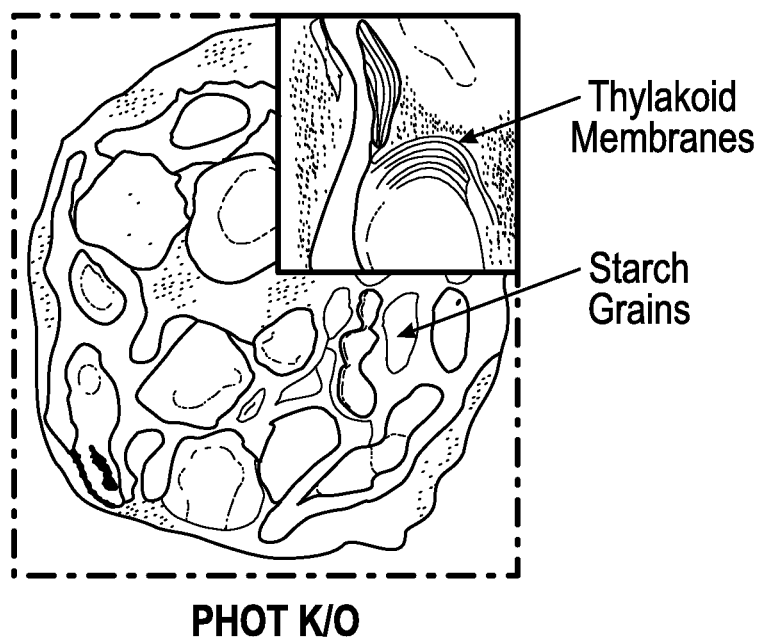

Starch Biosynthesis Pathway Genes Upregulated in PHOT K/O Lines:

*Chlamydomonas reinhardtii* PHOT K/O mutants have higher starch accumulation due to up-regulation of the following genes involved in starch biosynthesis is FIG. 10. These results were consistent with the observed increase in starch content in PHOT K/O chloroplasts by EM.

1. AGPase: ADP glucose pyrophosphorylase catalyzes the rate-limiting step and first-dedicated step for starch biosynthesis. A 2-fold increase was observed for the PHOT K/O mutants.
2. Starch synthase 2, 3 and 4: A 5-fold increase was observed for the PHOT K/O mutants.
3. Starch branching enzyme: A 3-fold increase was observed for the PHOT K/O mutants.

A structural hallmark of thylakoid membranes in plants and microalgae is the stacking of the membranes associated with the localization of the PSII complex. The stromal membranes extending from the stacks are enriched in PSI and ATPase complexes. This arrangement of LHCII complexes provides functional flexibility, enabling their primary light harvesting function as well as ability to participate in multilevel regulatory mechanisms involving highly efficient energy dissipation through pigment interactions such as chlorophyll-xanthophyll interactions. These regulatory processes require a significant reorganization in the membrane, and a substantial degree of structural flexibility in thylakoid membranes to carry out short-term adaptations and long-term acclimations in response to change in light and environmental stimuli.

An electron micrograph illustration showing the thylakoid membrane structure in both parent strain and PHOT K/O line is drastically altered in PHOT K/O lines. These results are in concert with the phototropin involvement in regulation of LHC protein biosynthesis and pigment biosynthesis. When thylakoid membranes are tightly stacked, they are densely packed with proteins and inhibit efficient protein diffusion including diffusions of the electron transport carrier protein plastocyanin. This protein mobility is required for efficient photosynthetic electron transfer, as well as regulation and repair of photodamaged photosynthetic apparatus. In parent cells thylakoid membranes are very tightly stacked giving very little space for the movement of the molecules). In contrast, PHOT K/O lines have parallel grana stacks and wide luminal spacing Other Important Genes Upregulated in Transcriptomic Analysis:

Lipid Biosynthesis Pathway Genes:

The following genes involved in lipid metabolism are up regulated in PHOT K/O mutants:

1. Acyl carrier protein (ACP) is an important component in both FA and polyketide biosynthesis with the growing chain bound during synthesis as a thiol ester. A 3-fold increase was observed for the PHOT K/O mutants.

ω-3 fatty acid desaturase (FAD) A 4-fold increase was observed for the PHOT K/O mutants. Fatty acid biosynthesis (FAB). A 3-fold increase was observed for the PHOT K/O mutants.

Figure 12:
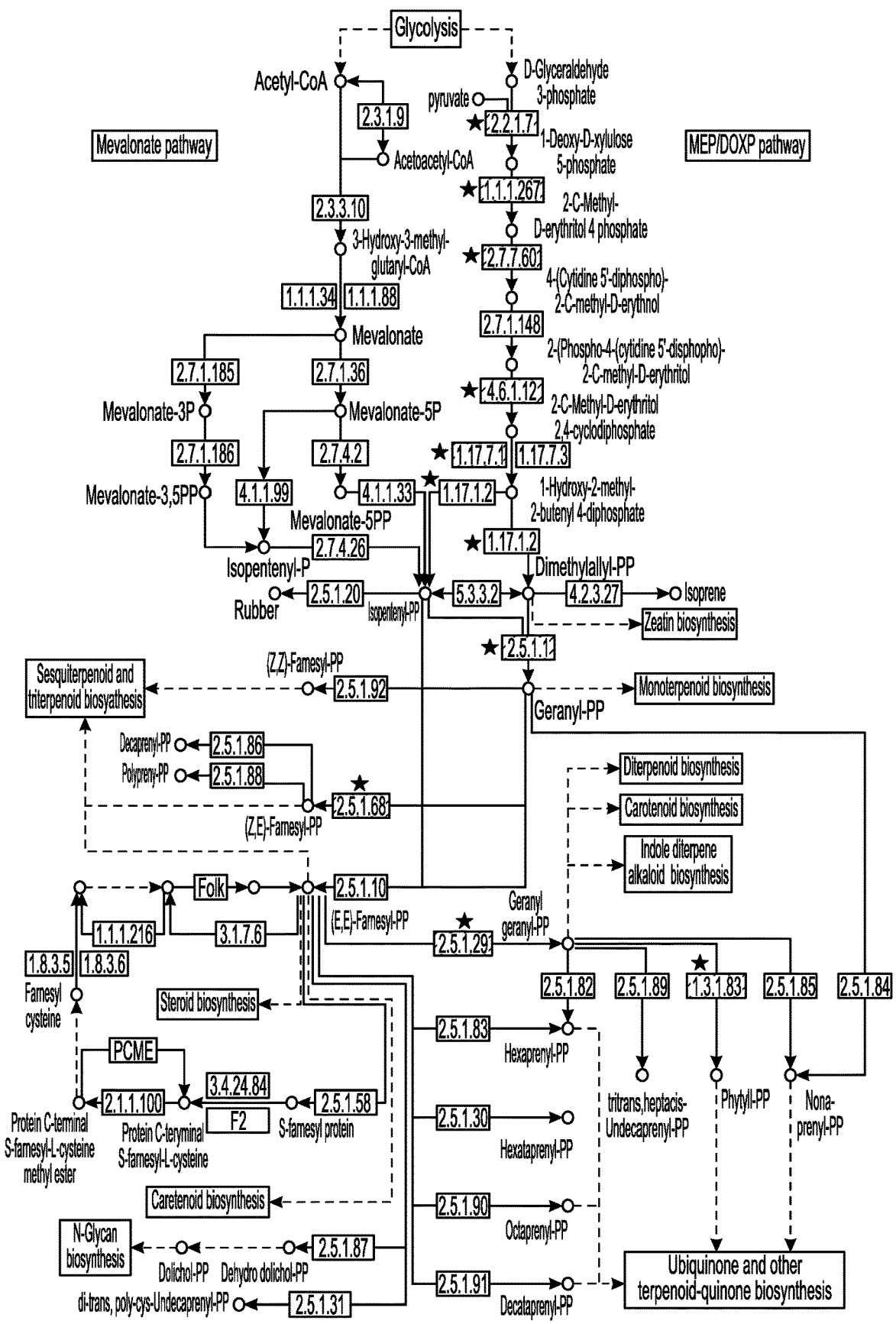
FIG. 12—KEGG pathway graphical data on terpenoid synthesis related gene expression *Chlamydomonas reinhardtii* PHOT K/O lines and parent lines. Star indicates up-regulated genes relative to parent line.

Terpenoid Biosynthesis Pathway Genes:

The methyl erythritol 4-phosphate (MEP) pathway is the source of isoprenoid precursors for the chloroplast. The precursors lead to the formation of various isoprenoids having diverse roles in different biological processes. Some isoprenoids have important commercial uses. Isoprene, which is made in surprising abundance by some trees, plays a significant role in atmospheric chemistry. Multiple genes involved in MEP/DOXP pathway were up regulated in PHOT K/O mutants (FIG. 12). In contrast, the mevalonate terpenoid pathway (cytoplasmic) genes were not up regulated in PHOT K/O mutants.

Note that all data so far were generated in cell wall free mutants of *Chlamydomonas reinhardtii*. Metabolomic analyses in *C. reinhardtii* clarified the pathways and gene up-regulation in high light in *C. reinhardtii* PHOT K/O mutants of this invention:

*Chlorella sp. sorokiniana* strain 1230. Is a UTEX strain. The amino acid sequence of phototropin A is provided as SEQ ID NO. 5 and the nucleotide sequence as SEQ ID NO. 6. The amino acid sequence of phototropin B is provided as SEQ ID NO. 7 and the nucleotide sequence as SEQ ID NO. 8.

*Chlorella sp. sorokiniana* strain 1228. The amino acid sequence of phototropin A is provided as SEQ ID NO. 9 and the nucleotide sequence as SEQ ID NO. 10. The amino acid sequence of phototropin B is provided as SEQ ID NO. 11 and the nucleotide sequence as SEQ ID NO. 12.

*Picochlorum soloecismus* (DOE101). The amino acid sequence is provided as SEQ. ID NO. 13 and the nucleotide sequence as SEQ. ID NO. 14.

TABLE 1

List of publically available sequences that may be phototropins or heterologous to phototropin genes based upon homology or function.

| GenBank # | Alga | Description | Aliases |
|---|---|---|---|
| 9688782 | *Micromonas pusila* CCMP1545 | Phototropin, blue light receptor | MICPUCDRAFT_49739 |
| 9617508 | *Volvox carteri f. nagariensis* | Phototropin | VOLCADRAFT_127319 |
| 23616146 | *Auxenochlorella protothecoides* | Phototropin 2 | F751_4755 |
| 23614975 | *Auxenochlorella protothecoides* | Phototropin-1B | F751_3584 |
| 19011210 | *Bathycoccus prasinos* | Phototropin | Bathy16g02310 |
| 9831018 | *Ostrecoccus tauri* | Putative blue light receptor | Ot16g02900 |
| 8249220 | *Micromonas sp*, RCC299 | Blue light receptor | MICPUN_105003 |
| 16998047 | *Cyanidioschyzon merolae* 10D | Serine/threonine kinase | MICPUT_105003 |
| 17089759 | *Galdieria sulphuraria* | Serine/threonine kinase | Gasu_15820 |
| 17087623 | *Galdieria sulphuraria* | Serine/threonine kinase | Gasu_38210 |
| 17041755 | *Coccomyxa subellipsoidea* C-169 | Putative blue light receptor | COCSUDRAFT_63287 |
| 17350696 | *Chlorella variabilis* | Hypothetical protein | CHLNCDRAF_141214 |
| 5005771 | *Ostreococcus lucimarinus* CCE9901 | Hypothetical protein | OSTLU_40751 |
| 17304390 | *Guillarida theta* CCMP2712 | Hypothetical protein | GUITHDRAFT_162563 |
| 7452793 | *Thalassiosira pseudonana* CCMP1355 | Hypothetical protein | THAPSDRAFT_33193 |
| 7442442 | *Thalassiosira pseudonana* CCMP1355 | Hypothetical protein, PAS domain | THAPSDRAFT_261631 |
| 7200921 | *Phaeodactylum tricornutum* CCAP 1055/1 | Hypothetical protein; one PAS domain | PHATRDRAFT_51933 |
| CBJ25875 | *Ectocarpus siliculosus* CCAP: 1310/4 | aureochrome 1 | AUR1; Esi_0017_0027 |
| XP_005854445 | *Nannochloropsis gaditana* CCMP526 | PAS and BZIP domain containing protein, putative aureochrome | GA_0015702 |
| BAF91488 | *Vaucheria frigida* | aureochrome1 | AUREO1 |

Heterologous Algal Phototropin Genes

The *Chlamydomonas reinhardtii* phototropin gene has already been sequenced and a provisional version is available publically (GenBank 5718965). Additional algal genes are available that have either been shown to be a phototropin, contain blue light receptors, have some homology to phototropin or are putative blue light receptors similar to phototropin (Table 1). Additional phototropin genes in two other production strains of microalgae are known.

*Chlorella sp.* Strain 1412. Is a strain developed by the National Alliance of Biofuels and Bio-products (NAABB) consortium and is housed at UTEX Culture Collection Of Algae at the University of Texas at Austin (UTEX). The amino acid sequence is provided as SEQ ID NO. 1 and the nucleotide sequence as SEQ ID NO. 2. The phototropin B gene of *Chlorella sorokiniana*. Strain 1412 is provide as SEQ ID NO. 3 and nucleotide as SEQ ID NO. 4.

Alternative Targets

Additional PHOT downstream signal transduction targets can be use as alternatives to the knockout or reduction in phot expression to generate the desirable phenotypes of this invention, including but not limited to improved photosynthetic efficiency, higher biomass productivity, increase yield of sink molecules/compounds, and improved genetic stability. An example of this could be the algal gene homologous to the *Arabidopsis* KIN10 and KIN11 kinases (Baena-Gonzalez, Rolland et al. 2007). Genes substantially homologous to the *Chlorella* genes in SEQ ID 15 to 27 and the *Chlamydomonas* genes in SEQ ID 28-34 would be applicable to this current invention.

Additional gene targets can be used as alternatives to the knockout or reduction in phot expression to generate the desirable phenotypes of this invention with desirable phenotypes having but not limited to improved photosynthetic efficiency, higher biomass productivity, increase yield of sink molecules. These genes could include the algal genes homologous to the *Arabidopsis* NADPH thioredoxin reductase C (NTRC) and NADPH thioredoxin reductase 2 genes (Toivola et al. 2013) Genes substantially homologous to the *Chlorella* genes in SEQ ID NO 35-40, 43-44 and 47 to 50 and the *Chlamydomonas* genes in SEQ ID 67-68 would be applicable to this current invention

TABLE 2

| Sequence No. ( ) | protein/dna(<212>); Organism/Strain(<213>)/protein |
|---|---|
| 1 | <212> PRT |
|   | <213> *Chlorella sorokiniana*, strain 1412; phototropin A |
| 2 | <212> DNA |
|   | <213> *Chlorella sorokiniana*, strain 1412; phototropin A |
| 3 | <212> PRT |
|   | <213> *Chlorella sorokiniana*, strain 1412; phototropin B |
| 4 | <212> DNA |
|   | <213> *Chlorella sorokiniana*, strain 1412; phototropin B |
| 5 | <212> PRT |
|   | <213> *Chlorella sorokiniana*, strain 1230; Phototropin A |
| 6 | <212> DNA |
|   | <213> *Chlorella sorokiniana*, strain 1230; Phototropin A |
| 7 | <212> PRT |
|   | <213> *Chlorella sorokiniana*, strain 1230; phototropin B |
| 8 | <212> DNA |
|   | <213> *Chlorella sorokiniana*, strain 1230; phototropin B |
| 9 | <212> PRT |
|   | <213> *Chlorella sorokiniana*, strain 1228; Phototropin A |
| 10 | <212> DNA <213> *Chlorella sorokiniana*, strain 1228; phototropin A |
| 11 | <212> PRT |
|   | <213> *Chlorella sorokiniana*, strain 1228; phototropin B |
| 12 | <212> DNA |
|   | <213> *Chlorella sorokiniana*, strain 1228; phototropin B |
| 13 | <212> PRT |
|   | <213> *Picochlorum soloecismus*, strain DOE101, phototropin |
| 14 | <212> DNA |
|   | <213> *Picochlorum soloecismus*, strain DOE101; phototropin |
| 15 | <212> PRT |
|   | <213> *Chlorella sorokiniana*, strain 1228; KIN11 SNF1-related |
| 16 | <212> DNA |
|   | <213> *Chlorella sorokiniana*, strain 1228; KIN11 SNF1-related |
| 17 | <212> PRT |
|   | <213> *Chlorella sorokiniana*, strain 1228; KIN11 SNF1-related protein kinase catalytic subunit alpha |
| 18 | <212> DNA <213> *Chlorella sorokiniana*, strain 1228; KIN11 SNF1-related protein kinase catalytic subunit alpha |
| 19 | <212> PRT |
|   | <213> *Chlorella sorokiniana*, strain UTEX 1230; KIN11 SNF1-related protein kinase catalytic subunit alpha |
| 20 | <212> DNA |
|   | <213> *Chlorella sorokiniana*, strain UTEX 1230; KIN11 SNF1-related protein kinase catalytic subunit alpha |
| 21 | <212> PRT |
|   | <213> *Chlorella sorokiniana*, strain UTEX1230; KIN11 SNF1-related protein kinase catalytic subunit |
| 22 | <212> DNA |
|   | <213> *Chlorella sorokiniana*, strain UTEX 1230; KIN11 SNF1-related protein kinase atalytic subunit |
| 23 | <212> PRT |
|   | <213> *Chlorella sorokiniana*, strain 1412; KIN11 SNF1-related protein kinase catalytic subunit |
| 24 | <212> DNA |
|   | <213> *Chlorella sorokiniana*, strain 1412; KIN11 SNF1-related protein kinase catalytic subunit |
| 25 | <212> PRT |
|   | <213> *Chlorella sorokiniana*, strain 1412; KIN11 SNF1-related protein kinase catalytic subunit homolog |
| 26 | <212> DNA |
|   | <213> *Chlorella sorokiniana*, strain 1412; KIN11 SNF1-related protein kinase catalytic subunit homolog |
| 27 | <212> PRT |
|   | <213> *Chlamydomonas reinhardtii*; SNF-1 KIN10/11 homolog |
| 28 | <212> DNA |
|   | <213> *Chlamydomonas reinhardtii*; SNF-1 KIN10/11 homolog |
| 29 | <212> PRT |
|   | <213> *Chlamydomonas reinhardtii*; SNF-1 KIN10/11 homolog |
| 30 | <212> DNA |
|   | <213> *Chlamydomonas reinhardtii*; SNF-1 KIN10/11 homolog |
| 31 | <212> PRT |
|   | <213> *Chlamydomonas reinhardtii*; SNF-1 KIN10/11 homolog |

TABLE 2-continued

Sequence ID and Type

Sequence No. ( )  protein/dna(<212>); Organism/Strain(<213>)/protein

| No. | Type / Organism |
|---|---|
| 32 | <212> DNA <213> *Chlamydomonas reinhardtii*; SNF-1 KIN10/11 homolog |
| 33 | <212> PRT <213> *Chlamydomonas reinhardtii*; SNF-1 KIN10/11 homolog |
| 34 | <212> DNA <213> *Chlamydomonas reinhardtii*; SNF-1 KIN10/11 homolog |
| 35 | <212> DNA <213> *Chlorella sorokiniana*, strain UTEX 1230; NTR2 |
| 36 | <212> PRT <213> *Chlorella sorokiniana*, strain UTEX 1230; NTR2 |
| 37 | <212> DNA <213> *Chlorella sorokiniana*, strain 1412; NTR2 |
| 38 | <212> PRT <213> *Chlorella sorokiniana*, strain 1412; NTR2 |
| 39 | <212> DNA <213> *Chlorella sorokiniana*, strain 1228; NTR2 |
| 40 | <212> PRT <213> *Chlorella sorokiniana*, strain 1228; NTR2 |
| 41 | <212> DNA <213> *Picochlorum soloecismus*, strain DOE101; NTR2 |
| 42 | <212> PRT <213> *Picochlorum soloecismus*, strain DOE101; NTR2 |
| 43 | <212> DNA <213> *Chlorella sorokiniana*, strain 1228; NTRC |
| 44 | 212> PRT <213> *Chlorella sorokiniana*, strain 1228; NTRC |
| 45 | <212> DNA <213> *Picochlorum soloecismus*, strain DOE101; NTRC |
| 46 | <212> PRT <213> *Picochlorum soloecismus*, strain DOE101; NTRC |
| 47 | <212> DNA <213> *Chlorella sorokiniana*, strain UTEX 1230; NTRC |
| 48 | <212> PRT <213> *Chlorella sorokiniana*, strain UTEX 1230; NTRC |
| 49 | <212> DNA <213> *Chlorella sorokiniana*, strain 1412; NTRC |
| 50 | <212> PRT <213> *Chlorella sorokiniana*, strain 1412; NTRC |
| 51 | <212> PRT <213> *Chlorella variabilis*; phototropin A |
| 52 | <212> PRT <213> *Chlamydomonas reinhardtii*, strain CC-503; phototropin |
| 53 | <212> PRT <213> *Botryococcus terribilis*; phototropin A homolog |
| 54 | <212> PRT <213> *Tetraselmis striata*; phototropin A |
| 55 | <212> PRT <213> *Micromonas pusilla*, strain CCMP 1545; phototropin A |
| 56 | <212> PRT <213> *Dunaliella salina*; phototropin A |
| 57 | <212> PRT <213> *Chlorella variabilis*; phototropin B homolog |
| 58 | <212> PRT <213> *Haematococcus lacustris*; phototropin B homolog |
| 59 | <212> PRT <213> *Tetraselmis striata*; phototropin B homolog |
| 60 | <212> PRT <213> *Coccomyxa subellipsoidea*, strain C-169; phototropin B homolog |
| 61 | <212> PRT <213> *Micromonas pusilla*, strain CCMP1545; phototropin B homolog |
| 62 | <212> PRT <213> *Vaucheria frigida*; aureochrome1 |
| 63 | <212> PRT <213> *Fucus distichus*; AUREOChrome-like protein |
| 64 | <212> PRT <213> *Nannochloropsis gaditana*; aureochrome1-like protein |
| 65 | <212> PRT <213> *Nannochloropsis gaditana*; aureohrome1-like protein |
| 66 | <212> PRT <213> *Sargassum fusiforme*; putative aurochrome, LOV domain-containing protein |
| 67 | <212> PRT <213> *Chlamydomonas reinhardtii*; NTR2 |
| 68 | <212> PRT <213> *Chlamydomonas reinhardtii*; NTRC |

EXAMPLES

Certain embodiments of the invention will be described in more detail through the following examples. The examples are intended solely to aid in more fully describing selected embodiments of the invention, and should not be considered to limit the scope of the invention in any way.

Example 1—Growth of *Chlamydomonas reinhardtii*

*Chlarnydomonas reinhardtii* parental strains (cw15 and UV4) and the phototropin knockout (PHOT K/0) mutants (CW15 and A4) were grown at 25° C. in 250 mL Erlenmeyer flasks containing 100 mL of High-Salt (HS) or Tris-Acetate-Phosphate (TAP) media and shaken at 150 rpm (world wide web at chlamy.org/media.html). Cultures were typically inoculated from a log phase culture using 1 mL of cells. Flasks were illuminated using fluorescent light at the light intensities as indicated for each experiment.

Example 2—Measurement of Photoautotrophic Growth and Biomass Estimation

Photoautotrophic growth of the parent strains CW15 and UV4) and the phototropin knock out mutants (G5 and A4) was measured in environmental photobioreactors ("ePBRs") (obtained from Phenometrics, Inc.) in 500 mL of liquid HS media. All experiments were done in triplicates for each time point and each treatment. Light intensity was programmed for a 12 h sinusoidal light period with a peak mid-day intensity of 2,000 µmol photons $m^{-2}$ $s^{-1}$. Temperature was a constant 25° C., and the ePBRs were stirred with a magnetic stir bar at 200 rpm. Filtered air was bubbled constantly through the growing cultures. The optical density of the cultures was monitored on a daily basis at 750 nm using a Cary 300 Bio UV-Vis spectrophotometer (Agilent). After completion of growth measurements, the total contents of individual ePBRs were harvested by centrifugation at 11,000 rpm for 15 min. Cell pellets were frozen immediately in liquid $N_2$ and later freeze-dried using a Microprocessor Controlled Lyophilizer (Flexi-Dry). After drying, pellets were weighed for total biomass.

Example 3—Measurement of Chlorophyll Fluorescence

For Chl fluorescence induction analysis, cell suspensions of the parental wild-type and transgenic *Chlamydomonas* strains were adjusted to a Chl concentration of ~2.5 µg/mL. Quenching of Chl fluorescence was measured using the FL-3500 fluorometer (Photon System Instruments) (Kaftan, Meszaros et al. 1999). The cells were dark adapted for 10 min prior to the measurement. Chl fluorescence was induced using non-saturating continuous illumination and Chl fluorescence levels were measured every 1 µs using a weak pulse-modulated measuring flash. For the state transition experiments, low light grown cultures were dark adapted or pre-illuminated with 715 nm light for 10 min prior to the induction of Chl fluorescence. The actinic flash duration for this experiment was set to 50 µs and Chl fluorescence was measured every 1 µs.

Example 4—Measurement of Photosynthetic Oxygen Evolution $CO_2$-supported rates of oxygen evolution were determined for low light (50 µmol photons $m^{-2}$ $s^{-1}$) HS grown log-phase cultures (0.4-0.6 $OD_{750\ nm}$) using a Clark-type oxygen electrode (Hansatech Instruments). Cells were re-suspended in 20 mM HEPES buffer (pH 7.4) and air-saturated rates of oxygen evolution were measured as a function of light intensity (650 nm) at 50, 150, 300, 450, 600, 750 and 850 µmol photons $m^{-2}$ $s^{-1}$. The same experiment was repeated in the presence of 10 mM $NaHCO_3$. Light saturation curves were normalized on the basis of Chl as well as cell density ($A_{750\ nm}$). Chl was determined by method described by Arnon (Arnon 1949).

Example 5—Measurement of Pigment Content by HPLC

*Chlamydomonas* cultures were grown at low (50 µmol photons $m^{-2}$ $s^{-1}$) and high (saturating) light (500 µmol photons $m^{-2}$ $s^{-1}$) intensities for 5 days in HS media in shaker flasks. Cells were centrifuged at 3,000 rpm for 3 min and immediately frozen in liquid nitrogen and lyophilized. Carotenoids and chlorophylls were extracted with 100% acetone in the dark for 20 min. After incubation samples were centrifuged at 14,000 rpm for 2 min in a microfuge and the supernatant was transferred to a glass tube and dried under vacuum. The dried samples were re-suspended in 1 mL of acetonitrile:water:triethylamine (900:99:1, v/v/v) for HPLC analysis. Pigment separation and chromatographic analysis were performed on a Beckman HPLC equipped with a UV-Vis detector, using a C18 reverse phase column at a flow rate of 1.5 ml/min. Mobile phases were (A) acetonitrile/$H_2O$/triethylamine (900:99:1, v/v/v) and (B) ethyl acetate. Pigment detection was carried out at 445 nm with reference at 550 nm (Tian and DellaPenna 2001). Individual algal pigments were identified on the basis of their retention times and optical absorbance properties and quantified on the basis of their integrated absorbance peaks relative to known carotenoid standards. Carotenoid standards were purchased from DHI, Denmark. Pigments were standardized on the basis of dry weight of three replicates.

Example 7—Transmission Electron Microscopy

Cells were prepared for electron microscopy by immobilizing cells in 3% sodium alginate (w/v) and the alginate beads were then solidified by incubation in cold 30 mM CaCl2 for 30 min. We used alginate encapsulated algal cells to keep cells intact as well as to protect from direct and harmful effect of chemicals during fixation processes. These cells were fixed using 2% glutaraldehyde for 1.5-2 hours and after fixation, these cells were post fixed in buffered 2% osmium tetroxide for 1.5 hours. After dehydration these cells were embedded in Spurr's resin. Thin sections were stained with uranyl acetate and lead citrate. LEO 912 transmission electron microscope was used to view and collect images at 120 kv and a Proscan digital camera.

Example 8—Transcriptome Analysis

Total RNA was extracted from 100 mg of cells/sample, flash frozen in liquid nitrogen, grown at high light (500 µmol photons $m^{-2}$ $s^{-1}$) intensities for 5 days in HS media in shaker flasks) using the Direct-zol RNA-miniprep kit (ZYMO, P/N 2051) according to the manufacturer's instructions. Each total RNA sample was enriched for mRNA by hybridizing the poly(A) tail to oligo d(T)25 probes covalently coupled to magnetic beads, followed by elution (NEB, P/N S1419S). The enriched mRNA fractions were prepared for Illumina sequencing using the ScriptSeq V.2 RNA-seq Library Preparation Kit (Epicentre, P/N SSV21106) and sequenced on a Hi-Seq 2000 (2×150 bp), multiplexed at 6 samples per lane. The resultant sequence reads were trimmed for quality and mapped to the coding sequences present in version 9 of the *Chlamydomonas reinhardtii* genome annotation at web address phytozome.jgi.doe.gov/pz/portal.html#!info?alias=Org_Creinhardtii using bowtie2. The relative transcript abundance of each gene (mean of 3 biological samples) was determined using RSEM and differential expression values (UV4 vs A4) were calculated using EdgeR. All genes identified as differentially expressed were mapped to KEGG biochemical maps using the v.9 annotation assignments.

Example 9—Identification of *Chlorella* Spp. Phototropin Coding Sequence

Phototropin genes were identified in three *Chlorella* species (herein designated as strain 1412, strain 1228 and *Chlorella sorokiniana* UTEX1230) and a *Picochiorum soloecismus* (DOE101) by conducting homologous BLASTp searches against the annotations of *Chlorella* species using *Chlamydomonas reinhardtii* phototropin genes/proteins (NP_851210) and *Arabidopsis thaliana* protein sequences (Accession # AED97002.1 and AEE78073) as query proteins. The *Chlorella* spp. and Picochiorum phototropin homologs were aligned to other phototropin amino acid sequences using CLUSTALW, then truncated based on conserved sequence alignments and phylogenetically analyzed using a Maximum-Likelihood algorithm. Each *Chlorella* strain contains two paralogous copies of photoropin and *Picochlorum soloecismus*. (DOE101) was found to contain 1 homolog of phototropin. These sequences are provided as SEQ ID Nos. 1-14. Additional phototropin sequences and functional homologs are provided in Table 1 and SEQ ID NO 51-66.

Example 10—Inducible Control of Phototropin Expression in *Chlamydomonas reinhardtii*

One method to reduce expression of algal PHOT gene(s) is to use RNAi technology driving the expression of double stranded, fold-back RNA elements to reduce the PHOT expression. A strong gene promoter such as psaD or other strong constitutive gene promoters could be used to drive expression of the RNAi construct similar to methods used previously in *Chlamydomonas* for modulation of light harvesting antennae complex (Perrine, Negi et al. 2012).

Example 11—Production of a *Chlorella* Phototropin Minus Mutant

PHOT gene knockouts could be potentially generated by traditional mutagenesis approaches including chemical, UV, random insertional mutagenesis screened by TILLING (Comai, Young et al. 2004, Nieto, Piron et al. 2007), and by targeted knock outs using CRISPR/cas9 (Wang, Yang et al. 2013, Xiao, Wang et al. 2013, Dubrow 2014). Pooled PHOT-based PCR screening coupled with sequencing of PHOT PCR products could be used to screen for PHOT mutants.

Example 12—Chemical Mutagenesis for Production of a Phototropin K/O Mutant in *Chlorella sorokiniana*

Classical chemical mutagenesis is carried out using N-methyl-N'-nitro-N-nitrosoguanidine (MNNG). This mutagen makes nucleotide changes in the DNA and these changes, depending on their position, can have effects that are either positive or negative in the use of the strain being treated. By careful observation of phenotypes produced, as well as implementation of selective pressure, one selects mutants with improved traits for the desired purpose. This method has been applied to algae previously (Yan, Aruga et al. 2000).

Identifying strains of algae that grow rapidly and produce high starch is used as a selection marker for PHOT K/O mutants. Because this approach does not involve adding foreign DNA (in fact is focused only on existing genetic potential of the strain being mutagenized), strains generated by chemical mutagenesis are not considered to be "genetically modified", allowing deployment in the field without additional government regulation.

N-methyl-N'-nitro-N-nitrosoguanidine (MNNG) was chosen based on its proven use for modifying blue-green algae, as well as its ability to eliminate toxicity by degradation in dilute acid. First, the conditions required to result in approximately 99% lethality for *Chlorella prototheocoides* are determined; this degree of lethality generated optimal mutation frequency in blue-green algae (Chapman and Meeks 1987). Two treatments, exposure to 0.25 mg/mL MNNG for 30 minutes and 0.025 mg/mL MNNG for 60 minutes, result in approximately 99% lethality for this strain (unpublished data). Both treatments are used to generate mutagenized populations of *Chlorella* using enrichment strategies.

Approximately $10^8$ cells are mutagenized with four concentrations of MNNG and incubated for three different durations. After rinsing out the mutagen, approximately $10^4$ cells are spread plated on nutrient plates, and the number of colonies scored after 12 days. Treatments with approximately 100 surviving colonies, representing 99% lethality, are chosen as optimal for generating mutations.

PHOT K/O mutants are expected to be more rapidly growing and to produce excess sink molecules/material. In *C. prototheocoides* the sink is lipid which could be used as a screen for selection of cells representing high lipid cells. Numerous methods are in the literature for such selection such as Nile red (Pick and Rachutin-Zalogin 2012) and BODIPY 493/503 (Ohsaki, Shinohara et al. 2010). High lipid cells are selected by flow cytometry and then placed in flask for cell culture. Rapid growing high lipid cells will dominate the culture and should be PHOT K/O as determined in this invention.

Example 13—Genome Editing Using CRISPR/Cas9 to Reduce Expression of Phototropin in *Chlamydomonas reinhardtii*

Recently, it has been demonstrated that CRISPR/cas9 genome editing techniques can be used to knock out genes of interest in *Chlamydomonas* when the Cas9 gene is expressed constitutively. By incorporating multiple guide RNA elements to specifically recognize the PHOT gene high efficiencies of gene mutagenesis can occur during miss-repair of the double stranded break in the target gene catalyzed by Cas/9 by the endogenous repair enzymes. By targeting repair of a recognized restriction endonuclease site, inhibition of the digestion of the PHOT-specific PCR product by the diagnostic restriction endonuclease can be used as an effective screen for PHOT mutants. Similarly, DNA repair mistakes that occur following double stranded DNA breaks in the PHOT gene generated by TALEN complexes can be used to generate PHOT-specific mutants.

REFERENCES CITED

The following references and others cited herein, to the extent that they provide exemplary procedural and other details supplementary to those set forth herein, are specifically incorporated herein by reference and include US published patent applications and published patents: US 20130116165; US 20140249295; US 20130330718; U.S. Pat. No. 8,859,232 and other patent related documents EP2682469; WO 2011133493; WO 201408626; and WO 2013056212 and other publications listed:

OTHER PUBLICATIONS

Arnon, D. I. (1949). "Copper Enzymes in Isolated Chloroplasts. Polyphenoloxidase in *Beta Vulgaris*." *Plant Physiol* 24(1): 1-15.

Ausubel, F. M., R. Brent, R. Kingston, D. Moore, J. Seidman, J. Smith and K. Struhl (1997). *Short Protocols in Molecular Biology*. New York, Wiley.

Baena-Gonzalez, E., F. Rolland, J. M. Thevelein and J. Sheen (2007). "A central integrator of transcription networks in plant stress and energy signalling." *Nature* 448(7156): 938-942.

Briggs, W. R. and M. A. Olney (2001). "Photoreceptors in plant photomorphogenesis to date. Five phytochromes, two cryptochromes, one phototropin, and one superchrome." *Plant Physiol* 125(1): 85-88.

Chapman, J. and J. Meeks (1987). "Conditions for mutagenesis of the nitrogen-fixing cyanobacterium *Anabaena variabilis*." *J Gen Microbiol* 131: 111-118.

Chen, M., J. Chory and C. Fankhauser (2004). "Light signal transduction in higher plants." *Annu Rev Genet* 38: 87-117.

Comai, L., K. Young, B. J. Till, S. H. Reynolds, E. A. Greene, C. A. Codomo, L. C. Enns, J. E. Johnson, C. Burtner, A. R. Odden and S. Henikoff (2004). "Efficient discovery of DNA polymorphisms in natural populations by Ecotilling." *Plant J* 37(5): 778-786.

Dubrow, Z. (2014). The develpment and application of the CRISPR/CAS system as a powerful new tool for genome editing: A case study.

Ermilova, E. V., Z. M. Zalutskaya, K. Huang and C. F. Beck (2004). "Phototropin plays a crucial role in controlling changes in chemotaxis during the initial phase of the sexual life cycle in *Chlamydomonas*." *Planta* 219(3): 420-427.

Folta, K. M., E. J. Lieg, T. Durham and E. P. Spalding (2003). "Primary inhibition of hypocotyl growth and phototropism depend differently on phototropin-mediated increases in cytoplasmic calcium induced by blue light." *Plant Physiol* 133(4): 1464-1470.

Fu, X., D. Wang, X. Yin, P. Du and B. Kan (2014). "Time course transcriptome changes in *Shewanella algae* in response to salt stress." *PLoS One* 9(5): e96001.

Gaj, T., C. A. Gersbach and C. F. Barbas, 3rd (2013). "ZFN, TALEN, and CRISPR/Cas-based methods for genome engineering." *Trends Biotechnol* 31(7): 397-405.

Green, M. and J. Sambrook (2012). *Molecular cloning: A laboratory manual*. Cold Spring Habor, N.Y., Cold Spring Harbor Laboratory Press.

Grossman, A. R. (2005). "Paths toward Algal Genomics." *Plant Physiology* 137(2): 410-427.

Huang, K. and C. F. Beck (2003). "Phototropin is the blue-light receptor that controls multiple steps in the sexual life cycle of the green alga *Chlamydomonas reinhardtii*." *Proc Natl Acad Sci USA* 100(10): 6269-6274.

Huang, K. and C. F. Beck (2003). "Phototropin is the blue-light receptor that controls multiple steps in the sexual life cycle of the green alga *Chlamydomonas reinhardtii*." *Proceedings of the National Academy of Sciences* 100(10): 6269-6274.

Huang, K., T. Kunkel and C. F. Beck (2004). "Localization of the blue-light receptor phototropin to the flagella of the green alga *Chlamydomonas reinhardtii*." *Mol Biol Cell* 15(8): 3605-3614.

Hwang, Y. S., G. Jung and E. Jin (2008). "Transcriptome analysis of acclimatory responses to thermal stress in Antarctic algae." *Biochem Bioghys Res Commun* 367(3): 635-641.

Im, C. S., S. Eberhard, K. Huang, C. F. Beck and A. R. Grossman (2006). "Phototropin involvement in the expression of genes encoding chlorophyll and carotenoid biosynthesis enzymes and LHC apoproteins in *Chlamydomonas reinhardtii*." *Plant J* 48(1): 1-16.

Kaftan, D., T. Meszaros, J. Whitmarsh and L. Nedbal (1999). "Characterization of photosystem II activity and heterogeneity during the cell cycle of the green alga *scenedesmus quadricauda*." *Plant Physiol* 120(2): 433-442.

Kagawa, T., M. Kimura and M. Wada (2009). "Blue Light-Induced Phototropism of Inflorescence Stems and Petioles is Mediated by Phototropin Family Members phot1 and phot2." *Plant and Cell Physiology* 50(10): 1774-1785.

Kanehisa, M. and S. Goto (2000). "KEGG: kyoto encyclopedia of genes and genomes." *Nucleic Acids Res* 28(1): 27-30.

Kanehisa, M., S. Goto, Y. Sato, M. Kawashima, M. Furumichi and M. Tanabe (2014). "Data, information, knowledge and principle: back to metabolism in KEGG." *Nucleic Acids Res* 42 (Database issue): D199-205.

Koid, A. E., Z. Liu, R. Terrado, A. C. Jones, D. A. Caron and K. B. Heidelberg (2014). "Comparative transcriptome analysis of four prymnesiophyte algae." *PLoS One* 9(6): e97801.

Kozuka, T., S. G. Kong, M. Doi, K. Shimazaki and A. Nagatani (2011). "Tissue-autonomous promotion of palisade cell development by phototropin 2 in *Arabidopsis*." *Plant Cell* 23(10): 3684-3695.

Matsuoka, D., T. Iwata, K. Zikihara, H. Kandori and S. Tokutomi (2007). "Primary processes during the light-signal transduction of phototropin." *Photochem Photobiol* 83(1): 122-130.

Moni, A., A. Y. Lee, W. R. Briggs and I. S. Han (2015). "The blue light receptor Phototropin 1 suppresses lateral root growth by controlling cell elongation." *Plant Biol (Stuttg)* 17(1): 34-40.

Nieto, C., F. Piron, M. Dalmais, C. F. Marco, E. Moriones, M. L. Gomez-Guillamon, V. Truniger, P. Gomez, J. Garcia-Mas, M. A. Aranda and A. Bendahmane (2007). "EcoTILLING for the identification of allelic variants of melon eIF4E, a factor that controls virus susceptibility." *BMC Plant Biol* 7: 34.

Ohsaki, Y., Y. Shinohara, M. Suzuki and T. Fujimoto (2010). "A pitfall in using BODIPY dyes to label lipid droplets for fluorescence microscopy." *Histochem Cell Biol* 133(4): 477-480.

Onodera, A., Kong, S-G, M. Doi, K.-I. Shimazaki, J. Christie, N. Mochizuki and A. Nagatani (2005). "Phototropin from *Chlamydomonas reinhardtii* is functional in *Arabidopsis thaliana.*" *Plant Cell Physiol* 46(2): 367-374.

Perrine, Z., S. Negi and R. Sayre (2012). "Optimization of photosynthetic light energy utilization by microalgae." *Algal Res* 134-142.

Pick, U. and T. Rachutin-Zalogin (2012). "Kinetic anomalies in the interactions of Nile red with microalgae." *Journal of microbiological methods* 88(2): 189-196.

Reeck, G. R., C. de Haen, D. C. Teller, R. F. Doolittle, W. M. Fitch, R. E. Dickerson, P. Chambon, A. D. McLachlan, E. Margoliash, T. H. Jukes and et al. (1987). ""Homology" in proteins and nucleic acids: a terminology muddle and a way out of it." *Cell* 50(5): 667.

Rismani-Yazdi, H., B. Z. Haznedaroglu, K. Bibby and J. Peccia (2011). "Transcriptome sequencing and annotation of the microalgae *Dunaliella tertiolecta*: pathway description and gene discovery for production of next-generation biofuels." *BMC Genomics* 12: 148.

Sambrook, J., E. Fritsch and T. Maniatis (1989). *Molecular cloning: a laboratory manual*. Cold Spring Harbor, N.Y., Cold Spring Harbor Laboratory Press.

Sethi, P., M. Prasad and S. Roy (2009). *All-optical switching in LOV2-C250S protein mutant from Chlamydomonas reinhardtii green algae*. Emerging Trends in Electronic and Photonic Devices & Systems, 2009. ELECTRO '09. International Conference on.

Sizova, I., A. Greiner, M. Awasthi, S. Kateriya and P. Hegemann (2013). "Nuclear gene targeting in *Chlamydomonas* using engineered zinc-finger nucleases." *Plant J* 73(5): 873-882.

Suetsugu, N. and M. Wada (2007). "Phytochrome-dependent Photomovement Responses Mediated by Phototropin Family Proteins in Cryptogam Plants†." *Photochemistry and Photobiology* 83(1): 87-93.

Sullivan, S., C. E. Thomson, D. J. Lamont, M. A. Jones and J. M. Christie (2008). "In vivo phosphorylation site mapping and functional characterization of *Arabidopsis* phototropin 1." *Mol Plant* 1(1): 178-194.

Takemiya, A., S. Inoue, M. Doi, T. Kinoshita and K. Shimazaki (2005). "Phototropins promote plant growth in response to blue light in low light environments." *Plant Cell* 17(4): 1120-1127.

Tian, L. and D. DellaPenna (2001). "Characterization of a second carotenoid beta-hydroxylase gene from *Arabidopsis* and its relationship to the LUT1 locus." *Plant Mol Biol* 47(3): 379-388.

Trippens, J., A. Greiner, J. Schellwat, M. Neukam, T. Rottmann, Y. Lu, S. Kateriya, P. Hegemann and G. Kreimer (2012). "Phototropin Influence on Eyespot Development and Regulation of Phototactic Behavior in *Chlamydomonas reinhardtii.*" *The Plant Cell* 24(11): 4687-4702.

Veetil, S. K., C. Mittal, P. Ranjan and S. Kateriya (2011). "A conserved isoleucine in the LOV1 domain of a novel phototropin from the marine alga *Ostreococcus tauri* modulates the dark state recovery of the domain." *Biochim Biophys Acta* 1810(7): 675-682.

Wang, H., H. Yang, C. S. Shivalila, M. M. Dawlaty, A. W. Cheng, F. Zhang and R. Jaenisch (2013). "One-step generation of mice carrying mutations in multiple genes by CRISPR/Cas-mediated genome engineering." *Cell* 153 (4): 910-918.

Xiao, A., Z. Wang, Y. Hu, Y. Wu, Z. Luo, Z. Yang, Y. Zu, W. Li, P. Huang, X. Tong, Z. Zhu, S. Lin and B. Zhang (2013). "Chromosomal deletions and inversions mediated by TALENs and CRISPR/Cas in zebrafish." *Nucleic Acids Res* 41(14): e141.

Yan, X.-H., Y. Aruga and Y. Fujita (2000). "Induction and characterization of pigmentation mutants in *Porphyra yezoensis* (Bangiales, Rhodophyta)." *Journal of Applied Phycology* 12(1): 69-81.

Zorin, B., Y. Lu, I. Sizova and P. Hegemann (2009). "Nuclear gene targeting in *Chlamydomonas* as exemplified by disruption of the PHOT gene." *Gene* 432(1-2): 91-96.

Toivola, J., Nikkanen, L., Dahlström, K. M., Salminen, T. A., Lepisto, A., Vignols, F., and Rintamäki, E. (2013). "Overexpression of chloroplast NADPH dependent thioredoxin reductase in *Arabidopsis* enhances leaf growth and elucidates in vivo function of reductase and thioredoxin domains." Frontiers in plant sciences doi: 10.3389/fpls.2013.00389

Takahashi F (2016) Blue-light-regulated transcription factor, Aureochrome, in photosynthetic stramenopiles. *J Plant Res* 129(2):189-97.

---

What is claimed is:

1. A method for increasing a biomass productivity of an algal strain as compared to the productivity of a wild-type parental strain wherein an expression or function of a gene comprising a nucleotide sequence with at least 85% homology to a nucleotide sequence encoding any of SEQ ID NO 15, 21, 25, 31, and 33 or a polypeptide sequence having at least 85% homology to any of SEQ ID NO 15, 21, 25, 31, and 33 is over expressed in the algal strain as compared to the wild-type parental strain, and wherein the function is homologous to the *Arabidopsis* SNF1-related protein kinase KIN10 or KIN11
and wherein the biomass productivity is selected from bioproducts or storage products.

2. The method of claim 1, wherein the gene has at least 90% sequence homology to the nucleotide sequence encoding any of SEQ ID NO 15, 21, 25, 31, and 33 or the polypeptide sequence has at least 90% homology to any of SEQ ID NO 15, 21, 25, 31, and 33.

3. The method of claim 1, wherein the homologous gene has at least 95% sequence homology to the nucleotide sequence encoding any of SEQ ID NO 15, 21, 25, 31, and 33 or the polypeptide sequence has at least 95% homology to any of SEQ ID NO 15, 21, 25, 31, and 33.

4. The method of claim 1, wherein the biomass productivity of the algal strain is increased as compared to the wildtype parental strain.

5. The method of claim 1, wherein the biomass productivity of storage products in the algal strain is increased as compared to the wildtype parental strain.

6. The method of claim 5, wherein the storage product is selected from starch, lipid, pigments and other sink molecules.

7. The method of claim 1, wherein the biomass productivity is increased as compared to the wildtype parental strain for bioproducts or storage products selected from lipids, waxes, polysaccharides, and photoprotective pigments.

8. The method of claim 7 wherein the polysaccharides are selected from the group consisting of: starch, glycogen, mannans, glycans, cellulose, and hemicellulose.

9. The method of claim 7 wherein the photoprotective pigments is xanthophyll.

* * * * *

UNITED STATES PATENT AND TRADEMARK OFFICE
CERTIFICATE OF CORRECTION

Page 1 of 1

PATENT NO. : 10,590,398 B2
APPLICATION NO. : 15/831178
DATED : March 17, 2020
INVENTOR(S) : Sangeeti Negi, Richard Thomas Sayre and Shawn Robert Starkenburg It is certified that error appears in the above-identified patent and that said Letters Patent is hereby corrected as shown below:

In the Specification

Column 1, Lines 23-26 are replaced as shown:
This invention was made with government support under contract/grant Nos. Prime Contract No. DE-AC52-06NA25396 and NMC. Inc, subcontract No. 277529 awarded by Department of Energy (DOE); DE-EE0006316 awarded by DOE-REAP; DE-EE0007089-40101-5804 awarded by DOE-PACE. The U.S. government has certain rights in the invention.

Signed and Sealed this
First Day of September, 2020

Andrei Iancu
*Director of the United States Patent and Trademark Office*